United States Patent
Menet et al.

(10) Patent No.: US 9,440,929 B2
(45) Date of Patent: Sep. 13, 2016

(54) COMPOUNDS AND PHARMACEUTICAL COMPOSITIONS THEREOF FOR THE TREATMENT OF INFLAMMATORY DISORDERS

(71) Applicant: GALAPAGOS NV, Mechelen (BE)

(72) Inventors: Christel Jeanne Marie Menet, Mechelen (BE); Oscar Mammoliti, Mechelen (BE); Javier Blanc, Mechelen (BE); Mislav Orsulic, Zagreb (HR); Maja Roscic, Zagreb (HR)

(73) Assignee: GALAPAGOS NV, Mechelen (BE)

( * ) Notice: Subject to any disclaimer, the term of this patent is extended or adjusted under 35 U.S.C. 154(b) by 0 days.

(21) Appl. No.: 14/599,644

(22) Filed: Jan. 19, 2015

(65) Prior Publication Data

US 2015/0203455 A1    Jul. 23, 2015

(51) Int. Cl.

| | |
|---|---|
| *C07D 401/06* | (2006.01) |
| *C07D 401/12* | (2006.01) |
| *C07D 235/08* | (2006.01) |
| *C07D 401/14* | (2006.01) |
| *C07D 405/12* | (2006.01) |
| *A61K 31/4184* | (2006.01) |
| *A61K 31/4439* | (2006.01) |
| *A61K 31/5377* | (2006.01) |
| *A61K 45/06* | (2006.01) |
| *C07D 413/14* | (2006.01) |

(52) U.S. Cl.
CPC ......... *C07D 235/08* (2013.01); *A61K 31/4184* (2013.01); *A61K 31/4439* (2013.01); *A61K 31/5377* (2013.01); *A61K 45/06* (2013.01); *C07D 401/12* (2013.01); *C07D 401/14* (2013.01); *C07D 405/12* (2013.01); *C07D 413/14* (2013.01)

(58) Field of Classification Search
CPC .......................... C07D 401/06; C07D 401/12
USPC .............................. 546/273.4, 273.7; 514/338
See application file for complete search history.

(56) References Cited

FOREIGN PATENT DOCUMENTS

| EP | 2226315 | 9/2010 |
|---|---|---|
| WO | WO2005124342 | 12/2005 |
| WO | WO2012044090 | 4/2012 |
| WO | WO2013117645 | 8/2013 |

OTHER PUBLICATIONS

Kirk-Othmer Encyclopedia of Chemical Technology, 8, pp. 95-147 (2002).*
Vippagunta et al., "Crystalline Solids", Advanced Drug Delivery Reviews 48 (2001) 3-26.*
Guillory (in Brittain ed.), "Polymorphism in Pharmaceutical Solids. ," NY: Marcel Dekker, Inc., 1999, 1-2, 125-181, 183-226.*
Yu et al., "Physical characterization of, etc.," PSTT, vl. 1(3), 118-127 (1998).*
Braga et al., "Making crystals from . . . " J. Royal Soc. Chem. Commun. p. 3635-3645 (2005).*
Bernstein, "Polymorphism in . . . " p. 115-118, 272 (2002).*
Davidovich et al., "Detection of polymorphism . . . " Am. Pharm. Rev. v.&(1) p. 10, 12, 14, 16, 100 (2004).*
Dean "Analytical Chem . . . " p. 10.24-10.26 (1995).*
Invanisevic et al. "Use of X-ray . . . " Pharm. Sci. Encycl. p. 1-42 (2010).*
Seddon "Pseudopolymorph. . . " Crystal Growth & design v.4(6) p. 1087 (2004) (2 pages from internet).*
Firestein G. S., Evolving concepts of rheumatoid arthritis, Nature, vol. 423, May 15, 2003, 356-361.
Kopf et al., Averting inflammation by targeting the cytokine environment Nature Reviews, Drug Discovery, vol. 9, Sep. 2010, 703-718.
Legendre et al., JAK/STAT but Not ERK1/ERK2 Pathway Mediates Interleukin (IL)-6/Soluble IL-6R Down-regulation of Type II Collagen, Aggrecan Core, and Link Protein Transcription in Articular Chondrocytes, The Journal of Biological Chemistry, vol. 278, No. 5, 2003, pp. 2903-62912.
Levy et al., STAT3 Signaling and the Hyper-IgE Syndrome, N Eng J Med, Oct. 18, 2007, 357, 16, 1655-1658.
Li et al., Oncostatin M-Induced Matrix Metalloproteinase and Tissue Inhibitor of Metalloproteinase-3 Genes Expression in Chondrocytes Requires Janus Kinase/STAT Signaling Pathway, The Journal of Immunology, 2001, 166 (5):3491-8.

(Continued)

*Primary Examiner* — Patricia L Morris
(74) *Attorney, Agent, or Firm* — Klauber & Jackson LLC

(57) ABSTRACT

The present invention discloses compounds according to Formula I:

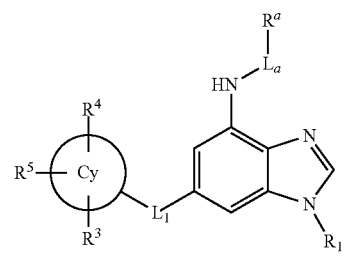

wherein Cy, $R^1$, $L_1$, $R^3$, $R^4$, $R^5$, $L_a$, and $R^a$ are as defined herein.

Novel benzimidazoles according to Formula I, able to inhibit JAK are disclosed, these compounds may be prepared as a pharmaceutical composition, and may be used for the prevention and treatment of a variety of conditions in mammals including humans, including by way of non-limiting example, allergic diseases, inflammatory diseases, autoimmune diseases, proliferative diseases, transplantation rejection, diseases involving impairment of cartilage turnover, congenital cartilage malformations, and/or diseases associated with hypersecretion of IL6 or hypersecretion of interferons.

14 Claims, No Drawings

(56) References Cited

OTHER PUBLICATIONS

Mullighan, et al., JAK mutations in high-risk childhood acute lymphoblastic leukemia, PNAS, 2009, 106(23), 9414-18.
O'Shea et al., A new modality for immunosuppression: targeting the JAK/STAT pathway, Nature Reviews, Jul. 2004, vol. 3, 555-564.
O'Sullivan et al., Cytokine receptor signaling through the Jak-Stat-Socs pathway in disease, Molecular Immunology 44 (2007) 2497-2506.
Osaki et al., The TATA-containing core promoter of the type II collagen gene (COL2A1) is the target of interferon-c-mediated inhibition in human chondrocytes: requirement for Stat1a, Jak1 and Jak2, Biochem. J, 2003, 369, 103-115.
Otero et al., Signalling pathway involved in nitric oxide synthase type II activation in chondrocytes: synergistic effect of leptin with interleukin-1, Arthritis Research & Therapy 2005, 7:R581-R591.
Rodig et al., Disruption of the Jak1 Gene Demonstrates Obligatory and Nonredundant Roles of the Jaks in Cytokine-Induced Biologic Responses, Cell, vol. 93, 373-383, May 1, 1998.
Vainchenker et al., JAKs in pathology: Role of Janus kinases in hematopoietic malignancies and immunodeficiencies, Seminars in Cell & Developmental Biology, 2008, 19, 385-393.
Xiang et al., Identification of somatic JAK1 mutations in patients with acute myeloid leukemia, Blood, 2008, 111: 4809-4812.
O'Dell, Therapeutic Strategies for Rheumatoid Arthritis;2004 N Eng J Med, 350, 2591-602.
Naka T et al., The paradigm of IL-6: from basic science to medicine. Arthritis Res,2002; 4 (suppl 3), S233-S242.
Choy et al., Cytokine Pathways and Joint Inflammation in Rheumatoid Arthritis, N Engl J Med, Mar. 22, 2001, vol. 344, No. 12 . 907-916.
Clegg et al., Glucosamine, Chondroitin Sulfate, and the Two in Combination for Painful Knee Osteoarthritis, N Engl J Med 2006, 354, 795-808.
Lee et al., Rheumatoid arthritis, The Lancet, Sep. 2001, vol. 358, p. 903-911.
Smolen J.S. et al, Therapeutic strategies for rheumatoid arthritis, Nat Rev Drug Discov, 2003, 2(6), 473-88.
Wieland et al., Osteoarthritis—an untreatable disease?, Nature Reviews, 2005, vol. 4, 331-344.
Tam et al, Expression levels of the JAK/STAT pathway in the transition from hormone-sensitive to hormone-refractory prostate cancer, British Journal of Cancer, 2007, vol. 97, 378-383.

* cited by examiner

COMPOUNDS AND PHARMACEUTICAL COMPOSITIONS THEREOF FOR THE TREATMENT OF INFLAMMATORY DISORDERS

CROSS REFERENCE TO RELATED APPLICATION

The present application claims the priority of co-pending United Kingdom Application No. GB 1401086.2 filed on Jan. 23, 2014, and the disclosure of said application is incorporated herein by reference in its entirety. Applicants claim the benefits of said application under 35 U.S.C. §119.

FIELD OF THE INVENTION

The present invention relates to compounds that are inhibitors of JAK, a family of tyrosine kinases that are involved in allergic diseases, inflammatory diseases, autoimmune diseases, proliferative diseases, transplantation rejection, diseases involving impairment of cartilage turnover, congenital cartilage malformations, and/or diseases associated with hypersecretion of IL6 or hypersecretion of interferons. In particular, the compounds of the invention inhibit JAK1 and/or TYK2. The present invention also provides methods for the production of the compounds of the invention, pharmaceutical compositions comprising the compounds of the invention, methods for the prevention and/or treatment of diseases involving allergic diseases, inflammatory diseases, autoimmune diseases, proliferative diseases, transplantation rejection, diseases involving impairment of cartilage turnover, congenital cartilage malformations, and/or diseases associated with hypersecretion of IL6 or hypersecretion of interferons by administering a compound of the invention.

BACKGROUND OF THE INVENTION

Janus kinases (JAKs) are cytoplasmic tyrosine kinases that transduce cytokine signaling from membrane receptors to STAT transcription factors. Four JAK family members are described, JAK1, JAK2, JAK3 and TYK2. Upon binding of the cytokine to its receptor, JAK family members auto- and/or transphosphorylate each other, followed by phosphorylation of STATs that then migrate to the nucleus to modulate transcription. JAK-STAT intracellular signal transduction serves the interferons, most interleukins, as well as a variety of cytokines and endocrine factors such as EPO, TPO, GH, OSM, LIF, CNTF, GM-CSF and PRL. (Vainchenker et al., 2008)

The combination of genetic models and small molecule JAK inhibitor research revealed the therapeutic potential of several JAKs. JAK3 is validated by mouse and human genetics as an immune-suppression target. (O'Shea et al., 2004) JAK3 inhibitors were successfully taken into clinical development, initially for organ transplant rejection but later also in other immuno-inflammatory indications such as rheumathoid arthritis (RA), psoriasis and Crohn's disease (http://clinicaltrials.gov/).

TYK2 is a potential target for immuno-inflammatory diseases, being validated by human genetics and mouse knock-out studies. (Levy and Loomis, 2007)

JAK1 is a target in the immuno-inflammatory disease area. JAK1 heterodimerizes with the other JAKs to transduce cytokine-driven pro-inflammatory signaling. Therefore, inhibition of JAK1 is of interest for immuno-inflammatory diseases with pathology-associated cytokines that use JAK1 signaling, such as IL-6, IL-4, IL-5, IL-13, or IFNgamma, as well as for other diseases driven by JAK-mediated signal transduction.

The degeneration of cartilage is the hallmark of various diseases, among which rheumatoid arthritis and osteoarthritis are the most prominent. Rheumatoid arthritis (RA) is a chronic joint degenerative disease, characterized by inflammation and destruction of the joint structures. When the disease is unchecked, it leads to substantial disability and pain due to loss of joint functionality and even premature death. The aim of an RA therapy, therefore, is not only to slow down the disease but to attain remission in order to stop the joint destruction. Besides the severity of the disease outcome, the high prevalence of RA (~0.8% of adults are affected worldwide) means a high socio-economic impact. (Choy and Panayi, 2001; Firestein, 2003; Lee and Weinblatt, 2001; O'Dell, 2004; Smolen and Steiner, 2003).

JAK1 and JAK2 are implicated in intracellular signal transduction for many cytokines and hormones. Pathologies associated with any of these cytokines and hormones can be ameliorated by JAK1 and JAK2 inhibitors. Hence, several allergic or inflammatory conditions and autoimmune diseases might benefit from treatment with compounds described in this invention including rheumatoid arthritis, systemic lupus erythematosis, juvenile idiopathic arthritis, osteoarthritis, asthma, chronic obstructive pulmonary disease COPD, tissue fibrosis, eosinophilic inflammation, eosophagitis, inflammatory bowel diseases (e.g. Crohn's, ulcerative colitis), transplantation, graft-versus-host disease, psoriasis, myositis, multiple sclerosis. (Kopf et al., 2010)

Osteoarthritis (also referred to as OA, or wear-and-tear arthritis) is the most common form of arthritis and is characterized by loss of articular cartilage, often associated with hypertrophy of the bone and pain. (Wieland et al., 2005)

Osteoarthritis is difficult to treat. At present, no cure is available and treatment focuses on relieving pain and preventing the affected joint from becoming deformed. Common treatments include the use of non-steroidal anti-inflammatory drugs (NSAIDs). Although dietary supplements such as chondroitin and glucosamine sulphate have been advocated as safe and effective options for the treatment of osteoarthritis, a recent clinical trial revealed that both treatments did not reduce pain associated with osteoarthritis. (Clegg et al., 2006)

Stimulation of the anabolic processes, blocking catabolic processes, or a combination of these two, may result in stabilization of the cartilage, and perhaps even reversal of the damage, and therefore prevent further progression of the disease. Therapeutic methods for the correction of the articular cartilage lesions that appear during the osteoarthritic disease have been developed, but so far none of them have been able to mediate the regeneration of articular cartilage in situ and in vivo. Taken together, no disease modifying osteoarthritic drugs are available.

Vandeghinste et al. (Vandeghinste et al., 2005) discovered JAK1 as a target whose inhibition might have therapeutic relevance for several diseases including OA. Knockout of the JAK1 gene in mice demonstrated that JAK1 plays essential and non-redundant roles during development: JAK1-/- mice died within 24 h after birth and lymphocyte development was severely impaired. Moreover, JAK1-/- cells were not, or less, reactive to cytokines that use class II cytokine receptors, cytokine receptors that use the gamma-c subunit for signaling and the family of cytokine receptors that use the gp130 subunit for signaling. (Rodig et al., 1998)

Various groups have implicated JAK-STAT signaling in chondrocyte biology. Li et al. (Li et al., 2001) showed that Oncostatin M induces MMP and TIMP3 gene expression in primary chondrocytes by activation of JAK/STAT and MAPK signaling pathways. Osaki et al. (Osaki et al., 2003) showed that interferon-gamma mediated inhibition of collagen II in chondrocytes involves JAK-STAT signaling. IL1-beta induces cartilage catabolism by reducing the expression of matrix components, and by inducing the expression of collagenases and inducible nitric oxide synthase (N052), which mediates the production of nitric oxide (NO). Otero et al. (Otero et al., 2005) showed that leptin and IL1-beta synergistically induced NO production or expression of NOS2 mRNA in chondrocytes, and that that was blocked by a JAK inhibitor. Legendre et al. (Legendre et al., 2003) showed that IL6/IL6 Receptor induced downregulation of cartilage-specific matrix genes collagen II, aggrecan core and link protein in bovine articular chondrocytes, and that this was mediated by JAK/STAT signaling. Therefore, these observations suggest a role for JAK kinase activity in cartilage homeostasis and therapeutic opportunities for JAK kinase inhibitors.

JAK family members have been implicated in additional conditions including myeloproliferative disorders (O'Sullivan et al., 2007), where mutations in JAK2 have been identified. This indicates that inhibitors of JAK in particular JAK2 may also be of use in the treatment of myeloproliferative disorders. Additionally, the JAK family, in particular JAK1, JAK2 and JAK3, has been linked to cancers, in particular leukaemias e.g. acute myeloid leukaemia (O'Sullivan et al., 2007; Xiang et al., 2008), and acute lymphoblastic leukaemia (Mullighan et al., 2009) or solid tumours e.g. uterine leiomyosarcoma (Constantinescu et al., 2008), prostate cancer (Tam et al., 2007). These results indicate that inhibitors of JAK, in particular of JAK1 and/or JAK2, may also have utility in the treatment of cancers (leukaemias and solid tumours e.g. uterine leiomyosarcoma, prostate cancer).

In addition, Castleman's disease, multiple myeloma, mesangial proliferative glomerulonephritis, psoriasis, and Kaposi's sarcoma are likely due to hypersecretion of the cytokine IL-6, whose biological effects are mediated by intracellular JAK-STAT signalling (Naka et al., 2002). This result shows that inhibitors of JAK may also find utility in the treatment of said diseases.

The current therapies are not satisfactory and therefore there remains a need to identify further compounds that may be of use in the treatment of allergic diseases, inflammatory diseases, autoimmune diseases, proliferative diseases, transplantation rejection, diseases involving impairment of cartilage turnover, congenital cartilage malformations, and/or diseases associated with hypersecretion of IL6 or hypersecretion of interferons. The present invention therefore provides compounds, methods for their manufacture and pharmaceutical compositions comprising the compounds of the invention together with a suitable pharmaceutical carrier. The present invention also provides for the use of a compound of the invention in the preparation of a medicament for the treatment of allergic diseases, inflammatory diseases, autoimmune diseases, proliferative diseases, transplantation rejection, diseases involving impairment of cartilage turnover, congenital cartilage malformations, and/or diseases associated with hypersecretion of IL6 or hypersecretion of interferons.

SUMMARY OF THE INVENTION

The present invention is based on the discovery that the compounds of the invention are able to act as inhibitors of JAK and that they are useful for the treatment of allergic diseases, inflammatory diseases, autoimmune diseases, proliferative diseases, transplantation rejection, diseases involving impairment of cartilage turnover, congenital cartilage malformations, and/or diseases associated with hypersecretion of IL6 or hypersecretion of interferons. In a specific aspect the compounds of the invention are inhibitors of JAK1 and/or TYK2. The present invention also provides methods for the production of these compounds, pharmaceutical compositions comprising these compounds and methods for treating allergic diseases, inflammatory diseases, autoimmune diseases, proliferative diseases, transplantation rejection, diseases involving impairment of cartilage turnover, congenital cartilage malformations, and/or diseases associated with hypersecretion of IL6 or hypersecretion of interferons by administering a compound of the invention.

Accordingly, in a first aspect of the invention, the compounds of the invention are provided according to Formula (I):

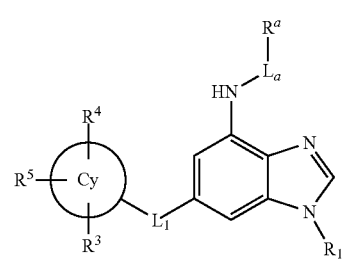

wherein $R^1$ is H, or Me;

$L_1$ is —$NR^2$—; —O—, or —$CH_2$—;

Cy is phenyl, or 5-9 membered monocyclic or fused bicyclic heteroaryl comprising 1 to 4 heteroatoms independently selected from N, O, and S;

$R^2$ is H, or $C_{1-4}$ alkyl;

$R^3$ is H, halo, $C_{1-4}$ alkyl optionally substituted with one or more halo, or $C_{1-4}$ alkoxy optionally substituted with one or more halo;

$R^4$ is H, or halo;

$R^5$ is —CN, halo, or is -$L_2$-$R^6$

-$L_2$ is absent, or is —C(=O)—, —C(=O)$NR^7$—, —$NR^7$C(=O)—, —$SO_2$—, —$SO_2NR^7$—, or —$NR^7SO_2$—;

$R^6$ is H, or $C_{1-6}$ alkyl optionally substituted with one or more independently selected $R^8$ groups;

$R^7$ is H, or $C_{1-4}$ alkyl;

$R^8$ is OH, CN, halo, or $C_{1-4}$ alkoxy, $L_a$ is absent, or is —C(=O)—, —C(=O)O—, or —C(=O)NH—;

$R^a$ is:
  H,
  $C_{1-4}$ alkyl optionally substituted with one or more independently selected $R^b$,
  $C_{3-7}$ monocyclic cycloalkyl optionally substituted with one or more independently selected $R^c$, or
  4-7 membered monocyclic heterocycloalkyl comprising one or more heteroatoms independently selected from O, N, and S, or
  5-6 membered monocyclic heteroaryl comprising one or more heteroatoms independently selected from O, N, and S;

$R^b$ is
halo,
CN,
OH,
$C_{1-4}$ alkoxy,
$C_{3-7}$ cycloalkyl,
4-7 membered monocyclic heterocycloalkyl comprising one or more heteroatoms independently selected from O, N, and S (which heterocycloalkyl is optionally substituted with one or more independently selected halo, or oxo),
—SO$_2$—C$_{1-4}$ alkyl, or
—C(=O)NR$^{b1}$R$^{b2}$
$R^c$ is
halo,
CN,
OH,
$C_{1-4}$ alkyl,
—C(=O)OH, or
—C(=O)NR$^{c1}$R$^{c2}$; and
each R$^{b1}$, R$^{b2}$, R$^{c1}$ and R$^{c2}$ is independently selected from H, and C$_{1-4}$ alkyl.

In a particular embodiment the compounds of the invention are inhibitors of JAK1 and/or TYK2.

Surprisingly, it has now been found that the compounds of the invention may exhibit improved in vitro activity when compared to closely related analogues.

Furthermore, in a particular aspect, the compounds of the invention may exhibit improved stability in vitro, when compared to closely related analogues. This improvement may result in vivo in a lower dosage of the drug being required, and thereby may result in decreased toxicity and/or drug-drug interaction.

In a further aspect, the present invention provides pharmaceutical compositions comprising the compounds of the invention, and a pharmaceutical carrier, excipient or diluent. Moreover, the compounds of the invention, useful in the pharmaceutical compositions and treatment methods disclosed herein, are pharmaceutically acceptable as prepared and used. In this aspect of the invention, the pharmaceutical composition may additionally comprise further active ingredients suitable for use in combination with the compounds of the invention.

In a further aspect, the invention provides a compound of the invention or a pharmaceutical composition comprising a compound of the invention for use as a medicament. In a specific embodiment, said pharmaceutical composition additionally comprises a further active ingredient.

In a further aspect of the invention, this invention provides a method of treating a mammal susceptible to or afflicted with a condition from among those listed herein, and particularly, such condition as may be associated with aberrant JAK activity, e.g. allergic diseases, inflammatory diseases, autoimmune diseases, proliferative diseases, transplantation rejection, diseases involving impairment of cartilage turnover, congenital cartilage malformations, and/or diseases associated with hypersecretion of IL6 or hypersecretion of interferons, which method comprises administering an effective amount of the pharmaceutical composition or compound of the invention as described herein. In a specific embodiment the condition is associated with aberrant JAK1 and/or TYK2 activity.

In a further aspect, the present invention provides a compound of the invention for use in the treatment or prophylaxis of a condition selected from those listed herein, particularly such conditions as may be associated with aberrant JAK activity, e.g. allergic diseases, inflammatory diseases, autoimmune diseases, proliferative diseases, transplantation rejection, diseases involving impairment of cartilage turnover, congenital cartilage malformations, and/or diseases associated with hypersecretion of IL6 or hypersecretion of interferons.

In yet another method of treatment aspect, this invention provides a method for treating a mammal susceptible to or afflicted with a condition that is causally related to abnormal JAK activity as described herein, and comprises administering an effective condition-treating or condition-preventing amount of the pharmaceutical composition or a compound of the invention described herein. In a specific aspect the condition is causally related to abnormal JAK1 and/or TYK2 activity.

In a further aspect, the present invention provides a compound of the invention, or a pharmaceutical composition comprising a compound of the invention, for use as a medicament.

In a further aspect, the present invention provides a compound of the invention for use in the treatment or prophylaxis of a condition that is causally related to abnormal JAK activity.

In additional aspects, this invention provides methods for synthesizing the compounds of the invention, with representative synthetic protocols and pathways disclosed later on herein.

Accordingly, it is a principal object of this invention to provide novel compounds, which can modify the activity of JAK and thus prevent or treat any conditions that may be causally related thereto. In a specific aspect the compounds of the invention modulate the activity of JAK1 and/or TYK2.

It is a further object of this invention to provide compounds that can treat or alleviate conditions or symptoms of same, such as allergic diseases, inflammatory diseases, autoimmune diseases, proliferative diseases, transplantation rejection, diseases involving impairment of cartilage turnover, congenital cartilage malformations, and/or diseases associated with hypersecretion of IL6 or hypersecretion of interferons, that may be causally related to the activity of JAK, in particular JAK1 and/or TYK2.

A still further object of this invention is to provide a pharmaceutical composition that may be used in the treatment or prophylaxis of a variety of conditions, including the diseases associated with JAK activity such as allergic diseases, inflammatory diseases, autoimmune diseases, proliferative diseases, transplantation rejection, diseases involving impairment of cartilage turnover, congenital cartilage malformations, and/or diseases associated with hypersecretion of IL6 or hypersecretion of interferons. In a specific embodiment the disease is associated with JAK1 and/or TYK2 activity.

Other objects and advantages will become apparent to those skilled in the art from a consideration of the ensuing detailed description.

DETAILED DESCRIPTION OF THE INVENTION

Definitions

The following terms are intended to have the meanings presented therewith below and are useful in understanding the description and intended scope of the present invention.

When describing the invention, which may include compounds, pharmaceutical compositions containing such compounds and methods of using such compounds and compositions, the following terms, if present, have the following meanings unless otherwise indicated. It should also be understood that when described herein any of the moieties defined forth below may be substituted with a variety of substituents, and that the respective definitions are intended to include such substituted moieties within their scope as set out below. Unless otherwise stated, the term "substituted" is to be defined as set out below. It should be further understood that the terms "groups" and "radicals" can be considered interchangeable when used herein.

The articles 'a' and 'an' may be used herein to refer to one or to more than one (i.e. at least one) of the grammatical objects of the article. By way of example 'an analogue' means one analogue or more than one analogue.

'Alkyl' means straight or branched aliphatic hydrocarbon with the number of carbon atoms specified. Particular alkyl groups have 1 to 8 carbon atoms. More particular is lower alkyl which has 1 to 6 carbon atoms. A further particular group has 1 to 4 carbon atoms. Exemplary straight chained groups include methyl, ethyl n-propyl, and n-butyl. Branched means that one or more lower alkyl groups such as methyl, ethyl, propyl or butyl is attached to a linear alkyl chain, exemplary branched chain groups include isopropyl, iso-butyl, t-butyl and isoamyl.

'Alkoxy' refers to the group —OR$^{26}$ where R$^{26}$ is alkyl with the number of carbon atoms specified. Particular alkoxy groups are methoxy, ethoxy, n-propoxy, isopropoxy, n-butoxy, tert-butoxy, sec-butoxy, n-pentoxy, n-hexoxy, and 1,2-dimethylbutoxy. Particular alkoxy groups are lower alkoxy, i.e. with between 1 and 6 carbon atoms. Further particular alkoxy groups have between 1 and 4 carbon atoms.

'Alkenyl' refers to monovalent olefinically (unsaturated) hydrocarbon groups with the number of carbon atoms specified. Particular alkenyl has 2 to 8 carbon atoms, and more particularly, from 2 to 6 carbon atoms, which can be straight-chained or branched and having at least 1 and particularly from 1 to 2 sites of olefinic unsaturation. Particular alkenyl groups include ethenyl (—CH=CH$_2$), n-propenyl (—CH$_2$CH=CH$_2$), isopropenyl (—C(CH$_3$)=CH$_2$) and the like.

'Amino' refers to the radical —NH$_2$.

'Aryl' refers to a monovalent aromatic hydrocarbon group derived by the removal of one hydrogen atom from a single carbon atom of a parent aromatic ring system. In particular aryl refers to an aromatic ring structure, monocyclic or fused polycyclic, with the number of ring atoms specified. Specifically, the term includes groups that include from 6 to 10 ring members. Where the aryl group is a monocyclic ring system it preferentially contains 6 carbon atoms. Particularly aryl groups include phenyl, and naphthyl.

'Cycloalkyl' refers to a non-aromatic hydrocarbyl ring structure, monocyclic, fused polycyclic, bridged polycyclic, or spirocyclic, with the number of ring atoms specified. A cycloalkyl may have from 3 to 12 carbon atoms, in particular from 3 to 10, and more particularly from 3 to 7 carbon atoms. Such cycloalkyl groups include, by way of example, single ring structures such as cyclopropyl, cyclobutyl, cyclopentyl, cyclohexyl, and cycloheptyl.

'Cyano' refers to the radical —CN.

'Halo' or 'halogen' refers to fluoro (F), chloro (Cl), bromo (Br) and iodo (I). Particular halo groups are either fluoro or chloro.

'Hetero' when used to describe a compound or a group present on a compound means that one or more carbon atoms in the compound or group have been replaced by a nitrogen, oxygen, or sulfur heteroatom. Hetero may be applied to any of the hydrocarbyl groups described above such as alkyl, e.g. heteroalkyl, cycloalkyl, e.g. heterocycloalkyl, aryl, e.g. heteroaryl, and the like having from 1 to 4, and particularly from 1 to 3 heteroatoms, more typically 1 or 2 heteroatoms, for example a single heteroatom.

'Heteroaryl' means an aromatic ring structure, monocyclic or fused polycyclic, that includes one or more heteroatoms independently selected from O, N and S and the number of ring atoms specified. In particular, the aromatic ring structure may have from 5 to 9 ring members. The heteroaryl group can be, for example, a five membered or six membered monocyclic ring or a fused bicyclic structure formed from fused five and six membered rings or two fused six membered rings or, by way of a further example, two fused five membered rings. Each ring may contain up to four heteroatoms typically selected from nitrogen, sulphur and oxygen. Typically the heteroaryl ring will contain up to 4 heteroatoms, more typically up to 3 heteroatoms, more usually up to 2, for example a single heteroatom. In one embodiment, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five.

Examples of five membered monocyclic heteroaryl groups include but are not limited to pyrrolyl, furanyl, thiophenyl, imidazolyl, furazanyl, oxazolyl, oxadiazolyl, oxatriazolyl, isoxazolyl, thiazolyl, isothiazolyl, pyrazolyl, triazolyl and tetrazolyl groups.

Examples of six membered monocyclic heteroaryl groups include but are not limited to pyridinyl, pyrazinyl, pyridazinyl, pyrimidinyl and triazinyl. Particular examples of bicyclic heteroaryl groups containing a five membered ring fused to another five-membered ring include but are not limited to imidazothiazolyl and imidazoimidazolyl. Particular examples of bicyclic heteroaryl groups containing a six membered ring fused to a five membered ring include but are not limited to benzfuranyl, benzthiophenyl, benzimidazolyl, benzoxazolyl, isobenzoxazolyl, benzisoxazolyl, benzothiazolyl, benzisothiazolyl, isobenzofuranyl, indolyl, isoindolyl, indolizinyl, purinyl (e.g. adenine, guanine), indazolyl, pyrazolopyrimidinyl, triazolopyrimidinyl, and pyrazolopyridinyl groups. Particular examples of bicyclic heteroaryl groups containing two fused six membered rings include but are not limited to quinolinyl, isoquinolinyl, pyridopyridinyl, quinoxalinyl, quinazolinyl, cinnolinyl, phthalazinyl, naphthyridinyl, and pteridinyl groups. Particular heteroaryl groups are those derived from thiophenyl, pyrrolyl, benzothiophenyl, benzofuranyl, indolyl, pyridinyl, quinolinyl, imidazolyl, oxazolyl and pyrazinyl. Examples of representative heteroaryls include the following:

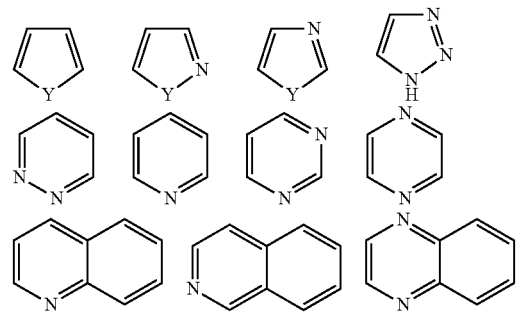

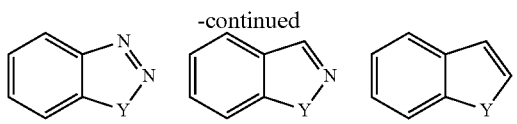

wherein each Y is selected from >C(=O), NH, O and S.

'Heterocycloalkyl' means a non-aromatic fully saturated ring structure, monocyclic, fused polycyclic, spirocyclic, or bridged polycyclic, that includes one or more heteroatoms independently selected from O, N and S and the number of ring atoms specified. The heterocycloalkyl ring structure may have from 4 to 12 ring members, in particular from 4 to 10 ring members and more particularly from 4 to 7 ring members. Each ring may contain up to four heteroatoms typically selected from nitrogen, sulphur and oxygen. Typically the heterocycloalkyl ring will contain up to 4 heteroatoms, more typically up to 3 heteroatoms, more usually up to 2, for example a single heteroatom. Examples of heterocyclic rings include, but are not limited to azetidinyl, oxetanyl, thietanyl, pyrrolidinyl (e.g. 1-pyrrolidinyl, 2-pyrrolidinyl and 3-pyrrolidinyl), morpholinyl, thiomorpholinyl, tetrahydrofuranyl, tetrahydrothiophenyl, imidazolinyl, oxazolinyl, thiazolinyl, piperidinyl (e.g. 1-piperidinyl, 2-piperidinyl, 3-piperidinyl and 4-piperidinyl), pyranyl, dioxanyl, tetrahydropyranyl (e.g. 4-tetrahydro pyranyl), 2-pyrazolinyl, pyrazolidinyl, or piperazinyl.

Particular examples of monocyclic heterocycloalkyl groups are shown in the following illustrative examples:

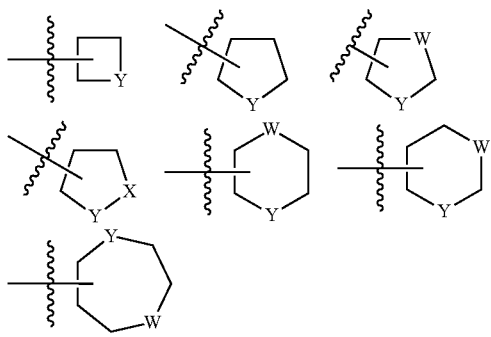

wherein each W and Y is independently selected from CH$_2$, NH, O and S.

Particular examples of fused bicyclic heterocycloalkyl groups are shown in the following illustrative examples:

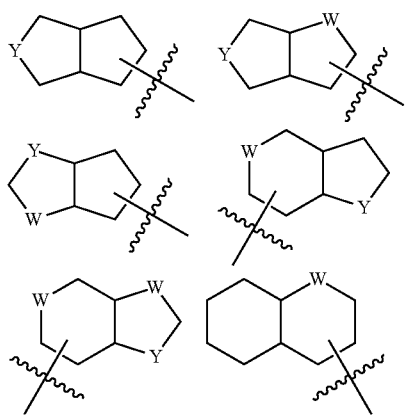

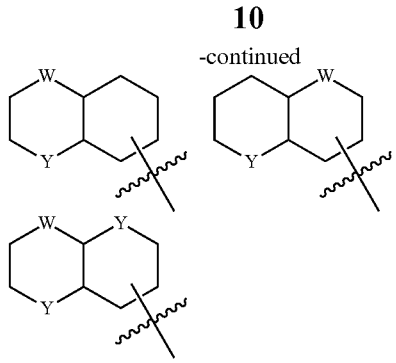

wherein each W and Y is independently selected from CH$_2$, NH, O and S.

Particular examples of bridged bicyclic heterocycloalkyl groups are shown in the following illustrative examples:

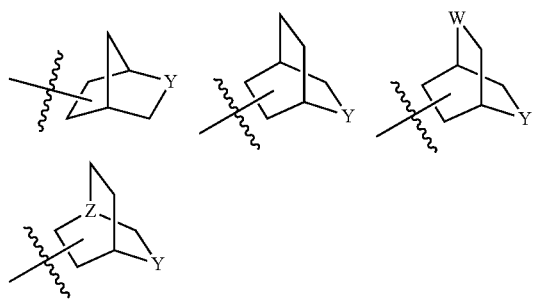

wherein each W and Y is independently selected from CH$_2$, NH, O and S, and Z is N or CH.

Particular examples of spirocyclic heterocycloalkyl groups are shown in the following illustrative examples:

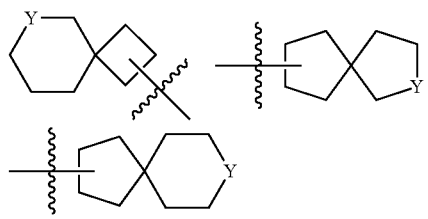

wherein each Y is selected from NH, O and S.

'Hydroxyl' refers to the radical —OH.

'Oxo' refers to the radical =O.

'Substituted' refers to a group in which one or more hydrogen atoms are each independently replaced with the same or different substituent(s).

'Sulfo' or 'sulfonic acid' refers to a radical such as —SO$_3$H.

'Thiol' refers to the group —SH.

As used herein, term 'substituted with one or more' refers to one to four substituents. In one embodiment it refers to one to three substituents. In further embodiments it refers to one or two substituents. In a yet further embodiment it refers to one substituent.

'Thioalkoxy' refers to the group —SR$^{26}$ where R$^{26}$ has the number of carbon atoms specified and particularly C$_1$-C$_8$ alkyl. Particular thioalkoxy groups are thiomethoxy, thioethoxy, n-thiopropoxy, isothiopropoxy, n-thiobutoxy, tert-thiobutoxy, sec-thiobutoxy, n-thiopentoxy, n-thiohexoxy, and 1,2-dimethylthiobutoxy. Particular thioalkoxy groups are lower thioalkoxy, i.e. with between 1 and 6 carbon atoms. Further particular alkoxy groups have between 1 and 4 carbon atoms.

One having ordinary skill in the art of organic synthesis will recognize that the maximum number of heteroatoms in a stable, chemically feasible heterocyclic ring, whether it is aromatic or non aromatic, is determined by the size of the ring, the degree of unsaturation and the valence of the heteroatoms. In general, a heterocyclic ring may have one to four heteroatoms so long as the heteroaromatic ring is chemically feasible and stable.

'Pharmaceutically acceptable' means approved or approvable by a regulatory agency of the Federal or a state government or the corresponding agency in countries other than the United States, or that is listed in the U.S. Pharmacopoeia or other generally recognized pharmacopoeia for use in animals, and more particularly, in humans.

'Pharmaceutically acceptable salt' refers to a salt of a compound of the invention that is pharmaceutically acceptable and that possesses the desired pharmacological activity of the parent compound. In particular, such salts are non-toxic may be inorganic or organic acid addition salts and base addition salts. Specifically, such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g. an alkali metal ion, an alkaline earth ion, or an aluminum ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like; and when the compound contains a basic functionality, salts of non toxic organic or inorganic acids, such as hydrochloride, hydrobromide, tartrate, mesylate, acetate, maleate, oxalate and the like. The term 'pharmaceutically acceptable cation' refers to an acceptable cationic counterion of an acidic functional group. Such cations are exemplified by sodium, potassium, calcium, magnesium, ammonium, tetraalkylammonium cations, and the like.

'Pharmaceutically acceptable vehicle' refers to a diluent, adjuvant, excipient or carrier with which a compound of the invention is administered.

'Prodrugs' refers to compounds, including derivatives of the compounds of the invention, which have cleavable groups and become by solvolysis or under physiological conditions the compounds of the invention which are pharmaceutically active in vivo. Such examples include, but are not limited to, choline ester derivatives and the like, N-alkylmorpholine esters and the like.

'Solvate' refers to forms of the compound that are associated with a solvent, usually by a solvolysis reaction. This physical association includes hydrogen bonding. Conventional solvents include water, EtOH, acetic acid and the like. The compounds of the invention may be prepared e.g. in crystalline form and may be solvated or hydrated. Suitable solvates include pharmaceutically acceptable solvates, such as hydrates, and further include both stoichiometric solvates and non-stoichiometric solvates. In certain instances the solvate will be capable of isolation, for example when one or more solvent molecules are incorporated in the crystal lattice of the crystalline solid. 'Solvate' encompasses both solution-phase and isolable solvates. Representative solvates include hydrates, ethanolates and methanolates.

'Subject' includes humans. The terms 'human', 'patient' and 'subject' are used interchangeably herein.

'Effective amount' means the amount of a compound of the invention that, when administered to a subject for treating a disease, is sufficient to effect such treatment for the disease. The "effective amount" can vary depending on the compound, the disease and its severity, and the age, weight, etc., of the subject to be treated.

'Preventing' or 'prevention' refers to a reduction in risk of acquiring or developing a disease or disorder (i.e. causing at least one of the clinical symptoms of the disease not to develop in a subject that may be exposed to a disease-causing agent, or predisposed to the disease in advance of disease onset.

The term 'prophylaxis' is related to 'prevention', and refers to a measure or procedure the purpose of which is to prevent, rather than to treat or cure a disease. Non-limiting examples of prophylactic measures may include the administration of vaccines; the administration of low molecular weight heparin to hospital patients at risk for thrombosis due, for example, to immobilization; and the administration of an anti-malarial agent such as chloroquine, in advance of a visit to a geographical region where malaria is endemic or the risk of contracting malaria is high.

'Treating' or 'treatment' of any disease or disorder refers, in one embodiment, to ameliorating the disease or disorder (i.e. arresting the disease or reducing the manifestation, extent or severity of at least one of the clinical symptoms thereof). In another embodiment 'treating' or 'treatment' refers to ameliorating at least one physical parameter, which may not be discernible by the subject. In yet another embodiment, 'treating' or 'treatment' refers to modulating the disease or disorder, either physically, (e.g. stabilization of a discernible symptom), physiologically, (e.g. stabilization of a physical parameter), or both. In a further embodiment, "treating" or "treatment" relates to slowing the progression of the disease.

As used herein the term 'allergic disease(s)' refers to the group of conditions characterized by a hypersensitivity disorder of the immune system including, allergic airway disease (e.g. asthma, rhinitis), sinusitis, eczema and hives, as well as food allergies or allergies to insect venom.

As used herein the term 'asthma' as used herein refers to any disorder of the lungs characterized by variations in pulmonary gas flow associated with airway constriction of whatever cause (intrinsic, extrinsic, or both; allergic or non-allergic). The term asthma may be used with one or more adjectives to indicate the cause.

As used herein the term 'inflammatory disease(s)' refers to the group of conditions including, rheumatoid arthritis, osteoarthritis, juvenile idiopathic arthritis, psoriasis, psoriatic arthritis, ankylosing spondylitis, allergic airway disease (e.g. asthma, rhinitis), chronic obstructive pulmonary disease (COPD), inflammatory bowel diseases (e.g. Crohn's disease, ulcerative colitis), endotoxin-driven disease states (e.g. complications after bypass surgery or chronic endotoxin states contributing to e.g. chronic cardiac failure), and related diseases involving cartilage, such as that of the joints. Particularly the term refers to rheumatoid arthritis, osteoarthritis, allergic airway disease (e.g. asthma), chronic obstructive pulmonary disease (COPD) and inflammatory bowel diseases. More particularly the term refers to rheumatoid arthritis, chronic obstructive pulmonary disease (COPD) and inflammatory bowel diseases As used herein the term 'autoimmune disease(s)' refers to the group of diseases including obstructive airways disease, including conditions such as COPD, asthma (e.g intrinsic asthma, extrinsic asthma, dust asthma, infantile asthma) particularly chronic or inveterate asthma (for example late asthma and airway hyperreponsiveness), bronchitis, including bronchial asthma, systemic lupus erythematosus (SLE), cutaneous lupus erythrematosis, lupus nephritis, dermatomyositis, Sjogren's syndrome, multiple sclerosis, psoriasis, dry eye disease, type I diabetes mellitus and complications associated therewith, atopic eczema (atopic dermatitis), thyroiditis (Hashimoto's and autoimmune thyroiditis), contact dermatitis and further eczematous dermatitis, inflammatory bowel disease (e.g. Crohn's disease and ulcerative colitis), atherosclerosis and amyotrophic lateral sclerosis. Particularly the term refers to COPD, asthma, systemic lupus erythematosus, type I diabetes mellitus and inflammatory bowel disease. As used herein the term 'proliferative disease(s)' refers to conditions such as cancer (e.g. uterine leiomyosarcoma or prostate cancer), myeloproliferative disorders (e.g. polycythemia vera, essential thrombocytosis and myelofibrosis), leukemia (e.g. acute myeloid leukaemia, acute and chronic lymphoblastic leukemia), multiple myeloma, psoriasis, restenosis, scleroderma or fibrosis. In particular the term refers to cancer, leukemia, multiple myeloma and psoriasis.

As used herein, the term 'cancer' refers to a malignant or benign growth of cells in skin or in body organs, for example but without limitation, breast, prostate, lung, kidney, pancreas, stomach or bowel. A cancer tends to infiltrate into adjacent tissue and spread (metastasise) to distant organs, for example to bone, liver, lung or the brain. As used herein the term cancer includes both metastatic tumour cell types (such as but not limited to, melanoma, lymphoma, leukaemia, fibrosarcoma, rhabdomyosarcoma, and mastocytoma) and types of tissue carcinoma (such as but not limited to, colorectal cancer, prostate cancer, small cell lung cancer and non-small cell lung cancer, breast cancer, pancreatic cancer, bladder cancer, renal cancer, gastric cancer, glioblastoma, primary liver cancer, ovarian cancer, prostate cancer and uterine leiomyosarcoma). In particular, the term 'cancer' refers to acute lymphoblastic leukemia, acute myeloidleukemia, adrenocortical carcinoma, anal cancer, appendix cancer, astrocytomas, atypical teratoid/rhabdoid tumor, basal cell carcinoma, bile duct cancer, bladder cancer, bone cancer (osteosarcoma and malignant fibrous histiocytoma), brain stem glioma, brain tumors, brain and spinal cord tumors, breast cancer, bronchial tumors, Burkitt lymphoma, cervical cancer, chronic lymphocytic leukemia, chronic myelogenous leukemia, colon cancer, colorectal cancer, craniopharyngioma, cutaneous T-Cell lymphoma, embryonal tumors, endometrial cancer, ependymoblastoma, ependymoma, esophageal cancer, ewing sarcoma family of tumors, eye cancer, retinoblastoma, gallbladder cancer, gastric (stomach) cancer, gastrointestinal carcinoid tumor, gastrointestinal stromal tumor (GIST), gastrointestinal stromal cell tumor, germ cell tumor, glioma, hairy cell leukemia, head and neck cancer, hepatocellular (liver) cancer, hodgkin lymphoma, hypopharyngeal cancer, intraocular melanoma, islet cell tumors (endocrine pancreas), Kaposi sarcoma, kidney cancer, Langerhans cell histiocytosis, laryngeal cancer, leukemia, Acute lymphoblastic leukemia, acute myeloid leukemia, chronic lymphocytic leukemia, chronic myelogenous leukemia, hairy cell leukemia, liver cancer, non-small cell lung cancer, small cell lung cancer, Burkitt lymphoma, cutaneous T-cell lymphoma, Hodgkin lymphoma, non-Hodgkin lymphoma, lymphoma, Waldenstrom macroglobulinemia, medulloblastoma, medulloepithelioma, melanoma, mesothelioma, mouth cancer, chronic myelogenous leukemia, myeloid leukemia, multiple myeloma, asopharyngeal cancer, neuroblastoma, non-Hodgkin lymphoma, non-small cell lung cancer, oral cancer, oropharyngeal cancer, osteosarcoma, malignant fibrous histiocytoma of bone, ovarian cancer, ovarian epithelial cancer, ovarian germ cell tumor, ovarian low malignant potential tumor, pancreatic cancer, papillomatosis, parathyroid cancer, penile cancer, pharyngeal cancer, pineal parenchymal tumors of intermediate differentiation, pineoblastoma and supratentorial primitive neuroectodermal tumors, pituitary tumor, plasma cell neoplasm/multiple myeloma, pleuropulmonary blastoma, primary central nervous system lymphoma, prostate cancer, rectal cancer, renal cell (kidney) cancer, retinoblastoma, rhabdomyosarcoma, salivary gland cancer, sarcoma, Ewing sarcoma family of tumors, sarcoma, kaposi, Sezary syndrome, skin cancer, small cell Lung cancer, small intestine cancer, soft tissue sarcoma, squamous cell carcinoma, stomach (gastric) cancer, supratentorial primitive neuroectodermal tumors, testicular cancer, throat cancer, thymoma and thymic carcinoma, thyroid cancer, urethral cancer, uterine cancer, uterine sarcoma, vaginal cancer, vulvar cancer, Waldenstrom macroglobulinemia, and Wilms tumor. In another particular embodiment, the term cancer refers to pancreatic cancer, liver cancer, hepatocellular carcinoma (HCC), breast cancer, or colon cancer.

As used herein the term 'leukemia' refers to neoplastic diseases of the blood and blood forming organs. Such diseases can cause bone marrow and immune system dysfunction, which renders the host highly susceptible to infection and bleeding. In particular the term leukemia refers to acute myeloid leukaemia (AML), and acute lymphoblastic leukemia (ALL) and chronic lymphoblastic leukaemia (CLL). In another particular embodiment, the term leukemia refers to T-cell acute lymphoblastic leukemia (T-ALL), chronic lymphocytic leukemia (CLL), or diffuse large B-cell lymphoma (DLBCL).

As used herein the term 'transplantation rejection' refers to the acute or chronic rejection of cells, tissue or solid organ allo- or xenografts of e.g. pancreatic islets, stem cells, bone marrow, skin, muscle, corneal tissue, neuronal tissue, heart, lung, combined heart-lung, kidney, liver, bowel, pancreas, trachea or oesophagus, or graft-versus-host diseases.

As used herein the term 'diseases involving impairment of cartilage turnover' includes conditions such as osteoarthritis, psoriatic arthritis, juvenile rheumatoid arthritis, gouty arthritis, septic or infectious arthritis, reactive arthritis, reflex sympathetic dystrophy, algodystrophy, Tietze syndrome or costal chondritis, fibromyalgia, osteochondritis, neurogenic or neuropathic arthritis, arthropathy, endemic forms of arthritis like osteoarthritis deformans endemica, Mseleni disease and Handigodu disease; degeneration resulting from fibromyalgia, systemic lupus erythematosus, scleroderma and ankylosing spondylitis.

As used herein the term 'congenital cartilage malformation(s)' includes conditions such as hereditary chondrolysis, chondrodysplasias and pseudochondrodysplasias, in particular, but without limitation, microtia, anotia, metaphyseal chondrodysplasia, and related disorders.

As used herein the term 'disease(s) associated with hypersecretion of IL6' includes conditions such as Castleman's disease, multiple myeloma, psoriasis, Kaposi's sarcoma and/or mesangial proliferative glomerulonephritis.

As used herein the term 'disease(s) associated with hypersecretion of interferons includes conditions such as systemic and cutaneous lupus erythematosis, lupus nephritis, dermatomyositis, Sjogren's syndrome, psoriasis, rheumatoid arthritis.

'Compound(s) of the invention', and equivalent expressions, are meant to embrace compounds of the Formula(e) as herein described, which expression includes the pharmaceutically acceptable salts, and the solvates, e.g. hydrates, and the solvates of the pharmaceutically acceptable salts where the context so permits. Similarly, reference to intermediates, whether or not they themselves are claimed, is meant to embrace their salts, and solvates, where the context so permits.

When ranges are referred to herein, for example but without limitation, $C_{1-8}$ alkyl, the citation of a range should be considered a representation of each member of said range.

Other derivatives of the compounds of this invention have activity in both their acid and acid derivative forms, but in the acid sensitive form often offers advantages of solubility, tissue compatibility, or delayed release in the mammalian organism (Bundgaard, 1985). Prodrugs include acid derivatives well know to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the compounds of this invention are particularly useful prodrugs. In some cases it is desirable to prepare double ester type prodrugs such as (acyloxy)alkyl esters or ((alkoxycarbonyl)oxy)alkylesters. Particular such prodrugs are the $C_{1-8}$ alkyl, $C_{2-8}$ alkenyl, $C_{6-10}$ optionally substituted aryl, and $(C_{6-10}$ aryl)-$(C_{1-4}$ alkyl) esters of the compounds of the invention.

As used herein, the term 'isotopic variant' refers to a compound that contains unnatural proportions of isotopes at one or more of the atoms that constitute such compound. For example, an 'isotopic variant' of a compound can contain one or more non-radioactive isotopes, such as for example, deuterium ($^2H$ or D), carbon-13 ($^{13}C$), nitro ($^{15}N$), or the like. It will be understood that, in a compound where such isotopic substitution is made, the following atoms, where present, may vary, so that for example, any hydrogen may be $^2H$/D, any carbon may be $^{13}C$, or any nitrogen may be $^{15}N$, and that the presence and placement of such atoms may be determined within the skill of the art. Likewise, the invention may include the preparation of isotopic variants with radioisotopes, in the instance for example, where the resulting compounds may be used for drug and/or substrate tissue distribution studies. The radioactive isotopes tritium, i.e. $^3H$, and carbon-14, i.e. $^{14}C$, are particularly useful for this purpose in view of their ease of incorporation and ready means of detection. Further, compounds may be prepared that are substituted with positron emitting isotopes, such as $^{11}C$, $^{18}F$, $^{15}O$ and $^{13}N$, and would be useful in Positron Emission Topography (PET) studies for examining substrate receptor occupancy.

All isotopic variants of the compounds provided herein, radioactive or not, are intended to be encompassed within the scope of the invention.

It is also to be understood that compounds that have the same molecular formula but differ in the nature or sequence of bonding of their atoms or the arrangement of their atoms in space are termed 'isomers'. Isomers that differ in the arrangement of their atoms in space are termed 'stereoisomers'.

Stereoisomers that are not mirror images of one another are termed 'diastereomers' and those that are non-superimposable mirror images of each other are termed 'enantiomers'. When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e. as (+) or (−)-isomers respectively). A chiral compound can exist as either individual enantiomer or as a mixture thereof. A mixture containing equal proportions of the enantiomers is called a 'racemic mixture'.

'Tautomers' refer to compounds that are interchangeable forms of a particular compound structure, and that vary in the displacement of hydrogen atoms and electrons. Thus, two structures may be in equilibrium through the movement of π electrons and an atom (usually H). For example, enols and ketones are tautomers because they are rapidly interconverted by treatment with either acid or base. Another example of tautomerism is the aci- and nitro-forms of phenylnitromethane, that are likewise formed by treatment with acid or base.

Tautomeric forms may be relevant to the attainment of the optimal chemical reactivity and biological activity of a compound of interest.

The compounds of the invention may possess one or more asymmetric centers; such compounds can therefore be produced as individual (R)- or (S)-stereoisomers or as mixtures thereof.

Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art.

It will be appreciated that compounds of the invention may be metabolized to yield biologically active metabolites.

THE INVENTION

The present invention is based on the identification that the compounds of the invention are inhibitors of JAK and that they are useful for the treatment of allergic diseases, inflammatory diseases, autoimmune diseases, proliferative diseases, transplantation rejection, diseases involving impairment of cartilage turnover, congenital cartilage malformations, and/or diseases associated with hypersecretion of IL6 or hypersecretion of interferons. In a specific embodiment the compounds of the invention are inhibitors of JAK1 and/or TYK2.

The present invention also provides methods for the production of the compounds of the invention, pharmaceutical compositions comprising a compound of the invention and methods for treating allergic diseases, inflammatory diseases, autoimmune diseases, proliferative diseases, transplantation rejection, diseases involving impairment of cartilage turnover, congenital cartilage malformations, and/or diseases associated with hypersecretion of IL6 or hypersecretion of interferons by administering a compound of the invention. In a specific embodiment the compounds of the invention are inhibitors of JAK1 and/or TYK2.

Accordingly, in a first aspect of the invention, the compounds of the invention are provided according to Formula (I):

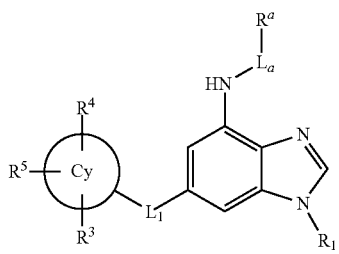

wherein
$R^1$ is H, or Me;
$L_1$ is $-NR^2-$; $-O-$, or $-CH_2-$;
Cy is phenyl, or 5-9 membered monocyclic or fused bicyclic heteroaryl comprising 1 to 4 heteroatoms independently selected from N, O, and S;
$R^2$ is H, or $C_{1-4}$ alkyl;
$R^3$ is H, halo, $C_{1-4}$ alkyl optionally substituted with one or more independently selected halo, or $C_{1-4}$ alkoxy optionally substituted with one or more independently selected halo;
$R^4$ is H, or halo;
$R^5$ is $-CN$, halo, or is $-L_2-R^6$;
$-L_2$ is absent, or is $-C(=O)-$, $-C(=O)NR^7-$, $-NR^7C(=O)-$, $-SO_2-$, $-SO_2NR^7-$, or $-NR^7SO_2-$;
$R^6$ is H, or $C_{1-6}$ alkyl optionally substituted with one or more independently selected $R^8$ groups;
$R^7$ is H, or $C_1$ alkyl;
$R^8$ is OH, CN, halo, or $C_{1-4}$ alkoxy;
$L_a$ is absent, or is $-C(=O)-$, $-C(=O)O-$, or $-C(=O)NH-$;
$R^a$ is:
  H,
  $C_{1-4}$ alkyl optionally substituted with one or more independently selected $R^b$,
  $C_{3-7}$ monocyclic cycloalkyl optionally substituted with one or more independently selected $R^c$,
  4-7 membered monocyclic heterocycloalkyl comprising one or more heteroatoms independently selected from O, N, and S, or
  5-6 membered monocyclic heteroaryl comprising one or more heteroatoms independently selected from O, N, and S;
$R^b$ is
  halo,
  CN,
  OH,
  $C_{1-4}$ alkoxy,
  $C_{3-7}$ cycloalkyl,
  4-7 membered monocyclic heterocycloalkyl comprising one or more heteroatoms independently selected from O, N, and S (which heterocycloalkyl is optionally substituted with one or more independently selected halo, or oxo),
  $-SO_2-C_{1-4}$ alkyl, or
  $-C(=O)NR^{b1}R^{b2}$;
$R^c$ is
  halo,
  CN,
  OH,
  $C_{1-4}$ alkyl,
  $-C(=O)OH$, or
  $-C(=O)NR^{c1}R^{c2}$; and
each $R^{b1}$, $R^{b2}$, $R^{c1}$ and $R^{c2}$ is independently selected from H, and $C_{1-4}$ alkyl.

In one embodiment, a compound of the invention is according to Formula I, wherein $R^1$ is Me.

In another embodiment, a compound of the invention is according to Formula I, wherein Cy is phenyl.

In one embodiment, a compound of the invention is according to Formula I, wherein Cy is 5-9 membered monocyclic or fused bicyclic heteroaryl comprising 1 to 4 heteroatoms independently selected from N, O, and S. In another embodiment, a compound of the invention is according to Formula I, wherein Cy is 5-9-membered monocyclic or fused bicyclic heteroaryl comprising 1 or 2 heteroatoms independently selected from N, O, and S. In a particular embodiment, Cy is pyrazolyl, pyrrolyl, imidazolyl, triazolyl, thiophenyl, thiazolyl, furanyl, pyridyl, pyrazinyl, pyrimidyl, pyridazinyl, benzofuranyl, benzothiophenyl, benzothiazolyl, benzothiadiazolyl, benzoxazolyl, indolyl or indazolyl.

In another embodiment, a compound of the invention is according to Formula I, wherein Cy is 5-6 membered monocyclic heteroaryl comprising 1 to 4 heteroatoms independently selected from N, O, and S. In yet another embodiment, a compound of the invention is according to Formula I, wherein Cy is 5-6 membered monocyclic heteroaryl comprising 1 or 2 heteroatoms independently selected from N, O, and S. In a particular embodiment, Cy is pyrazolyl, pyrrolyl, imidazolyl, furanyl, thiophenyl, triazolyl, tetrazolyl, thiazolyl, oxazolyl, thiadiazolyl, or oxadiazolyl. In another particular embodiment, Cy is pyridinyl, pyrazinyl, pyrimidinyl, or pyridazolyl. In a more particular embodiment, Cy is pyridyl.

In one embodiment, a compound of the invention is according to Formula IIa, IIb, or IIc:

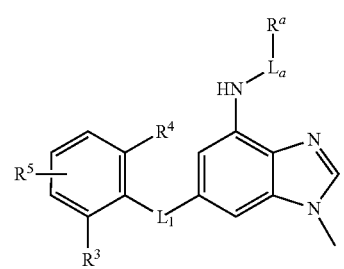

-continued

IIb
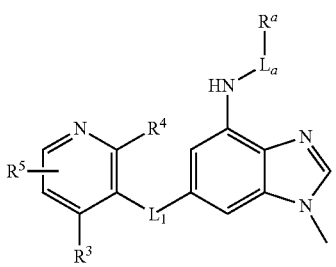

IIc
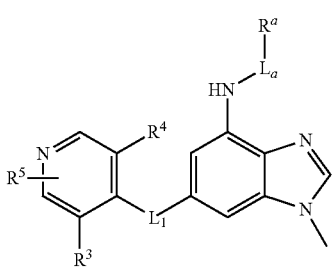

wherein $L_1$, $R^3$, $R^4$, $L_a$, $R^a$ and $R^5$ are as described in any of the embodiments above.

In one embodiment, a compound of the invention is according to Formula IIIa, IIIb, or IIIc:

IIIa
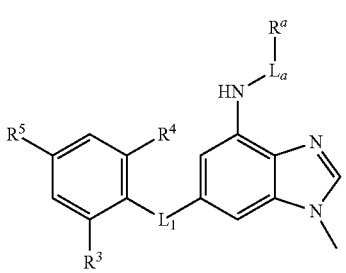

IIIb
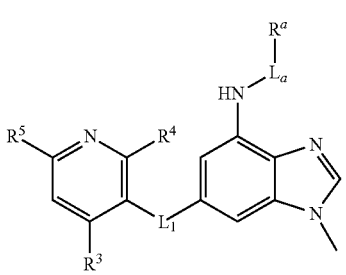

IIIc
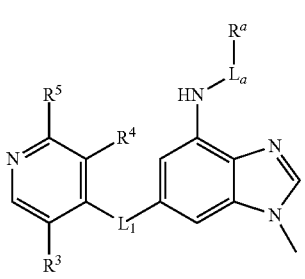

wherein $L_1$, $R^3$, $R^4$, $L_a$, $R^a$ and $R^5$ are as described in any of the embodiments above.

In one embodiment, a compound of the invention is according to any one of Formulae I-IIIc, wherein $L_1$ is —$CH_2$—.

In one embodiment, a compound of the invention is according to any one of Formulae I-IIIc, wherein $L_1$ is —O—.

In one embodiment, a compound of the invention is according to any one of Formulae I-IIIc, wherein $L_1$ is —$NR^2$—, and $R^2$ is as described in any of the embodiments above.

In one embodiment, a compound of the invention is according to any one of Formulae I-IIIc, wherein $L_1$ is —$NR^2$—, wherein $R^2$ is H.

In one embodiment, a compound of the invention is according to any one of Formulae I-IIIc, wherein $L_1$ is —$NR^2$—, wherein $R^2$ is $C_{1-4}$ alkyl. In a particular embodiment, $R^2$ is Me, Et, or iPr. In a more particular embodiment, $R^2$ is Me. In another more particular embodiment, $R^2$ is Et.

In one embodiment, a compound of the invention is according to Formula IVa, IVb, IVc, IVd, IVe or IVf:

IVa
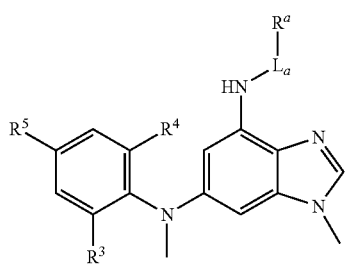

IVb
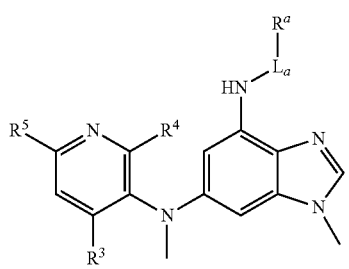

IVc
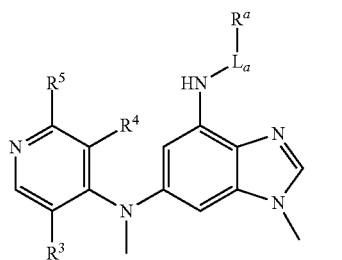

IVd
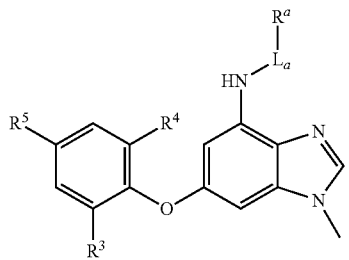

wherein $R^3$, $R^4$, $R^5$, $L_a$, and $R^a$ are as described in any of the embodiments above.

In one embodiment, a compound of the invention is according to any one of Formula I-IVf, wherein $L_a$ is absent.

In one embodiment, a compound of the invention is according to any one of Formula I-IVf, wherein $L_a$ is —C(═O)—, —C(═O)O—, or —C(═O)NH—. In a particular embodiment, $L_a$ is —C(═O)—.

In one embodiment, a compound of the invention is according to Formula Va, Vb, Vc, Vd, Ve or Vf:

wherein $R^3$, $R^4$, $R^5$, and $R^a$ are as described in any of the embodiments above.

In one embodiment, a compound of the invention is according to any one of Formula I-Vf, wherein $R^4$ is H, or halo. In a particular embodiment, $R^4$ is F, or Cl. In another particular embodiment, $R^4$ is H.

In one embodiment, a compound of the invention is according to any one of Formulae I-Vf, wherein $R^3$ is H.

In one embodiment, a compound of the invention is according to any one of Formulae I-Vf, wherein $R^3$ is halo. In a particular embodiment, $R^3$ is F, or Cl. In more particular embodiment, $R^3$ is Cl.

In one embodiment, a compound of the invention is according to any one of Formulae I-Vf, wherein $R^3$ is $C_{1-4}$ alkyl. In a particular embodiment, $R^3$ is Me, Et, or n-Pr. In more particular embodiment, $R^3$ is Me or Et. In a most particular embodiment, $R^3$ is Et. In another most particular embodiment, $R^3$ is Me.

In another embodiment, a compound of the invention is according to any one of Formulae I-Vf, wherein $R^3$ is $C_{1-4}$ alkyl substituted with one or more independently selected halo. In a particular embodiment, $R^3$ is —CHF$_2$, —CF$_3$, —$CH_2$—$CHF_2$ or —$CH_2$—$CF_3$. In more particular embodiment, $R^3$ is —$CF_3$, or —$CH_2$—$CF_3$.

In one embodiment, a compound of the invention is according to any one of Formulae I-Vf, wherein $R^3$ is $C_{1-4}$ alkoxy. In a particular embodiment, $R^3$ is —OMe, —OEt, or —On-Pr. In more particular embodiment, $R^3$ is —OMe or —OEt.

In another embodiment, a compound of the invention is according to any one of Formulae I-Vf, wherein $R^3$ is $C_{1-4}$ alkoxy substituted with one or more independently selected halo. In a particular embodiment, $R^3$ is —$OCHF_2$, —$OCF_3$, or —$OCH_2$—$CHF_2$. In more particular embodiment, $R^3$ is —$OCHF_2$.

In one embodiment, a compound of the invention is according to any one of Formulae I-Vf, wherein $R^5$ is CN.

In one embodiment, a compound of the invention is according to any one of Formulae I-Vf, wherein $R^5$ is halo. In a particular embodiment, $R^5$ is F, or Cl. In a more particular embodiment, $R^5$ is F.

In one embodiment, a compound of the invention is according to any one of Formulae I-Vf, wherein $R^5$ is -$L_2$-$R^6$, $R^6$ is as described above, $L_2$ is —C(=O)$NR^7$—, —$NR^7$C(=O)—, —$SO_2NR^7$—, or —$NR^7SO_2$—, and $R^7$ is as defined in any of the preceding embodiments. In a particular embodiment, $R^7$ is H. In another particular embodiment, $R^7$ is $C_{1-4}$ alkyl. In a more particular embodiment, $R^7$ is Me, or Et. In a most particular embodiment, $R^7$ is Me.

In one embodiment, a compound of the invention is according to any one of Formulae I-Vf, wherein $R^5$ is -$L_2$-$R^6$, $L_2$ is as described above, and $R^6$ is H.

In one embodiment, a compound of the invention is according to any one of Formulae I-Vf, wherein $R^5$ is -$L_2$-$R^6$, $L_2$ is as described above, and $R^6$ is $C_{1-6}$ alkyl. In a particular embodiment, $R^6$ is Me, Et, iPr, or tBu. In a more particular embodiment, $R^6$ is Me, or Et.

In one embodiment, a compound of the invention is according to any one of Formulae I-Vf, wherein $R^5$ is -$L_2$-$R^6$, $L_2$ is as described above, and $R^6$ is $C_{1-6}$ alkyl substituted with one or more independently selected $R^8$ groups. In another embodiment, $R^6$ is Me, Et, iPr, or tBu, each of which is substituted with one or more independently selected $R^8$ groups. In a particular embodiment, $R^6$ is $C_{1-6}$ alkyl substituted with one, two or three independently selected $R^8$ groups. In another particular embodiment, $R^6$ is Me, Et, iPr, or tBu, each of which is substituted with one, two or three independently selected $R^8$ groups. In a more particular embodiment, $R^6$ is $C_{1-6}$ alkyl substituted with one $R^8$ group. In another particular embodiment, $R^6$ is Me, Et, iPr, or tBu, each of which is substituted with one $R^8$ group.

In one embodiment, a compound of the invention is according to any one of Formulae I-Vf, wherein $R^8$ is OH, CN, halo, or $C_{1-4}$ alkoxy. In a particular embodiment, $R^8$ is OH, CN, F, Cl, —OMe, or —OEt.

In a particular embodiment, $R^5$ is -$L_2$-$R^6$, $L_2$ is —C(=O)—, or —$SO_2$—, and $R^6$ is $C_{1-6}$ alkyl. In a more particular embodiment, $R^5$ is -$L_2$-$R^6$, $L_2$ is —C(=O)—, or —$SO_2$, and $R^6$ is Me, Et, iPr, or tBu. In a most particular embodiment, $R^5$ is —C(=O)Me, —C(=O)Et, —$SO_2$Me or —$SO_2$Et.

In one embodiment, a compound of the invention is according to any one of Formulae I-Vf, wherein $R^5$ is -$L_2$-$R^6$, $L_2$ is —C(=O)$NR^7$—, —$NR^7SO_2$—, —$SO_2NR^7$—, or —$NR^7SO_2$—, $R^6$ and $R^7$ are as defined in any of the preceding embodiments. In a particular embodiment, $R^7$ is H, Me, or Et, and $R^6$ is as defined in any of the preceding embodiments. In another particular embodiment, $R^7$ is as defined in any of the preceding embodiments, and $R^6$ is H. In yet another particular embodiment, $R^7$ is as defined in any of the preceding embodiments, and $R^6$ is $C_{1-6}$ alkyl optionally substituted with one or more independently selected OH, CN, halo, or $C_{1-4}$ alkoxy. In a more particular embodiment, $R^7$ is H, Me, or Et, and $R^6$ is H. In another more particular embodiment, $R^7$ is H, Me, or Et, and $R^6$ is Me, Et, iPr or tBu, each of which is optionally substituted with one or more independently selected OH, CN, halo, or $C_{1-4}$ alkoxy. In yet another more particular embodiment, $R^7$ is H, Me, or Et, and $R^6$ is Me, Et, iPr or tBu, each of which is optionally substituted with one or more independently selected OH, CN, F, Cl, OMe, or OEt. In a most particular embodiment, $R^5$ is —C(=O)$NH_2$, or —$SO_2NH_2$.

In one embodiment, a compound of the invention is according to any one of Formula I-Vf, wherein $R^a$ is H.

In one embodiment, a compound of the invention is according to any one of Formula I-Vf, wherein $R^a$ is $C_{1-4}$ alkyl. In a particular embodiment, $R^a$ is Me, Et, iPr, or tBu. In a more particular embodiment, $R^a$ is Me, or Et. In a most particular embodiment, $R^a$ is Me.

In one embodiment, a compound of the invention is according to any one of Formula I-Vf, wherein $R^a$ is $C_{1-4}$ alkyl substituted with one or more independently selected $R^b$. In another embodiment, $R^a$ is Me, Et, iPr, or tBu, each of which is substituted with one or more independently selected $R^b$. In a particular embodiment, $R^a$ is $C_{1-4}$ alkyl substituted with one, two, or three independently selected $R^b$. In another particular embodiment, $R^a$ is Me, Et, iPr, or tBu, each of which is substituted with one, two, or three independently selected $R^b$. In a more particular embodiment, $R^a$ is $C_{1-4}$ alkyl substituted with one $R^b$. In another more particular embodiment, $R^a$ is Me, Et, iPr, or tBu, each of which is substituted with one $R^b$.

In one embodiment, a compound of the invention is according to any one of Formula I-Vf, wherein $R^b$ is halo, CN, or OH. In a particular embodiment, $R^b$ is F, Cl, CN, or OH.

In one embodiment, a compound of the invention is according to any one of Formula I-Vf, wherein $R^b$ is $C_{1-4}$ alkoxy. In a particular embodiment, $R^b$ is OMe, OEt, or OiPr. In a more particular embodiment, $R^b$ is OMe.

In one embodiment, a compound of the invention is according to any one of Formula I-Vf, wherein $R^b$ is $C_{3-7}$ cycloalkyl. In a particular embodiment, $R^b$ is cyclopropyl, cyclobutyl, cyclopentyl, or cyclohexyl. In a more particular embodiment, $R^b$ is cyclopropyl.

In one embodiment, a compound of the invention is according to any one of Formula I-Vf, wherein $R^b$ is 4-7 membered monocyclic heterocycloalkyl comprising one or more heteroatoms independently selected from O, N, and S. In a particular embodiment, $R^b$ is oxetanyl, tetrahydrofuranyl, tetrahydropyranyl, azetidinyl, pyrrolidinyl, piperidinyl, piperazinyl, morpholinyl, or thiomorpholinyl.

In one embodiment, a compound of the invention is according to any one of Formula I-Vf, wherein $R^b$ is 4-7 membered monocyclic heterocycloalkyl comprising one or more heteroatoms independently selected from O, N, and S, substituted with one or more independently selected halo, or oxo. In a particular embodiment, $R^b$ is oxetanyl, tetrahydrofuranyl, tetrahydropyranyl, azetidinyl, pyrrolidinyl, piperidinyl, piperazinyl, morpholinyl, or thiomorpholinyl, each of which is substituted with one or more independently selected halo, or oxo. In another particular embodiment, $R^b$ is 4-7 membered monocyclic heterocycloalkyl comprising one or more heteroatoms independently selected from O, N, and S, substituted with one or more independently selected F, Cl, or oxo. In a more particular embodiment, $R^b$ is oxetanyl, tetrahydrofuranyl, tetrahydropyranyl, azetidinyl, pyrrolidinyl, piperidinyl, piperazinyl, morpholinyl, or thiomorpholinyl, each of which is substituted with one or more independently selected F, Cl, or oxo. In a most particular embodiment, $R^b$ is 4-7 membered monocyclic heterocycloalkyl comprising one or more heteroatoms independently selected from O, N, and S, substituted with one, two or three independently selected F, Cl, or oxo. In another most particular embodiment, $R^b$ is oxetanyl, tetrahydrofuranyl, tetrahydropyranyl, azetidinyl, pyrrolidinyl, piperidinyl, piperazinyl, morpholinyl, or thiomorpholinyl, each of which is substituted with one, two or three independently selected F, Cl, or oxo.

In one embodiment, a compound of the invention is according to any one of Formula I-Vf, wherein $R^b$ is —SO$_2$—C$_1$ alkyl. In a particular embodiment, $R^b$ is —SO$_2$CH$_3$, or —SO$_2$CH$_2$CH$_3$.

In one embodiment, a compound of the invention is according to any one of Formula I-Vf, wherein $R^b$ is —C(=O)NR$^{b1}$R$^{b2}$, wherein each R$^{b1}$, or R$^{b2}$ is independently selected from H, and C$_{1-4}$ alkyl. In a particular embodiment, each R$^{b1}$, or R$^{b2}$ is independently selected from H, —CH$_3$, and —CH$_2$CH$_3$. In a more particular embodiment, $R^b$ is —C(=O)NH$_2$, —C(=O)NMeH, or —C(=O)NMe$_2$.

In one embodiment, a compound of the invention is according to any one of Formula I-Vf, wherein $R^a$ is C$_{3-7}$ monocyclic cycloalkyl. In a particular embodiment, $R^a$ is cyclopropyl, cyclobutyl, or cyclopentyl. In a more particular embodiment, $R^a$ is cyclopropyl.

In one embodiment, a compound of the invention is according to any one of Formula I-Vf, wherein $R^a$ is C$_{3-7}$ monocyclic cycloalkyl substituted with one or more independently selected R$^c$ groups. In another embodiment, $R^a$ is cyclopropyl, cyclobutyl, or cyclopentyl, each of which is substituted with one or more independently selected R$^c$ groups. In a particular embodiment, $R^a$ is C$_{3-7}$ monocyclic cycloalkyl substituted with one, two or three independently selected R$^c$ groups. In another particular embodiment, $R^a$ is cyclopropyl, cyclobutyl, or cyclopentyl, each of which is substituted with one, two or three independently selected R$^c$ groups. In a more particular embodiment, $R^a$ is C$_{3-7}$ monocyclic cycloalkyl substituted with one R$^c$ group. In another particular embodiment, $R^a$ is cyclopropyl, cyclobutyl, or cyclopentyl, each of which is substituted with one R$^c$ group.

In one embodiment, a compound of the invention is according to any one of Formula I-Vf, wherein R$^c$ is halo, CN, or OH. In a particular embodiment, R$^c$ is F, Cl, CN, or OH. In a more particular embodiment, R$^c$ is F.

In one embodiment, a compound of the invention is according to any one of Formula I-Vf, wherein R$^c$ is C$_{1-4}$ alkyl. In a particular embodiment, R$^c$ is -Me, -Et, or -iPr.

In one embodiment, a compound of the invention is according to any one of Formula I-Vf, wherein R$^c$ is —C(=O)OH.

In one embodiment, a compound of the invention is according to any one of Formula I-Vf, wherein R$^c$ is —C(=O)NR$^{c1}$R$^{c2}$ wherein each R$^{c1}$ or R$^{c2}$ is independently selected from H, and C$_{1-4}$ alkyl. In a particular embodiment, each R$^{c1}$, or R$^{c2}$ is independently selected from H, —CH$_3$, and —CH$_2$CH$_3$. In a more particular embodiment, R$^c$ is —C(=O)NH$_2$, —C(=O)NMeH, or —C(=O)NMe$_2$.

In one embodiment, a compound of the invention is according to any one of Formula I-Vf, wherein $R^a$ is:

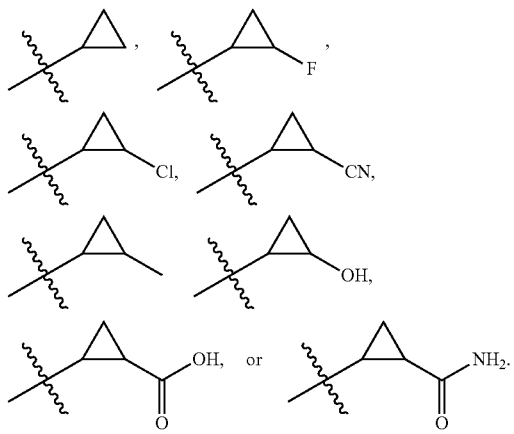

In one embodiment, a compound of the invention is according to any one of Formula I-Vf, wherein $R^a$ is:

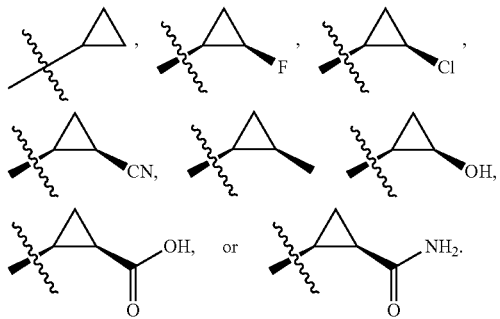

In one embodiment, a compound of the invention is according to any one of Formula I-Vf, wherein $R^a$ is 4-7 membered monocyclic heterocycloalkyl comprising one or more heteroatoms independently selected from O, N, and S. In a particular embodiment, $R^a$ is oxetanyl, tetrahydropyranyl, tetrahydropyranyl, azetidinyl, pyrrolidinyl, piperidinyl, piperazinyl, morpholinyl, or thiomorpholinyl.

In one embodiment, a compound of the invention is according to any one of Formula I-Vf, wherein $R^a$ is 5-6 membered monocyclic heteroaryl comprising one or more heteroatoms independently selected from O, N, and S. In a particular embodiment, $R^a$ is furanyl, thienyl, pyrrolyl, oxazolyl, thiazolyl, imidazolyl, triazolyl, oxadiazolyl, tetrazole, pyridinyl, pyrazinyl, or pyrimidinyl.

In one embodiment, a compound of the invention is according to Formula I, wherein the compound is selected from:

N-(6-(((6-cyano-4-ethylpyridin-3-yl)(methyl)amino)-1-methyl-1H-benzo[d]imidazol-4-yl)cyclopropanecarboxamide, N-(6-(4-cyano-2-ethyl-6-fluorophenylamino)-1-methyl-1H-benzo[d]imidazol-4-yl)cyclopropanecarboxamide, N-(6-((4-cyano-2-ethyl-6-fluorophenyl)(methyl)amino)-1-methyl-1H-benzo[d]imidazol-4-yl)cyclopropanecarboxamide, methyl 6-((6-cyano-4-ethylpyridin-3-yl)(methyl)amino)-1-methyl-1H-benzo[d]imidazol-4-ylcarbamate, methyl 6-((4-cyano-2-ethyl-6-fluorophenyl)(methyl) amino)-1-methyl-1H-benzo[d]imidazol-4-ylcarbamate, (1R,2R)—N-[6-[(6-cyano-4-ethyl-3-pyridyl)oxy]-1-methyl-benzimidazol-4-yl]-2-fluoro-cyclopropanecarboxamide, N-(6-((4-cyano-2-ethyl-6-fluorophenyl)(methyl)amino)-1-methyl-1H-benzo[d]imidazol-4-yl)-2-fluorocyclopropanecarboxamide (1S,2S)/(1R,2R) racemic mixture, (1R,2R)—N-(6-((6-cyano-4-ethylpyridin-3-yl)(methyl)amino)-1-methyl-1H-benzo[d]imidazol-4-yl)-2-fluorocyclopropanecarboxamide, (1R,2R)—N-(6-((6-cyano-4-methylpyridin-3-yl)(methyl)amino)-1-methyl-1H-benzo[d]imidazol-4-yl)-2-fluorocyclopropanecarboxamide, (1R,2R)—N-[6-(4-cyano-2-ethyl-phenoxy)-1-methyl-benzimidazol-4-yl]-2-fluoro-cyclopropanecarboxamide, (1R,2R)—N-[6-(2-chloro-4-cyano-6-fluoro-N-methyl-anilino)-1-methyl-benzimidazol-4-yl]-2-fluoro-cyclopropanecarboxamide, (1R,2R)-2-fluoro-N-[6-[(6-fluoro-4-methyl-3-pyridyl)-methyl-amino]-1-methyl-benzimidazol-4-yl]cyclopropanecarboxamide, (1R,2R)—N-[6-[(2,6-difluoro-3-pyridyl)-methyl-amino]-1-methyl-benzimidazol-4-yl]-2-fluoro-cyclopropanecarboxamide, (1R,2R)—N-[6-[(6-cyano-2-fluoro-3-pyridyl)-methyl-amino]-1-methyl-benzimidazol-4-yl]-2-fluoro-cyclopropanecarboxamide, (1R,2R)—N-[6-(4-cyano-2-fluoro-N-methyl-anilino)-1-methyl-benzimidazol-4-yl]-2-fluoro-cyclopropanecarboxamide, (1R,2R)-2-fluoro-N-[6-(2-fluoro-N,6-dimethyl-4-methylsulfonyl-anilino)-1-methyl-benzimidazol-4-yl]cyclopropanecarboxamide, (1R,2R)-2-fluoro-N-[6-(2-fluoro-N-methyl-4-methylsulfonyl-anilino)-1-methyl-benzimidazol-4-yl]cyclopropanecarboxamide, N-[6-[(4-ethyl-6-methylsulfonyl-3-pyridyl)-methyl-amino]-1-methyl-benzimidazol-4-yl]cyclopropanecarboxamide, N-[6-(2-fluoro-N,6-dimethyl-4-methylsulfonyl-anilino)-1-methyl-benzimidazol-4-yl]cyclopropanecarboxamide, (1R,2R)—N-[6-[(6-cyano-4-methyl-3-pyridyl)oxy]-1-methyl-benzimidazol-4-yl]-2-fluoro-cyclopropanecarboxamide, (1R,2R)—N-[6-[(6-cyano-2-fluoro-4-methyl-3-pyridyl)-methyl-amino]-1-methyl-benzimidazol-4-yl]-2-fluoro-cyclopropanecarboxamide, (1R,2R)—N-[6-[(2-cyano-3-fluoro-5-methyl-4-pyridyl)-methyl-amino]-1-methyl-benzimidazol-4-yl]-2-fluoro-cyclopropanecarboxamide, N-[6-[(6-cyano-4-methyl-3-pyridyl)oxy]-1-methyl-benzimidazol-4-yl]cyclopropanecarboxamide, 5-((4-(cyclopropanecarboxamido)-1-methyl-1H-benzo[d]imidazol-6-yl)(methyl)amino)-4-ethylpicolinamide, 4-ethyl-5-((4-((1R,2R)-2-fluorocyclopropanecarboxamido)-1-methyl-1H-benzo[d]imidazol-6-yl)(methyl)amino)picolinamide, (1R,2R)—N-[6-(N,2-dimethyl-4-methylsulfonyl-anilino)-1-methyl-benzimidazol-4-yl]-2-fluoro-cyclopropanecarboxamide, (1R,2R)—N-[6-(4-ethylsulfonyl-N,2-dimethyl-anilino)-1-methyl-benzimidazol-4-yl]-2-fluoro-cyclopropanecarboxamide, 5-(7-amino-3-methyl-benzimidazol-5-yl)oxy-4-methyl-pyridine-2-carbonitrile, N-[6-[(4-ethyl-6-methylsulfonyl-3-pyridyl)oxy]-1-methyl-benzimidazol-4-yl]cyclopropanecarboxamide, N-[6-[4-(cyanomethyl)anilino]-1-methyl-benzimidazol-4-yl]cyclopropanecarboxamide, N-[6-(2,3-dihydro-1,4-benzodioxin-6-ylamino)-1-methyl-benzimidazol-4-yl]cyclopropanecarboxamide, and 5-[7-[[(1R,2R)-2-fluorocyclopropanecarbonyl]amino]-3-methyl-benzimidazol-5-yl]oxy-4-methyl-pyridine-2-carboxamide.

In one embodiment, a compound of the invention is according to Formula I, wherein the compound is selected from 1-[6-[(6-cyano-4-methyl-3-pyridyl)oxy]-1-methyl-benzimidazol-4-yl]-3-isopropyl-urea, 4-methyl-5-[3-methyl-7-(methylamino)benzimidazol-5-yl]oxy-pyridine-2-carbonitrile, 5-[7-(dimethylamino)-3-methyl-benzimidazol-5-yl]oxy-4-methyl-pyridine-2-carbonitrile, N-[6-[(6-cyano-4-methyl-3-pyridyl)oxy]-1-methyl-benzimidazol-4-yl]-3-hydroxy-azetidine-1-carboxamide, N-[6-[(6-cyano-4-methyl-3-pyridyl)oxy]-1-methyl-benzimidazol-4-yl]morpholine-4-carboxamide, and 1-[6-[(6-cyano-4-methyl-3-pyridyl)oxy]-1-methyl-benzimidazol-4-yl]-3-isopropyl-urea.

In one embodiment, a compound of the invention is according to Formula I, wherein the compound is N-[6-[(6-cyano-4-methyl-3-pyridyl)oxy]-1-methyl-benzimidazol-4-yl]-2-fluoro-cyclopropanecarboxamide. In a more particular embodiment, a compound of the invention is according to Formula I, wherein the compound is (1R,2R)—N-[6-[(6-cyano-4-methyl-3-pyridyl)oxy]-1-methyl-benzimidazol-4-yl]-2-fluoro-cyclopropanecarboxamide.

In one embodiment, a compound of the invention is according to Formula I, wherein the compound is not N-[6-[(6-cyano-4-methyl-3-pyridyl)oxy]-1-methyl-benzimidazol-4-yl]-2-fluoro-cyclopropanecarboxamide. In a more particular embodiment, a compound of the invention is according to Formula I, wherein the compound is not (1R,2R)—N-[6-[(6-cyano-4-methyl-3-pyridyl)oxy]-1-methyl-benzimidazol-4-yl]-2-fluoro-cyclopropanecarboxamide.

In one embodiment, a compound of the invention is according to Formula I, wherein the compound is N-(6-((6-cyano-4-methylpyridin-3-yl)(methyl)amino)-1-methyl-1H-benzo[d]imidazol-4-yl)-2-fluorocyclopropanecarboxamide. In a more particular embodiment, a compound of the invention is according to Formula I, wherein the compound is (1R,2R)—N-(6-((6-cyano-4-methylpyridin-3-yl)(methyl)amino)-1-methyl-1H-benzo[d]imidazol-4-yl)-2-fluorocyclopropanecarboxamide.

In one embodiment, a compound of the invention is according to Formula I, wherein the compound is not N-(6-((6-cyano-4-methylpyridin-3-yl)(methyl)amino)-1-methyl-1H-benzo[d]imidazol-4-yl)-2-fluorocyclopropanecarboxamide. In a more particular embodiment, a compound of the invention is according to Formula I, wherein the compound is not (1R,2R)—N-(6-((6-cyano-4-methylpyridin-3-yl)(methyl)amino)-1-methyl-1H-benzo[d]imidazol-4-yl)-2-fluorocyclopropanecarboxamide.

In one embodiment a compound of the invention is not an isotopic variant.

In one aspect a compound of the invention according to any one of the embodiments herein described is present as the free base.

In one aspect a compound of the invention according to any one of the embodiments herein described is a pharmaceutically acceptable salt.

In one aspect a compound of the invention according to any one of the embodiments herein described is a solvate of the compound.

In one aspect a compound of the invention according to any one of the embodiments herein described is a solvate of a pharmaceutically acceptable salt of a compound.

While specified groups for each embodiment have generally been listed above separately, a compound of the invention includes one in which several or each embodiment in the above Formula, as well as other formulae presented herein, is selected from one or more of particular members or groups designated respectively, for each variable. Therefore, this invention is intended to include all combinations of such embodiments within its scope.

While specified groups for each embodiment have generally been listed above separately, a compound of the invention may be one for which one or more variables (for example, R groups) is selected from one or more embodiments according to any of the Formula(e) listed above. Therefore, the present invention is intended to include all combinations of variables from any of the disclosed embodiments within its scope.

Alternatively, the exclusion of one or more of the specified variables from a group or an embodiment, or combinations thereof is also contemplated by the present invention.

In certain aspects, the present invention provides prodrugs and derivatives of the compounds according to the formulae above. Prodrugs are derivatives of the compounds of the invention, which have metabolically cleavable groups and become by solvolysis or under physiological conditions the compounds of the invention, which are pharmaceutically active, in vivo. Such examples include, but are not limited to, choline ester derivatives and the like, N-alkylmorpholine esters, and the like.

Other derivatives of the compounds of this invention have activity in both their acid and acid derivative forms, but the acid sensitive form often offers advantages of solubility, tissue compatibility, or delayed release in the mammalian organism (Bundgard, H, 1985). Prodrugs include acid derivatives well know to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the compounds of this invention are preferred prodrugs. In some cases it is desirable to prepare double ester type prodrugs such as (acyloxy)alkyl esters or ((alkoxycarbonyl)oxy)alkylesters. Particularly useful are the $C_1$ to $C_8$ alkyl, $C_2$-$C_8$ alkenyl, aryl, $C_7$-$C_{12}$ substituted aryl, and $C_7$-$C_{12}$ arylalkyl esters of the compounds of the invention.

CLAUSES

1) A compound according to Formula I:

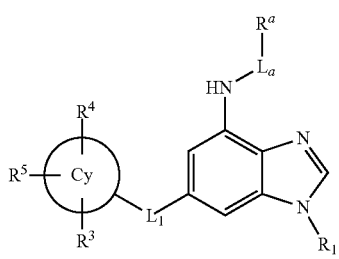

I wherein
$R^1$ is H, or Me;
$L_1$ is —NR—, —O—, or —$CH_2$—;

Cy is phenyl, or 5-9 membered monocyclic or fused bicyclic heteroaryl comprising 1 to 4 heteroatoms independently selected from N, O, and S;
$R^2$ is H, or $C_{1-4}$ alkyl;
$R^3$ is H, halo, $C_{1-4}$ alkyl optionally substituted with one or more independently selected halo, or $C_{1-4}$ alkoxy optionally substituted with one or more independently selected halo;
$R^4$ is H, or halo;
$R^5$ is —CN, halo, or is -$L_2$-$R^6$;
-$L_2$ is absent, or is —C(=O)—, —C(=O)$NR^7$—, —$NR^7$C(=O)—, —$SO_2$—, —$SO_2NR^7$—, or —$NR^7SO_2$—;
$R^6$ is H, or $C_{1-6}$ alkyl optionally substituted with one or more independently selected $R^8$ groups;
$R^7$ is H, or $C_{1-4}$ alkyl;
$R^8$ is OH, CN, halo, or $C_{1-4}$ alkoxy;
$L_a$ is absent, or is —C(=O)—, —C(=O)O—, or —C(=O)NH—;
$R^a$ is:
  H,
  $C_{1-4}$ alkyl optionally substituted with one or more independently selected $R^b$,
  $C_{3-7}$ monocyclic cycloalkyl optionally substituted with one or more independently selected Re,
  4-7 membered monocyclic heterocycloalkyl comprising one or more heteroatoms independently selected from O, N, and S, or
  5-6 membered monocyclic heteroaryl comprising one or more heteroatoms independently selected from O, N, and S;
$R^b$ is
  halo,
  CN,
  OH,
  $C_{1-4}$ alkoxy,
  $C_{3-7}$ cycloalkyl,
  4-7 membered monocyclic heterocycloalkyl comprising one or more heteroatoms independently selected from O, N, and S (which heterocycloalkyl is optionally substituted with one or more independently selected halo, or oxo),
  —$SO_2$—$C_{1-4}$ alkyl, or
  —C(=O)$NR^{b1}R^{b2}$;
$R^c$ is
  halo,
  CN,
  OH,
  $C_{1-4}$ alkyl,
  —C(=O)OH, or
  —C(=O)$NR^{c1}R^{c2}$; and
each $R^{b1}$, $R^{b2}$, $R^{c1}$ and $R^{c2}$ is independently selected from H, and $C_{1-4}$ alkyl;
or a pharmaceutically acceptable salt, or a solvate, or a solvate of the pharmaceutically acceptable salts.

2) A compound or pharmaceutically acceptable salt according to clause 1, wherein $R^1$ is Me.

3) A compound or pharmaceutically acceptable salt according to any one of clauses 1-2, wherein Cy is phenyl.

4) A compound or pharmaceutically acceptable salt thereof according to any one of clauses 1-2, wherein Cy is 5-9 membered monocyclic or fused bicyclic heteroaryl comprising 1 to 4 heteroatoms independently selected from N, O, and S.

5) A compound or pharmaceutically acceptable salt thereof according to any one of clauses 1-2, wherein 5-6 membered monocyclic heteroaryl comprising 1 to 4 heteroatoms independently selected from N, O, and S.

6) A compound or pharmaceutically acceptable salt according to any one of clauses 1-2, wherein Cy is pyridyl.

7) A compound or pharmaceutically acceptable salt according to any one of clauses 1, wherein the compound is according to Formula IIa, IIb, or IIc:

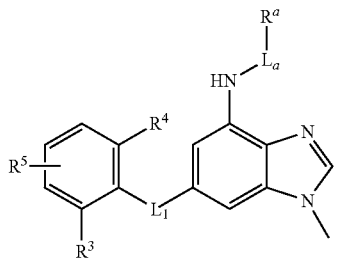
IIa

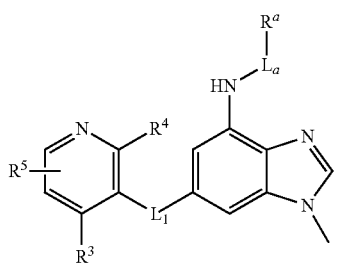
IIb

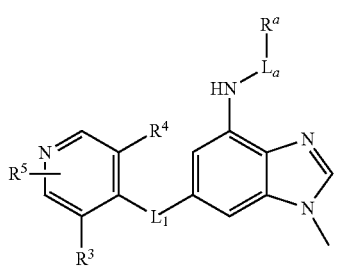
IIc wherein $L_1$, $R^3$, $R^4$, $L_a$, $R^a$ and $R^5$ are as described in clause 1.

8) A compound or pharmaceutically acceptable salt according to any one of clauses 1, wherein the compound is according to Formula IIIa, IIIb, or IIIc:

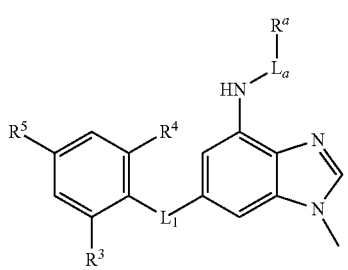
IIIa

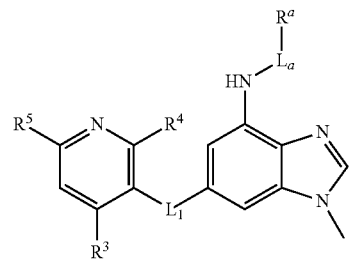
IIIb

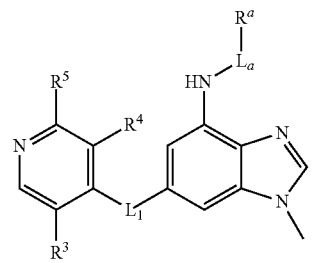
IIIc wherein $L_1$, $R^3$, $R^4$, $L_a$, $R^a$ and $R^5$ are as described in clause 1.

9) A compound or pharmaceutically acceptable salt according to any one of clauses 1-8, wherein $L_1$ is —CH$_2$—.

10) A compound or pharmaceutically acceptable salt according to any one of clauses 1-8, wherein $L_1$ is O.

11) A compound or pharmaceutically acceptable salt according to any one of clauses 1-8, wherein $L_1$ is —NR$^2$—.

12) A compound or pharmaceutically acceptable salt according to clause 11, wherein $R^2$ is H.

13) A compound or pharmaceutically acceptable salt according to clause 11, wherein $R^2$ is $C_{1-4}$ alkyl.

14) A compound or pharmaceutically acceptable salt according to clause 11, wherein $R^2$ is Me.

15) A compound or pharmaceutically acceptable salt according to any one of clauses 1, wherein the compound is according to Formula IVa, IVb, IVc, IVd, IVe or IVf:

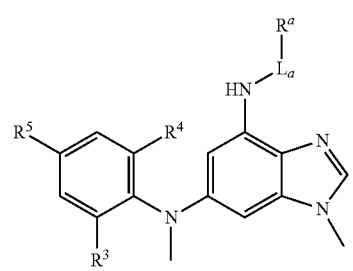
IVa

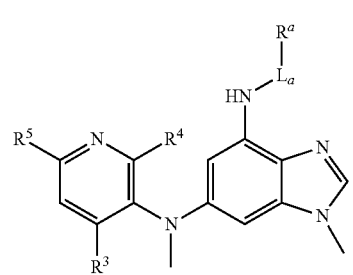
IVb

-continued

IVc 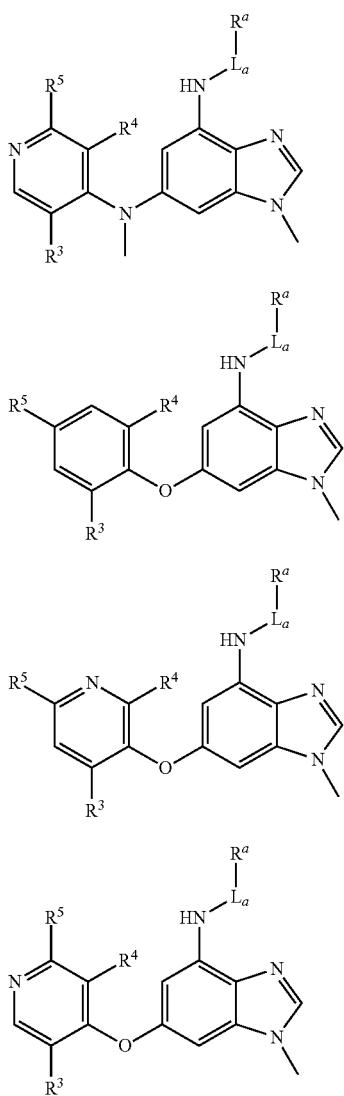

IVd

IVe

IVf wherein $R^3$, $R^4$, $R^5$, $L_a$, and $R^a$ are as described in clause 1.

16) A compound or pharmaceutically acceptable salt according to any one of clauses 1-15, wherein $L_a$ is absent.
17) A compound or pharmaceutically acceptable salt according to any one of clauses 1-15, wherein $L_a$ is —C(=O)—.
18) A compound or pharmaceutically acceptable salt according to any one of clauses 1, wherein the compound is according to Formula Va, Vb, Vc, Vd, Ve or Vf:

Va 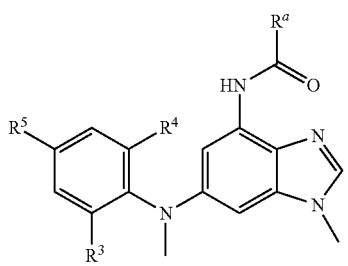

Vb 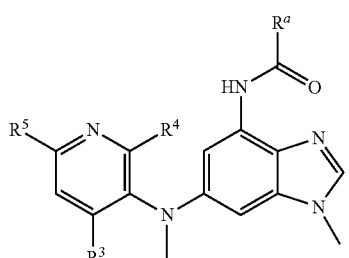

Vc 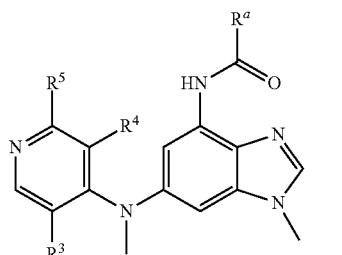

Vd 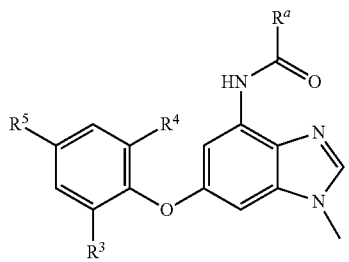

Ve 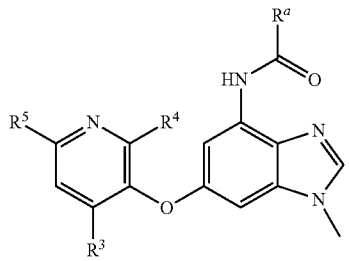

Vf 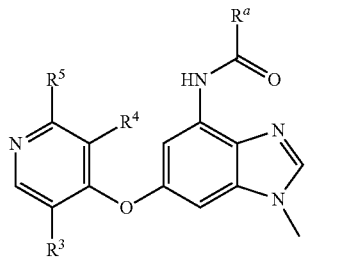

wherein $R^3$, $R^4$, $R^5$, $L_a$, and $R^a$ are as described in clause 1.

19) A compound or pharmaceutically acceptable salt according to any one of clauses 1-18, wherein $R^4$ is H.
20) A compound or pharmaceutically acceptable salt according to any one of clauses 1-18, wherein $R^4$ is F, or Cl.
21) A compound or pharmaceutically acceptable salt according to any one of clauses 1-18, wherein $R^3$ is H.
22) A compound or pharmaceutically acceptable salt according to any one of clauses 1-18, wherein $R^3$ is $C_{1-4}$ alkyl.
23) A compound or pharmaceutically acceptable salt according to clause 22, wherein $R^3$ is Me or Et.

24) A compound or pharmaceutically acceptable salt according to any one of clauses 1-23, wherein $R^5$ is CN.
25) A compound or pharmaceutically acceptable salt according to any one of clauses 1-23, wherein $R^5$ is halo.
26) A compound or pharmaceutically acceptable salt according to clause 25, wherein $R^5$ is F, or Cl.
27) A compound or pharmaceutically acceptable salt according to any one of clauses 1-23, wherein $R^5$ is -$L_2$-$R^6$, $R^6$ is as described in clause 1, and $L_2$ is —C(=O)NR$^7$—, —NR$^7$C(=O)—, —SO$_2$NR$^7$—, or —NR$^7$SO$_2$—.
28) A compound or pharmaceutically acceptable salt according to clause 27, wherein $R^7$ is H.
29) A compound or pharmaceutically acceptable salt according to any one of clauses 1-23, wherein $R^5$ is -$L_2$-$R^6$, $L_2$ is as described in clause 1, and $R^6$ is H.
30) A compound or pharmaceutically acceptable salt according to any one of clauses 1-26, wherein $R^5$ is -$L_2$-$R^6$, $L_2$ is as described in clause 1, and $R^6$ is $C_{1-6}$ alkyl.
31) A compound or pharmaceutically acceptable salt according to clause 30, wherein $R^6$ is Me.
32) A compound or pharmaceutically acceptable salt according to any one of clauses 1-23, wherein $R^5$ is -$L_2$-$R^6$, $L_2$ is as described in clause 1, and $R^6$ is $C_{1-6}$ alkyl substituted with one or more independently selected $R^8$ groups.
33) A compound or pharmaceutically acceptable salt according to clause 32, wherein $R^6$ is Me, Et, iPr, or tBu, each of which is substituted with one or more independently selected $R^8$ groups.
34) A compound or pharmaceutically acceptable salt according to clause 33, wherein $R^8$ is OH, CN, F, Cl, —OMe, or —OEt.
35) A compound or pharmaceutically acceptable salt according to any one of clauses 1-23, wherein $R^5$ is -$L_2$-$R^6$, wherein $L_2$ is —C(=O)—, or —SO$_2$—, and $R^6$ is $C_{1-6}$ alkyl.
36) A compound or pharmaceutically acceptable salt according to clause 35, wherein $R^5$ is —C(=O)Me, —C(=O)Et, —SO$_2$Me or —SO$_2$Et.
37) A compound or pharmaceutically acceptable salt according to any one of clauses 1-23, wherein $R^5$ is -$L_2$-$R^6$, wherein $L_2$ is —C(=O)NR$^7$—, —NR$^7$C(=O)—, —SO$_2$NR$^7$—, or —NR$^7$SO$_2$—, wherein $R^7$ is H, Me, or Et, and $R^6$ is Me, Et, iPr or tBu, each of which is optionally substituted with one or more independently selected OH, CN, halo, or $C_{1-4}$ alkoxy.
38) A compound or pharmaceutically acceptable salt according to clause 37, wherein $R^5$ is —C(=O)NH$_2$, or —SO$_2$NH$_2$.
39) A compound or pharmaceutically acceptable salt according to any one of clauses 1-38, wherein $R^a$ is $C_{1-4}$ alkyl.
40) A compound or pharmaceutically acceptable salt according to clause 39, wherein $R^a$ is Me, or Et.
41) A compound or pharmaceutically acceptable salt according to any one of clauses 1-38, wherein $R^a$ is $C_{1-4}$ alkyl substituted with one or more independently selected $R^b$.
42) A compound or pharmaceutically acceptable salt according to clause 41, wherein $R^a$ is Me, Et, iPr, or tBu.
43) A compound or pharmaceutically acceptable salt according to clause 41 or 42, wherein $R^b$ is F, Cl, CN, or OH.
44) A compound or pharmaceutically acceptable salt according to clause 41 or 42, wherein $R^b$ is OMe, OEt, or OiPr.
45) A compound or pharmaceutically acceptable salt according to clause 41 or 42, wherein $R^b$ is cyclopropyl, cyclobutyl, cyclopentyl, or cyclohexyl.
46) A compound or pharmaceutically acceptable salt according to clause 41 or 42, wherein $R^b$ is oxetanyl, tetrahydrofuranyl, tetrahydropyranyl, azetidinyl, pyrrolidinyl, piperidinyl, piperazinyl, morpholinyl, or thiomorpholinyl.
47) A compound or pharmaceutically acceptable salt according to clause 41 or 42, wherein $R^b$ is oxetanyl, tetrahydrofuranyl, tetrahydropyranyl, azetidinyl, pyrrolidinyl, piperidinyl, piperazinyl, morpholinyl, or thiomorpholinyl, each of which is substituted with one or more independently selected halo, or oxo.
48) A compound or pharmaceutically acceptable salt according to clause 41 or 42, wherein $R^b$ is —SO$_2$CH$_3$, or —SO$_2$CH$_2$CH$_3$.
49) A compound or pharmaceutically acceptable salt according to clause 41 or 42, wherein $R^b$ is —C(=O)NH$_2$, —C(=O)NMeH, or —C(=O)NMe$_2$.
50) A compound or pharmaceutically acceptable salt according to any one of clauses 1-38, wherein $R^a$ is $C_{3-7}$ monocyclic cycloalkyl.
51) A compound or pharmaceutically acceptable salt according to any one of clauses 1-38, wherein $R^a$ is $C_{3-7}$ monocyclic cycloalkyl substituted with one or more independently selected $R^c$ groups.
52) A compound or pharmaceutically acceptable salt according to clause 50, or 51, wherein $R^a$ is cyclopropyl, cyclobutyl, or cyclopentyl.
53) A compound or pharmaceutically acceptable salt according to clause 51, wherein $R^c$ is F, Cl, CN, or OH.
54) A compound or pharmaceutically acceptable salt according to clause 51, wherein $R^c$ is -Me, -Et, or -iPr.
55) A compound or pharmaceutically acceptable salt according to clause 51, wherein $R^c$ is —C(=O)OH.
56) A compound or pharmaceutically acceptable salt according to clause 51, wherein $R^c$ is —C(=O)NH$_2$, —C(=O)NMeH, or —C(=O)NMe$_2$.
57) A compound or pharmaceutically acceptable salt according to any one of clauses 1-38, wherein $R^a$ is:

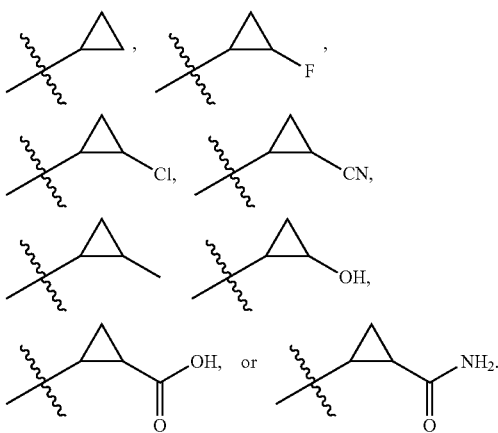

58) A compound or pharmaceutically acceptable salt according to any one of clauses 1-38, wherein $R^a$ is:

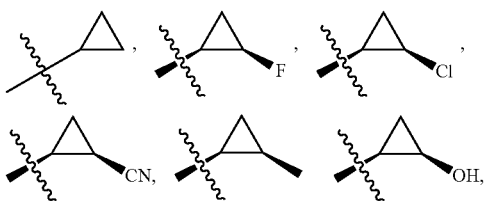

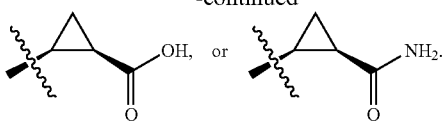

59) A compound or pharmaceutically acceptable salt according to any one of clauses 1-38, wherein $R^a$ is 4-7 membered monocyclic heterocycloalkyl comprising one or more heteroatoms independently selected from O, N, and S.

60) A compound or pharmaceutically acceptable salt according to clause 59, wherein $R^a$ is oxetanyl, tetrahydrofuranyl, tetrahydropyranyl, azetidinyl, pyrrolidinyl, piperidinyl, piperazinyl, morpholinyl, or thiomorpholinyl.

61) A compound or pharmaceutically acceptable salt according to any one of clauses 1-38, wherein $R^a$ is 5-6 membered monocyclic heteroaryl comprising one or more heteroatoms independently selected from O, N, and S.

62) A compound or pharmaceutically acceptable salt according to clause 61, wherein $R^a$ is furanyl, thienyl, pyrrolyl, oxazolyl, thiazolyl, imidazolyl, triazolyl, oxadiazolyl, tetrazole, pyridinyl, pyrazinyl, or pyrimidinyl.

63) A compound, or pharmaceutically acceptable salt thereof, according to clause 1 wherein the compound is selected from Table I 64) A compound, or pharmaceutically acceptable salt thereof, according to clause 1 wherein the compound is (1R,2R)—N-[6-[(6-cyano-4-methyl-3-pyridyl)oxy]-1-methyl-benzimidazol-4-yl]-2-fluoro-cyclopropanecarboxamide.

65) A compound, or pharmaceutically acceptable salt thereof, according to clause 1 wherein the compound is not (1R,2R)—N-[6-[(6-cyano-4-methyl-3-pyridyl)oxy]-1-methyl-benzimidazol-4-yl]-2-fluoro-cyclopropanecarboxamide.

66) A compound, or pharmaceutically acceptable salt thereof, according to clause 1 wherein the compound is (1R,2R)—N-(6-((6-cyano-4-methylpyridin-3-yl)(methyl)amino)-1-methyl-1H-benzo[d]imidazol-4-yl)-2-fluorocyclopropanecarboxamide.

67) A compound, or pharmaceutically acceptable salt thereof, according to clause 1 wherein the compound is not (1R,2R)—N-(6-((6-cyano-4-methylpyridin-3-yl)(methyl)amino)-1-methyl-1H-benzo[d]imidazol-4-yl)-2-fluorocyclopropanecarboxamide.

68) A pharmaceutical composition comprising a pharmaceutically acceptable carrier and a pharmaceutically effective amount of a compound according to any one of clauses 1-67.

69) The pharmaceutical composition according to clause 68 comprising a further therapeutic agent.

70) The compound or pharmaceutically acceptable salt thereof, according to any one of clauses 1-67, or the pharmaceutical composition according any one of clauses 68-69, for use in medicine.

71) A compound according to any one of clauses 1-67, or the pharmaceutical composition according any one of clauses 68-69, for use in the treatment, or prophylaxis of allergic diseases, inflammatory diseases, autoimmune diseases, proliferative diseases, transplantation rejection, diseases involving impairment of cartilage turnover, congenital cartilage malformations, and/or diseases associated with hypersecretion of IL6 or hypersecretion of interferons.

72) A compound according to any one of clauses 1-67, or the pharmaceutical composition according any one of clauses 68-69, for use in the treatment, or prophylaxis of proliferative diseases.

73) A compound according to clause 72, wherein the proliferative diseases is selected from myelofibrosis, T-cell acute lymphoblastic leukemia (T-ALL), multiple myeloma, chronic lymphocytic leukemia (CLL), diffuse large B-cell lymphoma (DLBCL), pancreatic cancer, liver cancer, hepatocellular carninoma (HCC), lung cancer, breast cancer, and colon cancer.

74) A method for the treatment, or prophylaxis of allergic diseases, inflammatory diseases, autoimmune diseases, proliferative diseases, transplantation rejection, diseases involving impairment of cartilage turnover, congenital cartilage malformations, and/or diseases associated with hypersecretion of IL6 or hypersecretion of interferons, comprising administering an amount of compound according to any one of clauses 1-67, or the pharmaceutical composition according any one of clauses 68-69, sufficient to effect said treatment, or prophylaxis.

75) A method for the treatment, or prophylaxis of proliferative diseases, comprising administering an amount of compound according to any one of clauses 1-67, or the pharmaceutical composition according any one of clauses 68-69, sufficient to effect said treatment, or prophylaxis.

76) A method of treatment according to clause 76, wherein the proliferative diseases is selected from myelofibrosis, T-cell acute lymphoblastic leukemia (T-ALL), multiple myeloma, chronic lymphocytic leukemia (CLL), diffuse large B-cell lymphoma (DLBCL), pancreatic cancer, liver cancer, hepatocellular carninoma (HCC), lung cancer, breast cancer, and colon cancer.

77) The method according to any one of clause 75-77, wherein the compound according to any one of clauses 1-67, or the pharmaceutical composition according any one of clauses 68-69, is administered in combination with a further therapeutic agent.

78) The pharmaceutical composition according to clause 69, or the method according to clause 78, wherein the further therapeutic agent is an agent for the treatment, or prophylaxis of allergic diseases, inflammatory diseases, autoimmune diseases, proliferative diseases, transplantation rejection, diseases involving impairment of cartilage turnover, congenital cartilage malformations, and/or diseases associated with hypersecretion of IL6 or hypersecretion of interferons.

79) The pharmaceutical composition according to clause 69, or the method according to clause 78, wherein the further therapeutic agent is an agent for the treatment, or prophylaxis of myelofibrosis, T-cell acute lymphoblastic leukemia (T-ALL), multiple myeloma, chronic lymphocytic leukemia (CLL), diffuse large B-cell lymphoma (DLBCL), pancreatic cancer, liver cancer, hepatocellular carninoma (HCC), lung cancer, breast cancer, and colon cancer.

Pharmaceutical Compositions

When employed as a pharmaceutical, a compound of the invention is typically administered in the form of a pharmaceutical composition. Such compositions can be prepared in a manner well known in the pharmaceutical art and comprise at least one active compound of the invention according to Formula I. Generally, a compound of the invention is administered in a pharmaceutically effective amount. The amount of compound of the invention actually administered will typically be determined by a physician, in the light of the relevant circumstances, including the condition to be treated, the chosen route of administration, the actual compound of the invention administered, the age, weight, and response of the individual patient, the severity of the patient's symptoms, and the like.

The pharmaceutical compositions of this invention can be administered by a variety of routes including oral, rectal, transdermal, subcutaneous, intra-articular, intravenous, intramuscular, and intranasal. Depending on the intended route of delivery, a compound of the invention is preferably formulated as either injectable or oral compositions or as salves, as lotions or as patches all for transdermal administration.

The compositions for oral administration can take the form of bulk liquid solutions or suspensions, or bulk powders. More commonly, however, the compositions are presented in unit dosage forms to facilitate accurate dosing. The term 'unit dosage forms' refers to physically discrete units suitable as unitary dosages for human subjects and other mammals, each unit containing a predetermined quantity of active material calculated to produce the desired therapeutic effect, in association with a suitable pharmaceutical excipient, vehicle or carrier. Typical unit dosage forms include prefilled, premeasured ampules or syringes of the liquid compositions or pills, tablets, capsules or the like in the case of solid compositions. In such compositions, the compound of the invention according to Formula I is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or non-aqueous vehicle with buffers, suspending and dispensing agents, colorants, flavors and the like. Solid forms may include, for example, any of the following ingredients, or compound of the inventions of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint or orange flavoring.

Injectable compositions are typically based upon injectable sterile saline or phosphate-buffered saline or other injectable carriers known in the art. As before, the active compound of the invention according to Formula I in such compositions is typically a minor component, often being from about 0.05 to 10% by weight with the remainder being the injectable carrier and the like.

Transdermal compositions are typically formulated as a topical ointment or cream containing the active ingredient(s), generally in an amount ranging from about 0.01 to about 20% by weight, preferably from about 0.1 to about 20% by weight, preferably from about 0.1 to about 10% by weight, and more preferably from about 0.5 to about 15% by weight. When formulated as an ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the dermal penetration of stability of the active ingredients or the formulation. All such known transdermal formulations and ingredients are included within the scope of this invention.

A compound of the invention can also be administered by a transdermal device. Accordingly, transdermal administration can be accomplished using a patch either of the reservoir or porous membrane type, or of a solid matrix variety.

The above-described components for orally administrable, injectable or topically administrable compositions are merely representative. Other materials as well as processing techniques and the like are set forth in Part 8 of Remington's Pharmaceutical Sciences, $17^{th}$ edition, 1985, Mack Publishing Company, Easton, Pa., which is incorporated herein by reference.

A compound of the invention can also be administered in sustained release forms or from sustained release drug delivery systems. A description of representative sustained release materials can be found in Remington's Pharmaceutical Sciences.

The following formulation examples illustrate representative pharmaceutical compositions that may be prepared in accordance with this invention. The present invention, however, is not limited to the following pharmaceutical compositions.

Formulation 1—Tablets

A compound of the invention according to Formula I may be admixed as a dry powder with a dry gelatin binder in an approximate 1:2 weight ratio. A minor amount of magnesium stearate may be added as a lubricant. The mixture may be formed into 240-270 mg tablets (80-90 mg of active compound of the invention according to Formula I per tablet) in a tablet press.

Formulation 2—Capsules

A compound of the invention according to Formula I may be admixed as a dry powder with a starch diluent in an approximate 1:1 weight ratio. The mixture may be filled into 250 mg capsules (125 mg of active compound of the invention according to Formula I per capsule).

Formulation 3—Liquid

A compound of the invention according to Formula I (125 mg), may be admixed with sucrose (1.75 g) and xanthan gum (4 mg) and the resultant mixture may be blended, passed through a No. 10 mesh U.S. sieve, and then mixed with a previously made solution of microcrystalline cellulose and sodium carboxymethyl cellulose (11:89, 50 mg) in water. Sodium benzoate (10 mg), flavor, and color may be diluted with water and added with stirring. Sufficient water may then be added with stirring. Further sufficient water may be then added to produce a total volume of 5 mL.

Formulation 4—Tablets

A compound of the invention according to Formula I may be admixed as a dry powder with a dry gelatin binder in an approximate 1:2 weight ratio. A minor amount of magnesium stearate may be added as a lubricant. The mixture may be formed into 450-900 mg tablets (150-300 mg of active compound of the invention according to Formula I) in a tablet press.

Formulation 5—Injection

A compound of the invention according to Formula I may be dissolved or suspended in a buffered sterile saline injectable aqueous medium to a concentration of approximately 5 mg/mL.

Formulation 6—Topical

Stearyl alcohol (250 g) and a white petrolatum (250 g) may be melted at about 75° C. and then a mixture of A compound of the invention according to Formula I (50 g) methylparaben (0.25 g), propylparaben (0.15 g), sodium lauryl sulfate (10 g), and propylene glycol (120 g) dissolved in water (about 370 g) may be added and the resulting mixture may be stirred until it congeals.

Methods of Treatment

A compound of the invention may be used as a therapeutic agent for the treatment of conditions in mammals that are causally related or attributable to aberrant activity of JAK. In particular, conditions related to aberrant activity of JAK1 and/or TYK2. Accordingly, the compounds and pharmaceutical compositions of the invention find use as therapeutics for preventing and/or treating allergic diseases, inflammatory diseases, autoimmune diseases, proliferative diseases, transplantation rejection, diseases involving impairment of cartilage turnover, congenital cartilage malformations, and/or diseases associated with hypersecretion of IL6 or hypersecretion of interferons in mammals including humans.

In one aspect, the present invention provides a compound of the invention, or a pharmaceutical composition comprising a compound of the invention for use as a medicament.

In another aspect, the present invention provides a compound of the invention, or a pharmaceutical composition comprising a compound of the invention for use in the manufacture of a medicament.

In yet another aspect, the present invention provides a method of treating a mammal having, or at risk of having a disease disclosed herein, said method comprising administering an effective condition-treating or condition-preventing amount of one or more of the pharmaceutical compositions or compounds of the invention herein described. In a particular aspect, the present invention provides a method of treating a mammal having, or at risk of having allergic diseases, inflammatory diseases, autoimmune diseases, proliferative diseases, transplantation rejection, diseases involving impairment of cartilage turnover, congenital cartilage malformations, and/or diseases associated with hypersecretion of IL6 or hypersecretion of interferons.

In a method of treatment aspects, this invention provides methods of treatment and/or prophylaxis of a mammal susceptible to or afflicted with an allergic reaction, said method comprising administering an effective condition-treating or condition-preventing amount of one or more of the pharmaceutical compositions or compounds of the invention as herein described. In a specific embodiment, the allergic reaction is selected from allergic airway disease, sinusitis, eczema and hives, food allergies and allergies to insect venom.

In another aspect the present invention provides a compound of the invention for use in the treatment, and/or prophylaxis of an allergic reaction. In a specific embodiment, the allergic reaction is selected from allergic airway disease, sinusitis, eczema and hives, food allergies and allergies to insect venom.

In yet another aspect, the present invention provides a compound of the invention, or a pharmaceutical composition comprising a compound of the invention for use in the manufacture of a medicament for the treatment, or prophylaxis of an allergic reaction. In a specific embodiment, the allergic reaction is selected from allergic airway disease, sinusitis, eczema and hives, food allergies and allergies to insect venom.

In additional method of treatment aspects, this invention provides methods of treatment and/or prophylaxis of a mammal susceptible to or afflicted with an inflammatory condition. The methods comprise administering an effective condition-treating or condition-preventing amount of one or more of the pharmaceutical compositions or compounds of the invention as herein described. In a specific embodiment, the inflammatory condition is selected from rheumatoid arthritis, osteoarthritis, allergic airway disease (e.g. asthma) and inflammatory bowel diseases.

In another aspect the present invention provides a compound of the invention for use in the treatment, and/or prophylaxis of an inflammatory condition. In a specific embodiment, the inflammatory condition is selected from rheumatoid arthritis, osteoarthritis, allergic airway disease (e.g. asthma) and inflammatory bowel diseases.

In yet another aspect, the present invention provides the compound of the invention, or a pharmaceutical composition comprising a compound of the invention for use in the manufacture of a medicament for the treatment, and/or prophylaxis of an inflammatory condition. In a specific embodiment, the inflammatory condition is selected from rheumatoid arthritis, osteoarthritis, allergic airway disease (e.g. asthma) and inflammatory bowel diseases.

In additional method of treatment aspects, this invention provides methods of treatment and/or prophylaxis of a mammal susceptible to or afflicted with an autoimmune disease. The methods comprise administering an effective condition-treating or condition-preventing amount of one or more of the pharmaceutical compositions or compounds of the invention herein described. In a specific embodiment, the autoimmune disease is selected from COPD, asthma, systemic lupus erythematosis, type I diabetes mellitus and inflammatory bowel disease.

In another aspect the present invention provides a compound of the invention for use in the treatment, and/or prophylaxis of an autoimmune disease. In a specific embodiment, the autoimmune disease is selected from COPD, asthma, systemic lupus erythematosis, type I diabetes mellitus and inflammatory bowel disease. In a more specific embodiment, the autoimmune disease is systemic lupus erythematosis.

In yet another aspect, the present invention provides a compound of the invention, or a pharmaceutical composition comprising a compound of the invention for use in the manufacture of a medicament for the treatment, and/or prophylaxis of an autoimmune disease. In a specific embodiment, the autoimmune disease is selected from COPD, asthma, systemic lupus erythematosis, type I diabetes mellitus and inflammatory bowel disease.

In further method of treatment aspects, this invention provides methods of treatment and/or prophylaxis of a mammal susceptible to or afflicted with a proliferative disease, said methods comprising administering an effective condition-treating or condition-preventing amount of one or more of the pharmaceutical compositions or compounds of the invention herein described. In a specific embodiment, the proliferative disease is selected from cancer (e.g. solid tumors such as uterine leiomyosarcoma or prostate cancer), leukemia (e.g. AML, ALL or CLL), multiple myeloma and psoriasis. In a more specific embodiment, the proliferative disease is selected from myelofibrosis, T-cell acute lymphoblastic leukemia (T-ALL), multiple myeloma, chronic lymphocytic leukemia (CLL), diffuse large B-cell lymphoma (DLBCL), pancreatic cancer, liver cancer, hepatocellular carcinoma (HCC), lung cancer, breast cancer, and colon cancer.

In another aspect the present invention provides a compound of the invention for use in the treatment, and/or prophylaxis of a proliferative disease. In a specific embodiment, the proliferative disease is selected from cancer (e.g. solid tumors such as uterine leiomyosarcoma or prostate cancer), leukemia (e.g. AML, ALL or CLL), multiple myeloma and psoriasis. In a more specific embodiment, the proliferative disease is selected from myelofibrosis, T-cell acute lymphoblastic leukemia (T-ALL), multiple myeloma, chronic lymphocytic leukemia (CLL), diffuse large B-cell lymphoma (DLBCL), pancreatic cancer, liver cancer, hepatocellular carcinoma (HCC), lung cancer, breast cancer, and colon cancer.

In yet another aspect, the present invention provides a compound of the invention, or a pharmaceutical composition comprising a compound of the invention for use in the manufacture of a medicament for the treatment, and/or prophylaxis of a proliferative disease. In a specific embodiment, the proliferative disease is selected from cancer (e.g. solid tumors such as uterine leiomyosarcoma or prostate cancer), leukemia (e.g. AML, ALL or CLL), multiple myeloma and psoriasis. In a more specific embodiment, the proliferative disease is selected from myelofibrosis, T-cell acute lymphoblastic leukemia (T-ALL), multiple myeloma, chronic lymphocytic leukemia (CLL), diffuse large B-cell lymphoma (DLBCL), pancreatic cancer, liver cancer, hepatocellular carcinoma (HCC), lung cancer, breast cancer, and colon cancer.

In further method of treatment aspects, this invention provides methods of treatment and/or prophylaxis of a mammal susceptible to or afflicted with transplantation rejection, said methods comprising administering an effective condition-treating or condition-preventing amount of one or more of the pharmaceutical compositions or compounds of the invention herein described. In a specific embodiment, the transplantation rejection is organ transplant rejection.

In another aspect the present invention provides a compound of the invention for use in the treatment, and/or prophylaxis of transplantation rejection. In a specific embodiment, the transplantation rejection is organ transplant rejection.

In yet another aspect, the present invention provides a compound of the invention, or a pharmaceutical composition comprising a compound of the invention for use in the manufacture of a medicament for the treatment and/or prophylaxis of of transplantation rejection. In a specific embodiment, the transplantation rejection is organ transplant rejection.

In a method of treatment aspect, this invention provides a method of treatment, and/or prophylaxis in a mammal susceptible to or afflicted with diseases involving impairment of cartilage turnover, which method comprises administering a therapeutically effective amount of a compound of the invention, or one or more of the pharmaceutical compositions herein described.

In another aspect the present invention provides a compound of the invention for use in the treatment, and/or prophylaxis of diseases involving impairment of cartilage turnover.

In yet another aspect, the present invention provides a compound of the invention, or a pharmaceutical composition comprising a compound of the invention for use in the manufacture of a medicament for the treatment, and/or prophylaxis of diseases involving impairment of cartilage turnover.

The present invention also provides a method of treatment and/or prophylaxis of congenital cartilage malformations, which method comprises administering an effective amount of one or more of the pharmaceutical compositions or compounds of the invention herein described.

In another aspect the present invention provides a compound of the invention for use in the treatment, and/or prophylaxis of congenital cartilage malformations.

In yet another aspect, the present invention provides a compound of the invention, or a pharmaceutical composition comprising a compound of the invention for use in the manufacture of a medicament for the treatment, and/or prophylaxis of congenital cartilage malformations.

In further method of treatment aspects, this invention provides methods of treatment and/or prophylaxis of a mammal susceptible to or afflicted with diseases associated with hypersecretion of IL6, said methods comprising administering an effective condition-treating or condition-preventing amount of one or more of the pharmaceutical compositions or compounds of the invention herein described. In a specific embodiment, the disease associated with hypersecretion of IL6 is selected from Castleman's disease and mesangial proliferative glomerulonephritis.

In another aspect the present invention provides a compound of the invention for use in the treatment, and/or prophylaxis of diseases associated with hypersecretion of IL6. In a specific embodiment, the disease associated with hypersecretion of IL6 is selected from Castleman's disease and mesangial proliferative glomerulonephritis.

In yet another aspect, the present invention provides a compound of the invention, or a pharmaceutical composition comprising a compound of the invention for use in the manufacture of a medicament for the treatment, and/or prophylaxis of diseases associated with hypersecretion of IL6. In a specific embodiment, the disease associated with hypersecretion of IL6 is selected from Castleman's disease and mesangial proliferative glomerulonephritis.

In further method of treatment aspects, this invention provides methods of treatment and/or prophylaxis of a mammal susceptible to or afflicted with diseases associated with hypersecretion of interferons, said methods comprising administering an effective condition-treating or condition-preventing amount of one or more of the pharmaceutical compositions or compounds of the invention herein described. In a specific embodiment, the disease associated with hypersecretion of interferons is selected from systemic and cutaneous lupus erythematosis, lupus nephritis, dermatomyositis, Sjogren's syndrome, psoriasis, and rheumatoid arthritis.

In another aspect the present invention provides a compound of the invention for use in the treatment, and/or prophylaxis of diseases associated with hypersecretion of interferons. In a specific embodiment, the disease associated with hypersecretion of interferons is selected from systemic and cutaneous lupus erythematosis, lupus nephritis, dermatomyositis, Sjogren's syndrome, psoriasis, and rheumatoid arthritis.

In yet another aspect, the present invention provides a compound of the invention, or a pharmaceutical composition comprising a compound of the invention for use in the manufacture of a medicament for the treatment, and/or prophylaxis of diseases associated with hypersecretion of interferons. In a specific embodiment, the disease associated with hypersecretion of interferons is selected from systemic and cutaneous lupus erythematosis, lupus nephritis, dermatomyositis, Sjogren's syndrome, psoriasis, and rheumatoid arthritis.

As a further aspect of the invention there is provided a compound of the invention for use as a pharmaceutical especially in the treatment and/or prophylaxis of the aforementioned conditions and diseases. Also provided herein is the use of the present compounds in the manufacture of a medicament for the treatment and/or prophylaxis of one of the aforementioned conditions and diseases.

A particular regimen of the present method comprises the administration to a subject suffering from a disease involving inflammation, of an effective amount of a compound of the invention for a period of time sufficient to reduce the level of inflammation in the subject, and preferably terminate the processes responsible for said inflammation. A special embodiment of the method comprises administering of an effective amount of a compound of the invention to a subject patient suffering from or susceptible to the development of rheumatoid arthritis, for a period of time sufficient to reduce or prevent, respectively, inflammation in the joints of said patient, and preferably terminate, the processes responsible for said inflammation.

A further particular regimen of the present method comprises the administration to a subject suffering from a disease condition characterized by cartilage or joint degradation (e.g. rheumatoid arthritis and/or osteoarthritis) of an effective amount of a compound of the invention for a period of time sufficient to reduce and preferably terminate the self-perpetuating processes responsible for said degradation. A particular embodiment of the method comprises administering of an effective amount of a compound of the invention to a subject patient suffering from or susceptible to the development of osteoarthritis, for a period of time sufficient to reduce or prevent, respectively, cartilage degradation in the joints of said patient, and preferably terminate, the self-perpetuating processes responsible for said degradation. In a particular embodiment said compound may exhibit cartilage anabolic and/or anti-catabolic properties.

Injection dose levels range from about 0.1 mg/kg/h to at least 10 mg/kg/h, all for from about 1 to about 120 h and especially 24 to 96 h. A preloading bolus of from about 0.1 mg/kg to about 10 mg/kg or more may also be administered to achieve adequate steady state levels. The maximum total dose is not expected to exceed about 2 g/day for a 40 to 80 kg human patient.

For the prophylaxis and/or treatment of long-term conditions, such as degenerative conditions, the regimen for treatment usually stretches over many months or years so oral dosing is preferred for patient convenience and tolerance. With oral dosing, one to five and especially two to four and typically three oral doses per day are representative regimens. Using these dosing patterns, each dose provides from about 0.01 to about 20 mg/kg of a compound of the invention, with particular doses each providing from about 0.1 to about 10 mg/kg and especially about 1 to about 5 mg/kg.

Transdermal doses are generally selected to provide similar or lower blood levels than are achieved using injection doses.

When used to prevent the onset of a condition, a compound of the invention will be administered to a patient at risk for developing the condition, typically on the advice and under the supervision of a physician, at the dosage levels described above. Patients at risk for developing a particular condition generally include those that have a family history of the condition, or those who have been identified by genetic testing or screening to be particularly susceptible to developing the condition.

A compound of the invention can be administered as the sole active agent or it can be administered in combination with other therapeutic agents, including other compounds that demonstrate the same or a similar therapeutic activity and that are determined to be safe and efficacious for such combined administration. In a specific embodiment, co-administration of two (or more) agents allows for significantly lower doses of each to be used, thereby reducing the side effects seen.

In one embodiment, a compound of the invention or a pharmaceutical composition comprising a compound of the invention is administered as a medicament. In a specific embodiment, said pharmaceutical composition additionally comprises a further active ingredient.

In one embodiment, a compound of the invention is co-administered with another therapeutic agent for the treatment and/or prophylaxis of a disease involving inflammation; particular agents include, but are not limited to, immunoregulatory agents e.g. azathioprine, corticosteroids (e.g. prednisolone or dexamethasone), cyclophosphamide, cyclosporin A, tacrolimus, Mycophenolate Mofetil, muromonab-CD3 (OKT3, e.g. Orthocolone®), ATG, aspirin, acetaminophen, ibuprofen, naproxen, and piroxicam.

In one embodiment, a compound of the invention is co-administered with another therapeutic agent for the treatment and/or prophylaxis of arthritis (e.g. rheumatoid arthritis); particular agents include but are not limited to analgesics, non-steroidal anti-inflammatory drugs (NSAIDS), steroids, synthetic DMARDS (for example but without limitation methotrexate, leflunomide, sulfasalazine, auranofin, sodium aurothiomalate, penicillamine, chloroquine, hydroxychloroquine, azathioprine, and ciclosporin), and biological DMARDS (for example but without limitation Infliximab, Etanercept, Adalimumab, Rituximab, and Abatacept).

In one embodiment, a compound of the invention is co-administered with another therapeutic agent for the treatment and/or prophylaxis of proliferative disorders; particular agents include but are not limited to: methotrexate, leukovorin, adriamycin, prenisone, bleomycin, cyclophosphamide, 5-fluorouracil, paclitaxel, docetaxel, vincristine, vinblastine, vinorelbine, doxorubicin, tamoxifen, toremifene, megestrol acetate, anastrozole, goserelin, anti-HER2 monoclonal antibody (e.g. Herceptin™), capecitabine, raloxifene hydrochloride, EGFR inhibitors (e.g. Iressa®, Tarceva™, Erbitux™), VEGF inhibitors (e.g. Avastin™), proteasome inhibitors (e.g. Velcade™), Glivec® and hsp90 inhibitors (e.g. 17-AAG). Additionally, a compound of the invention may be administered in combination with other therapies including, but not limited to, radiotherapy or surgery. In a specific embodiment the proliferative disorder is selected from cancer, myeloproliferative disease and leukaemia.

In one embodiment, a compound of the invention is co-administered with another therapeutic agent for the treatment and/or prophylaxis of autoimmune diseases, particular agents include but are not limited to: glucocorticoids, cytostatic agents (e.g. purine analogs), alkylating agents, (e.g nitrogen mustards (cyclophosphamide), nitrosoureas, platinum compounds, and others), antimetabolites (e.g. methotrexate, azathioprine and mercaptopurine), cytotoxic antibiotics (e.g. dactinomycin anthracyclines, mitomycin C, bleomycin, and mithramycin), antibodies (e.g. anti-CD20, anti-CD25 or anti-CD3 (OTK3) monoclonal antibodies, Atgam® and Thymoglobuline®), cyclosporin, tacrolimus, rapamycin (sirolimus), interferons (e.g. IFN-β), TNF binding proteins (e.g. infliximab (Remicade™), etanercept (Enbrel™), or adalimumab (Humira™)), mycophenolate, Fingolimod and Myriocin.

In one embodiment, a compound of the invention is co-administered with another therapeutic agent for the treatment and/or prophylaxis of transplantation rejection, particular agents include but are not limited to: calcineurin inhibitors (e.g. cyclosporin or tacrolimus (FK506)), mTOR inhibitors (e.g. sirolimus, everolimus), anti-proliferatives (e.g. azathioprine, mycophenolic acid), corticosteroids (e.g. prednisolone, hydrocortisone), Antibodies (e.g. monoclonal anti-IL-2Rα receptor antibodies, basiliximab, daclizumab), polyclonal anti-T-cell antibodies (e.g. anti-thymocyte globulin (ATG), anti-lymphocyte globulin (ALG)).

In one embodiment, a compound of the invention is co-administered with another therapeutic agent for the treatment and/or prophylaxis of asthma and/or rhinitis and/or COPD, particular agents include but are not limited to: beta2-adrenoceptor agonists (e.g. salbutamol, levalbuterol, terbutaline and bitolterol), epinephrine (inhaled or tablets), anticholinergics (e.g. ipratropium bromide), glucocorticoids (oral or inhaled) Long-acting β2-agonists (e.g. salmeterol, formoterol, bambuterol, and sustained-release oral albuterol), combinations of inhaled steroids and long-acting bronchodilators (e.g. fluticasone/salmeterol, budesonide/formoterol), leukotriene antagonists and synthesis inhibitors (e.g. montelukast, zafirlukast and zileuton), inhibitors of mediator release (e.g. cromoglycate and ketotifen), biological regulators of IgE response (e.g. omalizumab), antihistamines (e.g. ceterizine, cinnarizine, fexofenadine) and vasoconstrictors (e.g. oxymethazoline, xylomethazoline, nafazoline and tramazoline).

Additionally, a compound of the invention may be administered in combination with emergency therapies for asthma and/or COPD, such therapies include oxygen or heliox administration, nebulized salbutamol or terbutaline (optionally combined with an anticholinergic (e.g. ipratropium), systemic steroids (oral or intravenous, e.g. prednisone, prednisolone, methylprednisolone, dexamethasone, or hydrocortisone), intravenous salbutamol, non-specific beta-agonists, injected or inhaled (e.g. epinephrine, isoetharine, isoproterenol, metaproterenol), anticholinergics (IV or nebulized, e.g. glycopyrrolate, atropine, ipratropium), methylxanthines (theophylline, aminophylline, bamiphylline), inhalation anesthetics that have a bronchodilatory effect (e.g. isoflurane, halothane, enflurane), ketamine and intravenous magnesium sulfate.

In one embodiment, a compound of the invention is co-administered with another therapeutic agent for the treatment and/or prophylaxis of inflammatory bowel disease (IBD), particular agents include but are not limited to: glucocorticoids (e.g. prednisone, budesonide) synthetic disease modifying, immunomodulatory agents (e.g. methotrexate, leflunomide, sulfasalazine, mesalazine, azathioprine, 6-mercaptopurine and ciclosporin) and biological disease modifying, immunomodulatory agents (infliximab, adalimumab, rituximab, and abatacept).

In one embodiment, a compound of the invention is co-administered with another therapeutic agent for the treatment and/or prophylaxis of SLE, particular agents include but are not limited to: Disease-modifying antirheumatic drugs (DMARDs) such as antimalarials (e.g. plaquenil, hydroxychloroquine), immunosuppressants (e.g. methotrexate and azathioprine), cyclophosphamide and mycophenolic acid; immunosuppressive drugs and analgesics, such as nonsteroidal anti-inflammatory drugs, opiates (e.g. dextropropoxyphene and co-codamol), opioids (e.g. hydrocodone, oxycodone, MS Contin, or methadone) and the fentanyl duragesic transdermal patch.

In one embodiment, a compound of the invention is co-administered with another therapeutic agent for the treatment and/or prophylaxis of psoriasis, particular agents include but are not limited to: topical treatments such as bath solutions, moisturizers, medicated creams and ointments containing coal tar, dithranol (anthralin), corticosteroids like desoximetasone (Topicort™), fluocinonide, vitamin D3 analogues (for example, calcipotriol), Argan oiland retinoids (etretinate, acitretin, tazarotene), systemic treatments such as methotrexate, cyclosporine, retinoids, tioguanine, hydroxyurea, sulfasalazine, mycophenolate mofetil, azathioprine, tacrolimus, fumaric acid esters or biologics such as Amevive™ Enbrel™, Humira™, Remicade™, Raptiva™ and ustekinumab (a IL-12 and IL-23 blocker). Additionally, a compound of the invention may be administered in combination with other therapies including, but not limited to phototherapy, or photochemotherapy (e.g. psoralen and ultraviolet A phototherapy (PUVA)).

In one embodiment, a compound of the invention is co-administered with another therapeutic agent for the treatment and/or prophylaxis of allergic reaction, particular agents include but are not limited to: antihistamines (e.g. cetirizine, diphenhydramine, fexofenadine, levocetirizine), glucocorticoids (e.g. prednisone, betamethasone, beclomethasone, dexamethasone), epinephrine, theophylline or anti-leukotrienes (e.g. montelukast or zafirlukast), anti-cholinergics and decongestants.

By co-administration is included any means of delivering two or more therapeutic agents to the patient as part of the same treatment regime, as will be apparent to the skilled person. Whilst the two or more agents may be administered simultaneously in a single formulation this is not essential. The agents may be administered in different formulations and at different times.

Chemical Synthetic Procedures

General

The compounds of the invention can be prepared from readily available starting materials using the following general methods and procedures. It will be appreciated that where typical or preferred process conditions (i.e. reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art (Greene, T W; Wuts, P G M; 1991).

The following methods are presented with details as to the preparation of a compound of the invention as defined hereinabove and the comparative examples. A compound of the invention may be prepared from known or commercially available starting materials and reagents by one skilled in the art of organic synthesis.

All reagents were of commercial grade and were used as received without further purification, unless otherwise stated. Commercially available anhydrous solvents were used for reactions conducted under inert atmosphere. Reagent grade solvents were used in all other cases, unless otherwise specified. Column chromatography was performed on silica gel 60 (35-70 μm). Thin layer chromatography was carried out using pre-coated silica gel F-254 plates (thickness 0.25 mm). $^1$H NMR spectra were recorded on a Bruker DPX 400 NMR spectrometer (400 MHz or a Bruker Advance 300 NMR spectrometer (300 MHz). Chemical shifts (δ) for 1H NMR spectra are reported in parts per million (ppm) relative to tetramethylsilane (δ 0.00) or the appropriate residual solvent peak, i.e. CHCl$_3$ (δ 7.27), as internal reference. Multiplicities are given as singlet (s), doublet (d), triplet (t), quartet (q), quintuplet (quin), multiplet (m) and broad (br). Electrospray MS spectra were obtained on a Waters platform LC/MS spectrometer or with Waters Acquity H-Class UPLC coupled to a Waters Mass detector 3100 spectrometer. Columns used: Waters Acquity UPLC BEH C18 1.7 μm, 2.1 mm ID×50 mm L, Waters Acquity UPLC BEH C18 1.7 μm, 2.1 mm ID×30 mm L, or Waters Xterra MS 5 μm C18, 100×4.6 mm. The methods are using either MeCN/H$_2$O gradients (H$_2$O contains either 0.1% TFA or 0.1% NH$_3$) or MeOH/H$_2$O gradients (H$_2$O contains 0.05% TFA). Microwave heating was performed with a Biotage Initiator.

The preparative HPLC purifications were performed with a mass-directed auto-purification system coupled with a ZQ single quadrupole mass spectrometer. All HPLC purifications were performed with a gradient of H$_2$O (different pHs)/MeCN. Preparative HPLC separations under basic conditions were usually carried out using a BEH XBrigde C18 (5 μm, 19×5 mm) precolumn and a BEH XBrigde C18 (5 μm, 19×100 mm) Separations under acidic conditions were usually carried out using CSH Select C18 (5 μm, 19×5 mm) precolumn and a CSH Select C18 (5 μm, 19×100 mm) The focused gradient was from x % to x+25% acetonitrile in water in 5 min with a cycle time of 10 min. The column flow rate was 20 mL/min. The injection volume ranged from 200 to 750 μL. A capillary splitter was used to divert flow after column separation to the mass spectrometer which was diluted by 1 mL/min of make-up flow. The make-up flow is 0.1% formic acid in methanol. All samples were purified by a Waters mass directed fraction collection.

TABLE I

| \multicolumn{2}{c}{List of abbreviations used in the experimental section:} | |
| --- | --- |
| Abbreviation | Definition |
| AcOH | acetic acid |
| ATP | adenosine tri-phosphate |
| BINAP | 2,2'-bis(diphenylphosphino)-1,1'-binaphthyl |
| br s | broad singlet |
| Brettphos | 2-(dicyclohexylphosphino)3,6-dimethoxy-2',4',6'-triisopropyl-1,1'-biphenyl |
| BSA | bovine serum albumin |
| C'ial | commercially available |
| Conc | concentrated |
| Cpd | compound |
| DCM | dichloromethane |
| DMF | dimethyl formamide |
| DMSO | dimethyl sulfoxide |
| DPPA | diphenylphosphoryl azide |
| Dsc'd | fully described above |
| DTT | dithiothreitol |

TABLE I-continued

| \multicolumn{2}{c}{List of abbreviations used in the experimental section:} | |
| --- | --- |
| Abbreviation | Definition |
| EDTA | ethylenediaminetetraacetic acid |
| EGTA | ethylene glycol tetraacetic acid |
| Et$_2$O | diethyl ether |
| Et$_3$B | triethylborane |
| Et$_3$N | triethylamine |
| EtOAc | ethyl acetate |
| EtOH | ethanol |
| FACS | Fluorescence-Activated Cell Sorting |
| FBS | fetal bovine serum |
| g | gram |
| h | hour |
| HEPES | 4-(2-hydroxyethyl)-1-piperazineethanesulfonic acid |
| HPLC | high pressure liquid chromatography |
| Int | intermediate |
| iPrOH | iso-Propanol |
| m | multiplet |
| M | mass |
| MC | methyl cellulose |
| MeCN | acetonitrile |
| MeI | iodomethane |
| MeNH$_2$ | methyl amine |
| MeOH | methanol |
| mg | milligram |
| min | minute |
| mL | milliliter |
| mmol | millimoles |
| MOPS | 3-(N-morpholino) propanesulfonic acid |
| MS Ms'd | mass spectrometry measured molecular weight |
| Mtd | method |
| MW | molecular weight |
| NCS | N-chlorosuccinimide |
| NMP | N-methylpyrrolidone |
| NMR | nuclear Magnetic Resonnance |
| PBS | phosphate buffered saline |
| pBSK | pBluescript phagemid |
| Pd(OAc)$_2$ | palladium(II) acetate |
| Pd(PPh$_3$)$_4$ | tetrakis(triphenylphosphine)palladium(0) |
| Pd$_2$(dba)$_3$ | tris(dibenzylideneacetone)dipalladium(0) |
| PdCl$_2$(dppf)•DCM | [1,1'-bis(diphenylphosphino)ferrocene]dichloropalladium (II), complex with dichloromethane |
| PDX | patient-derived xenografts |
| PET | positron emission topography |
| PMB | para-methoxybenzyl |
| ppm | parts per million |
| p-TsOH•H$_2$O | para-toluenesulfonic acid monohydrate |
| rt | room temperature |
| s | singlet |
| sat | saturated |
| SiO$_2$ | silica |
| SM | starting material |
| TFA | trifluoroacetic acid |
| THF | tetrahydrofuran |
| Xantphos | 4,5-Bis(diphenylphosphino)-9,9-dimethylxanthene |
| XPhos | 2-dicyclohexylphosphino-2',4',6'-triisopropylbiphenyl |

Synthetic Preparation of the Compound of the Invention

Example 1

Synthesis of the Intermediate Compounds of the Invention

1.1. Synthesis of bis-(4-methoxy-benzyl)-amine (Int. 1)

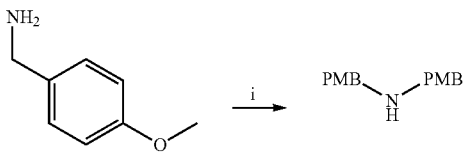

p-Anisaldehyde (411 mmol), 4-methoxybenzylamine (411 mmol) and toluene (500 mL) were combined in a round bottomed flask fitted with a condenser and a Dean-Stark trap. The reaction was refluxed for 1 h during which water was removed from the reaction mixture. The reaction was cooled and concentrated. The residue was dissolved in MeOH (120 mL). The mixture was cooled to 5° C. and NaBH$_4$ (205 mmol) was added in portions over 45 min. The reaction was slowly heated to reflux. After 2 h at reflux, the reaction was cooled to room temperature and concentrated. The residue was dissolved in EtOAc. The organic layer was washed (3×H$_2$O and brine), dried (Na$_2$SO$_4$) and concentrated to yield the desired product.

1.2. Synthesis of (6-Bromo-1-methyl-1H-benzoimidazol-4-yl)-bis-(4-methoxy-benzyl)-amine (Int.2)

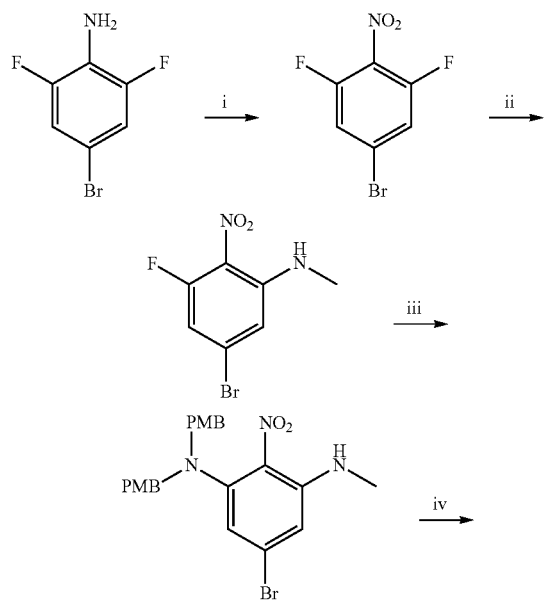

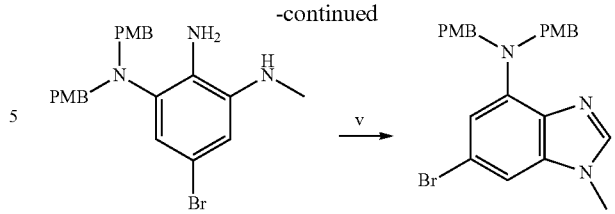

1.2.1. Step i: 5-Bromo-1,3-difluoro-2-nitro-benzene

A solution of 4-bromo-2,6-difluoroaniline (240 mmol) in AcOH (150 mL) was added dropwise to a suspension of NaBO$_3$.4 H$_2$O (325 mmol) in AcOH (450 mL) at 70° C. during 30 min. Another 2080 mmol of NaBO$_3$.4 H$_2$O were added over 5 h to the mixture. During this period the mixture was stirred at 70° C. The mixture was poured into water and extracted with Et$_2$O. The organic layer was combined with another Et$_2$O solution obtained from another reaction using the same conditions described above. The mixture was concentrated. A precipitate was formed and separated by filtration. The filtrate was concentrated to afford the desired product after flash column chromatography (SiO$_2$, petroleum ether).

1.2.2. Step ii: (5-Bromo-3-fluoro-2-nitro-phenyl)-methyl-amine

2 M MeNH$_2$ in THF (82 mL) was added dropwise to a solution of 5-bromo-1,3-difluoro-2-nitrobenzene (164 mmol) and Cs$_2$CO$_3$ (197 mmol) in THF (1 L). The reaction mixture was stirred at 0° C. for 1 h and then at room temperature for 1 h. The solvent was removed under reduced pressure. The residue was partitioned between EtOAc and H$_2$O. The two phases were separated and the organic layer was dried (Na$_2$SO$_4$) and concentrated to afford the desired product.

1.2.3. Step iii: 5-Bromo-N,N-bis-(4-methoxy-benzyl)-N'-methyl-2-nitro-benzene-1,3-diamine A mixture of bis-(4-methoxy-benzyl)-amine (346 mmol), 5-bromo-3-fluoro-N-methyl-2-nitroaniline (297 mmol) and Et$_3$N (891 mmol) was stirred at 120° C. for 16 h. The mixture was then cooled. The crude was combined with another one obtained following the same procedure described above. The resulting mixture was diluted in EtOAc and washed (2×0.2 M HCl, H$_2$O and sat. NaHCO$_3$). The organic phase was dried (Na$_2$SO$_4$) and concentrated to afford the desired product.

1.2.4. Step iv: 5-Bromo-N,N-bis-(4-methoxy-benzyl)-N''-methyl-benzene-1,2,3-triamine A mixture of 5-Bromo-N,N-bis-(4-methoxy-benzyl)-N'-methyl-2-nitro-benzene-1,3-diamine (170 mmol), NH$_4$Cl (2038 mmol) and Zn (2034 mmol) in 1:1 MeOH/THF (1 L) was stirred at room temperature for 1 h. The mixture was cooled to 0° C. and HCOOH (20 mL) was added slowly. The mixture was allowed to reach room temperature and stirred for 1 h. The mixture was filtered and combined with another one obtained following the procedure described above. The resulting mixture was concentrated. The residue was dissolved in DCM. The organic mixture was washed (sat. NH₄Cl), dried (Na₂SO₄) and concentrated to afford the desired product.

1.2.5. Step v: (6-Bromo-1-methyl-1H-benzoimidazol-4-yl)-bis-(4-methoxy-benzyl)-amine 5-Bromo-N,N-bis-(4-methoxy-benzyl)-N'''-methyl-benzene-1,2,3-triamine (170 mmol) was dissolved in a mixture of HC(OEt)₃ (100 mol) and MeCN (500 mL). The mixture was stirred at 85° C. for 0.5 h and then at room temperature for approximately 16 h. The mixture was combined with another one obtained following the same procedure described above. The resulting mixture was concentrated and the residue was purified by flash column chromatography (SiO₂, 15:85 to 60:40 EtOAc/petroleum ether) to obtain the desired product.

1.3. Synthesis of 5-{7-[Bis-(4-methoxy-benzyl)-amino]-3-methyl-3H-benzoimidazol-5-yloxy}-4-methyl-pyridine-2-carbonitrile (Int.3)

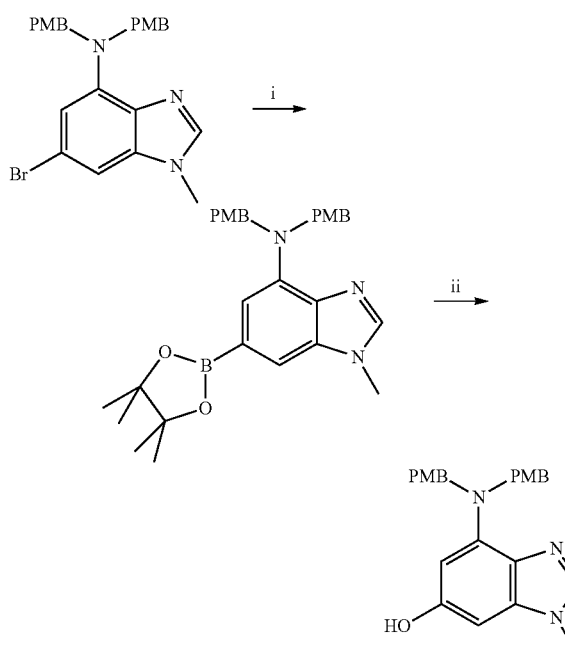

1.3.1. Step i: Bis-(4-methoxy-benzyl)-[1-methyl-6-(4,4,5,5-tetramethyl-[1,3,2]dioxaborolan-2-yl)-1H-benzoimidazol-4-yl]amine A mixture of (6-bromo-1-methyl-1H-benzoimidazol-4-yl)-bis-(4-methoxy-benzyl)-amine (54 mmol), bis(pinacolato)diboron (81 mmol), PdCl₂(dppf).DCM (2.71 mmol) and KOAc (162.5 mmol) in DMF (150 mL) was sonicated for 5 min under a stream of nitrogen. The mixture was then stirred at 110° C. in a round bottomed flask equipped with a condenser for 1 h. The mixture was filtered through a celite pad and the filtrate was concentrated. The residue was dissolved in EtOAc and the organic layer was washed (H₂O), dried (Na₂SO₄) and concentrated to afford the desired product.

1.3.2. Step ii: 5-{7-[Bis-(4-methoxy-benzyl)-amino]-3-methyl-3H-benzoimidazol-5-yloxy}-4-methyl-pyridine-2-carbonitrile H₂O₂ 30% wt. in H₂O (20 mL) was added to a solution of N,N-bis(4-methoxybenzyl)-1-methyl-6-(4,4,5,5-tetramethyl-1,3,2-dioxaborolan-2-yl)-1H-benzo[d]imidazol-4-amine (58.5 mmol) in DMF (600 mL) and the mixture was stirred for approximately 16 h at room temperature. The reaction was quenched with 5% aqueous Na₂SO₃. The mixture was extracted with EtOAc. The organic layer was washed (H₂O), dried (Na₂SO₄) and concentrated to afford the desired product.

1.4. General Method: Ortho-Directed Iodination

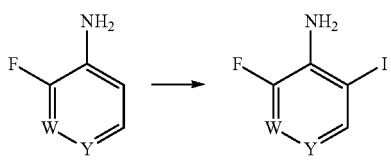

Where W can be: —N═, —CH═, —C(Cl)═; Y can be: —N═, —C(CN)═

1.4.1. Method A1

A mixture of the amino aromatic or heteroaromatic starting material (1 eq), Ag₂SO₄ (1 eq) and I₂ (1 eq) in EtOH is stirred at temperatures ranging from room temperature to 50° C. for a period which can vary from 1 h to approximately 16 h. The mixture is filtered, concentrated and diluted in an organic solvent. The organic mixture undergoes aqueous work up. The solvent is removed under reduced pressure and the residue is purified by flash column chromatography to yield the desired product.

1.4.2. Illustrative example of method A1: synthesis of 4-Amino-3-fluoro-5-iodo-benzonitrile (Int.4)

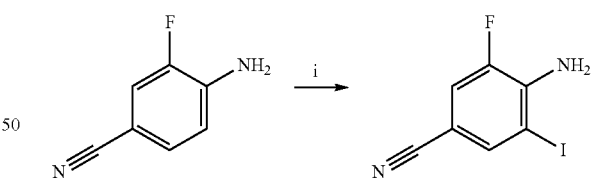

A mixture of 4-amino-3-fluorobenzonitrile (147 mmol), I₂ (147 mmol) and Ag₂SO₄ (147 mmol) in EtOH (700 mL) was stirred at room temperature for 1.5 h. The mixture was filtered and concentrated. The residue was dissolved in EtOAc and washed (sat. Na₂S₂O₃×3). The organic layer was dried (Na₂SO₄) and concentrated. The residue was purified by flash column chromatography (SiO₂, 95:5 to 70:30 cyclohexane/EtOAc) to yield the desired product.

1.4.3. Method A2

A mixture of the amino aromatic or heteroaromatic starting material (1 eq), Ag₂SO₄ (3 to 4 eq) and I₂ (3 to 4 eq) in EtOH is stirred at 70° C. for 16 h. More equivalents of I₂ and

1.5. Illustrative example of method A2: synthesis of 5-amino-6-fluoro-4-iodo-pyridine-2-carbonitrile (Int.5)

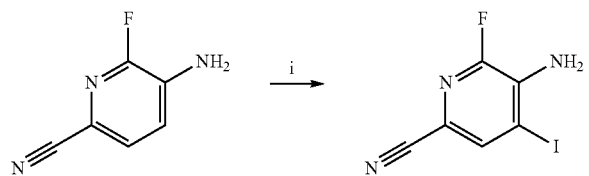 [SMILES: N#Cc1ccc(N)c(F)n1 ; N#Cc1cc(I)c(N)c(F)n1]

A mixture of Int.11 (3.62 mmol), I₂ (14.5 mmol) and Ag₂SO₄ (14.5 mmol) in EtOH (200 mL) was stirred at 70° C. for 16 h. 5 more equivalents of I₂ and Ag₂SO₄ were added and the reaction was stirred at 70° C. for a further 72 h. The mixture was filtered, concentrated and purified by flash column chromatography (SiO₂, 20:80 to 40:60 EtOAc/cyclohexane) to yield the desired product.

1.6. General Method: Introduction of Nitrile Group by Negishi Reaction

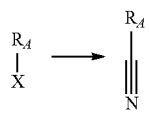

Where $R_A$ can be aryl or heteroaryl; and X can be Cl, Br or I.

1.6.1. Method B

A mixture of aryl/heteroaryl halide (1 eq), zinc cyanide (1 to 3 eq), Pd(PPh₃)₄ (0.1 to 0.2 eq) in DMF is heated at 150° C. in a microwave apparatus for a period ranging from 5 min to 0.5 h. The mixture is filtered and concentrated. The residue is diluted with an organic solvent. The organic mixture undergoes work up and the solvent is removed under reduced pressure. The residue is triturated or purified by flash column chromatography to yield the desired product.

1.6.2. Illustrative example of method B: synthesis of 5-fluoro-4-methyl-pyridine-2-carbonitrile (Int.7)

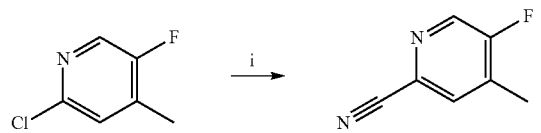

A microwave tube was charged with 2-chloro-5-fluoro-4-methylpyridine (5.5 mmol), Zn(CN)₂ (16.6 mmol), Pd(PPh₃)₄ (1.1 mmol) in DMF (20 mL). The mixture was stirred at 150° C. for 5 min in a microwave reactor. The mixture was combined with other crudes obtained following the procedure described above. The resulting mixture was filtered. The filtrate was concentrated under reduced pressure. The residue was diluted with EtOAc, washed (sat. NH₄Cl), dried (Na₂SO₄) and concentrated. The residue was purified by flash column chromatography (SiO₂, 5:95 to 15:85 EtOAc/petroleum ether) to yield the desired product.

1.7. General Method: Suzuki with Methyl Boronic Acid

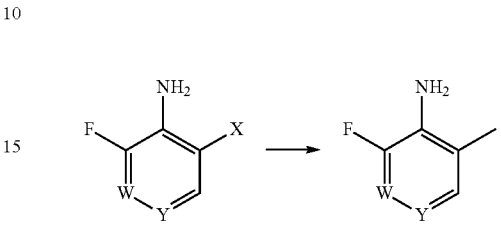

Where W can be: —N═, —CH═, —C(Cl)═; and Y can be: —N═, —C(CN)═; and X can be —I or —Br

1.7.1. Method C

A mixture of the aromatic/heteroaromatic halide (1 eq), methyl boronic acid (1.3 to 3 eq), Pd(dppf)Cl₂.DCM (0.11 to 0.2 eq) and Cs₂CO₃ (3 to 5 eq) in 1,4-dioxane is stirred at 100° C. The mixture is diluted with an organic solvent. The organic mixture undergoes aqueous work up and the solvent is removed under reduced pressure. The residue is purified by flash column chromatography to yield the desired product.

1.7.2. Illustrative example of method C, synthesis of 5-amino-6-fluoro-4-methyl-pyridine-2-carbonitrile (Int.12)

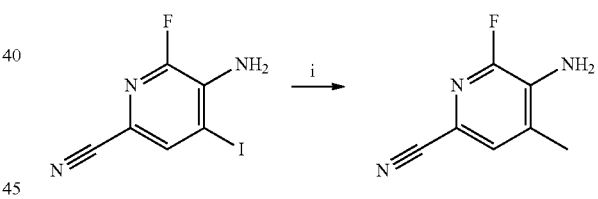

A mixture of Int.5 (3 mmol), methyl boronic acid (9.1 mmol), Pd(dppf)Cl₂.DCM (0.32 mmol) and Cs₂CO₃ (15.2 mmol) in 1,4-dioxane (8 mL) was stirred at 105° C. for 5 h. The mixture was diluted (EtOAc), washed (sat. NaHCO₃), dried (Na₂SO₄) and concentrated. The residue was purified by flash column chromatography (SiO₂, 10:90 to 50:50 EtOAc/petroleum ether) to yield the desired product.

1.8. Synthesis of 6-bromo-2-fluoro-pyridin-3-ylamine (Int.15)

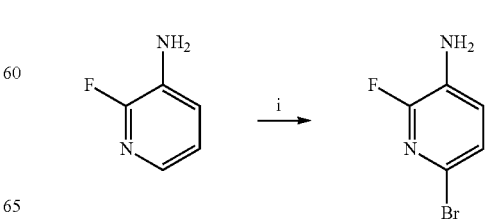

A mixture of 2-fluoropyridin-3-amine (44.6 mmol) and KOAc (44.6 mmol) in AcOH was stirred at room temperature for 1 h. The mixture was cooled to 0 C and Br$_2$ (44.6 mmol) was added dropwise. The mixture was stirred at 0° C. for 15 min. The mixture was concentrated and the residue was dissolved in EtOAc/MeOH. The organic solution was washed (sat. NaHCO$_3$, sat. Na$_2$S$_2$O$_3$), dried (Na$_2$SO$_4$) and concentrated. The residue was purified by flash column chromatography (SiO$_2$, 100:0 to 80:20 petroleum ether/EtOAc) to yield the desired product.

1.9. Synthesis of 2-bromo-6-fluoro-4-methanesulfonyl-phenylamine (Int.16)

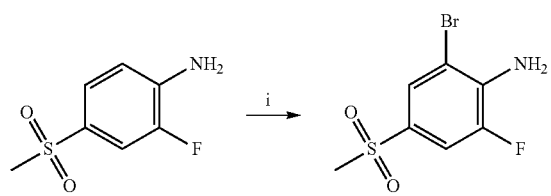

A mixture of 2-fluoro-4-methylsulfonyl-aniline (22.76 mmol) and KOAc (22.7 mmol) in AcOH was stirred at room temperature. The mixture was cooled to 0° C. and Br$_2$ (22.7 mmol) was added dropwise. The mixture was stirred for 30 min at 0° C. The mixture was concentrated and the residue was taken up in EtOAc. The organic mixture was washed (sat. NaHCO$_3$, sat. Na$_2$S$_2$O$_3$), dried (Na$_2$SO$_4$) and concentrated to yield the desired product.

1.10. Synthesis of 4-amino-3-ethyl-5-fluoro-benzonitrile (Int.17)

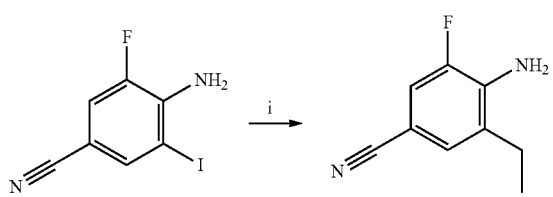

A mixture of Cs$_2$CO$_3$ (46 mmol) and Pd(dppf)Cl$_2$.DCM (0.76 mmol) was suspended in DMF (35 mL) and degassed with nitrogen. H$_2$O (400 µL), 1 M Et$_3$B in THF (11.5 mL) and a solution of Int.4 (7.63 mmol) in DMF (5 mL) were added to the mixture and the reaction was stirred at 60° C. for 30 min. The mixture was concentrated and the residue was taken up in EtOAc, washed (sat. NaHCO$_3$, H$_2$O), dried (Na$_2$SO$_4$) and concentrated. The residue was purified by flash column chromatography (SiO2, 100:0 to 95:5 petroleum ether/EtOAc) to yield the desired product.

1.11. General Method: Conversion of NH$_2$ into Iodide

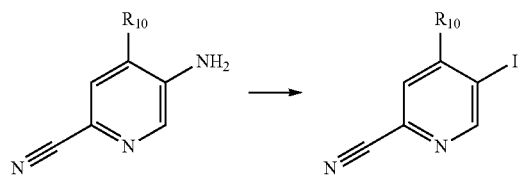

Where R$_{10}$ can be Me or Et.

1.11.1. Method D

Conc. HCl (6 eq) is added dropwise to a mixture of the amino aromatic/heteroaromatic compound (1 eq) in H$_2$O at 0 C. A solution of NaNO$_2$ (1.05 eq) in H$_2$O is added dropwise. The resulting mixture is stirred at 0 C for 15 min. A solution of KI (1.05 eq) in H$_2$O is added dropwise. The mixture is stirred at 0° C. for 15 min and for 1 h at room temperature. The mixture is extracted with an organic solvent. After aqueous work up and removal of the solvent under reduced pressure, the residue can undergo trituration or chromatography to yield the desired product.

1.11.2. Illustrative example of method D: synthesis of 5-iodo-4-methyl-pyridine-2-carbonitrile (Int.18)

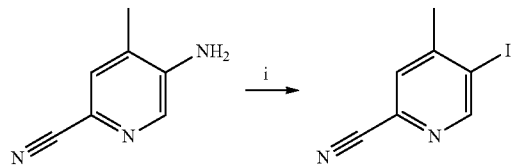

Conc. HCl (0.9 mL) was added dropwise to a mixture of Int.8 (1.88 mmol) in H$_2$O (10 mL) at 0° C. followed by the dropwise addition of a solution of NaNO$_2$ (1.97 mmol) in H$_2$O (0.5 mL). The resulting mixture was stirred at 0 C for 15 min. A solution of KI (1.97 mmol) in H$_2$O (1 mL) was added dropwise. The resulting mixture was stirred at 0° C. for 15 min and for 1 h at room temperature. The mixture was extracted with EtOAc. The organic layer was washed (H$_2$O), dried and concentrated. The residue was purified by flash column chromatography (SiO$_2$, 100:0 to 75:25 cyclohexane/EtOAc) to yield the desired product.

1.12. Synthesis of 6-bromo-4-methyl-pyridin-3-ylamine (Int.20)

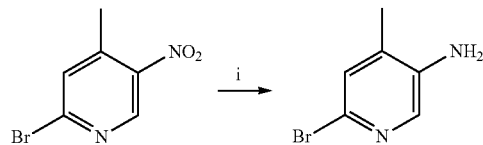

A mixture of NH$_4$Cl (14.9 mmol) and iron powder (18.4 mmol) in H$_2$O (5 mL) was stirred at 90° C. 2-bromo-4-methyl-5-nitropyridine (2.3 mmol) was added in portions.

The mixture was stirred at 90° C. for 1 h and 15 min. The reaction was stopped and extracted with EtOAc. The organic layer was dried (Na₂SO₄) and concentrated to yield the desired product.

1.13. Synthesis of 4-amino-3-chloro-5-fluoro-benzonitrile (Int.21)

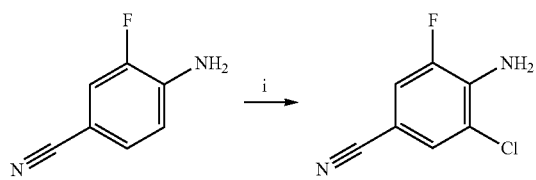 [SMILES: N#Cc1ccc(N)c(F)c1 ; N#Cc1cc(F)c(N)c(Cl)c1]

A mixture of 4-amino-3-fluorobenzonitrile (184 mmol) and NCS (276 mmol) in AcOH (300 mL) was stirred at 70° C. for approximately 16 h. The mixture was concentrated. $H_2O$ was added to the residue and the solid product was filtered off and washed (sat. NaHCO₃ and $H_2O$). To eliminate $H_2O$, THF was added and removed under reduced pressure to yield the desired product.

1.14. Synthesis of 3-ethyl-4-hydroxy-benzonitrile (Int.22)

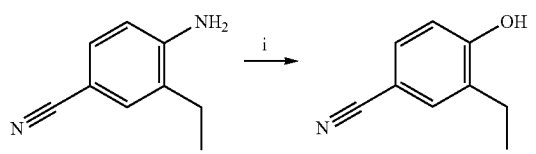

Concentrated $H_2SO_4$ (3.4 mL) was added dropwise to a solution of 4-amino-3-ethylbenzonitrile (6.84 mmol) in $H_2O$ (12 mL) at 0° C. A solution of NaNO₂ (7.52 mmol) in $H_2O$ (5 mL) was added dropwise at 0° C. to the resulting mixture. The reaction was stirred at 0° C. for 30 min and at 100° C. for 2 h. The mixture was cooled to room temperature and extracted with EtOAc. The organic layer was washed ($H_2O$), dried and concentrated to yield the desired product.

1.15. Synthesis of 2-chloro-3-fluoro-pyridin-4-ylamine (Int.23)

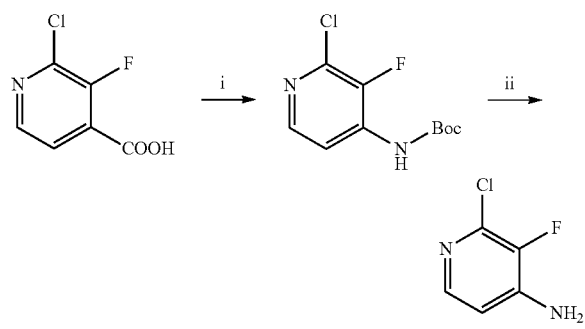

1.15.1. Step i: tert-butyl N-(2-chloro-3-fluoro-4-pyridyl)carbamate

Diphenylphosphoryl azide (DPPA) (129 mmol) was added to a mixture of 2-chloro-3-fluoro-pyridine-4-carboxylic acid (85.7 mmol), Et₃N (257 mmol) in 1:1 tert-BuOH/toluene (200 mL). The mixture was heated at 110° C. for 4 h. Mixture was diluted with $H_2O$ and extracted with DCM. The organic layer was dried (Na₂SO₄) and concentrated. The residue was purified by flash column chromatography (SiO₂, 100:0 to 80:20 DCM/EtOAc) to yield the desired product tert-butyl N-(2-chloro-3-fluoro-4-pyridyl)carbamate.

1.15.2. Step ii: 2-Chloro-3-fluoro-pyridin-4-ylamine

A solution of tert-butyl N-(2-chloro-3-fluoro-4-pyridyl)carbamate (20.2 mmol) in 1:2 TFA/DCM (45 mL) was stirred at room temperature for 6 h. The reaction mixture was concentrated and the residue was purified by flash column chromatography (SiO₂, 100:0 to 90:10 DCM/7N NH₃ in MeOH) to yield the desired product.

1.16. General method: Buchwald coupling with (6-Bromo-1-methyl-1H-benzoimidazol-4-yl)-bis-(4-methoxy-benzyl)-amine (Int.2)

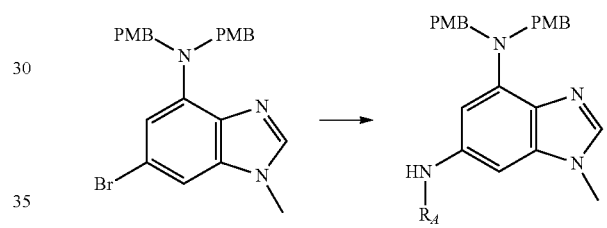

Where $R_A$ can be optionally substituted aryl or heteroaryl.

1.16.1. Method E1

A mixture of Int.2 (1 eq), the corresponding aniline (1.1 eq), Cs₂CO₃ (2 eq) and XPhos (0.3 eq) in dry toluene is purged with an inert gas before Pd(OAc)₂ (0.1 to 0.15 eq) is added. The mixture is stirred at 110° C. for approximately 16 h. The mixture may be partitioned between an organic solvent and an aqueous phase. The two layers are separated and the organic layer is dried and concentrated. Alternatively the reaction mixture can be filtered and concentrated. The residue may be kept as such or purified by chromatography to yield the desired product.

1.16.2. Illustrative example of method E1: synthesis of 5-{7-[Bis-(4-methoxy-benzyl)-amino]-3-methyl-3H-benzoimidazol-5-ylamino}-4-ethyl-pyridine-2-carbonitrile (Int.24)

-continued

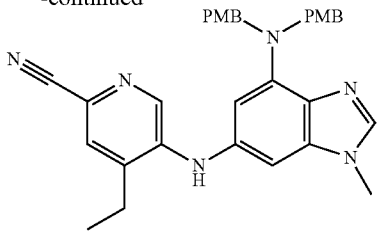

A mixture of Int.2 (0.75 mmol), Int.10 (0.79 mmol), Cs₂CO₃ (1.5 mmol) and XPhos (0.225 mmol) in dry toluene (6.3 mL) was purged with argon before Pd(OAc)₂ (0.075 mmol) was added. The mixture was stirred at 110° C. for approximately 16 h. The mixture was diluted with H₂O and extracted with DCM. The organic layer was washed (brine), dried (Na₂SO₄) and concentrated. The residue was purified by flash column chromatography (SiO₂, 100:0 to 50:50 cyclohexane/EtOAc) to yield the desired product.

1.16.3. Method E2

A mixture of Int.2 (1 eq), the corresponding aniline (1.1 eq), Cs₂CO₃ (4 to 5 eq) and XPhos (0.4 eq) in dry toluene is purged with an inert gas before Pd(OAc)₂ (0.2 to 0.3 eq) is added. The mixture is stirred at 110° C. for a period ranging from 1 h to 24 h. The mixture may be partitioned between an organic solvent and an aqueous phase. The two layers are separated and the organic layer is dried and concentrated. Alternatively the reaction mixture can be filtered and concentrated. The residue may be kept as such or purified by chromatography to yield the desired product.

1.16.4. Illustrative example of method E2: synthesis of 5-{7-[Bis-(4-methoxy-benzyl)-amino]-3-methyl-3H-benzoimidazol-5-ylamino}-4-methyl-pyridine-2-carbonitrile (Int.27)

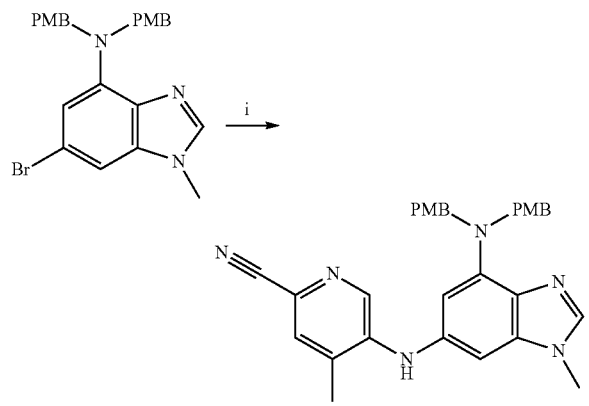

A mixture of Int.2 (4 mmol), Int.8 (4.3 mmol), Cs₂CO₃ (20 mmol) and XPhos (1.6 mmol) in dry toluene (35 mL) was purged with argon for 10 min before Pd(OAc)₂ (1.2 mmol) was added. The mixture was stirred at 110° C. for approximately 16 h. The mixture was filtered through a celite pad and concentrated. The residue was purified by flash column chromatography (SiO₂, 98:2 to 25:75 cyclohexane/EtOAc) to yield the desired product.

1.16.5. Method E3

A mixture of Int.2 (1 eq), the aniline (1.1 eq), BINAP (0.3 eq), Cs₂CO₃ (4 eq) and Pd(OAc)₂ (0.2 eq) in dry 1,4-dioxane is degassed with an inert gas. The reaction is stirred for a period ranging from 4 h to approximately 16 h at 100-110° C. The mixture may be partitioned between an organic solvent and an aqueous phase. The two layers are separated and the organic layer is dried and concentrated. Alternatively the reaction mixture can be filtered and concentrated. The residue may be kept as such or purified by chromatography to yield the desired product.

1.16.6. Illustrative example of method E3: synthesis of N6-(2-Fluoro-4-methanesulfonyl-phenyl)-N4,N4-bis-(4-methoxy-benzyl)-1-methyl-1H-benzoimidazole-4,6-diamine (Int.34)

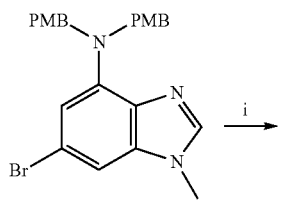

A mixture of Int.2 (1.48 mmol), 2-fluoro-4-methylsulfonyl-aniline (1.58 mmol), BINAP (0.47 mmol), Cs₂CO₃ (6.32 mmol) and Pd(OAc)₂ (0.32 mmol) in dry 1,4-dioxane (15 mL) was degassed with nitrogen. The reaction was stirred at 100° C. for approximately 16 h. The mixture was diluted with EtOAc and the organic layer was washed (H₂O), dried (Na₂SO₄) and concentrated to yield the desired product.

1.16.7. Method E4

A mixture of Int.2 (1 eq), the aniline (1.1 eq), Brettphos (0.1 eq), Cs₂CO₃ (5 eq) and Pd(OAc)₂ (0.05 eq) in dry 1,4-dioxane is degassed with an inert gas. The reaction is stirred for a period ranging from 2 h to approximately 8 h at 85-95° C. The mixture may be partitioned between an organic solvent and an aqueous phase. The two layers are separated and the organic layer is dried and concentrated. Alternatively the reaction mixture can be filtered and concentrated. The residue may be kept as such or purified by chromatography to yield the desired product.

1.16.8. Illustrative example of method E4: synthesis of N6-(2,3-dihydro-1,4-benzodioxin-6-yl)-N4,N4-bis[(4-methoxyphenyl)methyl]-1-methyl-benzimidazole-4,6-diamine (Int.78)

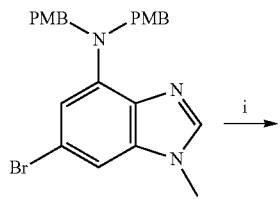

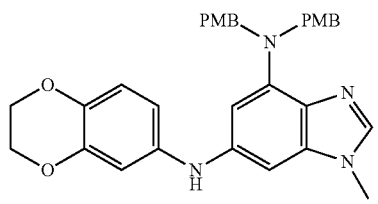

A mixture of Int.2 (1.17 mmol), 2,3-dihydro-1,4-benzodioxin-6-amine (1.29 mmol), Brettphos (0.117 mmol), Cs₂CO₃ (6.32 mmol) and Pd(OAc)₂ (0.058 mmol) in dry 1,4-dioxane (15 mL) was degassed with nitrogen. The reaction was stirred at 90° C. for approximately 5 h. The mixture was diluted with EtOAc and the organic layer was washed (H₂O), dried (Na₂SO₄) and concentrated to yield the desired product.

1.17. General Method: Methylation of Buchwald Product

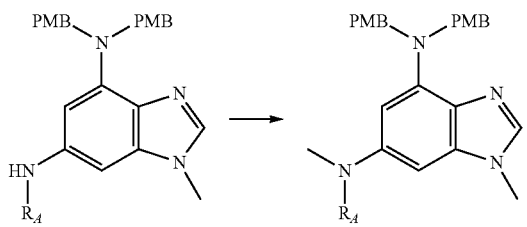

Where R$_A$ can be optionally substituted aryl or heteroaryl.

1.17.1. Method F

NaH (60% in mineral oil, 1.1 to 3 eq) is added to a solution of the intermediate obtained from the Buchwald coupling (1 eq) in THF or DMF at 0° C. The mixture is stirred at 0° C. for 30 min. MeI (1.1 to 3 eq) is added and the mixture is stirred at room temperature for a period ranging from 1 h to approximately 16 h. The mixture is partitioned between an organic solvent and an aqueous phase. The two layers are separated and the organic layer is dried and concentrated. The residue is purified by silica chromatography or used as such without further purification.

1.17.2. Illustrative example of method F: synthesis of N6-(2-Fluoro-4-methanesulfonyl-6-methyl-phenyl)-N4,N4-bis-(4-methoxy-benzyl)-1,N6-dimethyl-1H-benzoimidazole-4,6-diamine (Int.37)

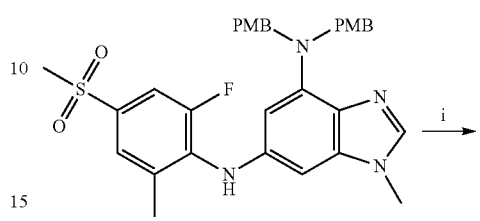

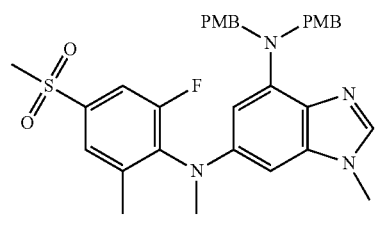

NaH (60% in mineral oil, 6.76 mmol) was added to a solution of Int.35 (2.25 mmol) in THF (10 mL) at 0° C. The mixture was stirred at 0° C. for 30 min. MeI (6.76 mmol) was added and the mixture was stirred at room temperature for approximately 16 h. The mixture was diluted with EtOAc and washed with H₂O. The organic layer was dried (Na₂SO₄) and concentrated. The residue was purified by flash column chromatography (SiO₂, 20:80 to 80:20 EtOAc/petroleum ether) to yield the desired product.

1.17.3. Illustrative example of method F: synthesis of N4,N4-bis[(4-methoxyphenyl)methyl]-N6,1-dimethyl-N6-(2-methyl-4-methylsulfonyl-phenyl)benzimidazole-4,6-diamine (Int.49A) and N6-(4-ethylsulfonyl-2-methyl-phenyl)-N4,N4-bis[(4-methoxyphenyl)methyl]-N6,1-dimethyl-benzimidazole-4,6-diamine (Int.49B)

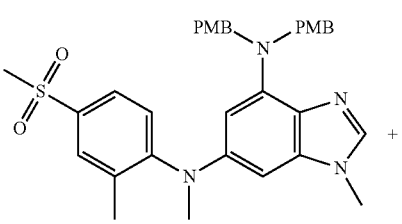

-continued

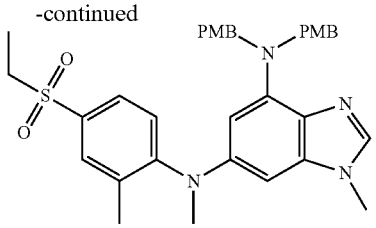

NaH (60% in mineral oil, 4.86 mmol) was added to a solution of Int.36 (1.62 mmol) in THF (10 mL) at 0° C. The mixture was stirred at 0° C. for 30 min. MeI (4.86 mmol) was added and the mixture was stirred at room temperature for 1 h. The mixture was diluted with EtOAc and washed with H₂O. The organic layer was dried (Na₂SO₄) and concentrated. Flash column chromatography (SiO₂, 20:80 to 80:20 EtOAc/petroleum ether) gelded a mixture of the desired product (Int.49A, major product) together with the a side product (Int.49B, minor product).

1.18. Synthesis of 4-{7-[Bis-(4-methoxy-benzyl)-amino]-3-methyl-3H-benzoimidazol-5-yloxy}-3-ethylbenzonitrile (Int.50)

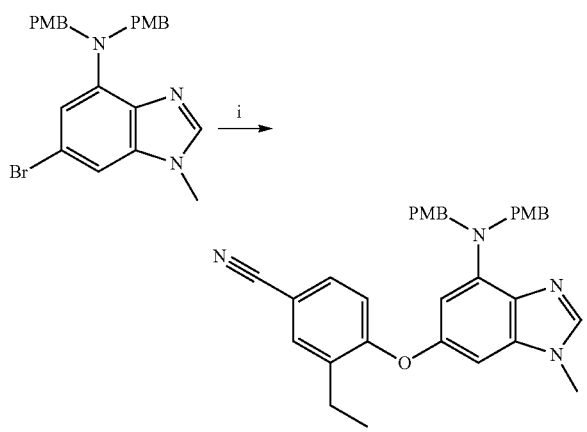

A mixture of Int.2 (0.4 mmol), Int.22 (0.4 mmol), CuI (0.06 mmol) and Cs₂CO₃ (1 mmol) in pyridine (2 mL) was flushed with argon, sealed and heated in a microwave reactor for 3 h at 200° C. The mixture was diluted with H₂O and extracted with EtOAc. The organic layer was dried and concentrated to yield the desired product.

1.19. General method: Ullmann coupling between 5-{7-[bis-(4-methoxy-benzyl)-amino]-3-methyl-3H-benzoimidazol-5-yloxy}-4-methyl-pyridine-2-carbonitrile (Int.3) and aromatic or heteroaromatic halides

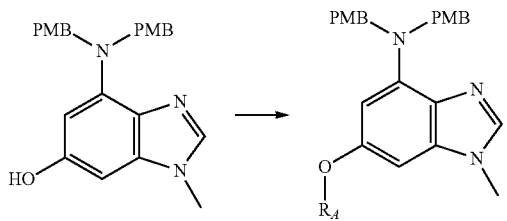

Where R_A can be optionally substituted aryl or heteroaryl.

1.19.1. Method G

A mixture of Int.3 (1 eq), the aryl halide (1.2 to 1.3 eq), CuI (0.1 to 0.2 eq), N,N-dimethyl glycine (0.3 to 0.5 eq) and Cs₂CO₃ (3 eq) in 1:1 DMF/1,4-dioxane is flushed with an inert gas and stirred at 110° C. for a period ranging from 4.5 h to 16 h. The mixture is filtered, partitioned between an organic solvent and an aqueous phase. The two layers are separated and the organic layer is dried and concentrated. The residue is purified by silica chromatography.

1.19.2. Illustrative example of method G: synthesis of 5-{7-[bis-(4-methoxy-benzyl)-amino]-3-methyl-3H-benzoimidazol-5-yloxy}-4-methyl-pyridine-2-carbonitrile (Int.51)

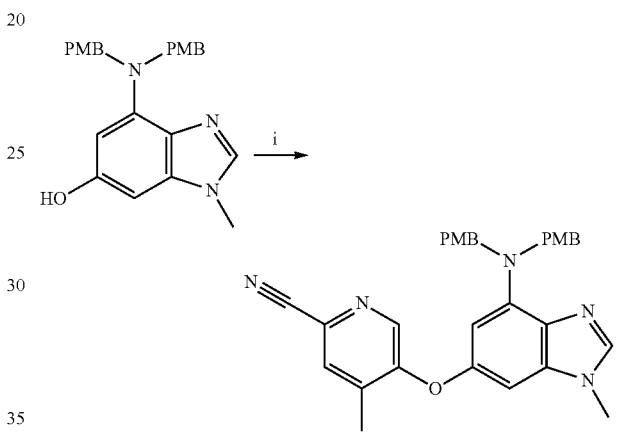

A mixture of Int.3 (0.39 mmol), Int.18 (0.47 mmol), CuI (0.08 mmol), N,N-dimethyl glycine (0.2 mmol) and Cs₂CO₃ (1.17 mmol) in 1:1 DMF/1,4-dioxane (4 mL) was flushed with argon and stirred at 110° C. for approximately 16 h in a sealed tube. The reaction mixture was cooled to room temperature and filtered through a Celite pad. The filtrate was concentrated. Water was added and the mixture was extracted with EtOAc. The organic layer was washed with water, dried and concentrated. The residue was purified by flash column chromatography (SiO₂, 100:0 to 40:60 cyclohexane/EtOAc) to yield the desired product.

1.20. General method: SNAr coupling between 5-{7-[bis-(4-methoxy-benzyl)-amino]-3-methyl-3H-benzoimidazol-5-yloxy}-4-methyl-pyridine-2-carbonitrile (Int.3) and aromatic or heteroaromatic halides

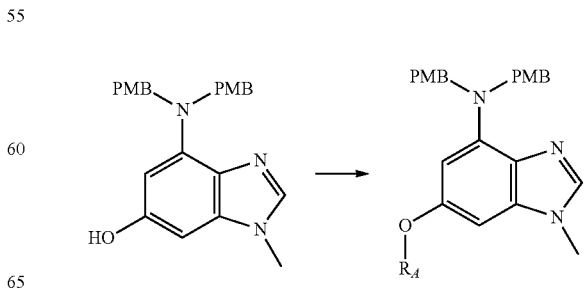

Where R_A can be optionally substituted aryl or heteroaryl.

1.20.1. Method H

A mixture of Int.3 (1 eq), the aryl/heteroaryl halide (1.2 to 1.5 eq) and $K_2CO_3$ (2 eq) in DMF is stirred at 100° C. for a period ranging from 3 h to approximately 16 h. The mixture is diluted with EtOAc, washed several times with $H_2O$, dried and concentrated. The residue is purified by flash column chromatography.

1.20.2. Illustrative example of method H: synthesis of 5-{7-[bis-(4-methoxy-benzyl)-amino]-3-methyl-3H-benzoimidazol-5-yloxy}-4-methyl-pyridine-2-carbonitrile (Int.51)

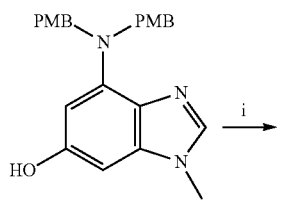

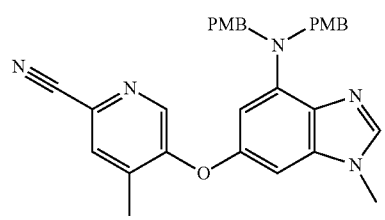

A mixture of Int.3 (58 mmol), Int.7 (70 mmol) and $K_2CO_3$ (116 mmol) in DMF (160 mL) was stirred at 100° C. After 3 h a further 7.35 mmol of Int.7 were added to the reaction and the mixture was stirred for an additional 1 h at 100° C. The resulting mixture was diluted with EtOAc, washed several times with $H_2O$, dried ($Na_2SO_4$) and concentrated. The residue was purified by flash column chromatography ($SiO_2$, 15:85 to 35:75 EtOAc/petroleum ether) to yield the desired product.

1.21. General Method: Bis-PMB Deprotection

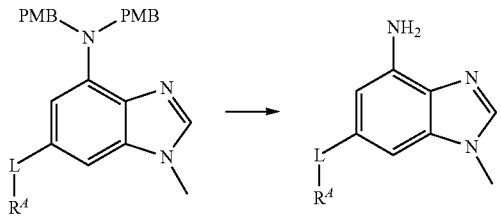

Where $R_A$ can be optionally substituted aryl or heteroaryl; and -L- can be: —NH—, —NMe- or —O—.

1.21.1. Method I1

A mixture of protected bis-PMB amine (1 eq) in TFA is stirred at room temperature for a period ranging from 30 min to approximately 16 h. The temperature is increased to 50 or 60° C. and the mixture is further stirred for a period ranging from 0.5 to 3 h. The mixture undergoes work up using a basic aqueous solution and an organic solvent. The two phases are separated and the organic layer is dried and concentrated. Alternatively, the reaction mixture can be first concentrated and then the residue undergoes the above described work up. The residue obtained from the work up can be purified by silica chromatography or by ISOLUTE® SCX-3 (Biotage) ion exchange resin or kept as such.

1.21.2. Illustrative example of method I1: synthesis of N6-(2-Fluoro-4-methanesulfonyl-6-methyl-phenyl)-1,N6-dimethyl-1H-benzoimidazole-4,6-diamine (Int.53)

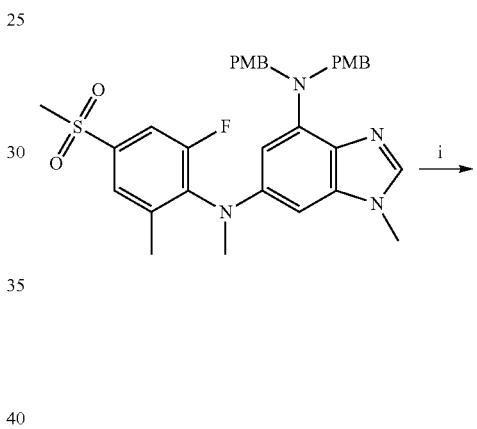

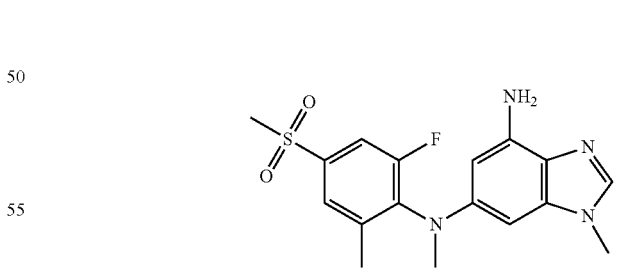

A mixture of Int.37 (0.33 mmol) in TFA (5 mL) was stirred at room temperature for 1 h and at 50° C. for 0.5 h. the mixture was concentrated. The residue was partitioned between sat. $NaHCO_3$ and DCM. The two phases were separated and the organic layer was dried ($Na_2SO_4$) and concentrated. The residue was purified by flash column chromatography ($SiO_2$, 20:80 to 100:0 EtOAc/petroleum ether) to yield the desired product.

1.21.3. Illustrative example of method I1: synthesis of N6,1-dimethyl-N6-(2-methyl-4-methylsulfonyl-phenyl)benzimidazole-4,6-diamine (Int.56A) and N6-(4-ethylsulfonyl-2-methyl-phenyl)-N6,1-dimethyl-benzimidazole-4,6-diamine (Int.56B)

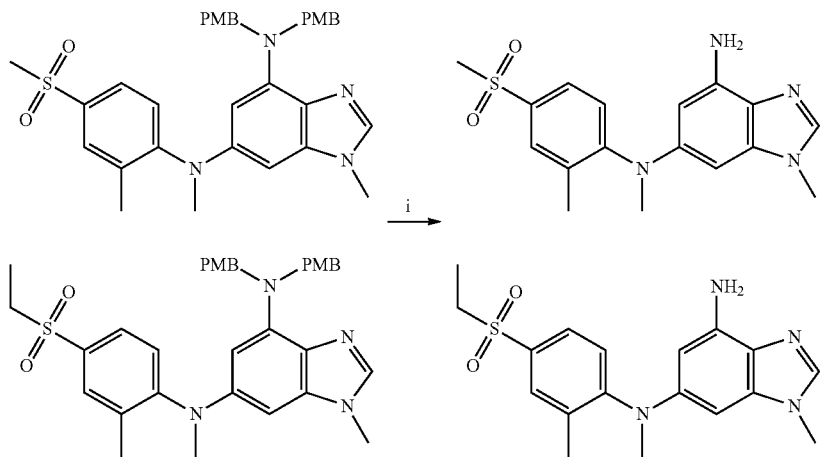

A mixture of Int.49A and 49B (ca 0.61 mmol in total) in TFA (5 mL) was stirred at room temperature for approximately 16 h and at 50° C. for 3 h. the mixture was concentrated. The residue was partitioned between sat. NaHCO$_3$ and DCM. The two phases were separated and the organic layer was dried (Na$_2$SO$_4$) and concentrated. Flash column chromatography (SiO$_2$, 20:80 to 100:0 EtOAc/petroleum ether) yielded a mixture of the desired product (Int.56A, major product) together with the a side product (Int.56B, minor product) deriving from the deprotection of Int.49B.

1.21.4. Method I2

A mixture of protected bis-PMB amine (1 eq) in DCM/TFA (3:1 to 1:1 ratio) is stirred at room temperature for a period ranging from 20 min to 3 h. The mixture undergoes work up using a basic aqueous solution and an organic solvent. The two phases are separated and the organic layer is dried and concentrated. Alternatively, the reaction mixture can be first concentrated and then the residue undergoes the above described work up. The residue obtained from the work up can be purified by silica chromatography or by ISOLUTE® SCX-3 (Biotage) ion exchange resin or kept as such.

1.21.5. Illustrative example of method I2: synthesis of 5-(7-amino-3-methyl-benzimidazol-5-yl)oxy-4-methyl-pyridine-2-carbonitrile (Cpd 28)

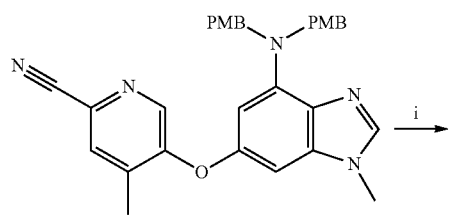

-continued

TFA (55 mL) was added to a solution of Int.51 (23.1 mmol) in DCM (55 mL) at 0° C. The mixture was stirred at room temperature for 20 min. Toluene was added and the mixture was concentrated. The residue was partitioned between DCM and sat. NaHCO$_3$. The two phases were separated and the organic layer was dried (Na$_2$SO$_4$) and concentrated. The residue was purified by flash column chromatography (SiO$_2$, 100:0 to 95:5 EtOAc/MeOH). The product obtained from the column was washed with THF to yield the desired product (Int 79).

1.21.6. Method I3

A mixture of protected bis-PMB amine (1 eq) in TFA is stirred at room temperature for a period ranging from 30 min to approximately 16 h. The mixture is diluted in an organic solvent and washed using a basic aqueous solution. The two phases are separated and the organic layer is dried and concentrated. Alternatively, before washing, the reaction mixture can be first concentrated. The organic layer is then concentrated, and the residue can be either purified by silica chromatography or by ISOLUTE® SCX-3 (Biotage) ion exchange resin or used as such. without any further purification

1.21.7. Illustrative example of method I3: synthesis of 5-[(7-amino-3-methyl-3H-benzoimidazol-5-yl)-methyl-amino]-4-methyl-pyridine-2-carbonitrile (Int.62)

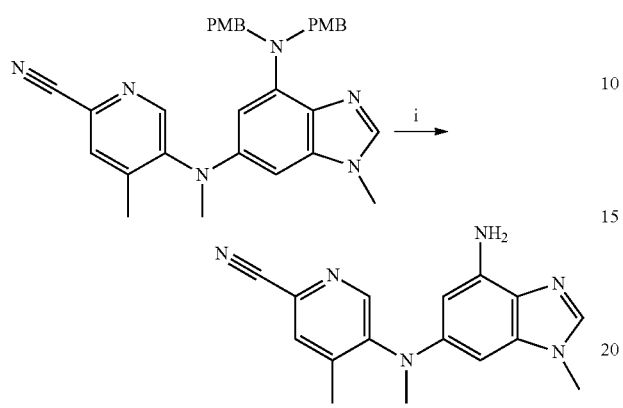

A solution of Int.41 (2.4 mmol) in TFA (10 mL) was stirred at room temperature for 3 h. The mixture was diluted (DCM), washed with sat. NaHCO₃ and then with 5 N NaOH. The two layers were separated and the aqueous layer was further extracted with DCM. The organic layers were combined, dried (filtration through phase separator) and concentrated. The residue was purified by flash column chromatography (SiO₂, 100:0 to 90:10 EtOAc/MeOH) to yield the desired product.

1.22. Synthesis of 4-Ethyl-6-methanesulfonyl-pyridin-3-ylamine (Int.70)

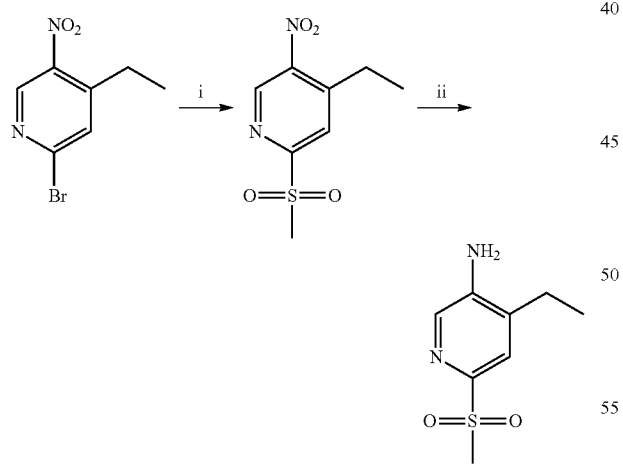

1.22.1. Step i: 4-ethyl-2-methylsulfonyl-5-nitro-pyridine

A mixture of 2-bromo-4-ethyl-5-nitro-pyridine (4.35 mmol) and sodium methanesulfinate (4.35 mmol) in DMSO (10 mL) was stirred at room temperature for 1.5 h. The mixture was poured into ice-water and stirred until the ice had melted. The mixture was filtered and the solid (the desired product) was collected.

1.22.2. Step ii: 4-ethyl-6-methylsulfonyl-pyridin-3-amine

A mixture of 4-ethyl-2-methylsulfonyl-5-nitro-pyridine (4.1 mmol), NH₄Cl (26.65 mmol) and iron powder (33 mmol) in H₂O (10 mL) was stirred at 90° C. for 1 h. The reaction was stopped, filtered and extracted with EtOAc. The organic layer was dried (Na₂SO₄) and concentrated to yield the desired product.

1.23. Synthesis of 4-ethyl-5-iodo-2-methylsulfonyl-pyridine (Int.74)

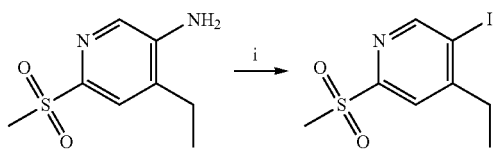

A solution of KI (15 mmol) and NaNO₂ (12 mmol) in H₂O (1.8 mL) was added dropwise to a mixture of Int.70 (6 mmol) and p-TsOH.H₂O (18 mmol) in MeCN (12 mL) keeping the temperature at 10 to 15° C. The mixture was stirred for 10 min at 10 to 15° C. and then at room temperature for 1 h. The mixture was cooled to 0° C., neutralized (sat. NaHCO₃) and extracted (DCM). The organic layer was dried (Na₂SO₄) and concentrated. The residue was purified by flash column chromatography (SiO₂, 70:30 petroleum ether/EtOAc) to yield the desired product.

Example 2

Synthesis of the Compounds of the Invention

2.1. General Method: Acylation of the Amine Intermediate with a Carbonyl Chloride Derivative to Obtain a Final Compound

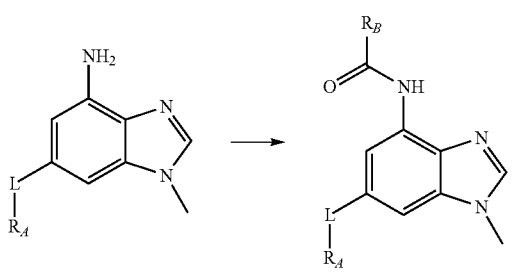

Where $R_A$ can be optionally substituted aryl or heteroaryl; L can be NH, NMe or O; and $R_B$ can be cycloalkyl, OMe.

2.1.1. Method J1

$R_B$COCl (1 eq) is added to a solution of the intermediate amine (1 eq) in DCM/pyridine (from 2:1 to 5:1 ratio) at 0° C. The mixture is stirred for a period ranging from 40 min to 2 h. The mixture is partitioned between an organic solvent and an aqueous solution. The two phases are separated and the organic layer is dried and concentrated. Alternatively, the reaction mixture can be concentrated without undergoing work up. The residue can be purified by silica chromatography or by preparative HPLC or by precipitation using the appropriate solvent mixture.

2.1.2. Illustrative example of method J1: synthesis of N-(6-((6-cyano-4-ethylpyridin-3-yl)(methyl)amino)-1-methyl-1H-benzo[d]imidazol-4-yl)cyclopropanecarboxamide (Cpd 1)

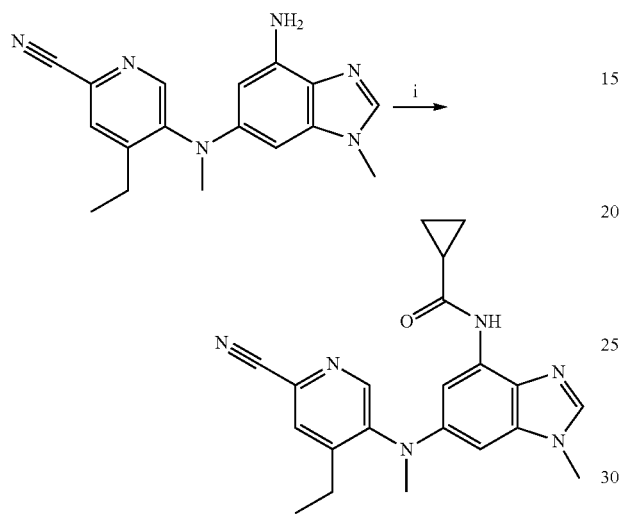

Cyclopropanecarbonyl chloride (0.39 mmol) was added to a solution of Int.63 (0.39 mmol) in 1:2 pyridine/DCM (2.55 mL) at 0° C. The mixture was stirred at room temperature for 40 min. The reaction mixture was concentrated and the residue was purified by flash column chromatography (SiO2, 100:0 to 97:3 DCM/MeOH) to afford the desired product.

2.1.3. Method J2

$R_B C(=O)Cl$ (1.5 to 3 eq) is added to a solution of the intermediate amine (1 eq) in DCM followed by pyridine (1.5 to 3 eq). The mixture is stirred for a period ranging from 2 h to approximately 16 h. The mixture is partitioned between an organic solvent and an aqueous solution. The two phases are separated and the organic layer is dried and concentrated. The residue can be purified by silica chromatography, by preparative HPLC or by precipitation using the appropriate solvent mixture.

2.1.4. Illustrative example of method J2: synthesis of methyl 6-((6-cyano-4-ethylpyridin-3-yl)(methyl)amino)-1-methyl-1H-benzo[d]imidazol-4-ylcarbamate (Cpd 4)

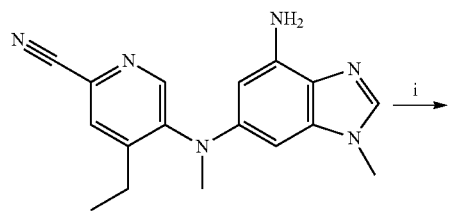

-continued

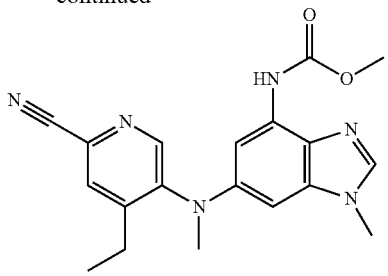

Methyl chloroformate (0.33 mmol) was added to a solution of Int.63 (0.22 mmol) in dry DCM (2.2 mL) followed by pyridine (0.33 mmol). The mixture was stirred at room temperature for 2 h. The mixture was partitioned between H2O and DCM. The two phases were separated and the organic layer was washed (sat. NaHCO3), dried (Na2SO4) and concentrated. The residue was purified by flash column chromatography (SiO2, 100:0 to 95:5 DCM/MeOH) to yield the desired product.

2.2. General Method: Acylation the Amine Intermediate with a Carboxylic Acid Derivative to Obtain a Final Compound

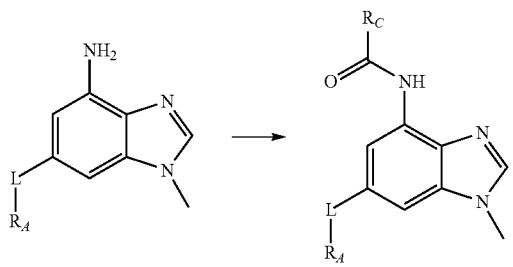

Where $R_A$ can be optionally substituted aryl or heteroaryl; L can be: NH, NMe or O; and $R_C$ can be: cycloalkyl, substituted cycloalkyl.

2.2.1. Method K1

(COCl)2 (1.4 to 2 eq) is added to a solution of the carboxylic acid (1.5 to 2 eq) in DCM at 0° C. A catalytic amount of DMF is added and the reaction is stirred at 0° C. for a period ranging from 30 min to 1 h. A solution of the intermediate amine (1 eq) and pyridine (2 to 4 eq) in DCM is added to the mixture. The resulting mixture is stirred at room temperature for a period ranging from 30 min to 2 h. The mixture is partitioned between an organic solvent and an aqueous solution. The two phases are separated and the organic layer is dried and concentrated. The residue can be purified by silica chromatography, by preparative HPLC or by precipitation using the appropriate solvent mixture.

2.2.2. Illustrative example of method K1: synthesis of (1R,2R)—N-[6-[(6-cyano-4-ethyl-3-pyridyl)oxy]-1-methyl-benzimidazol-4-yl]-2-fluoro-cyclopropanecarboxamide (Cpd 6)

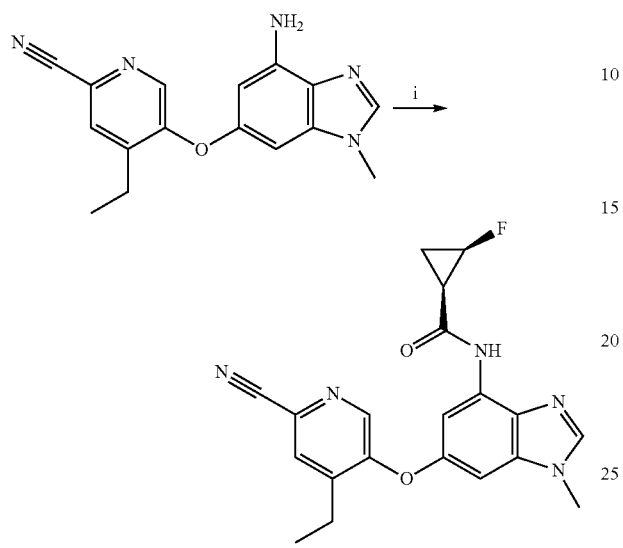

(COCl)₂ (0.186 mmol) was added to a solution of ((1R, 2R)-(−)-cis-2-fluoro-cyclopropanecarboxylic acid (ChemCollect, lot n. 1241399, 0.186 mmol) in DCM (1 mL) followed by DMF (2 drops). The reaction mixture was left to stir at 0° C. for 1 h. A solution of Int.65 (0.093 mmol) and pyridine (0.186 mmol) in DCM (1 mL) was added to the mixture and the reaction was stirred for 2 h at room temperature. Sat. NaHCO₃ was added and the two phases were separated. The organic layer was concentrated. The residue was purified by flash column chromatography (SiO₂, 100:0 to 95:5 DCM/MeOH) to yield the desired product.

2.2.3. Illustrative example of method K1: synthesis of (1R,2R)—N-[6-(N,2-dimethyl-4-methylsulfonyl-anilino)-1-methyl-benzimidazol-4-yl]-2-fluoro-cyclopropanecarboxamide (Cpd 26) and (1R,2R)—N-[6-(4-ethylsulfonyl-N,2-dimethyl-anilino)-1-methyl-benzimidazol-4-yl]-2-fluoro-cyclopropanecarboxamide (Cpd 27)

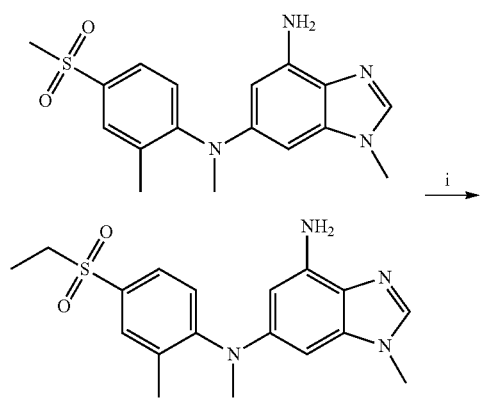

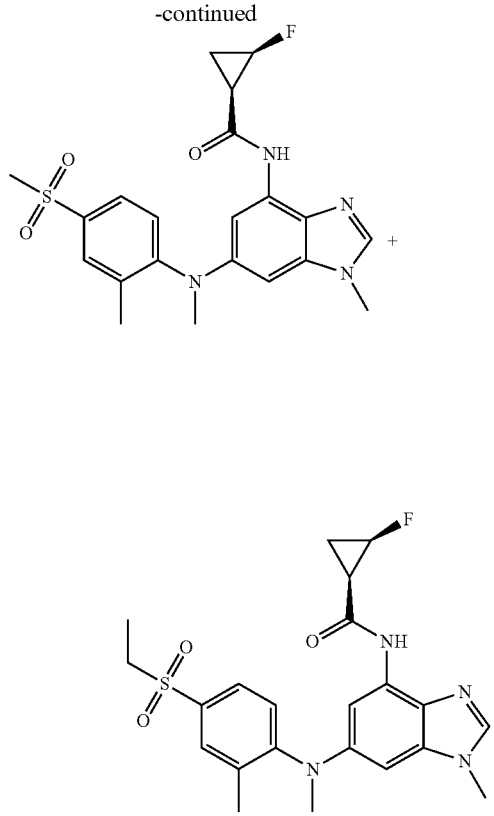

(COCl)₂ (0.82 mmol) was added to a solution of ((1R, 2R)-(−)-cis-2-fluoro-cyclopropanecarboxylic acid (ABCR, lot n. 1242863, 0.92 mmol) in DCM (1 mL) followed by DMF (1 drop). The reaction mixture was left to stir at 0° C. for 45 min. A solution of a mixture of Int.56A and Int.56B (approximately 0.46 mmol in total) and pyridine (1.85 mmol) in DCM (1 mL) was added to the mixture and the reaction was stirred for 2 h at room temperature. The mixture was diluted with DCM, washed (H₂O) and the two phases were separated. The organic layer was dried (Na₂SO₄) and concentrated. Flash column chromatography (SiO₂, 20:80 EtOAc/petroleum ether to 90:10 EtOAc/MeOH) gelded a mixture of Compound 26 and Compound 27. The two components were separated by prep. HPLC.

2.2.4. Method K2

(COCl)₂ (1.35 to 2.5 eq) is added to a solution of the carboxylic acid (1.4 to 3 eq) in DCM at 0° C. A catalytic amount of DMF is added and the reaction is stirred at 0° C. for a period ranging from 30 min to 1 h. A solution of the intermediate amine (1 eq) and pyridine (1.7 to 4 eq) in NMP or NMP/DCM is prepared separately making sure that the intermediate amine is fully dissolved. To help dissolution, heating can be applied (temperatures up to 70° C.). The latter solution is added dropwise to the solution containing the newly formed acyl chloride at 0° C. The resulting mixture is left to stir at room temperature for a period ranging from 1 to 2 h. The mixture is partitioned between an organic solvent and an aqueous solution. The two phases are separated and the organic layer is dried and concentrated. The residue can be purified by silica chromatography, by preparative HPLC or by precipitation using the appropriate solvent mixture.

2.2.5. Illustrative example of method K2: synthesis of (1R,2R)—N-[6-[(6-cyano-4-methyl-3-pyridyl)oxy]-1-methyl-benzimidazol-4-yl]-2-fluoro-cyclopropanecarboxamide (Cpd 20)

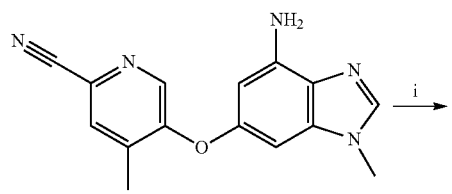

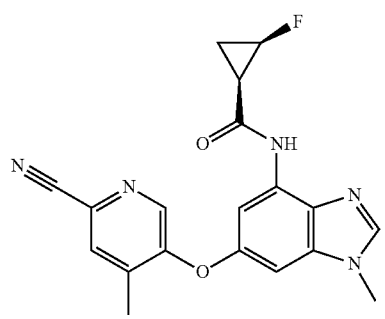

(CoCl)$_2$ (16.6 mmol) was added to a solution of ((1R,2R)-(−)-cis-2-fluoro-cyclopropanecarboxylic acid (ABCR, lot n. 1242863, 17.5 mmol) in DCM (70 mL) followed by DMF (200 µL). The reaction mixture was left to stir at 0° C. for 45 min. A solution of Compound 28 (12.5 mmol) and pyridine (21.3 mmol) in NMP (15 mL) was heated at 65° C., to help dissolution, and let cool down to room temperature. The solution containing Compound 28 and pyridine was added to the mixture containing the activated carboxylic derivative at 0° C. and the reaction was stirred for 45 min at room temperature. The mixture was partitioned between EtOAc and sat. NaHCO$_3$. The two phases were separated and the organic layer was washed further (sat. NaHCO$_3$, NH$_4$Cl, H$_2$O), dried (Na$_2$SO$_4$) and concentrated. The crude was purified by precipitation from DCM/iPrOH and the resulting solid was washed with Et$_2$O and dried under vacuum to afford the desired product.

2.3. General Method: Hydrolysis of a Nitrile Group to Obtain a Final Compound

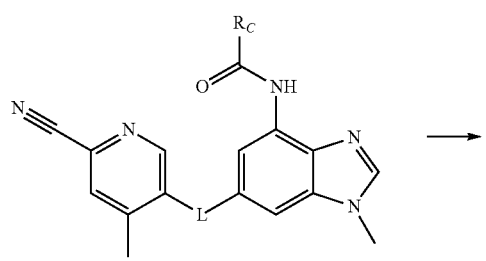

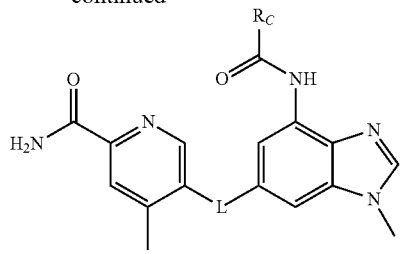

Where L is NH, NMe or O; R$_C$ is cycloalkyl, substituted cycloalkyl; Z is N or CH; and R$^{10}$ is Me or Et.

2.3.1. Method L

A solution of the nitrile starting material (1 eq) is dissolved in a 4:1 EtOH/DMSO mixture. The resulting organic solution is mixed with 30% H$_2$O$_2$/H$_2$O and 1 N NaOH with the following proportions 10:2:1 organic solution/H$_2$O$_2$/1N NaOH. The mixture is stirred at 50° C. for 1 h. The mixture is partitioned between an organic solvent and an aqueous solution. The two phases are separated and the organic layer is dried and concentrated. The residue can be purified by silica chromatography, by preparative HPLC or by precipitation using the appropriate solvent mixture.

2.3.2. Illustrative example of method L: synthesis of 5-((4-(cyclopropanecarboxamido)-1-methyl-1H-benzo[d]imidazol-6-yl)(methyl)amino)-4-ethylpicolinamide (Cpd 24)

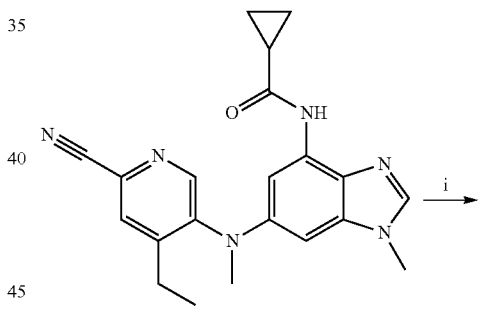

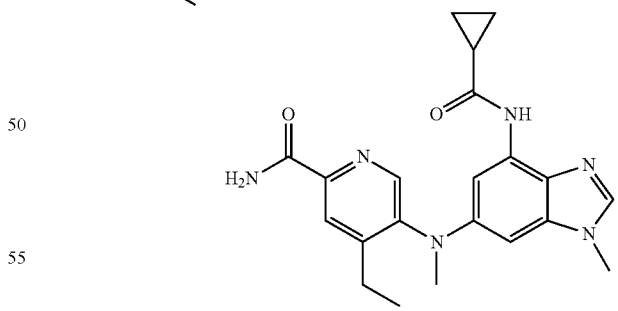

A solution of compound 1 (0.19 mmol) was dissolved in a 4:1 EtOH/DMSO mixture (2.3 mL). The resulting organic solution was mixed with 30% H$_2$O$_2$/H$_2$O (0.4 mL) and 1 N NaOH (0.23 mL). The mixture was stirred at 50° C. for 1 h. The reaction mixture was partitioned between dichloromethane and water. The layers were separated and the organic layer was filtered through a phase separator and concentrated. The residue was purified by preparative HPLC to yield the desired product.

2.3.3. Method M: General Method of Synthesis of Urea

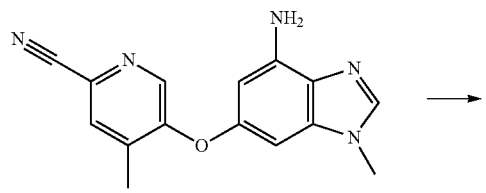

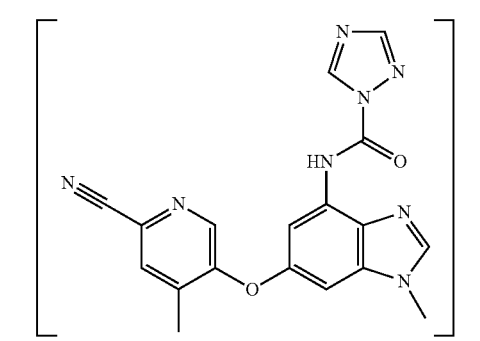

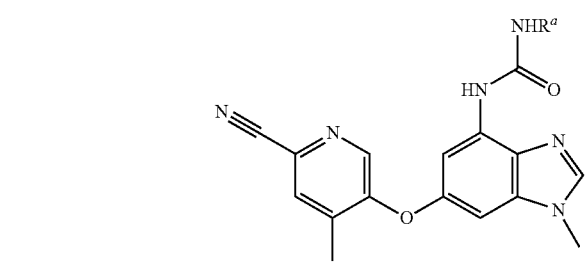

Carbonylditriazol (1.5 eq.) is added to a mixture of Cpd 28 (1.0 eq.) and pyridine (5 eq;) in DCM. The mixture is then stirred at 50° C. for 1 h. Without any further treatment the required amine $R^aNH_2$ is added to the solution at 50° C. and allowed to stir for another 1 h. After completion of the reaction by UPLC, the reaction mixture is cooled to room temperature and diluted with DCM, and ehe mixture is then partitioned in water. The two phases are separated and the organic layer is washed with 0.25 M HCl solution, sodium bicarbonate solution, dried and concentrated. The residue can be purified by silica chromatography, by preparative HPLC or by precipitation using the appropriate solvent mixture

2.3.4. Illustrative example of Method M: synthesis of 1-[6-[(6-cyano-4-methyl-3-pyridyl)oxy]-1-methyl-benzimidazol-4-yl]-3-isopropyl-urea (Cpd 33)

Carbonylditriazol (1.07 mmol) was added to a mixture of Cpd 28 (0.71 mmol) and pyridine (3.55 mmol) in DCM (3 mL) and the resulting mixture was stirred at 50° C. A precipitate formed after 2 min and the mixture was further stirred for 1 h. Methyl amine (2M solution in THF) (2.84 mmol) was then added to the solution at 50° C. and allowed to stir for another 1 h. After completion of the reaction by UPLC, the reaction mixture was cooled to room temperature and was diluted with DCM and partitioned in water. The two phases were separated and the organic layer was washed with 0.25 M HCl solution, sodium bicarbonate solution, dried and concentrated. The residue the used without any further purification.

2.4. Synthesis of 5-[7-[[(1R,2R)-2-fluorocyclopropanecarbonyl]amino]-3-methyl-benzimidazol-5-yl]oxy-4-methyl-pyridine-2-carboxamide (Cpd 32)

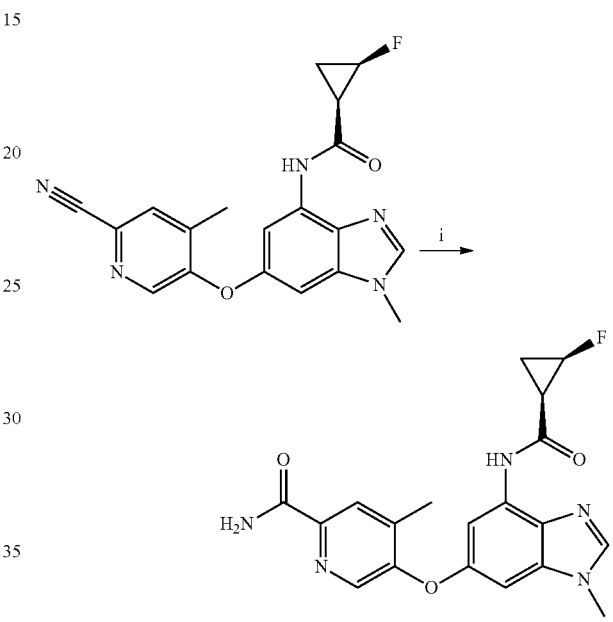

A mixture of Compound 20 (0.27 mmol) and DMSO (0.5 mL) in $H_2O$ (pH 13, 10 mL) was stirred at 50° C. for 72 h. The mixture was filtered. The solid was collected and purified by preparative HPLC to yield the desired product.

2.5. Synthesis of 4-methyl-5-[3-methyl-7-(methylamino)benzimidazol-5-yl]oxy-pyridine-2-carbonitrile (Cpd 34) and 5-[7-(dimethylamino)-3-methyl-benzimidazol-5-yl]oxy-4-methyl-pyridine-2-carbonitrile (Cpd 35)

NaH was added to a mixture of Cpd 28 (0.36 mmol) in THF (10 mL) at 0° C. After 30 min, MeI (0.36 mmol) was added and the reaction mixture was allowed to warm to room temperature and stirred until completion. After completion monitored by UPLC, the reaction was diluted in ethyl acetate and washed with water. The organic layer was dried over $Na_2SO_4$, filtered and evaporated. Cpd 34 and Cpd 35 were isolated by preparative HPLC.

Illustrative compounds of the invention listed in Table III below and comparative examples have been prepared according to the synthetic methods described herein using the intermediates listed in Table II. The NMR spectral data of the compounds of the invention and some of the comparative examples is given in Table IV.

TABLE II

Illustrative intermediates towards the compounds of the invention

| Int# | Structure | SM | Mtd | MW | MS Ms'd |
|---|---|---|---|---|---|
| 1 | PMB-NH-PMB | 4-Methoxy benzylamine | Dsc'd | 257.3 | 258.1 (M + 1) |
| 2 | PMB$_2$N-(6-bromo-1-methyl-benzimidazol-4-yl) | Int. 1 + 5-bromo-3-fluoro-N-methyl-2-nitro-aniline | Dsc'd - | 466.4 | 465.9/ 467.9 (M + 1) |
| 3 | PMB$_2$N-(6-hydroxy-1-methyl-benzimidazol-4-yl) | Int. 2 | Dsc'd - | 403.5 | 404.4 (M + 1) |
| 4 | 3-fluoro-4-amino-5-iodo-benzonitrile | 4-amino-3-fluoro-benzonitrile | A1 | 262.0 | 261.5 (M − 1) |
| 5 | 6-fluoro-5-amino-4-iodo-2-cyanopyridine | Int. 11 | A2 | 263.0 | 263.9 (M + 1) |
| 6 | 2-chloro-3-fluoro-4-amino-5-iodo-pyridine | Int. 23 | A1 | 272.4 | 272.8 (M + 1) |
| 7 | 2-cyano-5-fluoro-4-methyl-pyridine | 2-chloro-5-fluoro-4-methyl-pyridine | B | 136.1 | 137.1 (M + 1) |
| 8 | 2-cyano-4-methyl-5-amino-pyridine | Int. 20 | B | 133.2 | 134.1 (M + 1) |
| 9 | 2-cyano-3-fluoro-4-amino-5-methyl-pyridine | Int. 13 | B | 151.1 | 152.0 (M + 1) |

TABLE II-continued

Illustrative intermediates towards the compounds of the invention

| Int# | Structure | SM | Mtd | MW | MS Ms'd |
|---|---|---|---|---|---|
| 10 | 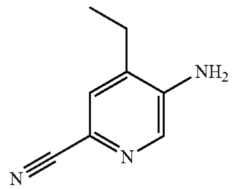 | 6-bromo-4-ethyl-pyridin-3-amine | B | 147.2 | 148.0 (M + 1) |
| 11 | 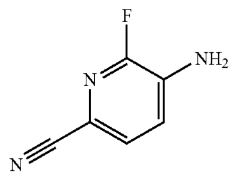 | Int. 15 | B | 137.1 | 138.0 (M + 1) |
| 12 | 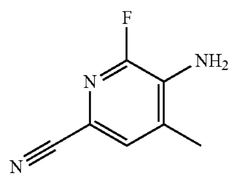 | Int. 5 | C | 151.1 | 152.0 (M + 1) |
| 13 | 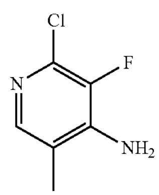 | Int. 6 | C | 160.6 | 161.0 (M + 1) |
| 14 | 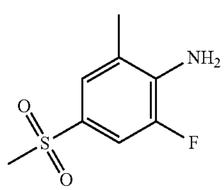 | Int. 16 | C | 203.2 | 204.0 (M + 1) |
| 15 | 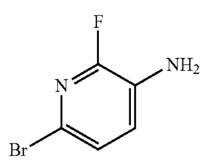 | 2-fluoropyridin-3-amine | Dsc'd | 191.0 | 190.9/ 192.9 (M + 1) |
| 16 | 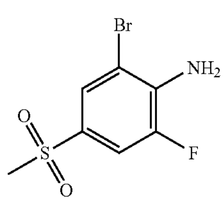 | 2-fluoro-4-methylsulfonyl-aniline | Dsc'd | 268.1 | 267.0/ 268.9 (M + 1) |
| 17 | 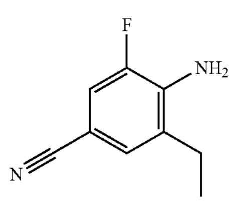 | Int. 4 | Dsc'd | 164.2 | 165.5 (M + 1) |

TABLE II-continued

*Illustrative intermediates towards the compounds of the invention*

| Int# | Structure | SM | Mtd | MW | MS Ms'd |
|---|---|---|---|---|---|
| 18 | (4-methyl-5-iodo-pyridine-2-carbonitrile) | Int. 8 | D | 244.0 | 245.0 (M + 1) |
| 19 | (4-ethyl-5-iodo-pyridine-2-carbonitrile) | Int. 10 | D | 258.1 | 259.1 (M + 1) |
| 20 | (2-bromo-4-methyl-5-amino-pyridine) | 2-bromo-4-methyl-5-nitro-pyridine | Dsc'd | 187.0 | 187.0/189.0 (M + 1) |
| 21 | (3-fluoro-4-amino-5-chloro-benzonitrile) | 4-amino-3-fluoro-benzonitrile | Dsc'd | 170.6 | Mass could not be detected by various methods |
| 22 | (4-hydroxy-3-ethyl-benzonitrile) | 4-amino-3-ethyl-benzonitrile | Dsc'd | 147.2 | 146.1 (M − 1) |
| 23 | (2-chloro-3-fluoro-4-amino-pyridine) | 2-chloro-3-fluoro-pyridine-4-carboxylic acid | Dsc'd | 146.6 | 147.0 (M + 1) |
| 24 | (PMB-protected intermediate) | Int. 2 + Int. 10 | E1 | 532.6 | 533.2 (M + 1) |
| 25 | (PMB-protected intermediate) | Int. 2 + Int. 17 | E1 | 549.6 | 550.4 (M + 1) |

TABLE II-continued

Illustrative intermediates towards the compounds of the invention

| Int# | Structure | SM | Mtd | MW | MS Ms'd |
|---|---|---|---|---|---|
| 26 | 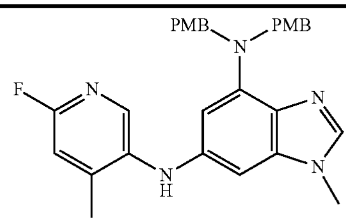 | Int. 2 + 6-fluoro-4-methyl-pyridin-3-amine | E1 | 511.6 | 512.5 (M + 1) |
| 27 | 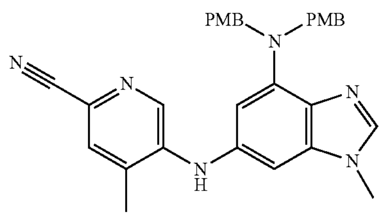 | Int. 2 + Int. 8 | E2 | 518.6 | 519.4 (M + 1) |
| 28 | 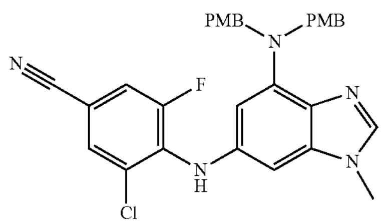 | Int. 2 + Int. 21 | E2 | 556.0 | 556.3 (M + 1) |
| 29 | 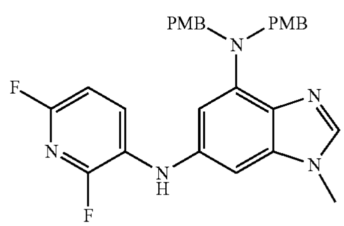 | Int. 2 + 2,6-difluoropyridin-3-amine | E2 | 515.6 | 516.4 (M + 1) |
| 30 | 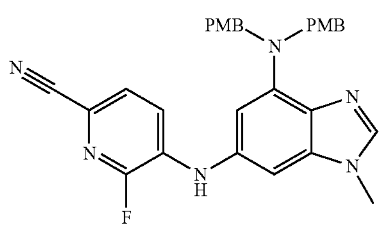 | Int. 2 + Int. 11 | E2 | 522.6 | 523.3 (M + 1) |
| 31 | 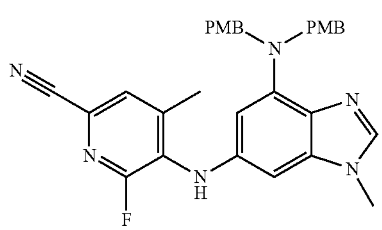 | Int. 2 + Int. 12 | E2 | 536.6 | 537.0 (M + 1) |
| 32 | 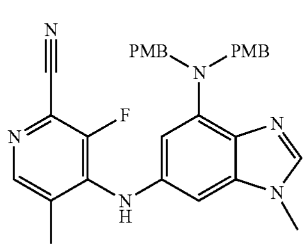 | Int. 2 + Int. 9 | E2 | 536.6 | 537.0 (M + 1) |

TABLE II-continued

Illustrative intermediates towards the compounds of the invention

| Int# | Structure | SM | Mtd | MW | MS Ms'd |
|---|---|---|---|---|---|
| 33 | 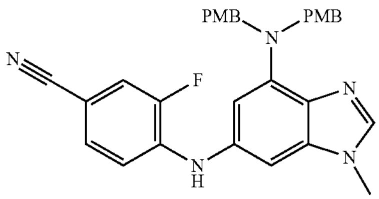 | Int. 2 + 4-amino-3-fluoro-benzonitrile | E2 | 521.6 | 522.4 (M + 1) |
| 34 | 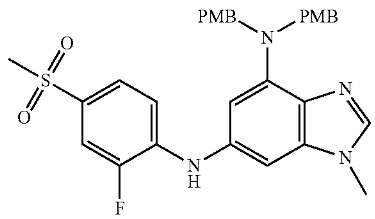 | Int. 2 + 2-fluoro-4-methylsulfonyl-aniline | E3 | 574.7 | 575.0 (M + 1) |
| 35 | 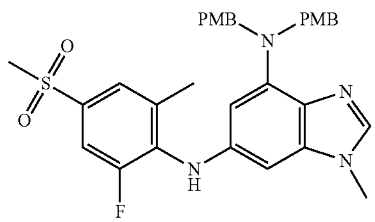 | Int. 2 + Int. 14 | E3 | 588.7 | 589.2 (M + 1) |
| 36 | 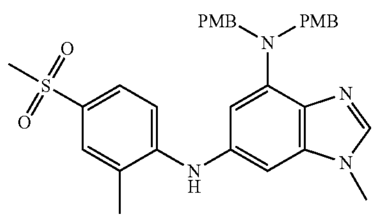 | Int.2 + 2-fluoro-4-methylsulfonyl-aniline | E3 | 570.7 | 571.4 (M + 1) |
| 37 | 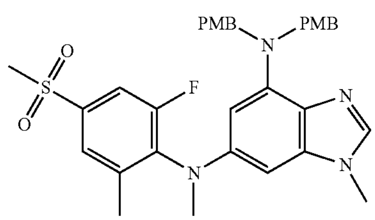 | Int. 35 | F | 602.7 | 603.3 (M + 1) |
| 38 | 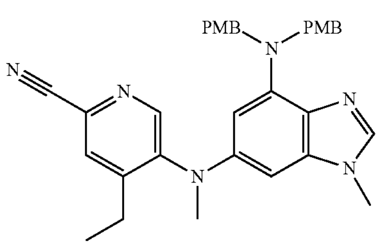 | Int. 24 | F | 546.7 | 547.2 (M + 1) |

TABLE II-continued

Illustrative intermediates towards the compounds of the invention

| Int# | Structure | SM | Mtd | MW | MS Ms'd |
|---|---|---|---|---|---|
| 39 | (structure) | Int. 25 | F | 563.7 | 564.3 (M + 1) |
| 40 | (structure) | Int. 26 | F | 525.6 | 526.4 (M + 1) |
| 41 | (structure) | Int. 27 | F | 532.6 | 533.5 (M + 1) |
| 42 | (structure) | Int. 28 | F | 570.1 | 570.4 (M + 1) |
| 43 | (structure) | Int. 29 | F | 529.6 | 530.5 (M + 1) |
| 44 | (structure) | Int. 30 | F | 536.6 | 536.5 (M + 1) |
| 45 | (structure) | Int. 31 | F | 550.6 | 551.0 (M + 1) |

TABLE II-continued

Illustrative intermediates towards the compounds of the invention

| Int# | Structure | SM | Mtd | MW | MS Ms'd |
|---|---|---|---|---|---|
| 46 | 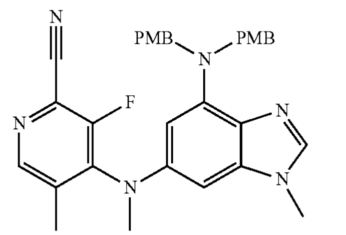 | Int. 32 | F | 550.6 | 551.0 (M + 1) |
| 47 | 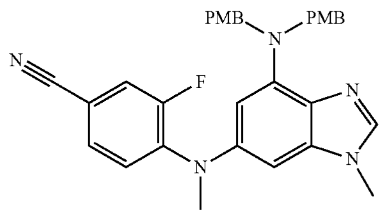 | Int. 33 | F | 535.6 | 522.4 (M + 1) |
| 48 | 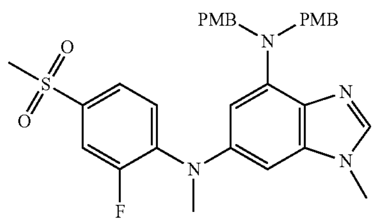 | Int. 34 | F | 588.7 | 589.5 (M + 1) |
| 49A | 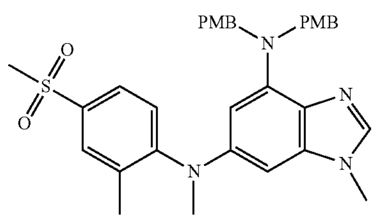 | Int. 36 | F | 584.7 | 585.1 (M + 1) |
| 49B | 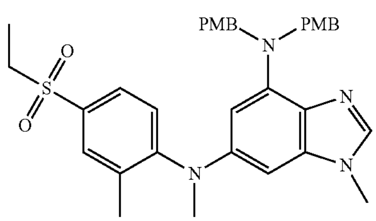 | Int. 36 | F (by product) | 598.8 | 599.1 (M + 1) |
| 50 | 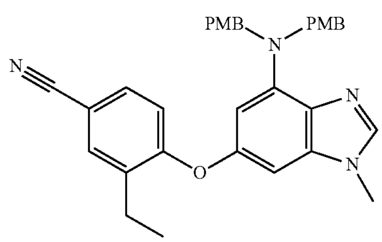 | Int. 2 + Int. 22 | Dsc'd | 532.6 | 533.4 (M + 1) |

TABLE II-continued

Illustrative intermediates towards the compounds of the invention

| Int# | Structure | SM | Mtd | MW | MS Ms'd |
|---|---|---|---|---|---|
| 51 | 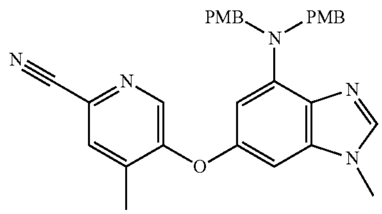 | Int. 3 + Int. 18 (method G), Int. 3 + Int. 7 (method H) | G or H | 519.6 | 520.4 (M + 1) |
| 52 | 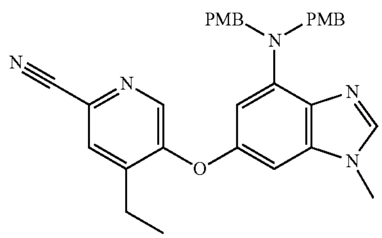 | Int. 3 + Int. 19 | G | 533.6 | 534.4 (M + 1) |
| 53 | 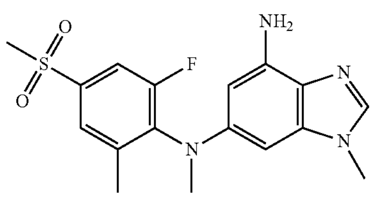 [SMILES: Cc1cc(S(C)(=O)=O)cc(F)c1N(C)c1cc(N)c2ncn(C)c2c1] | Int. 37 | I1 | 362.4 | 363.1 (M + 1) |
| 54 | 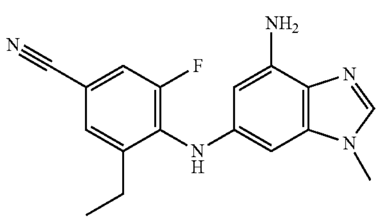 [SMILES: CCc1cc(C#N)cc(F)c1Nc1cc(N)c2ncn(C)c2c1] | Int. 25 | I1 | 309.3 | 310.3 (M + 1) |
| 55 | 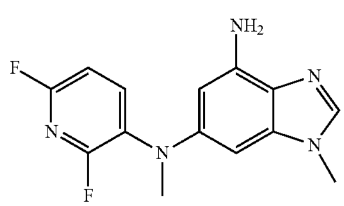 [SMILES: CN(c1cc(N)c2ncn(C)c2c1)c1ccc(F)nc1F] | Int. 43 | I1 | 289.3 | 290.0 (M + 1) |
| 56A | 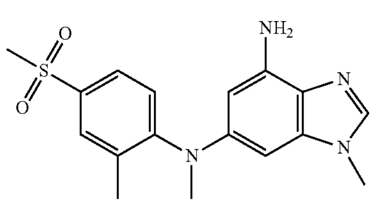 [SMILES: Cc1cc(S(C)(=O)=O)ccc1N(C)c1cc(N)c2ncn(C)c2c1] | Int. 49A | I1 | 344.4 | 344.9 (M + 1) |
| 56B | 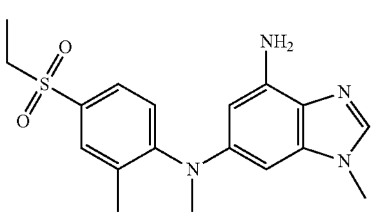 [SMILES: CCS(=O)(=O)c1ccc(N(C)c2cc(N)c3ncn(C)c3c2)c(C)c1] | Int. 49B | I1 | 358.5 | 359.0 (M + 1) |

TABLE II-continued

Illustrative intermediates towards the compounds of the invention

| Int# | Structure | SM | Mtd | MW | MS Ms'd |
|---|---|---|---|---|---|
| 57 | 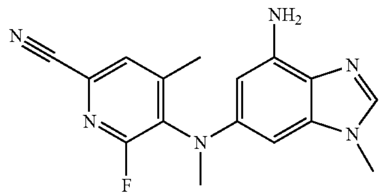 [SMILES: Cc1cc(C#N)nc(F)c1N(C)c1cc(N)c2ncn(C)c2c1] | Int. 45 | I1 | 310.3 | 311.0 (M + 1) |
| 58 | 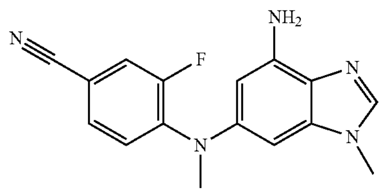 [SMILES: CN(c1cc(N)c2ncn(C)c2c1)c1ccc(C#N)cc1F] | Int. 47 | I1 | 295.3 | 296.0 (M + 1) |
| 59 | 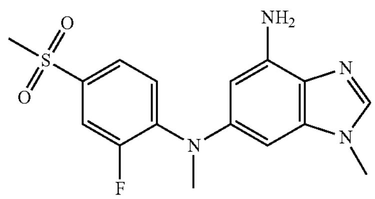 [SMILES: CN(c1cc(N)c2ncn(C)c2c1)c1ccc(S(C)(=O)=O)cc1F] | Int. 48 | I1 | 348.4 | 349.0 (M + 1) |
| 61 | 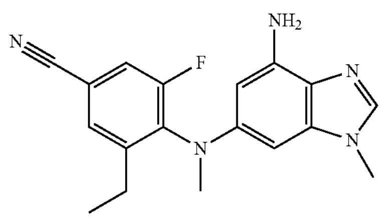 [SMILES: CCc1cc(C#N)cc(F)c1N(C)c1cc(N)c2ncn(C)c2c1] | Int. 39 | I2 | 323.4 | 324.3 (M + 1) |
| 62 | 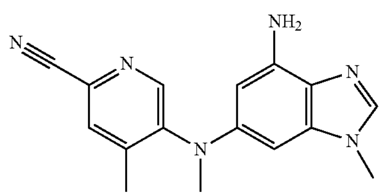 [SMILES: Cc1cc(C#N)ncc1N(C)c1cc(N)c2ncn(C)c2c1] | Int. 41 | I3 | 292.3 | 293.3 (M + 1) |
| 63 | 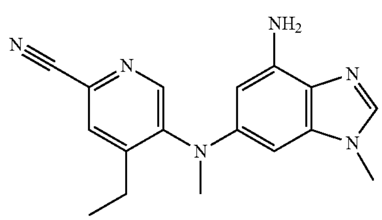 [SMILES: CCc1cc(C#N)ncc1N(C)c1cc(N)c2ncn(C)c2c1] | Int. 38 | I3 | 306.4 | 307.1 (M + 1) |
| 64 | 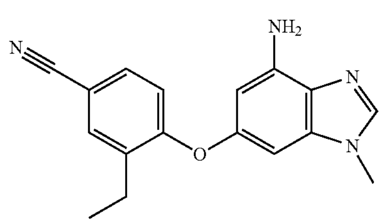 [SMILES: CCc1cc(C#N)ccc1Oc1cc(N)c2ncn(C)c2c1] | Int. 50 | I3 | 292.3 | 293.3 (M + 1) |

TABLE II-continued

Illustrative intermediates towards the compounds of the invention

| Int# | Structure | SM | Mtd | MW | MS Ms'd |
|---|---|---|---|---|---|
| 65 | 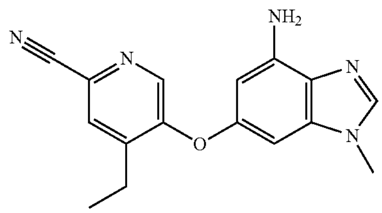 | Int. 52 | I3 | 293.3 | 294.2 (M + 1) |
| 66 | 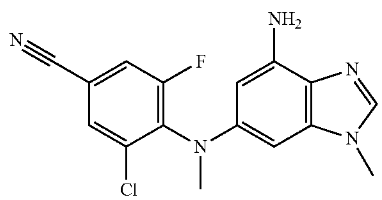 [SMILES: CN(c1cc(N)c2ncn(C)c2c1)c1c(F)cc(C#N)cc1Cl] | Int. 42 | I3 | 329.8 | 330.2 (M + 1) |
| 67 | 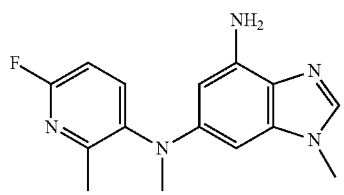 [SMILES: Cc1nc(F)ccc1N(C)c1cc(N)c2ncn(C)c2c1] | Int. 40 | I3 | 285.3 | 286.2 (M + 1) |
| 68 | 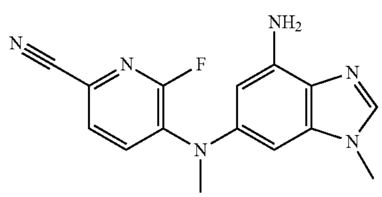 [SMILES: CN(c1cc(N)c2ncn(C)c2c1)c1ccc(C#N)nc1F] | Int. 44 | I3 | 296.3 | 297.0 (M + 1) |
| 69 | 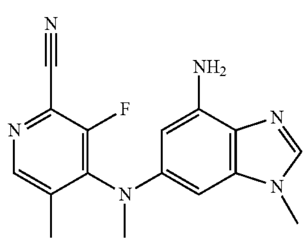 [SMILES: Cc1cnc(C#N)c(F)c1N(C)c1cc(N)c2ncn(C)c2c1] | Int. 32 | I3 | 310.3 | 311.0 (M + 1) |
| 70 | 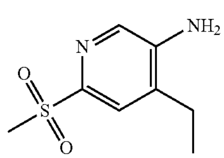 | 2-bromo-4-ethyl-5-nitro-pyridine | Dsc'd | 200.3 | 201.1 (M + 1) |
| 71 | 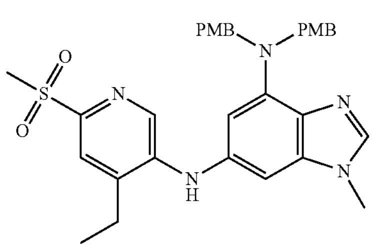 | Int.70 + Int. 2 | E2 | 585.7 | 586.0 (M + 1) |

TABLE II-continued

Illustrative intermediates towards the compounds of the invention

| Int# | Structure | SM | Mtd | MW | MS Ms'd |
|---|---|---|---|---|---|
| 72 | 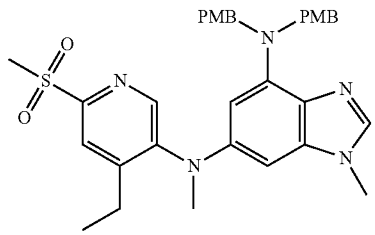 | Int. 71 | F | 599.8 | 600.1 (M + 1) |
| 73 | 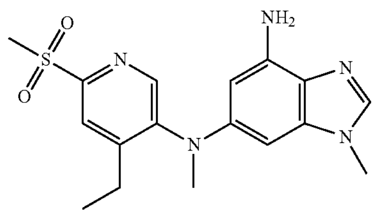 [SMILES: CCc1cc(S(C)(=O)=O)ncc1N(C)c1cc(N)c2ncn(C)c2c1] | Int. 72 | I3 | 359.5 | 360.0 (M + 1) |
| 74 | 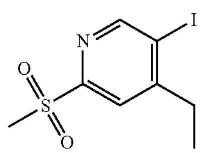 | Int. 70 | Dsc'd | 311.1 | 311.8 (M + 1) |
| 75 | 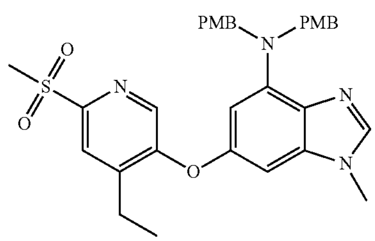 | Int. 3 + Int. 74 | G | 586.7 | 587.3 (M + 1) |
| 76 | 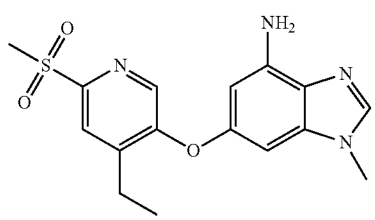 [SMILES: CCc1cc(S(C)(=O)=O)ncc1Oc1cc(N)c2ncn(C)c2c1] | Int. 75 | I2 | 346.4 | 347.0 (M + 1) |
| 77 | 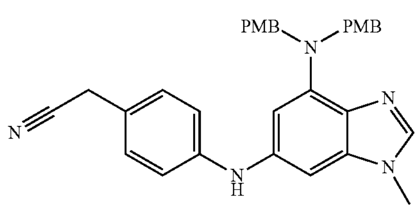 | Int. 2 + 2-(4-aminophenyl)acetonitrile | E4 | 517.6 | 518.0 (M + 1) |
| 78 | 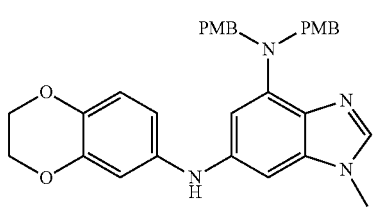 | Int. 2 + 2,3-dihydro-1,4-benzodioxin-6-amine | E4 | 536.6 | 537.33 (M + 1) |

TABLE II-continued

Illustrative intermediates towards the compounds of the invention

| Int# | Structure | SM | Mtd | MW | MS Ms'd |
|------|-----------|-----|-----|------|---------|
| 79 | 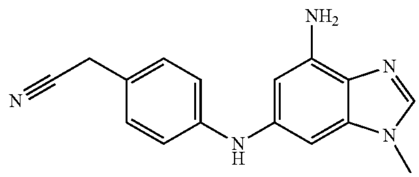 [SMILES: Cn1cnc2c(N)cc(Nc3ccc(CC#N)cc3)cc21] | Int. 77 | I2 | 277.3 | 278.0 (M + 1) |
| 80 | 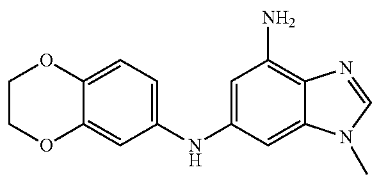 [SMILES: Cn1cnc2c(N)cc(Nc3ccc4c(c3)OCCO4)cc21] | Int. 78 | I2 | 296.3 | 297.0 (M + 1) |

TABLE III

Illustrative compounds of the invention

| Cpd # | Structure | Name | SM | Mtd | MW | MS Ms'd |
|-------|-----------|------|-----|-----|------|---------|
| 1 | 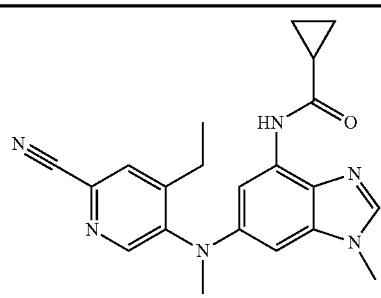 | N-(6-((6-cyano-4-ethylpyridin-3-yl)(methyl)amino)-1-methyl-1H-benzo[d]imidazol-4-yl)cyclopropanecarboxamide | Int 63 | J1 | 374.4 | 375.3 |
| 2 | 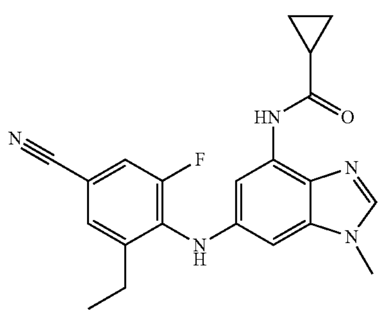 [SMILES: CCc1cc(C#N)cc(F)c1Nc1cc(NC(=O)C2CC2)c2ncn(C)c2c1] | N-(6-(4-cyano-2-ethyl-6-fluorophenylamino)-1-methyl-1H-benso[d]imidazol-4-yl)cyclopropanecarboxamide | Int 54 | J1 | 377.4 | 378.0 |
| 3 | 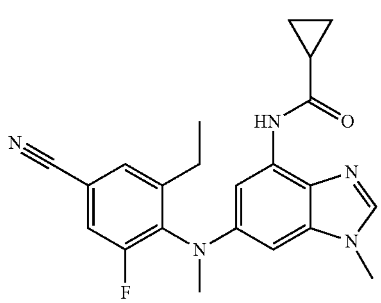 [SMILES: CCc1cc(C#N)cc(F)c1N(C)c1cc(NC(=O)C2CC2)c2ncn(C)c2c1] | N-(6-((4-cyano-2-ethyl-6-fluorophenyl)(methyl)amino)-1-methyl-1H benzo[d]imidazol-4-yl)cyclopropanecarboxamide | Int 61 | J1 | 391.4 | 392.4 |

TABLE III-continued

Illustrative compounds of the invention

| Cpd # | Structure | Name | SM | Mtd | MW | MS Ms'd |
|---|---|---|---|---|---|---|
| 4 | 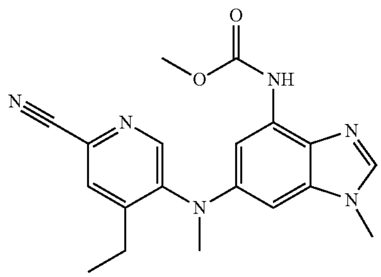 [SMILES: CCc1cc(C#N)ncc1N(C)c1cc(NC(=O)OC)c2ncn(C)c2c1] | methyl 6-((6-cyano-4-ethylpyridin-3-yl)(methyl)amino)-1-methyl-1H-benzo[d]imidazol-4-ylcarbamate | Int 63 | J2 | 364.4 | 365.1 |
| 5 | 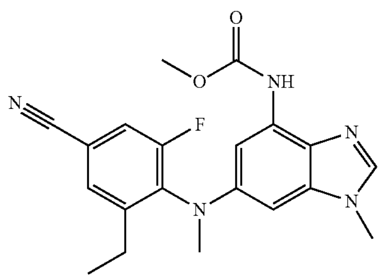 [SMILES: CCc1cc(C#N)cc(F)c1N(C)c1cc(NC(=O)OC)c2ncn(C)c2c1] | methyl 6-((4-cyano-2-ethyl-6-fluorophenyl)(methyl)amino)-1-methyl-1H-benzo[d]midazol-4-ylcarbamate | Int 61 | J2 | 381.4 | 382.1 |
| 6 | 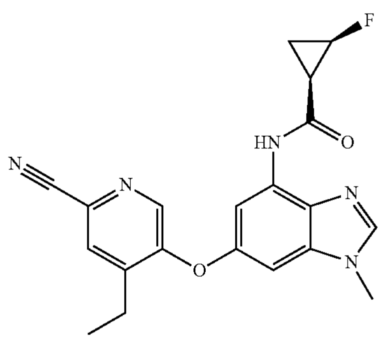 [SMILES: CCc1cc(C#N)ncc1Oc1cc(NC(=O)[C@H]2C[C@H]2F)c2ncn(C)c2c1] | (1R,2R)-N-[6-[(6-cyano-4-ethyl-3-pyridyl)oxy]-1-methyl-benzimidazol-4-yl]-2-fluoro-cyclopropanecarboxamide | Int 65 | K1 | 379.4 | 380.4 |
| 7 | 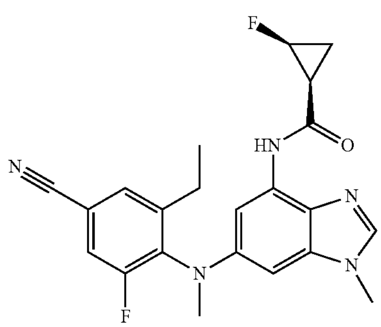 [SMILES: CCc1cc(C#N)cc(F)c1N(C)c1cc(NC(=O)[C@@H]2C[C@@H]2F)c2ncn(C)c2c1] | N-(6-((4-cyano-2-ethyl-6-flurorphenyl)(methyl)amino)-1-methyl-1H-benzo[d]imidazol-4-yl)-2-fluorocyclopropanecarboxamide (1S,2S)/(1R,2R) racemic mixture | Int 61 | K1 | 409.4 | 410.2 |
| 8 | 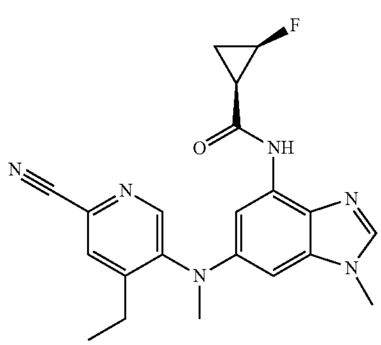 [SMILES: CCc1cc(C#N)ncc1N(C)c1cc(NC(=O)[C@H]2C[C@H]2F)c2ncn(C)c2c1] | (1R,2R)-N-(6-((6-cyano-4-ethylpyridin-3-yl)(methyl)amino)-1-methyl-1H-benzo[d]imidazol-4-yl)-2-fluorocyclopropanecarboxamide | Int 63 | K1 | 392.4 | 393.1 |

TABLE III-continued

Illustrative compounds of the invention

| Cpd # | Structure | Name | SM | Mtd | MW | MS Ms'd |
|---|---|---|---|---|---|---|
| 9 | 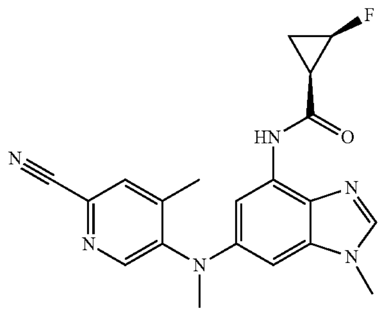 [SMILES: Cc1cc(C#N)ncc1N(C)c1cc(NC(=O)[C@H]2C[C@H]2F)c2ncn(C)c2c1] | (1R,2R)-N-(6-((6-cyano-4-methylpyridin-3-yl)(methyl)amino)-1-methyl-1H-benzo[d]imidazol-4-yl)-2-fluorocyclopropanecarboxamide | Int 62 | K1 | 378.4 | 378.9 |
| 10 | 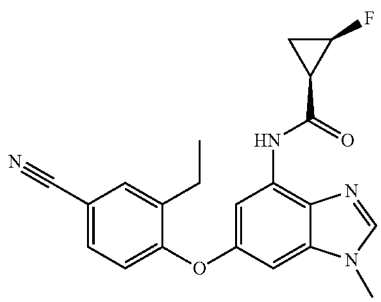 [SMILES: CCc1cc(C#N)ccc1Oc1cc(NC(=O)[C@H]2C[C@H]2F)c2ncn(C)c2c1] | (1R,2R)-N-[6-(4-cyano-2-ethyl-phenoxy)-1-methyl-benzimidazol-4-yl]-2-fluoro-cyclopropanecarboxamide | Int 64 | K1 | 378.4 | 379.4 |
| 11 | 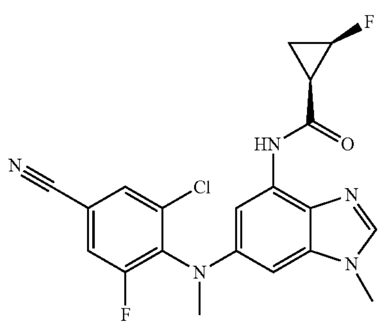 [SMILES: CN(c1cc(NC(=O)[C@H]2C[C@H]2F)c2ncn(C)c2c1)c1c(F)cc(C#N)cc1Cl] | (1R,2R)-N-[6-(2-chloro-4-cyano-6-fluoro-N-methyl-anilino)-1-methyl-benzimidazol-4-yl]-2-fluoro-cyclopropanecarboxamide | Int 66 | K1 | 415.8 | 416.0 |
| 12 | 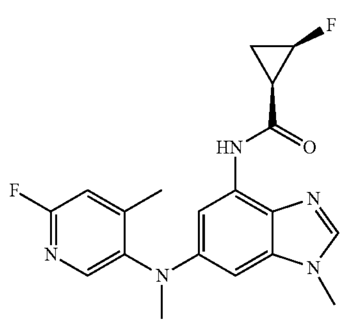 [SMILES: Cc1cc(F)ncc1N(C)c1cc(NC(=O)[C@H]2C[C@H]2F)c2ncn(C)c2c1] | (1R,2R)-2-fluoro-N-[6-[(6-fluoro-4-methyl-3-pyridyl)-methyl-amino]-1-methyl-benzimidazol-4-yl]cyclopropanecarboxamide | Int 67 | K1 | 371.4 | 372.5 |

TABLE III-continued

Illustrative compounds of the invention

| Cpd # | Structure | Name | SM | Mtd | MW | MS Ms'd |
|---|---|---|---|---|---|---|
| 13 | 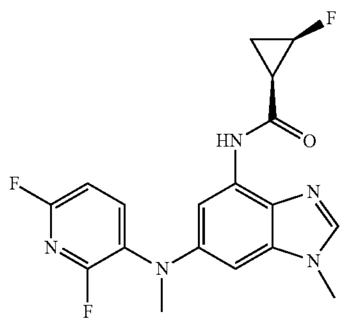 [SMILES: CN(c1cc(NC(=O)[C@H]2C[C@H]2F)c2ncn(C)c2c1)c1ccc(F)nc1F] | (1R,2R)-N-[6-[(2,6-difluoro-3-pyridyl)-methyl-amino]-1-methyl-benzimidazol-4-yl]-2-fluoro-cyclopropanecarboxamide | Int 55 | K1 | 375.4 | 376.1 |
| 14 | 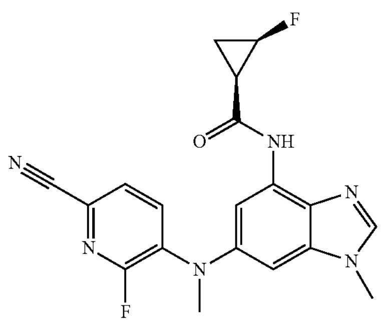 [SMILES: CN(c1cc(NC(=O)[C@H]2C[C@H]2F)c2ncn(C)c2c1)c1ccc(C#N)nc1F] | (1R,2R)-N-[6-[(6-cyano-2-fluoro-3-pyridyl)-methyl-amino]-1-methyl-benzimidazol-4-yl]-2-fluoro-cyclopropanecarboxamide | Int 68 | K1 | 382.4 | 383.0 |
| 15 | 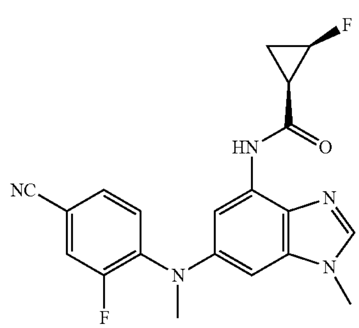 [SMILES: CN(c1cc(NC(=O)[C@H]2C[C@H]2F)c2ncn(C)c2c1)c1ccc(C#N)cc1F] | (1R,2R)-N-[6-(4-cyano-2-fluoro-N-methyl-anilino)-1-methyl-benzimidazol-4-yl]-2-fluoro-cyclopropanecarboxamide | Int 58 | K1 | 381.4 | 382.1 |
| 16 | 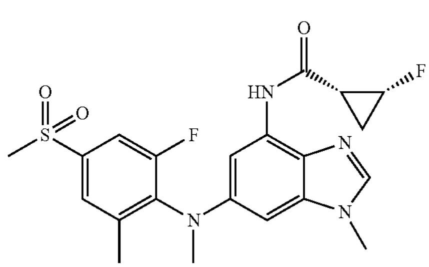 [SMILES: Cc1cc(S(C)(=O)=O)cc(F)c1N(C)c1cc(NC(=O)[C@H]2C[C@H]2F)c2ncn(C)c2c1] | (1R,2R)-2-fluoro-N-[6-(2-fluoro-N,6-dimethyl-4-methylsulfonyl-anilino)-1-methyl-benzimidazol-4-yl]cyclopropanecarboxamide | Int 53 | K1 | 448.5 | 448.9 |
| 17 | 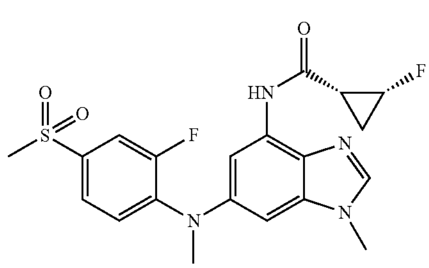 [SMILES: CN(c1cc(NC(=O)[C@H]2C[C@H]2F)c2ncn(C)c2c1)c1ccc(S(C)(=O)=O)cc1F] | (1R,2R)-2-fluoro-N-[6-(2-fluoro-N-methyl-4-methylsulfonyl-anilino)-1-methyl-benzimidazol-4-yl]cyclopropanecarboxamide | Int 59 | K1 | 434.5 | 435.1 |

TABLE III-continued

Illustrative compounds of the invention

| Cpd # | Structure | Name | SM | Mtd | MW | MS Ms'd |
|---|---|---|---|---|---|---|
| 18 | 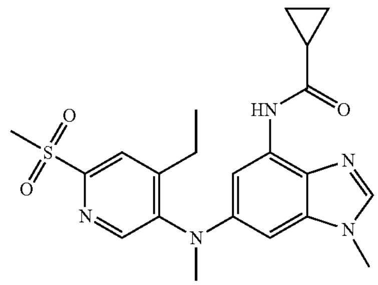 [SMILES: CCc1cc(S(C)(=O)=O)ncc1N(C)c1cc(NC(=O)C2CC2)c2ncn(C)c2c1] | N-[6-[(4-ethyl-6-methylsulfonyl-3-pyridyl)-methyl-amino]-1-methyl-benzimidazol-4-yl]cyclopropanecarboxamide | Int 73 | K1 | 427.5 | 428.2 |
| 19 | 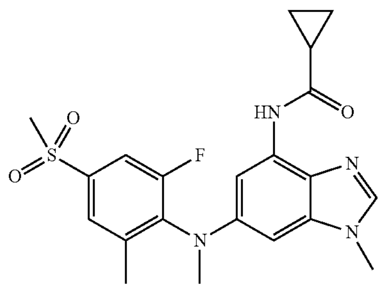 [SMILES: Cc1cc(S(C)(=O)=O)cc(F)c1N(C)c1cc(NC(=O)C2CC2)c2ncn(C)c2c1] | N-[6-(2-fluoro-N,6-dimethyl-4-methylsulfonyl-anilino)-1-methyl-benzimidazol-4-yl]cyclopropanecarboxamide | Int 53 | K1 | 430.5 | 431.0 |
| 20 | 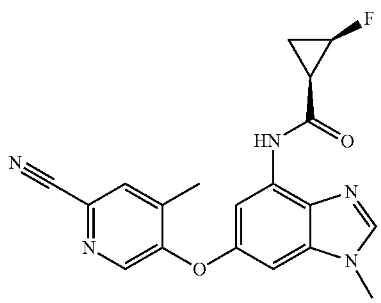 [SMILES: Cc1cc(C#N)ncc1Oc1cc(NC(=O)[C@H]2C[C@H]2F)c2ncn(C)c2c1] | (1R,2R)-N-[6-[(6-cyano-4-methyl-3-pyridyl)oxy]-1-methyl-benzimidazol-4-yl]-2-fluoro-cyclopropanecarboxamide | Cpd 28 | K2 | 365.4 | 366.0 |
| 21 | 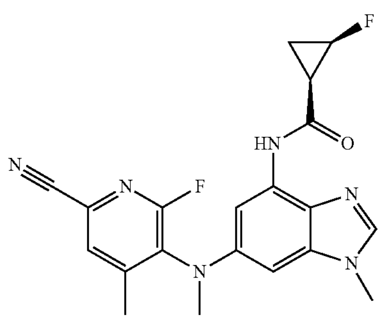 [SMILES: Cc1cc(C#N)nc(F)c1N(C)c1cc(NC(=O)[C@H]2C[C@H]2F)c2ncn(C)c2c1] | (1R,2R)-N-[6-[(6-cyano-2-fluoro-4-methyl-3-pyridyl)-methyl-amino]-1-methyl-benzimidazol-4-yl]-2-fluoro-cyclopropanecarboxamide | Int 57 | K2 | 396.4 | 397.1 |
| 22 | 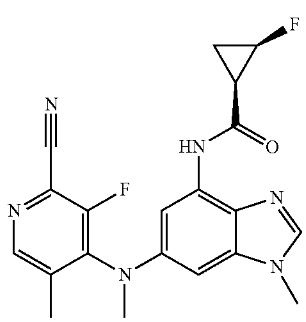 [SMILES: Cc1cnc(C#N)c(F)c1N(C)c1cc(NC(=O)[C@H]2C[C@H]2F)c2ncn(C)c2c1] | (1R,2R)-N-[6-[(2-cyano-3-fluoro-5-methyl-4-pyridyl)-methyl-amino]-1-methyl-benzimidazol-4-yl]-2-fluoro-cyclopropanecarboxamide | Int 69 | K2 | 396.4 | 397.1 |

TABLE III-continued

Illustrative compounds of the invention

| Cpd # | Structure | Name | SM | Mtd | MW | MS Ms'd |
|---|---|---|---|---|---|---|
| 23 | 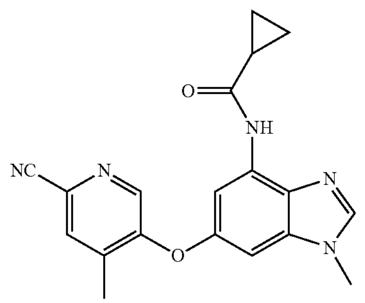 [SMILES: Cc1cc(C#N)ncc1Oc1cc(NC(=O)C2CC2)c2ncn(C)c2c1] | N-[6-[(6-cyano-4-methyl-3-pyridyl)oxy]-1-methyl-benzimidazol-4-yl]cyclopropanecarboxamide | Cpd 28 | K2 | 347.4 | 348.1 |
| 24 | 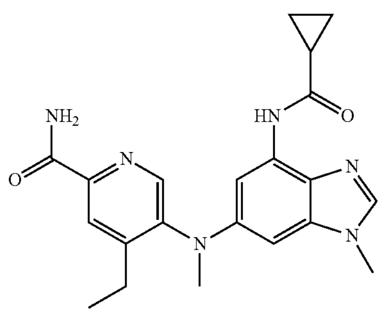 [SMILES: CCc1cc(C(N)=O)ncc1N(C)c1cc(NC(=O)C2CC2)c2ncn(C)c2c1] | 5-((4-(cyclopropanecarboxamido)-1-methyl-1H-benzo[d]imidazol-6-yl)(methyl)amino)-4-ethylpicolinamide | Cpd 1 | L | 392.5 | 393.3 |
| 25 | 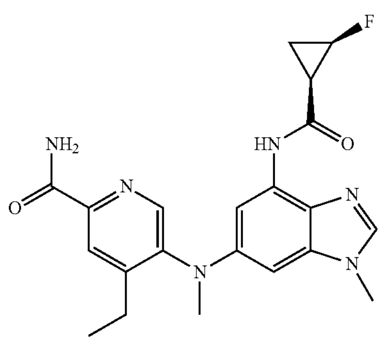 [SMILES: CCc1cc(C(N)=O)ncc1N(C)c1cc(NC(=O)[C@H]2C[C@H]2F)c2ncn(C)c2c1] | 4-ethyl-5-((4-((1R,2R)-2-fluorocyclopropanecarboxamido)-1-methyl-1H-benzo[d]imidazol-6-yl)(methyl)amino)picolinamide | Cpd 8 | L | 410.5 | 411.3 |
| 26 | 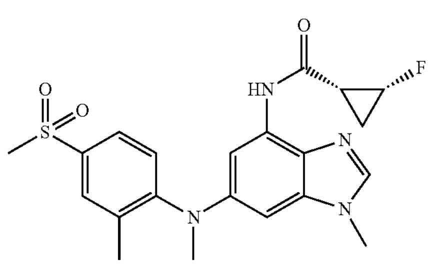 [SMILES: Cc1cc(S(C)(=O)=O)ccc1N(C)c1cc(NC(=O)[C@H]2C[C@H]2F)c2ncn(C)c2c1] | (1R,2R)-N-[6-(N,2-dimethyl-4-methylsulfonyl-anilino)-1-methyl-benzimidazol-4-yl]-2-fluoro-cyclopropanecarboxamide | Int 56A | — | 430.5 | 431.0 |
| 27 | 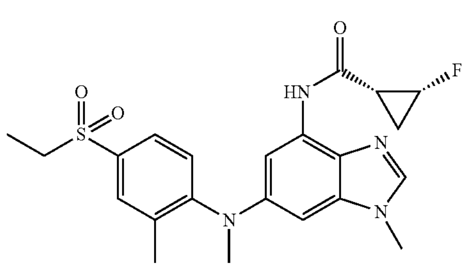 [SMILES: CCS(=O)(=O)c1ccc(N(C)c2cc(NC(=O)[C@H]3C[C@H]3F)c3ncn(C)c3c2)c(C)c1] | (1R,2R)-N-[6-(4-ethylsulfonyl-N,2-dimethyl-anilino)-1-methyl-benzimidazol-4-yl]-2-fluoro-cyclopropanecarboxamide | Int 56B | K1 | 444.5 | 445.0 |

TABLE III-continued

Illustrative compounds of the invention

| Cpd # | Structure | Name | SM | Mtd | MW | MS Ms'd |
|---|---|---|---|---|---|---|
| 28 | 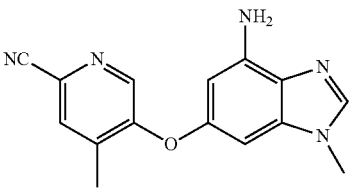 [SMILES: Cc1cc(C#N)ncc1Oc1cc(N)c2ncn(C)c2c1] | 5-(7-amino-3-methyl-benzimidazol-5-yl)oxy-4-methyl-pyridine-2-carbonitrile | Int 51 | I2 | 279.3 | 280.1 |
| 29 | 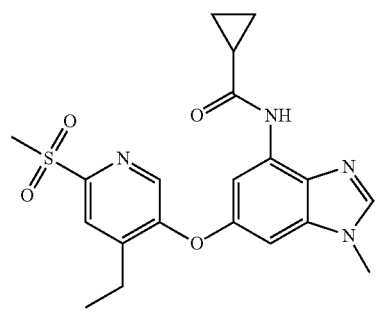 [SMILES: CCc1cc(S(C)(=O)=O)ncc1Oc1cc(NC(=O)C2CC2)c2ncn(C)c2c1] | N-[6-[(4-ethyl-6-methylsulfonyl-3-pyridyl)oxy]-1-methyl-benzimidazol-4-yl]cyclopropanecarbox-amide | Int 76 | K1 | 414.5 | 415.1 |
| 30 | 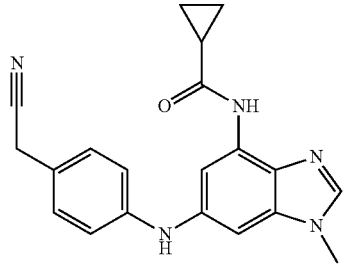 [SMILES: Cn1cnc2c(NC(=O)C3CC3)cc(Nc3ccc(CC#N)cc3)cc21] | N-[6-[4-(cyanomethyl)anilino]-1-methyl-benzimidazol-4-yl]cyclopropanecarbox-amide | Int 79 | K1 | 345.4 | 346.0 |
| 31 | 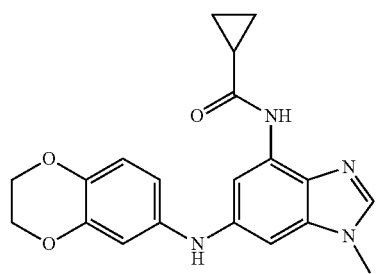 [SMILES: Cn1cnc2c(NC(=O)C3CC3)cc(Nc3ccc4c(c3)OCCO4)cc21] | N-[6-(2,3-dihydro-1,4-benzodioxin-6-ylamino)-1-methyl-benzimidazol-4-yl]cyclopropanecarbox-amide | Int 80 | K1 | 364.4 | 365.0 |
| 32 | 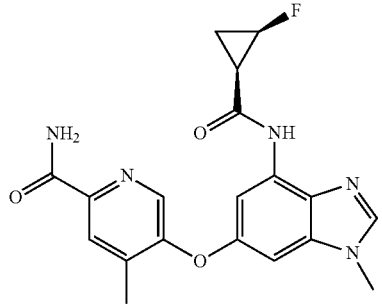 [SMILES: Cc1cc(C(N)=O)ncc1Oc1cc(NC(=O)[C@H]2C[C@H]2F)c2ncn(C)c2c1] | 5-[7 [[(1R,2R)-2-fluorocyclopropanecar-bonyl]amino]-3-methyl-benzimidazol-5-yl]oxy-4-methyl-pyridine-2-carboxamide | Cpd 20 | Dsc'd | 383.4 | 384.1 |

TABLE III-continued

Illustrative compounds of the invention

| Cpd # | Structure | Name | SM | Mtd | MW | MS Ms'd |
|---|---|---|---|---|---|---|
| 33 | 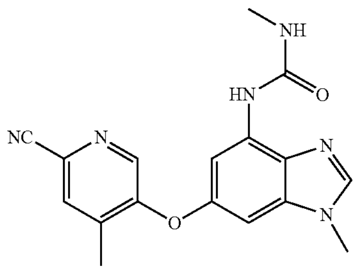 [SMILES: CNC(=O)Nc1cc(Oc2cnc(C#N)cc2C)cc2c1ncn2C] | 1-[6-[(6-cyano-4-methyl-3-pyrdyl)oxy]-1-methyl-benzimidazol-4-yl]-3-isopropyl-urea | Int 83 | M | 336.4 | 337.0 |
| 34 | 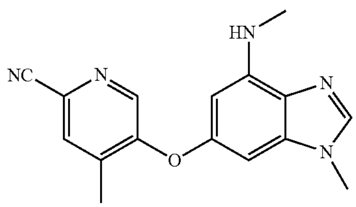 [SMILES: CNc1cc(Oc2cnc(C#N)cc2C)cc2c1ncn2C] | 4-methyl-5-[3-methyl-7-(methylamino)benzimidazol-5-yl]oxy-pyridine-2-carbonitrile | Int 83 | Dsc'd | 293.3 | 294.0 |
| 35 | 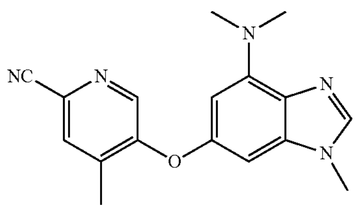 [SMILES: Cc1cc(C#N)ncc1Oc1cc(N(C)C)c2ncn(C)c2c1] | 5-[7-(dimethylamino)-3-methyl-benzimidazol-5-yl]oxy-4-methyl-pyridine-2-carbonitrile | Int 83 | Dsc'd | 307.4 | 308.0 |
| 36 | 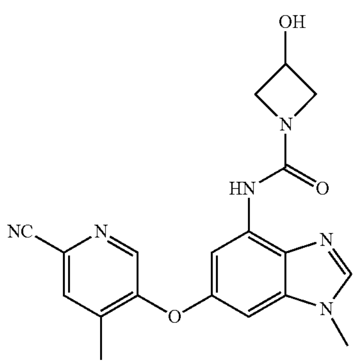 [SMILES: Cc1cc(C#N)ncc1Oc1cc(NC(=O)N2CC(O)C2)c2ncn(C)c2c1] | N-[6-[(6-cyano-4-methyl-3-pyridyl)oxy]-1-methyl-benzimidazol-4-yl]-3-hydroxy-azetidine-1-carboxamide | Int 83 | M | 378.1 | 379.0 |
| 37 | 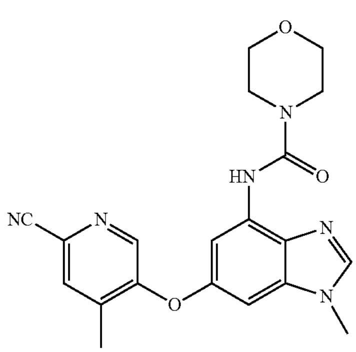 [SMILES: Cc1cc(C#N)ncc1Oc1cc(NC(=O)N2CCOCC2)c2ncn(C)c2c1] | N-[6-[(6-cyano-4-methyl-3-pyridyl)oxy]-1-methyl-benzimidazol-4-yl]morpholine-4-carboxamide | Int 83 | M | 392.2 | 393.1 |

TABLE III-continued

Illustrative compounds of the invention

| Cpd # | Structure | Name | SM | Mtd | MW | MS Ms'd |
|---|---|---|---|---|---|---|
| 38 | 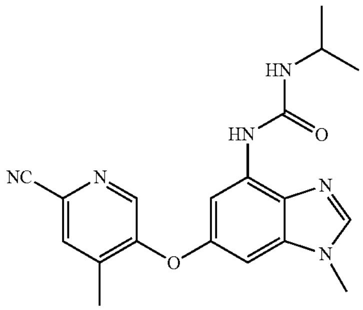 [SMILES: Cc1cc(C#N)ncc1Oc1cc(NC(=O)NC(C)C)c2ncn(C)c2c1] | 1-[6-[(6-cyano-4-methyl-3-pyridyl)oxy]-1-methyl-benzimidazol-4-yl]-3-isopropyl-urea | Int 83 | M | 364.2 | 365.1 |

TABLE IV

NMR data of illustrative compounds of the invention

Cpd# NMR

1. $^1$H NMR (600 MHz, DMSO-d$_6$): d = 0.69-0.77 (m, 4H), 1.04 (t, 3H), 2.15-2.24 (m, 1H), 2.34 (q, 2H), 3.34 (s, 3H), 3.74 (s, 3H), 6.72 (d, 1H), 7.49 (s, 1H), 7.94 (s, 1H), 8.04 (s, 1H), 8.48 (s, 1H), 10.05 (s, 1H).
2. $^1$H NMR (400 MHz, DMSO-d$_6$): δ = 0.70-0.80 (m, 4H), 1.09 (t, 3H), 2.19-2.27 (m, 1H), 2.64 (q, 2H), 3.68 (s, 3H), 6.42 (t, 1H), 7.55 (d, 1H), 7.64 (dd, 1H), 7.67 (br.s, 1H), 7.92 (s, 1H), 7.98 (s, 1H), 10.01 (s, 1H).
3. $^1$H NMR (300 MHz, DMSO-d$_6$): d = 9.93 (s, 1H), 7.96 (s, 1H), 7.81 (dd, 1H), 7.74 (s, 1 H), 7.29 (br s, 1H), 6.47 (d, finely split, 1H), 3.73 (s, 3H), 3.21 (s, 3H), 2.54-2.48 (m, partially obscured by solvent peak, 2H), 2.17 (m, 1H), 1.09 (t, 3H), 0.71-0.69 (m, 4H).
4. $^1$H NMR (300 MHz, DMSO-d$_6$): δ = 1.05 (t, 3H), 2.36 (q, 2H), 3.36 (s, 3H), 3.61 (s, 3H), 3.73 (s, 3H), 6.72 (d, 1H), 7.06 (d, 1H), 7.97 (s, 1H), 8.00 (dd, 1H), 8.50 (s, 1H), 8.91 (bs, 1H).
5. $^1$H NMR (300 MHz, DMSO-d$_6$): δ = 1.10 (t, 3H), 2.52 (q, 2H), 3.23 (s, 3H), 3.59 (s, 3H), 3.73 (s, 3H), 6.51 (d, 1H), 6.86 (d, 1H), 7.76 (bs, 1H), 7.82 (dd, 1H), 7.92 (s, 1H), 8.75 (s, 1H).
6. $^1$H NMR (400 MHz, DMSO-d$_6$): d = 1.14 (ddt, H), 1.24 (t, 3H), 1.53-1.67 (m, 1H), 2.51-2.55 (m, 1H), 2.75 (q, 2H), 3.79 (s, 3H), 4.77-5.03 (m, 1H), 7.13 (d, 1H), 7.85 (d, 1H), 8.07 (s, 1H), 8.11 (s, 1H), 8.22 (s, 1H), 10.43 (s, 1H).
7. $^1$H NMR (300 MHz, DMSO-d$_6$): δ = 0.99-1.15 (m, 1H), 1.09 (t, 3H), 1.54 (m, 1H), 2.39 (m, 1H), 2.52 (q, 2H), 3.22 (s, 3H), 3.73 (s, 3H), 4.85 (m, 1H), 6.49 (d, 1H), 7.32 (s, 1H), 7.75 (s, 1H), 7.82 (dd, 1H), 7.96 (s, 1H), 9.96 (s, 1H).
8. $^1$H NMR (300 MHz, DMSO-d$_6$): δ = 0.99-1.18 (m, 1H), 1.05 (t, 3H), 1.56 (m, 1H), 2.29-2.45 (m, 1H), 2.35 (q, 2H), 3.35 (s, 3H), 3.74 (s, 3H), 4.88 (m, 1H), 6.72 (d, 1H), 7.51 (bs, 1H), 7.95 (s, 1H), 8.05 (s, 1H), 8.49 (s, 1H), 10.09 (bs, 1H).
9. $^1$H NMR (300 MHz, DMSO-d$_6$): d = 10.13 (s, 1H), 8.49 (s, 1H), 8.07 (s, 1H), 7.87 (s, 1H), 7.55 (br s, 1H), 6.79 (d, finely split, 1H), 5.0-4.7(m, 1H), 3.75 (s, 3H), 3.38 (s, 3H), 2.5-2.3 (m, 1H), 1.97 (s, 3H), 1.6-1.5 (m, 1H), 1.2-1.0 (m, 1H).
10. $^1$H NMR (500 MHz, DMSO-d$_6$): d = 1.07-1.20 (m, 1H), 1.24 (t, 3H), 1.53-1.67 (m, 1H), 2.43-2.48 (m, 1H), 2.75 (q, 2H), 3.80 (s, 3H), 4.78-5.01 (m, 1H), 6.78 (d, 1H), 7.11 (d, 1H), 7.59 (dd, 1H), 7.78 (d, 1H), 7.80 (d, 1H), 8.22 (s, 1H), 10.40 (s, 1H).
11. $^1$H NMR (400 MHz, DMSO-d$_6$): d = 1.08 (ddt, 1H), 1.41-1.67 (m, 1H), 2.41 (dt, 1H), 3.27 (s, 3H), 3.75 (s, 3H), 4.65-5.05 (m, 1H), 6.61 (d, 1H), 7.42 (s, 1H), 8.00 (s, 1H), 8.04 (dd, 1H), 8.12 (t, 1H), 10.04 (s, 1H).
12. $^1$H NMR (500 MHz, DMSO-d$_6$): δ = 1.08 (ddt, 1H), 1.50-1.60 (m, 1H), 2.12 (s, 3H), 2.39 (dt, 1H), 3.25 (s, 3H), 3.73 (s, 3H), 4.76-4.96 (m, 1H), 6.49 (d, 1H), 7.19 (s, 1H), 7.35 (s, 1H), 7.97 (s, 1H), 8.00 (s, 1H), 10.02 (s, 1H).
13. $^1$H NMR (300 MHz, DMSO-d$_6$): 10.12 (s, 1H), 8.06-8.00 (m, 2H), 7.96 (s, 1H), 7.22-7.19 (m, 1H), 6.76 (s, 1H), 4.98-4.77 (d, 1H), 3.76 (s, 3H), 3.25 (s, 3H), 2.45-2.42 (m, 1H), 1.59-1.52 (m, 1H), 1.27-1.10 (m, 1H).
14. $^1$H NMR (400 MHz, DMSO-d$_6$) 10.30 (1 H, s), 8.20 (1 H, s), 7.92 (1 H, dd), 7.85 (1 H, d), 7.63 (1 H, dd), 7.17 (1 H, d), 4.92 (1H, dF), 3.79 (3 H, s), 3.40 (3 H, s), 2.48-2.44 (1H, m), 1.64-1.53 (1H, m), 1.19-1.15 (1H, m).
15. $^1$H NMR (300 MHz, DMSO-d$_6$): 10.22 (1H, s), 8.16 (1H, s), 7.80 (1H, s), 7.70-7.67 (1H, m), 7.59-7.58 (1H, d), 7.25-7.21 (1H, m), 7.07 (1H, s), 4.99-4.81 (1H, d), 3.79 (3H, s, CH3), 3.38 (3H, s, CH3), 2.46-2.42 (1H, m, CH), 1.61-1.55 (1H, m), 1.19-1.09 (1H, m)
16. $^1$H NMR (400 MHz, DMSO-d$_6$): 10.30 (1 H, s), 7.95 (1 H, s), 7.78(1 H, d), 7.74 (1 H, dd), 7.36 (1 H, d), 6.49 (1 H, d), 4.87 (1H, dF), 3.78 (3 H, s), 3.28 (3 H, s), 3.21 (3 H, s), 2.43-2.38 (1H, m), 2.22 (3 H, s), 1.62-1.51 (1H, m), 1.15-1.08 (1H, m).

TABLE IV-continued

NMR data of illustrative compounds of the invention

| Cpd# | NMR |
|---|---|
| 17 | $^1$H NMR (400 MHz, DMSO-d$_6$): 10.84 (1 H, s), 9.21 (1 H, s), 7.79 (2 H, dt), 7.55 (1 H, t), 7.42 (1 H, s), 7.26 (1 H, d), 4.95 (1H, dF), 3.96 (3 H, s), 3.43 (3 H, s), 3.28 (3 H, s), 2.43-2.38 (1 H, m), 1.62-1.51 (1 H, m), 1.15-1.08 (1 H, m). |
| 18 | $^1$H NMR (400 MHz, DMSO-d$_6$): 10.08 (1 H, s), 8.53 (1 H, s), 8.05 (1 H, s), 7.93 (1 H, s), 7.48 (1 H, br s), 6.69 (1 H, d), 3.75 (3 H, s), 3.29 (3 H, s), 3.21 (3 H, s), 2.46 (2 H, q), 2.25-2.17 (1 H, m), 1.08 (3 H, t), 0.76-0.69 (4 H, m). |
| 19 | $^1$H NMR (400 MHz, CDCl$_3$): 9.55 (1 H, br s), 8.05-8.00 (2 H, m), 7.70 (1 H, d), 7.61 (1 H, dd), 6.01 (1 H, d), 3.78 (3 H, s), 3.33 (3 H, s), 3.13 (3 H, s), 2.25 (3 H, s), 1.97-1.92 (1 H, m), 0.91-0.85 (4 H, m). |
| 20 | $^1$H NMR (500 MHz, DMSO-d$_6$): d = 1.15 (ddt, 1H), 1.54-1.66 (m, 1H), 2.36 (s, 3H), 2.52-2.54 (m, 1H), 3.80 (s, 3H), 4.77-5.03 (m, 1H), 7.12 (d, 1H), 7.86 (d, 1H), 8.08 (s, 1H), 8.12 (s, 1H), 8.23 (s, 1H), 10.44 (s, 1H). |
| 21 | $^1$H NMR (400 MHz, DMSO-d$_6$): 10.12 (1H, s), 8.11 (1H, s), 8.02 (1H, s), 7.41 (1H, s), 6.61 (1H, d), 4.88 (1H, m), 3.75 (3H, s), 3.26 (3H, s), 2.42 (1H, m), 2.22 (3H, s), 1.57 (1H, m), 1.09 (1H, m). |
| 22 | $^1$H NMR (400 MHz, DMSO-d$_6$): 10.18 (1H, s), 8.50 (1H, s), 8.06 (1H, s), 7.51 (1H, s), 6.73 (1H, d), 4.87 (1H, m), 3.75 (3H, s), 3.32 (3H, s), 2.45 (1H, m), 2.11 (3H, s), 1.60 (1H, m), 1.11 (1H, m). |
| 23 | $^1$H NMR (400 MHz, DMSO-d$_6$): 10.39 (1 H, s), 8.23 (1 H, s), 8.11 (1 H, s), 8.07 (1 H, s), 7.84 (1 H, d), 7.11 (1 H, d), 3.79 (3 H, s), 2.35 (3 H, s), 2.33-2.27 (1 H, m), 0.81-0.76 (4 H, m). |
| 24 | $^1$H NMR (600 MHz, DMSO-d$_6$): d = 0.56-0.78 (m, 4H), 1.09 (t, 3H), 2.18 (br. s., 1H), 2.46 (br. s., 2H), 3.30 (br. s., 3H), 3.73 (br. s., 3H), 6.56 (br. s., 1H), 7.38 (br. s., 1H), 7.59 (br. s., 1H), 7.98 (br. s., 2H), 8.05 (br. s., 1H), 8.33 (br. s., 1H), 9.96 (br. s., 1H). |
| 25 | $^1$H NMR (600 MHz, DMSO-d$_6$): d = 1.05-1.08 (m, 1H), 1.09 (t, 3H), 1.50-1.59 (m, 1H), 2.39 (dt, 1H), 2.45-2.49 (m, 2H), 3.31 (s, 3H), 3.73 (s, 3H), 4.70-4.97 (m, 1H), 6.57 (d, 1H), 7.42 (s, 1H), 7.59 (d, 1H), 7.99 (s, 2H), 8.06 (d, 1H), 8.34 (s, 1H), 10.00 (s, 1H). |
| 26 | $^1$H NMR (400 MHz, DMSO-d$_6$): 10.10 (1 H, s), 8.04 (1 H, s), 7.78 (1 H, s), 7.76 (1 H, dd), 7.51 (1 H, d), 7.35 (1 H, d), 6.68 (1 H, d), 4.90 (1H, d), 3.75 (3 H, s), 3.29 (3 H, s), 3.21 (3 H, s), 2.40 (1H, t), 2.08 (3 H, s), 1.64-1.53 (1H, m), 1.15-1.08 (1H, m). |
| 27 | $^1$H NMR (400 MHz, DMSO-d$_6$): 10.10 (1 H, s), 8.03 (1 H, s), 7.73-7.71 (2 H, m), 7.48 (1 H, d), 7.38 (1 H, d), 6.68 (1 H, dd), 4.90 (1H, dF), 3.74 (3 H, s), 3.29 (3 H, s), 3.23 (2 H, q), 2.40 (1H, t), 2.07 (3 H, s), 1.64-1.53 (1H, m), 1.15-1.08 (1H, m) 1.11 (3 H, t). |
| 28 | $^1$H NMR (400 MHz, DMSO-d$_6$): 8.09 (1 H, s), 8.05 (1 H, s), 7.95 (1 H, s), 6.53 (1 H, d), 6.11 (1 H, d), 5.60 (2 H, br s) 3.68 (3 H, s), 2.34 (3 H, s). |
| 29 | $^1$H NMR (400 MHz, DMSO-d$_6$): 10.42 (1 H, s), 8.23 (1 H, s), 8.13 (1 H, s), 8.03 (1 H, s), 7.86 (1 H, d), 7.13 (1 H, d), 3.80 (3 H, s), 3.24 (3 H, s), 2.83 (2 H, q), 2.33-2.27 (1 H, m), 1.26 (3 H, t), 0.81-0.76 (4 H, m). |
| 30 | $^1$H NMR (400 MHz, CDCl$_3$) 8.81 (1 H, s), 8.02 (1 H, d), 7.71 (1 H, s), 7.17 (2 H, d), 7.04 (2 H, d), 6.83 (1 H, d), 6.05 (1 H, s), 3.73 (3 H, s), 3.65 (2 H, s), 1.73-1.66 (1 H, m), 1.10-1.06 (2 H, m), 0.87-0.82 (2 H, m). |
| 31 | $^1$H NMR (400 MHz, CDCl$_3$) 8.77 (1 H, s), 7.89 (1 H, s), 7.66 (1 H, s), 6.78 (1 H, d), 6.68 (2 H, t), 6.63 (1 H, dd), 5.73 (1 H, br s), 4.25-4.21 (4 H, m), 3.69 (3 H, s), 1.73-1.66 (1 H, m), 1.11-1.06 (2 H, m), 0.87-0.82 (2 H, m). |
| 32 | $^1$H NMR (400 MHz, DMSO-d$_6$): 10.41 (1 H, br s), 8.20 (1 H, s), 8.07 (1 H, s), 8.03 (1 H, s), 7.98 (1 H, br s), 7.84 (1 H, d), 7.55 (1 H, br s), 7.01 (1 H, d), 5.02-4.80 (1 H, m), 3.78 (3 H, s), 2.34 (3 H, s), 1.66-1.55 (1 H, m), 1.21-1.02 (2 H, m). |
| 33 | $^1$H NMR (400 MHz, DMSO-d$_6$): 8.89 (1 H, br s), 8.23 (1 H, br s), 8.10 (2 H, m), 7.72 (1 H, br m), 6.4-6.8 (2 H, m), 3.78 (3 H, s), 2.65 (3 H, d), 2.36 (3 H, s). |
| 34 | $^1$H NMR (400 MHz, DMSO-d$_6$): 8.07 (1 H, s), 8.05 (1 H, s), 7.97 (1 H, s), 6.47 (1 H, d), 6.10 (1 H, m), 6.01 (1 H, d), 3.69 (3 h, s), 2.77 (3 H, d), 2.36 (3 H, s) |
| 35 | $^1$H NMR (400 MHz, DMSO-d$_6$): 8.07 (1 H, s), 8.05 (1 H, s), 8.01 (1 H, s), 6.63 (1 H, d), 6.16 (1 H, d), 3.70 (3 H, s), 3.19 (6H, s), 2.36 (3H, s) |
| 36 | $^1$H NMR (400 MHz, DMSO-d$_6$): 8.16 (1 H, s), 8.10 (1 H, s), 0.07 (1 H, s), 8.00 (1 H, s), 7.62 (1 H, d), 6.99 (1 H, d), 5.68 (1 H, m), 4.45 (1 H, m), 4.21 (2 H, m), 3.78 (4 H, m), 2.57 (3 H, s) |
| 37 | $^1$H NMR (400 MHz, DMSO-d$_6$): 8.42 (1 H, br s), 8.16 (1 H, s), 8.10 (1 H, s), 8.07 (1 H, s), 7.56 (1 H, d), 7.02 (1 H, d), 3.78 (3 H, s), 3.61 (4 H, m), 3.44 (4 H, m), 2.36 (3 H, s) |
| 38 | $^1$H NMR (400 MHz, DMSO-d$_6$): 8.68 (1 h, br, s), 8.13 (1 H, s), 8.08 (1 H, s), 8.06 (1 H, s), 7.73 (1 H, s), 6.99 (1 h, br d), 6.89 (1 H, d), 3.75 (3 H, s), 3.72 (1 H, m), 2.35 (3 H, s), 1.07 (6 H, d) |

Example 3

Comparative Compounds

3.1. Compound A 2-[4-[(3-methylbenzimidazol-5-yl)amino]phenyl]acetonitrile

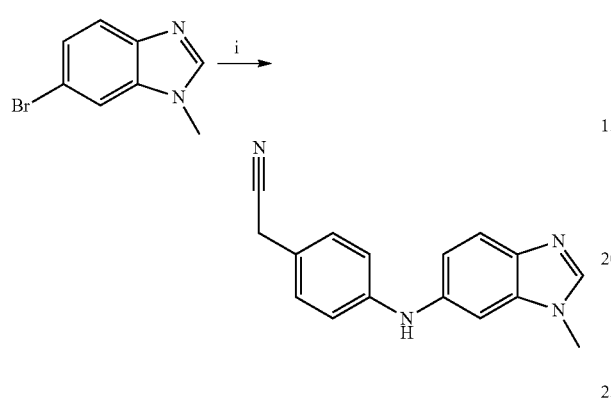

A mixture of Pd$_2$(dba)$_3$ (0.01 mmol) and Xantphos (0.01 mmol) in 1,4-dioxane (1 mL) was sonicated and added under nitrogen to a mixture of 6-bromo-1-methyl-benzimidazole (0.45 mmol), 2-(4-aminophenyl)acetonitrile (0.58 mmol) and Cs$_2$CO$_3$ (0.62 mmol) in 1,4-dioxane (2 mL). The mixture was stirred at 110° C. for 12 h. The mixture was diluted (DCM), washed (H$_2$O), dried (phase separator and concentrated. The residue was purified by prep HPLC to yield the desired product (Compound A).

MW: 262.3. MS Ms'd: 263.2.

NMR: 1H NMR (400 MHz, DMSO-d6): δ=8.13 (1H, s), 7.68 (1H, dd), 7.60 (1H, dd), 7.54 (1H, d), 7.32 (1H, d), 7.24 (1H, t), 6.91 (1H, dd), 3.77 (3H, s), 3.39 (3H, s).

3.2. Compound B

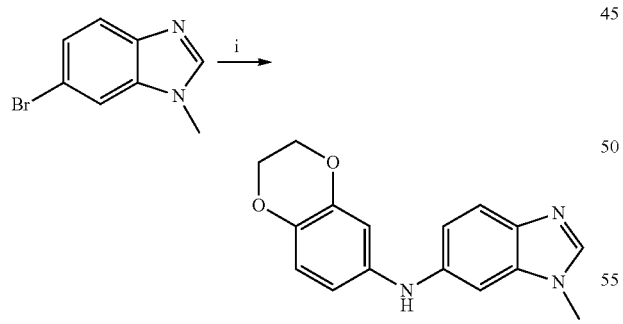

A mixture of Pd$_2$(dba)$_3$ (0.01 mmol) and Xantphos (0.01 mmol) in 1,4-dioxane (1 mL) was sonicated and added under nitrogen to a mixture of 6-bromo-1-methyl-benzimidazole (0.45 mmol), 2,3-dihydro-1,4-benzodioxin-6-amine (0.58 mmol) and Cs$_2$CO$_3$ (0.62 mmol) in 1,4-dioxane (2 mL). The mixture was stirred at 110° C. for 12 h. The mixture was diluted (DCM), washed (H$_2$O), dried (phase separator and concentrated. The residue was purified by prep HPLC to yield the desired product (Compound B).

MW: 281.3. MS Ms'd: 282.1.

NMR: 1H NMR (400 MHz, DMSO-d6): δ=7.94 (1H, s), 7.80 (1H, br s), 7.45 (1H, d), 7.05 (1H, d), 6.86 (1H, dd), 6.73 (1H, dd), 6.61-6.57 (2H, m), 4.22-4.16 (4H, m), 3.71 (3H, s).

3.3. Compound C 3-fluoro-4-[methyl-(3-methylbenzimidazol-5-yl)amino]benzonitrile

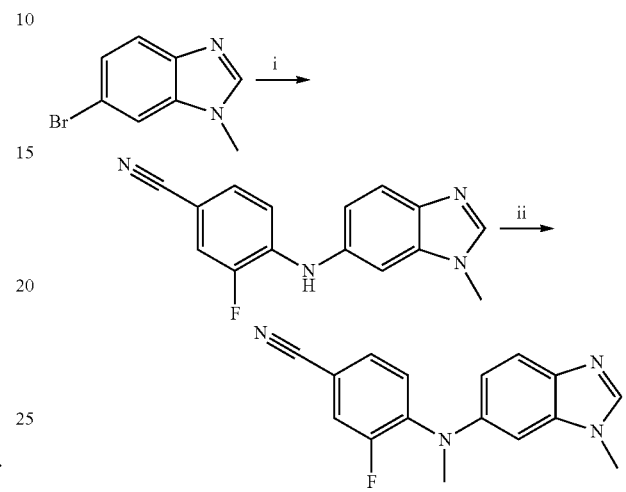

3.3.1. Step i: 3-fluoro-4-[(3-methylbenzimidazol-5-yl)amino]benzonitrile

A mixture containing 6-bromo-1-methyl-benzimidazole (2.38 mmol), 4-amino-3-fluoro-benzonitrile (3.57 mmol), XPhos (0.95 mmol), Cs$_2$CO$_3$ (7.14 mmol) and Pd(OAc)$_2$ (0.71 mmol) in dry toluene (8 mL) was stirred at 110° C. for approximately 16 h. The mixture was diluted (EtOAc), washed (H$_2$O), dried (Na$_2$SO$_4$) and concentrated to yield the desired product 3-fluoro-4-[(3-methylbenzimidazol-5-yl)amino]benzonitrile.

3.3.2. Step ii: 3-fluoro-4-[methyl-(3-methylbenzimidazol-5-yl)amino]benzonitrile (Compound C)

NaH (7.14 mmol) was added to a solution of 3-fluoro-4-[(3-methylbenzimidazol-5-yl)amino]benzonitrile (2.38 mmol) in THF (10 mL) at 0° C. The mixture was stirred for 30 min. MeI (4.76 mmol) was added and the mixture was stirred at room temperature during 3 h. The mixture was diluted (DCM), washed (H$_2$O) and concentrated. The residue was purified by prep HPLC to yield the desired product (Compound C).

MW: 280.1. MS Ms'd: 281.0.

NMR: 1H NMR (400 MHz, DMSO-d6): δ=8.13 (1H, s), 7.68 (1H, dd), 7.60 (1H, dd), 7.54 (1H, d), 7.32 (1H, d), 7.24 (1H, t), 6.91 (1H, dd), 3.77 (3H, s), 3.39 (3H, s).

3.4. Compound D

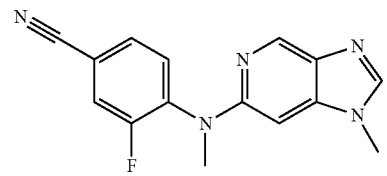 [SMILES: CN(c1cc2c(cn1)ncn2C)c1ccc(C#N)cc1F]

The synthesis of this compound was described in PCT Int. Appl. (2013) WO 2013117645. (Menet et al., 2013)

BIOLOGICAL EXAMPLES

Example 4

In Vitro Assays 4.1. JAK1 Inhibition Assay
4.1.1. JAK1 Assay polyGT Substrate

Recombinant human JAK1 catalytic domain (amino acids 850-1154; catalog number 08-144) was purchased from Carna Biosciences. 10 ng of JAK1 is incubated with 12.5 µg polyGT substrate (Sigma catalog number P0275) in kinase reaction buffer (15 mM Tris-HCl pH 7.5, 1 mM DTT, 0.01% Tween-20, 10 mM $MgCl_2$, 2 µM non-radioactive ATP, 0.25 µCi $^{33}$P-gamma-ATP (GE Healthcare, catalog number AH9968) final concentrations) with or without 5 µL containing test compound or vehicle (DMSO, 1% final concentration), in a total volume of 25 µL, in a polypropylene 96-well plate (Greiner, V-bottom). After 45 min at 30° C., reactions are stopped by adding of 25 µL/well of 150 mM phosphoric acid. All of the terminated kinase reaction is transferred to prewashed (75 mM phosphoric acid) 96 well filter plates (Perkin Elmer catalog number 6005177) using a cell harvester (Perkin Elmer). Plates are washed 6 times with 300 µL per well of a 75 mM phosphoric acid solution and the bottom of the plates is sealed. 40 µL/well of Microscint-20 is added, the top of the plates is sealed and readout is performed using the Topcount (Perkin Elmer). Kinase activity is calculated by subtracting counts per min (cpm) obtained in the presence of a positive control inhibitor (10 µM staurosporine) from cpm obtained in the presence of vehicle. The ability of a test compound to inhibit this activity is determined as:

$$\text{Percentage inhibition} = \frac{(RFU \text{ test compound} - RFU \text{ control})}{(RFU \text{ vehicle} - RFU \text{ control})} * 100$$

RFU test compound = RFU determined for sample with test compound present

RFU control = RFU determined for sample with positive control inhibitor

RFU vehicle = RFU determined in the presence of vehicle

Dose dilution series are prepared for the compounds enabling the testing of dose-response effects in the JAK1 assay and the calculation of the $IC_{50}$ for each compound. Each compound is routinely tested at concentration of 20 µM followed by a 1/3 serial dilution, 8 points (20 µM-6.67 µM-2.22 µM -740 nM-247 nM-82 nM-27 nM-9 nM) in a final concentration of 1% DMSO. When potency of compound series increased, more dilutions are prepared and/or the top concentration was lowered (e.g. 5 µM, 1 µM).

4.1.2. JAK1 Ulight-JAK1 Peptide Assay

Recombinant human JAK1 (catalytic domain, amino acids 866-1154; catalog number PV4774) was purchased from Invitrogen. 1 ng of JAK1 was incubated with 20 nM Ulight-JAK1 (tyr1023) peptide (Perkin Elmer catalog number TRF0121) in kinase reaction buffer (25 mM MOPS pH6.8, 0.01% Brij-35, 5 mM $MgCl_2$, 2 mM DTT, 7 µM ATP) with or without 4 µL containing test compound or vehicle (DMSO, 1% final concentration), in a total volume of 20 µL, in a white 384 Opti plate (Perkin Elmer, catalog number 6007290). After 60 min at room temperature, reactions were stopped by adding 20 µL/well of detection mixture (1× detection buffer (Perkin Elmer, catalog number CR97-100C), 0.5 nM Europium-anti-phosphotyrosine (PT66) (Perkin Elmer, catalog number AD0068), 10 mM EDTA). Readout is performed using the Envision with excitation at 320 nm and measuring emission at 615 nm (Perkin Elmer). Kinase activity was calculated by subtracting relative fluorescence units (RFU) obtained in the presence of a positive control inhibitor (10 µM staurosporine) from RFU obtained in the presence of vehicle. The ability of a test compound to inhibit this activity was determined as:

Percentage inhibition=((RFU determined for sample with test compound present−RFU determined for sample with positive control inhibitor) divided by (RFU determined in the presence of vehicle−RFU determined for sample with positive control inhibitor))*100.

Dose dilution series were prepared for the compounds enabling the testing of dose-response effects in the JAK1 assay and the calculation of the IC50 for the compound. Each compound is routinely tested at concentration of 20 µM followed by a 1/5 serial dilution, 10 points in a final concentration of 1% DMSO. When potency of compound series increases, more dilutions are prepared and/or the top concentration are lowered (e.g. 5 µM, 1 µM). The data are expressed as the average $IC_{50}$ from the assays±standard error of the mean.

TABLE V

JAK1 $IC_{50}$ Values of Illustrative Compounds of the invention

| Cpd# | JAK1 $IC_{50}$ |
|---|---|
| 1 | **** |
| 2 | **** |
| 3 | **** |
| 4 | **** |
| 5 | **** |
| 6 | **** |
| 7 | **** |
| 8 | **** |
| 9 | **** |
| 10 | **** |
| 11 | **** |
| 12 | **** |
| 13 | *** |
| 14 | **** |
| 15 | **** |
| 16 | **** |
| 17 | ** |
| 18 | **** |
| 19 | **** |
| 20 | **** |
| 21 | **** |
| 22 | **** |
| 23 | **** |
| 24 | **** |
| 25 | **** |
| 26 | **** |
| 27 | **** |
| 28 | *** |
| 29 | **** |
| 32 | *** |
| 33 | **** |
| 34 | ** |
| 35 | * |
| 36 | * |
| 37 | * |
| 38 | **** |

\* >500 nM
\*\* >100-500 nM
\*\*\* >50-100 nM
\*\*\*\* 0.1-50 nM

127

TABLE VI

JAK1 IC$_{50}$ Values of Comparative Compounds

| Cpd# | JAK1 IC$_{50}$ |
|---|---|
| A | * |
| B | * |
| C | * |
| D | * |

4.1.3. JAK1 Ki Determination Assay

For the determination of Ki, different amounts of compound are mixed with the enzyme and the enzymatic reaction is followed as a function of ATP concentration. The Ki is determined by means of double reciprocal plotting of Km vs compound concentration (Lineweaver-Burk plot). 1 ng of JAK1 (Invitrogen, PV4774) is used in the assay. The substrate was 50 nM Ulight-JAK-1 (Tyr1023) Peptide (Perkin Elmer, TRF0121) The reaction is performed in 25 mM MOPS pH 6.8, 0.01%, 2 mM DTT, 5 mM MgCl2 Brij-35 with varying concentrations of ATP and compound. Phosphorylated substrate is measured using an Eu-labeled anti-phosphotyrosine antibody PT66 (Perkin Elmer, AD0068) as described in 1.1.2. Readout is performed on the envision (Perkin Elmer) with excitation at 320 nm and emission followed at 615 nm and 665 nm.

4.2. JAK2 Inhibition Assay
4.2.1. JAK2 Assay polyGT Substrate

Recombinant human JAK2 catalytic domain (amino acids 808-1132; catalog number PV4210) was purchased from Invitrogen. 0.025 mU of JAK2 is incubated with 2.5 µg polyGT substrate (Sigma catalog number P0275) in kinase reaction buffer (5 mM MOPS pH 7.5, 9 mM MgAc, 0.3 mM EDTA, 0.06% Brij and 0.6 mM DTT, 1 µM non-radioactive ATP, 0.25 µCi $^{33}$P-gamma-ATP (GE Healthcare, catalog number AH9968) final concentrations) with or without 5 µL containing test compound or vehicle (DMSO, 1% final concentration), in a total volume of 25 µL, in a polypropylene 96-well plate (Greiner, V-bottom). After 90 min at 30° C., reactions are stopped by adding of 25 µL/well of 150 mM phosphoric acid. All of the terminated kinase reaction is transferred to prewashed (75 mM phosphoric acid) 96 well filter plates (Perkin Elmer catalog number 6005177) using a cell harvester (Perkin Elmer). Plates are washed 6 times with 300 µL per well of a 75 mM phosphoric acid solution and the bottom of the plates is sealed. 40 µL/well of Microscint-20 is added, the top of the plates is sealed and readout is performed using the Topcount (Perkin Elmer). Kinase activity is calculated by subtracting counts per min (cpm) obtained in the presence of a positive control inhibitor (10 µM staurosporine) from cpm obtained in the presence of vehicle. The ability of a test compound to inhibit this activity is determined as:

$$\text{Percentage inhibition} = \frac{(RFU \text{ test compound} - RFU \text{ control})}{(RFU \text{ vehicle} - RFU \text{ control})} * 100$$

RFU test compound = RFU determined for sample with test compound present

RFU control = RFU determined for sample with positive control inhibitor

RFU vehicle = RFU determined in the presence of vehicle

128

Dose dilution series are prepared for the compounds enabling the testing of dose-response effects in the JAK2 assay and the calculation of the IC$_{50}$ for each compound. Each compound is routinely tested at concentration of 20 µM followed by a 1/3 serial dilution, 8 points (20 µM-6.67 µM-2.22 µM-740 nM-247 nM-82 nM-27 nM-9 nM) in a final concentration of 1% DMSO. When potency of compound series increased, more dilutions are prepared and/or the top concentration is lowered (e.g. 5 µM, 1 µM).

4.2.2. JAK2 Ulight-JAK1 Peptide Assay

Recombinant human JAK2 (catalytic domain, amino acids 866-1154; catalog number PV4210) was purchased from Invitrogen. 0.0125 mU of JAK2 was incubated with 25 nM Ulight-JAK1 (tyr1023) peptide (Perkin Elmer catalog number TRF0121) in kinase reaction buffer (25 mM HEPES pH7.0, 0.01% Triton X-100, 7.5 mM MgCl$_2$, 2 mM DTT, 7.5 µM ATP) with or without 4 µL containing test compound or vehicle (DMSO, 1% final concentration), in a total volume of 20 µL, in a white 384 Opti plate (Perkin Elmer, catalog number 6007290). After 60 min at room temperature, reactions were stopped by adding 20 µL/well of detection mixture (1× detection buffer (Perkin Elmer, catalog number CR97-100C), 0.5 nM Europium-anti-phosphotyrosine (PT66) (Perkin Elmer, catalog number AD0068), 10 mM EDTA). Readout is performed using the Envision with excitation at 320 nm and measuring emission at 615 nm (Perkin Elmer). Kinase activity was calculated by subtracting relative fluorescence units (RFU) obtained in the presence of a positive control inhibitor (10 µM staurosporine) from RFU obtained in the presence of vehicle. The ability of a test compound to inhibit this activity was determined as:

Percentage inhibition=((RFU determined for sample with test compound present−RFU determined for sample with positive control inhibitor) divided by (RFU determined in the presence of vehicle−RFU determined for sample with positive control inhibitor))*100.

Dose dilution series are prepared for compound enabling the testing of dose-response effects in the JAK2 assay and the calculation of the IC$_{50}$ for the compound. Each compound is routinely tested at concentration of 20 µM followed by a 1/5 serial dilution, 10 points in a final concentration of 1% DMSO. When potency of compound series increases, more dilutions are prepared and/or the top concentration are lowered (e.g. 5 µM, 1 µM). The data are expressed as the average IC$_{50}$ from the assays±standard error of the mean.

The following compounds have been tested for their activity against JAK2 and the IC$_{50}$ values, as determined using the assays described herein, are given below in Table VII.

TABLE VII

JAK2 IC$_{50}$ Values of Illustrative Compounds of the invention

| Cpd# | JAK2 IC$_{50}$ |
|---|---|
| 1 | **** |
| 2 | **** |
| 3 | **** |
| 4 | **** |
| 5 | **** |
| 6 | **** |
| 7 | **** |
| 8 | **** |
| 9 | **** |
| 10 | **** |
| 11 | **** |
| 12 | *** |

TABLE VII-continued

JAK2 IC$_{50}$ Values of Illustrative Compounds of the invention

| Cpd# | JAK2 IC$_{50}$ |
|---|---|
| 13 | ** |
| 14 | *** |
| 15 | ** |
| 16 | **** |
| 17 | * |
| 18 | **** |
| 19 | **** |
| 20 | *** |
| 21 | **** |
| 22 | **** |
| 23 | *** |
| 24 | **** |
| 25 | **** |
| 26 | *** |
| 27 | ** |
| 28 | * |
| 29 | ** |
| 32 | *** |
| 33 | **** |
| 34 | * |
| 35 | * |
| 36 | * |
| 37 | * |
| 38 | ** |

\* >500 nM
\*\* >100-500 nM
\*\*\* >50-100 nM
\*\*\*\* 0.1-50 nM

TABLE VIII

JAK2 IC$_{50}$ Values of Comparative Compounds

| Cpd# | JAK2 IC$_{50}$ |
|---|---|
| A | * |
| B | * |
| C | * |
| D | * |

4.2.3. JAK2 Kd Determination Assay

JAK2 (Invitrogen, PV4210) is used at a final concentration of 5 nM. The binding experiment is performed in 50 mM Hepes pH 7.5, 0.01% Brij-35, 10 mM MgCl$_2$, 1 mM EGTA using 25 nM kinase tracer 236 (Invitrogen, PV5592) and 2 nM Eu-anti-GST (Invitrogen, PV5594) with varying compound concentrations. Detection of tracer is performed according to the manufacturer's procedure.

4.3. JAK3 Inhibition Assay
4.3.1. JAK3 Ulight-JAK1 Peptide Assay

Recombinant human JAK3 catalytic domain (amino acids 781-1124; catalog number PV3855) was purchased from Invitrogen. 0.5 ng JAK3 protein was incubated with 2.5 µg polyGT substrate (Sigma catalog number P0275) in kinase reaction buffer (25 mM Tris pH 7.5, 0.5 mM EGTA, 10 mM MgCl$_2$, 2.5 mM DTT, 0.5 mM Na$_3$VO$_4$, 5 mM b-glycerolphosphate, 0.01% Triton X-100, 1 µM non-radioactive ATP, 0.25 µCi $^{33}$P-gamma-ATP (GE Healthcare, catalog number AH9968) final concentrations) with or without 5 µL containing test compound or vehicle (DMSO, 1% final concentration), in a total volume of 25 µL, in a polypropylene 96-well plate (Greiner, V-bottom). After 45 min at 30° C., reactions were stopped by adding 25 µL/well of 150 mM phosphoric acid. All of the terminated kinase reaction was transferred to prewashed (75 mM phosphoric acid) 96 well filter plates (Perkin Elmer catalog number 6005177) using a cell harvester (Perkin Elmer). Plates were washed 6 times with 300 µL per well of a 75 mM phosphoric acid solution and the bottom of the plates was sealed. 40 µL/well of Microscint-20 was added, the top of the plates was sealed and readout was performed using the Topcount (Perkin Elmer). Kinase activity was calculated by subtracting counts per min (cpm) obtained in the presence of a positive control inhibitor (10 µM staurosporine) from cpm obtained in the presence of vehicle. The ability of a test compound to inhibit this activity was determined as:

$$\text{Percentage inhibition} = \frac{(RFU \text{ test compound} - RFU \text{ control})}{(RFU \text{ vehicle} - RFU \text{ control})} * 100$$

RFU test compound = RFU determined for sample with test compound present

RFU control = RFU determined for sample with positive control inhibitor

RFU vehicle = RFU determined in the presence of vehicle

Dose dilution series were prepared for the compounds enabling the testing of dose-response effects in the JAK3 assay and the calculation of the IC$_{50}$ for each compound. Each compound was routinely tested at concentration of 20 µM followed by a 1/5 serial dilution, 10 points in a final concentration of 1% DMSO. When potency of compound series increased, more dilutions were prepared and/or the top concentration was lowered (e.g. 5 µM, 1 µM).

The following compounds have been tested for their activity against JAK3 and the IC$_{50}$ values, as determined using the assays described herein, are given below in Table IX.

TABLE IX

JAK3 IC$_{50}$ Values of Illustrative Compounds of the invention

| Cpd# | JAK3 IC$_{50}$ |
|---|---|
| 1 | *** |
| 2 | **** |
| 3 | **** |
| 4 | ** |
| 5 | *** |
| 6 | * |
| 7 | **** |
| 8 | ** |
| 9 | ** |
| 10 | ** |
| 11 | ** |
| 12 | ** |
| 13 | * |
| 14 | ** |
| 15 | * |
| 16 | *** |
| 17 | * |
| 18 | ** |
| 19 | *** |
| 20 | * |
| 21 | *** |
| 22 | ** |
| 23 | * |
| 24 | ** |
| 25 | ** |
| 26 | ** |
| 27 | ** |
| 28 | * |
| 29 | * |
| 32 | * |
| 33 | ** |
| 34 | * |

TABLE IX-continued

JAK3 IC$_{50}$ Values of Illustrative Compounds of the invention

| Cpd# | JAK3 IC$_{50}$ |
|---|---|
| 35 | * |
| 36 | * |
| 37 | * |
| 38 | * |

\* >500 nM
\*\* >100-500 nM
\*\*\* >50-100 nM
\*\*\*\* 0.1-50 nM

TABLE X

JAK3 IC$_{50}$ Values of Comparative Compounds

| Cpd# | JAK3 IC$_{50}$ |
|---|---|
| C | * |
| D | * |

4.3.2. JAK3 Ki Determination Assay

For the determination of Ki, different amounts of compound are mixed with the enzyme and the enzymatic reaction is followed as a function of ATP concentration. The Ki is determined by means of double reciprocal plotting of Km vs compound concentration (Lineweaver-Burk plot). JAK3 (Carna Biosciences, 09CBS-0625B) is used at a final concentration of 10 ng/mL. The substrate is Poly(Glu,Tyr) sodium salt (4:1), MW 20 000-50 000 (Sigma, P0275) The reaction is performed in 25 mM Tris pH 7.5, 0.01% Triton X-100, 0.5 mM EGTA, 2.5 mM DTT, 0.5 mM Na$_3$VO$_4$, 5 mM b-glycerolphosphate, 10 mM MgCl$_2$ with varying concentrations of ATP and compound and stopped by addition of 150 mM phosphoric acid. Measurement of incorporated phosphate into the substrate polyGT is done by loading the samples on a filter plate (using a harvester, Perkin Elmer) and subsequent washing. Incorporated $^{33}$P in polyGT is measured in a Topcount scintillation counter after addition of scintillation liquid to the filter plates (Perkin Elmer).

4.4. TYK2 Inhibition Assay
4.4.1. TYK2 Ulight-JAK1 Peptide Assay

Recombinant human TYK2 catalytic domain (amino acids 871-1187; catalog number 08-147) was purchased from Carna biosciences. 5 ng of TYK2 was incubated with 12.5 µg polyGT substrate (Sigma catalog number P0275) in kinase reaction buffer (25 mM Hepes pH 7.2, 50 mM NaCl, 0.5 mM EDTA, 1 mM DTT, 5 mM MnCl$_2$, 10 mM MgCl$_2$, 0.1% Brij-35, 0.1 µM non-radioactive ATP, 0.125 µCi $^{33}$P-gamma-ATP (GE Healthcare, catalog number AH9968) final concentrations) with or without 5 µL containing test compound or vehicle (DMSO, 1% final concentration), in a total volume of 25 µL, in a polypropylene 96-well plate (Greiner, V-bottom). After 90 min at 30° C., reactions were stopped by adding 25 µL/well of 150 mM phosphoric acid. All of the terminated kinase reaction was transferred to prewashed (75 mM phosphoric acid) 96 well filter plates (Perkin Elmer catalog number 6005177) using a cell harvester (Perkin Elmer). Plates were washed 6 times with 300 µL per well of a 75 mM phosphoric acid solution and the bottom of the plates was sealed. 40 µL/well of Microscint-20 was added, the top of the plates was sealed and readout was performed using the Topcount (Perkin Elmer). Kinase activity was calculated by subtracting counts per min (cpm) obtained in the presence of a positive control inhibitor (10 µM staurosporine) from cpm obtained in the presence of vehicle. The ability of a test compound to inhibit this activity was determined as:

Percentage inhibition=((cpm determined for sample with test compound present–cpm determined for sample with positive control inhibitor) divided by (cpm determined in the presence of vehicle–cpm determined for sample with positive control inhibitor))*100.

Dose dilution series were prepared for the compounds enabling the testing of dose-response effects in the TYK2 assay and the calculation of the IC50 for each compound. Each compound was routinely tested at concentration of 20 µM followed by a 1/3 serial dilution, 8 points (20 µM-6.67 µM -2.22 µM-740 nM-247 nM-82 nM-27 nM-9 nM) in a final concentration of 1% DMSO. When potency of compound series increased, more dilutions were prepared and/or the top concentration was lowered (e.g. 5 µM, 1 µM).

The following compounds have been tested for their activity against TYK2; and the IC$_{50}$ values, as determined using the assays described herein, are given below in Table XI.

TABLE XI

TYK2 IC$_{50}$ Values of Illustrative Compounds of the invention

| Cpd# | TYK2 IC$_{50}$ |
|---|---|
| 1 | **** |
| 2 | **** |
| 3 | **** |
| 4 | **** |
| 5 | **** |
| 6 | **** |
| 7 | **** |
| 8 | **** |
| 9 | **** |
| 10 | **** |
| 11 | **** |
| 12 | **** |
| 13 | **** |
| 14 | **** |
| 15 | **** |
| 16 | **** |
| 17 | ** |
| 18 | **** |
| 19 | **** |
| 20 | **** |
| 21 | **** |
| 22 | **** |
| 23 | **** |
| 24 | **** |
| 25 | **** |
| 26 | **** |
| 27 | **** |
| 28 | ** |
| 29 | ** |
| 32 | *** |
| 33 | **** |
| 34 | * |
| 35 | * |
| 36 | * |
| 37 | * |
| 38 | ** |

\* >500 nM
\*\* >100-500 nM
\*\*\* >50-100 nM
\*\*\*\* 0.1-50 nM

TABLE XII

TYK2 IC$_{50}$ Values of Comparative Compounds

| Cpd# | TYK2 IC$_{50}$ |
|---|---|
| C | * |
| D | * |

4.4.2. TYK2 Kd Determination Assay

TYK2 (Carna Biosciences, 09CBS-0983D) is used at a final concentration of 5 nM. The binding experiment is performed in 50 mM Hepes pH 7.5, 0.01% Brij-35, 10 mM MgCl$_2$, 1 mM EGTA using 50 nM kinase tracer 236 (Invitrogen, PV5592) and 2 nM Eu-anti-GST (Invitrogen, PV5594) with varying compound concentrations. Detection of tracer is performed according to the manufacturers' procedure.

Example 5

Cellular Assays 5.1. JAK1, JAK2, and TYK2 Selectivity Cell Assays
5.1.1. Selective JAK1 Cell Assay, Activation of STAT1 by IFNα in PBMC Pheripheral blood mononuclear cells (PBMC) are isolated from buffy coats under sterile conditions by density gradient centrifugation using LymphoPrep™ medium (Axis-Shield) followed by 3 subsequent wash steps in PBS without Ca++ Mg++. PBMC are resuspended in plain RPMI 1640 medium containing 10% (v/v) heat inactivated FBS, 1% Pen-Strep (100 U/mL Penicilium and 100 μg/mL Streptomycin) and further cultured in a humidified incubator at 37° C. 5% CO$_2$.

PBMC are seeded in 24 well plates at 5.0 10$^{06}$ cells/well in a volume of 200 μL RPMI 1640 (Invitrogen) containing 10% (v/v) FBS and 1% Pen-Strep (Invitrogen).

PBMC are treated with test compound for 30 min at 37° C. 5% CO$_2$. 25 μL of 10× concentrated compound dilution is added to the medium. After 30 min of test compound/vehicle pre-treatment, PBMC are stimulated for 30 min at 37° C. 5% CO$_2$ with recombinant human IFNα (PeproTech) at final concentration of 100 ng/mL by addition of 25 μL (10× concentrated) cytokine trigger to obtain a final volume of 250 μL per well.

All compounds are tested in single starting from 20 μM followed by a 1/3 serial dilution, 8 doses in total (20 μM, 6.6 μM, 2.2 μM, 0.74 μM, 0.25 μM, 0.082 μM, 0.027 μM and 0.009 μM) in a final concentration of 0.2% DMSO.

After 30 min of cytokine stimulation, 250 μL of cell suspension is transferred to a 96-well V-bottom plate, centrifugated for 5 min at 1000 rpm to pellet cells, followed by removal of supernatant. The cell pellet is reconstituted in 100 μL 1× Lysis buffer supplemented with EDTA-free Protease Inhibitor Cocktail (Roche Applied Sciences, Product Number 11836170001) followed by sample freezing and storage at −80° C. 1× Lysis buffer is provided with the Phospho-STAT1 Elisa Kit and contains phosphatase inhibitors. Endogenous levels of phosphorylated STAT1 are quantified using a 96-well PathScan® Phospho-STAT1 (Tyr701) Sandwich ELISA Kit (Cell Signaling, Product Number #7234) according to manufacturer's instructions.

HRP activity (HRP is conjugated to the secondary antibody) is measured by addition of 100 μL of freshly prepared luminol substrate (BM Chemiluminescence ELISA Substrate (POD), Roche, Product Number 11582950001), incubation for 5 min at room temperature in the dark and measured in a Thermo Scientific Luminoskan Ascent Microplate Luminometer (integration time of 200 msec).

5.1.2. Selective JAK2 Cell Assay, Activation of STAT5 by GM-CSF in PBMC

Pheripheral blood mononuclear cells (PBMC) are isolated from buffy coats under sterile conditions by density gradient centrifugation using LymphoPrep™ medium (Axis-Shield) followed by 3 subsequent wash steps in PBS without Ca++ Mg++. PBMC are resuspended in plain RPMI 1640 medium containing 10% (v/v) heat inactivated FBS, 1% Pen-Strep (100 U/mL Penicilium and 100 μg/mL Streptomycin) and further cultured in a humidified incubator at 37° C. 5% CO$_2$.

PBMC are seeded in 24 well plates at 5.0E06 cells/well in a volume of 200 μL RPMI 1640 (Invitrogen) containing 10% (v/v) FBS and 1% Pen-Strep (Invitrogen).

PBMC are treated with test compound by adding 25 μL of 10× concentrated compound dilution to the medium and incubated for 30 min at 37° C. 5% CO$_2$. Subsequently, PBMC are stimulated with recombinant human GM-CSF (PeproTech) at final concentration of 0.5 ng/mL by addition of 25 μL (10× concentrated) cytokine trigger per well to obtain a final volume of 250 μL. Cells are triggered for 30 min at 37° C. 5% CO$_2$.

All compounds are tested in single starting from 20 μM followed by a 1/3 serial dilution, 8 doses in total (20 μM, 6.6 μM, 2.2 μM, 0.74 μM, 0.25 μM, 0.082 μM, 0.027 μM and 0.009 μM) in a final concentration of 0.2% DMSO.

After 30 min of cytokine stimulation 250 μL of cell suspension is transferred to a 96-well V-bottom plate following centrifugation for 5 min at 1000 rpm to pellet cells. Cell supernatant is removed and pellet is reconstituted in 100 μL 1× Lysis buffer supplemented with EDTA-free Protease Inhibitor Cocktail (Roche Applied Sciences, Product Number 11836170001) followed by sample freezing and strorage at −80° C. 1× Lysis buffer is provided with the Phospho-STAT5 Elisa Kit and contains phosphatase inhibitors. Endogenous levels of phosphorylated STAT5 are quantified using a 96-well PathScan® Phospho-STAT5 (Tyr694) Sandwich ELISA Kit (Cell Signaling, Product Number #7113) according to manufacturer's instructions.

HRP activity (HRP is conjugated to the secondary antibody) is measured by addition of 100 μL of freshly prepared luminol substrate (BM Chemiluminescence ELISA Substrate (POD), Roche, Product Number 11582950001), incubation for 5 min at room temperature in the dark and measured in a Thermo Scientific Luminoskan Ascent Microplate Luminometer (integration time of 200 msec).

5.1.3. Selective TYK2 Cell Assay, Activation of STAT4 by IL-12 in NK-92 Cells

NK-92 cells (human malignant non-Hodgkin's lymphoma, interleukin-2 (IL-2) dependent Natural Killer Cell line, ATCC #CRL-2407).

NK-92 cells are maintained in Minimum Essential Medium (MEM) Alpha medium w/o ribonucleosides and desoxyribonucleosides, 2 mM L-glutamine, 2.2 g/L sodium bicarbonate (Invitrogen, Product Number 22561-021) containing 0.2 mM myo-inositol, 0.1 mM 2-mercapto-EtOH, 0.1 mM folic acid, 12.5% heat inactivated horse serum (Invitrogen, Product Number 26050-088), 12.5% heat inactivated FBS, 1% Pen-Strep (100 U/mL Penicilium and 100 μg/mL Streptomycin) and 10 ng/mL recombinant human IL-2 (R&D Systems). IL-2 is added freshly to the medium with each medium refreshment step. Cells are cultured in a humidified incubator at 37° C. 5% CO$_2$.

A subcultured fraction of NK-92 cells are washed once in plain medium without rhIL-2 and seeded in 24-well plates at 0.5E06 cells/well in a volume of 400 μL of plain Alpha MEM medium w/o rhIL-2 containing 0.2 mM myo-inositol, 0.1 mM 2-mercaptoethanol, 0.1 mM folic acid, 12.5% heat inactivated horse serum (Invitrogen, Product Number 26050-088), 12.5% heat inactivated FBS, 1% Pen-Strep (Invitrogen).

NK-92 cells are treated with test compounds for 30 min prior to rhIL-12 stimulation by adding 50 μL of 10× concentrated compound dilution and incubation at 37° C. 5% $CO_2$. After 30 min of compound/vehicle pre-treatment, cells are stimulated with recombinant human IL-12 (R&D Systems, Product Number 219-IL) at final concentration of 25 ng/mL by addition of 50 μL (10× concentrated) cytokine trigger to obtain a final volume of 500 μL per well. NK-92 cells are triggered with rhIL-12 for 30 min at 37° C. 5% $CO_2$.

All compounds are tested in single starting from 20 μM followed by a 1/3 serial dilution, 8 doses in total (20 μM, 6.6 μM, 2.2 μM, 0.74 μM, 0.25 μM, 0.082 μM, 0.027 μM and 0.009 μM) in a final concentration of 0.2% DMSO.

The levels of phospho-STAT4 in rhIL-12 stimulated NK-92 cells are quantified using a flow cytometric analysis on a Gallios™ flow cytometer (Beckman Coulter). After 30 min of cytokine stimulation the cells are fixed by adding 500 μL of pre-warmed BD Cytofix Fixation Buffer (BD Phosflow™, Product Number 554655) immediately to the wells (fix cells immediately in order to maintain phosphorylation state, rather than spinning down the cells, it is recommended to fix the cells by adding an equal volume of pre-warmed BD Cytofix Buffer to the cell suspension). Cells are incubated for 10 min at 37° C. The fixed cell fraction is resuspended (1 mL) and transferred to FACS tubes followed by a centrifugation step (300×g, 10 min) and removal of the supernatant. The cell pellet is mixed (vortex) and the cells are permeabilized by adding 1 mL of BD Phosflow Perm Buffer III (BD Phosflow™ Product Number 558050) followed by incubation on ice for 30 min. After the permeabilization step, the cells are washed twice with BD Pharmingen™ Stain Buffer (BD Pharmingen, Product Number 554656) with intermediate centrifugation at 300×g for 10 min and removal of the supernatant. The pellet (0.5E06 cells) is resuspended in 100 μL of BD Pharmingen™ Stain Buffer and stained by mixing 20 μL of PE Mouse Anti-STAT4 (pY693) to the cells (BD Phosflow™, PE Mouse Anti-STAT4 (pY693), Product Number 558249), then incubated for 30 min at room temperature in the dark. The stained cells are washed once with 2 mL of BD Pharmingen™ Stain Buffer and resuspended in 500 μL of BD Pharmingen™ Stain Buffer and analyzed on a Gallios™ flow cytometer (Beckman Coulter).

For all analyses, dead cells and debris are excluded by forward scatter (FSC) and side scatter (SSC). Changes in phosphorylation of STAT4 proteins following cytokine stimulation are approximated by calculating the X-median or X-mean fluorescence intensity (MFI) per cell on 100% of the gated fraction for all cytokine stimulated, test compound and unstimulated samples.

5.1.4. Results JAK1, JAK2 and TYK2 Assays:

Unstimulated samples (no trigger/vehicle (0.2% DMSO) are used as a positive control (100% inhibition). As a negative control (0% inhibition), the stimulated samples (trigger/vehicle (0.2% DMSO)) are used. The positive and negative controls are used to calculate Z' and 'percent inhibition (PIN)' values.

Percentage inhibition is calculated from $$\text{Percentage inhibition} = \frac{RCLU(\text{trigger/veh}) - RCLU(\text{test compound})}{RCLU(\text{trigger/veh}) - RCLU(\text{no trigger/veh})} * 100$$

wherein
RCLU(trigger/veh): Relative Chemilumescent signal determined in presence of vehicle and trigger
RCLU(test compound): Relative Chemiluminescent signal determined in presence of test compounds)
RCLU(no trigger/veh): Relative Chemiluminescent signal determined in presence of vehicle without trigger.

In case the readout signal is expressed as X-mean values (flow cytometric analysis of pSTAT4 levels in cytokine stimulated NK-92 cells), the RCLU is replaced by X-mean value.

PIN values are plotted for compounds tested in dose-response and $EC_{50}$ values are derived using GraphPad Prism Software applying non-linear regression (sigmoidal) curve fitting.

5.2. JAK1 Mutations in Lung Cancer and Hepatocellular Carcinoma Cell Lines Assay.

5.2.1. JAK1 Mutation Induced Constitutive Signaling

Cancer cell lines with and without JAK1 mutations (Table I—Lung cancer cell lines) are cultured with or without serum for 4-6 h, stimulated or not with a cytokine cocktail (INFγ, IL2, IL4 and IL6) for 5, 10, 30 and 45 min. The phosphorylation of JAK1, STAT1, STAT3 and STAT5 are evaluated by immunoblot (Cell Signaling antibodies).

5.2.2. Targeting JAK1 Mutants Using JAK Inhibitors 5.2.2.1. JAK-STAT Pathway Phosphorylation:

Cancer cell lines with and without JAK1 mutations are cultured in the presence or absence of different concentrations of JAK inhibitors. Cells are analyzed at 24 and 48 h for effective JAK-STAT pathway inhibition by immunoblot.

TABLE XIII

Table I: Illustrative lung cancer cell lines

| Gene | Cell line | Tissue | Change | Protein domain | Present in primary tissue |
|---|---|---|---|---|---|
| JAK1 | NCIH1915 | Lung | I62V | FERM | — |
| JAK1 | SQ1 | Lung | N226S | FERM | — |
| JAK1 | HCC4006 | Lung | S383G | FERM | — |
| JAK1 | NCIH2066 | Lung | L423V | Interdomain (FERM and SH2) | — |
| JAK1 | NCIH1793 | Lung | H525Y | SH2 | — |
| JAK1 | HCC95 | Lung | N833S | Protein kinase 1 | Yes |
| JAK1 | VMRCLCD | Lung | E223* | — | — |
| JAK1 | NCIH1563 | Lung | Q161* | — | — |
| WT JAK1 | A549 | Lung | — | — | — |
| JAK1 −/− | U4C | Fibrosarcoma | — | — | — |

*truncation 5.2.2.2. Cell Viability 2D-assay: Cancer cell lines with and without JAK1 mutations are cultured in the presence or absence of increasing concentrations of JAK inhibitors. After 48-72 h, cell viability is measured using the Cell Titer-Glo Luminescent cell viability assay (Promega) or MTT assay. Alternatively, cancer cell lines at different culture time points with a fix concentration of JAK inhibitor are analyzed for cell viability using the Cell Titer-Glo Luminescent cell viability assay (Promega) or MTT assay.

3D-assay: Cancer cell lines with and without JAK1 mutations are seeded in semi-solid agar medium. Formation of multi-cellular colonies is measured by determining cell viability using a fluorescent dye at different culture time points. Addition of potential inhibitors after cell seeding allows for the analyses of anti-tumorigenic effects.

5.2.3. Investigating Human JAK1 Mutations in Murine Ba/F3 Cells (As illustrated in: Kan et al., 2013; Staerk et al., 2005; Zenatti et al., 2011)

Construction of JAK1 expression vectors: Wild type and mutant human JAK1 sequences are cloned into retroviral vectors and clones verified by sequencing.

Retroviral infection of Ba/F3 cells: Ba/F3 cells are infected with retroviral supernatants produced in 293T cells.

Ba/F3 cells expressing human WT or mutated JAK1 are cultured with or without IL-3 for 4 h and phosphorylation of the JAK-STAT pathway evaluated by immunoblot.

The transforming potential of JAK1 mutations is assessed by measuring the ability of each mutation to induce autonomous growth when expressed in cytokine-dependent Ba/F3 cells. Cell growth is assessed in the absence of the cytokine IL-3.

Mutant JAK1 transduced Ba/F3 cell lines are assessed for their sensitivity to the JAK inhibitors by culturing them in the presence or absence of increasing concentrations of JAK inhibitors. After 48-72 h, cell viability is measured using the Cell Titer-Glo Luminescent cell viability assay (Promega) or MTT assay. Alternatively, cancer cell lines at different culture time points with a fix concentration of JAK inhibitor are analyzed for cell viability using the Cell Titer-Glo Luminescent cell viability assay (Promega) or MTT assay.

5.2.4. In Vivo Tumorigenic Potential of JAK1 Mutations 5.2.4.1. Xenograft Model:

Mutant JAK1 expressing cells are injected subcutaneously in CD1 nu/nu mice or Rag1−/− mice and evaluated for tumor progression. Subcutaneous tumor volume growth curves are established. The transplantability of primary tumors into secondary recipient animals is determined.

5.2.4.2. PDX Model.

Patient-Derived Xenografts (PDXs) are based on the transfer of primary tumors (containing JAK1 mutations) directly from the patient into an immunodeficient mouse. To accomplish this, patient tumors must be obtained fresh from surgery, at which point they are mechanically or chemically digested, with a small portion saved as a primary stock and established in a NOD-SCID mouse. PDX models are maintained by passaging cells directly from mouse to mouse once the tumor burden becomes too high. Tumors can be engrafted heterotopically (implanting tumors into the subcutaneous flank of a mouse) or orthotopically (direct implantation to the mouse organ of choice).

The phosphorylation of JAK1, STAT1, STAT3 and STAT5 in primary and secondary tumors are evaluated by immunoblot.

5.3. PBL Proliferation Assay

Human peripheral blood lymphocytes (PBL) are stimulated with IL-2 and proliferation is measured using a BrdU incorporation assay. The PBL are first stimulated for 72 h with PHA to induce IL-2 receptor, then they are fasted for 24 h to stop cell proliferation followed by IL-2 stimulation for another 72 h (including 24 h BrdU labeling). Cells are preincubated with test compounds 1 h before IL-2 addition. Cells are cultured in RPMI 1640 containing 10% (v/v) FBS.

5.4. Human Whole Blood Assay (hWBA)

5.4.1. Protocol 1

5.4.1.1. IL-6 Stimulation Protocol

A flow cytometry analysis is performed to establish JAK1 over JAK2 compound selectivity ex vivo using human whole blood. Therefore, blood is taken from human volunteers who gave informed consent. Blood is then equilibrated for 30 min at 37° C. under gentle rocking, then aliquoted in Eppendorf tubes. Compound is added at different concentrations and incubated at 37° C. for 30 min under gentle rocking and subsequently stimulated for 20 min at 37° C. under gentle rocking with interleukin 6 (IL-6) for JAK1-dependent pathway stimulation or GM-CSF for JAK2-dependent pathway stimulation. Phospho-STAT1 and phospho-STAT5 are then evaluated using FACS analysis.

5.4.1.2. Phospho-STAT1 Assays 5.4.1.2.1. Preparation of Reagents

The 5× Lyse/Fix buffer (BD PhosFlow, Cat. no 558049) is diluted 5-fold with distilled water and pre-warmed at 37° C. The remaining diluted Lyse/Fix buffer is discarded.

10 μg rhIL-6 (R&D Systems, Cat no 206-IL) is dissolved in 1 mL of PBS 0.1% BSA to obtain a 10 μg/mL stock solution. The stock solution is aliquoted and stored at −80° C.

A 3-fold dilution series of the compound is prepared in DMSO (10 mM stock solution). Control-treated samples received DMSO instead of compound. All samples are incubated with a 1% final DMSO concentration.

5.4.1.2.2. Incubation of Blood with Compound and Stimulation with IL-6

Human blood is collected in heparinized tubes. The blood is divided in aliquots of 148.5 μL. Then, 1.5 μL of the test compound dilution is added to each blood aliquot and the blood samples are incubated for 30 min at 37° C. under gentle rocking. One and a half microliter of 10-fold diluted IL-6 stock solution is added to the blood samples (final concentration 10 ng/mL) and samples are incubated at 37° C. for 20 min under gentle rocking.

5.4.1.2.3. White Blood Cell Preparation

At the end of the stimulation period, 3 mL of 1× pre-warmed Lyse/Fix buffer is immediately added to the blood samples, vortexed briefly and incubated for 15 min at 37° C. in a water bath in order to lyse red blood cells and fix leukocytes.

Tubes are centrifuged for 5 min at 400×g at 4° C. The cell pellet is washed with 3 mL of cold 1×PBS, and after centrifugation the cell pellet is resuspended in 100 μL of ice-cold 1×PBS and 900 μL ice-cold 100% MeOH is added. Cells are then incubated at 4° C. for 30 min for permeabilization.

Permeabilized cells are then washed with 1×PBS containing 3% BSA and finally resuspended in 80 μL of 1×PBX containing 3% BSA.

5.4.1.2.4. Cell Labeling with Anti Phospho-STAT1 and Anti-CD4 Antibodies

20 μL of PE mouse anti-STAT1 (pY701) or PE mouse IgG2aκ isotype control antibody (BD Biosciences, Cat. no 612564 and 559319, respectively) and FITC-conjugated anti-CD4 antibody or control FITC-conjugated isotype antibody are added and mixed, then incubated for 30 min at 4° C., in the dark.

Cells are then washed once with 1×PBS and analyzed on a FACSCanto II flow cytometer (BD Biosciences).

5.4.1.2.5. Fluorescence Analysis on FACSCanto II 50,000 total events are counted and Phospho-STAT1 positive cells are measured after gating on CD4$^+$ cells, in the lymphocyte gate. Data are analyzed using the FACSDiva software and the percentage of inhibition of IL-6 stimulation calculated from the percentage of positive cells for phospho-STAT1 on CD4+ cells.

5.4.1.3. Phospho-STAT5 Assay

Preparation of Reagents

The 5× Lyse/Fix buffer (BD PhosFlow, Cat. no 558049) is diluted 5-fold with distilled water and pre-warmed at 37° C. Remaining diluted Lyse/Fix buffer is discarded.

10 μg rhGM-CSF (AbCys S.A., Cat no P300-03) is dissolved in 100 μL of PBS 0.1% BSA to obtain a 100 μg/mL stock solution. The stock solution is stored aliquoted at −80° C.

A 3-fold dilution series of the compound is prepared in DMSO (10 mM stock solution). Control-treated samples receive DMSO without the test compound. All samples are incubated with a 1% final DMSO concentration.

5.4.1.3.1. Incubation of Blood with Compound and Stimulation with GM-CSF

Human blood is collected in heparinized tubes. The blood is divided in aliquots of 148.5 μL. Then, 1.5 μL of compound dilution is added to each aliquot and the blood samples are incubated for 30 min at 37° C. under gentle rocking. A 5,000-fold dilution of the GM-CSF stock solution (1.5 μL) is added to the blood samples (final concentration 20 pg/mL) and samples are incubated at 37° C. for 20 min under gentle rocking.

5.4.1.3.2. White Blood Cell Preparation

At the end of the stimulation period, 3 mL of 1× pre-warmed Lyse/Fix buffer is immediately added to the blood samples, vortexed briefly and incubated for 15 min at 37° C. in a water bath in order to lyse red blood cells and fix leukocytes Tubes are centrifuged for 5 min at 400×g at 4° C. The cell pellet is washed with 3 mL of cold 1×PBS, and after centrifugation the cell pellet is resuspended in 100 μL of ice-cold 1×PBS and 900 μL ice-cold 100% MeOH is added. Cells are then incubated at 4° C. for 30 min for permeabilization. 5.4.1.3.3. Cell labeling with anti phospho-STAT5 and anti-CD33 antibodies 20 μL of PE mouse anti-STAT5 (pY694) or PE mouse IgG1κ isotype control antibody (BD Biosciences, Cat. no 612567 and 554680, respectively) and APC mouse anti CD33 antibody (BD Biosciences #345800) or control APC mouse IgG1 isotype antibody (BD Biosciences #345818) are added, mixed then incubated for 30 min at 4° C., in the dark.

Cells are then washed once with 1×PBS and analyzed on a FACSCanto II flow cytometer (BD Biosciences).

5.4.1.3.4. Fluorescence Analysis on FACSCanto II 50,000 total events are counted and Phospho-STAT5 positive cells are measured after gating on CD33$^+$ cells. Data are analyzed using the FACSDiva software and correspond to the percentage of inhibition of GM-CSF stimulation calculated from the percentage of positive cells for phosphor-STAT5 on CD33$^+$ cells.

5.5. Protocol 2

5.5.1. Stimulation Protocol

A flow cytometry analysis is performed to establish JAK1 over JAK2 compound selectivity ex vivo using human whole blood. Therefore, blood is taken from human volunteers who gave informed consent. Blood is then equilibrated for 30 min at 37° C. under gentle rocking, then aliquoted in Eppendorf tubes. Compound is added at different concentrations and incubated at 37° C. for 30 min under gentle rocking and subsequently stimulated for 20 min at 37° C. under gentle rocking with interleukin 6 (IL-6) for JAK1-dependent pathway stimulation, Interferon alpha (IFNα) for JAK1/TYK2 pathway stimulation, interleukin 2 (IL-2) for JAK1/JAK3 pathway stimulation or GM-CSF for JAK2-dependent pathway stimulation. Phospho-STAT1 (for IL-6- and IFNα-stimulated cells) and phospho-STAT5 (for IL-2- and GM-CSF-stimulated cells) levels are then evaluated using FACS analysis.

5.5.2. Phospho-STAT Assays

5.5.2.1. Preparation of Reagents

The 5× Lyse/Fix buffer (BD PhosFlow, Cat. no 558049) is diluted 5-fold with distilled water and pre-warmed at 37° C. The remaining diluted Lyse/Fix buffer is discarded.

10 μg rhIL-6 (R&D Systems, Cat no 206-IL) is dissolved in 1 mL of PBS+0.1% BSA to obtain a 10 μg/mL stock solution. The stock solution is aliquoted and stored at −80° C.

10 μg rhIL-2 (R&D Systems, Cat no 202-IL) is dissolved in 1 mL of PBS+0.1% BSA to obtain a 10 μg/mL stock solution. The stock solution is aliquoted and stored at −80° C.

5 μg rhGM-CSF (AbCys S.A., Cat no P300-03) is dissolved in 12.5 mL of PBS+0.1% BSA to obtain a 400 ng/mL stock solution. The stock solution is stored aliquoted at −80° C.

A 3-fold dilution series of the compound is prepared in DMSO (10 mM stock solution). Control-treated samples received DMSO instead of compound. All samples are incubated with a 1% final DMSO concentration.

5.5.2.2. Incubation of Blood with Compound and Stimulation with Triggers

Human blood is collected in heparinized tubes. The blood is divided in aliquots of 148.5 μL. Then, 1.5 μL of the test compound dilution is added to each blood aliquot and the blood samples are incubated for 30 min at 37° C. under gentle rocking. One and a half microliter of 10-fold diluted IL-6 stock solution, 1.5 μL of uIFNα (PBL Biomedical, Cat no 11200-1) stock solution, 1.5 μL of 25-fold diluted IL-2 stock solution or 1.5 μL of 200-fold dilution of the GM-CSF stock solution is added to the blood samples and samples are incubated at 37° C. for 20 min under gentle rocking.

5.5.2.3. White Blood Cell Preparation

At the end of the stimulation period, 3 mL of 1× pre-warmed Lyse/Fix buffer is immediately added to the blood samples, vortexed briefly and incubated for 15 min at 37° C. in a water bath in order to lyse red blood cells and fix leukocytes.

Tubes are centrifuged for 5 min at 400×g at 4° C. The cell pellet is washed with 3 mL of cold 1×PBS, and after centrifugation the cell pellet is resuspended in 100 μL of ice-cold 1×PBS and 900 μL ice-cold 100% MeOH is added. Cells are then incubated at 4° C. for 30 min for permeabilization.

Permeabilized cells are then washed with 1×PBS containing 3% BSA and finally resuspended in 80 μL of 1×PBX containing 3% BSA.

5.5.2.4. Cell Labeling

20 μL of PE mouse anti-STAT1 (pY701) or PE mouse IgG2aκ isotype control antibody (BD Biosciences, Cat. no 612564 and 559319, respectively) and APC-conjugated anti-CD4 antibody or control APC-conjugated isotype antibody (BD Biosciences, Cat. no 555349 and 555751, respectively) are added to IL-6- and IFNα-stimulated tubes and mixed, then incubated for 20 min at 4° C., in the dark.

20 μL of PE mouse anti-STAT5 (pY694) or PE mouse IgG1κ isotype control antibody (BD Biosciences, Cat. no 612567 and 554680, respectively) and APC-conjugated anti-CD4 antibody or control APC-conjugated isotype antibody (BD Biosciences, Cat. no 555349 and 555751, respectively) are added to IL-2-stimulated tubes, mixed then incubated for 20 min at 4° C., in the dark.

20 μL of PE mouse anti-STAT5 (pY694) or PE mouse IgG1κ isotype control antibody (BD Biosciences, Cat. no 612567 and 554680, respectively) and APC mouse anti CD33 antibody (BD Biosciences #345800) or control APC mouse IgG1 isotype antibody (BD Biosciences Cat. no 345818) are added to GM-CSF-stimulated tubes, mixed then incubated for 20 min at 4° C., in the dark.

Cells are then washed once with 1×PBS and analyzed on a FACSCanto II flow cytometer (BD Biosciences).

5.5.2.5. Fluorescence Analysis on FACSCanto II 50,000 total events are counted and Phospho-STAT1 positive cells are measured after gating on CD4+ cells, in the lymphocyte gate for IL-6- and IFNα-stimulated cells. Phospho-STAT5 positive cells are measured after gating on CD4+ cells, in the lymphocyte gate for IL-2-stimulated cells. Phospho-STAT5 positive cells are measured after gating on CD33+ cells. Data are analyzed using the FACSDiva software and the percentage of inhibition of IL-6 or IFNα stimulation calculated is from the percentage of positive cells for phospho-STAT1 on CD4+ cells. For the IL-2 stimulated cells, data are analyzed using the FACSDiva software and the percentage of inhibition of IL-2 stimulation is calculated from the percentage of positive cells for phospho-STAT1 on CD4+ cells. For the GM-CSF stimulated cells, the percentage of inhibition of GM-CSF stimulation is calculated from the percentage of positive cells for phosphor-STAT5 on CD33+ cells.

Example 6

In Vivo Models 6.1. CIA Model
6.1.1. Materials

Completed Freund's adjuvant (CFA) and incomplete Freund's adjuvant (IFA) were purchased from Difco. Bovine collagen type II (CII), lipopolysaccharide (LPS), and Enbrel was obtained from Chondrex (Isle d'Abeau, France); Sigma (P4252, L'Isle d'Abeau, France), Whyett (25 mg injectable syringe, France) Acros Organics (Palo Alto, Calif.), respectively. All other reagents used were of reagent grade and all solvents were of analytical grade.

6.1.2. Animals

Dark Agouti rats (male, 7-8 weeks old) were obtained from Harlan Laboratories (Maison-Alfort, France). Rats were kept on a 12 h light/dark cycle (0700-1900). Temperature was maintained at 22° C., and food and water were provided ad libitum.

6.1.3. Collagen Induced Arthritis (CIA)

One day before the experiment, CII solution (2 mg/mL) was prepared with 0.05 M acetic acid and stored at 4° C. Just before the immunization, equal volumes of adjuvant (IFA) and CII were mixed by a homogenizer in a pre-cooled glass bottle in an ice water bath. Extra adjuvant and prolonged homogenization may be required if an emulsion is not formed. 0.2 mL of the emulsion was injected intradermally at the base of the tail of each rat on day 1, a second booster intradermal injection (CII solution at 2 mg/mL in CFA 0.1 mL saline) was performed on day 9. This immunization method was modified from published methods (Jou et al., 2005; Sims et al., 2004).

6.1.4. Study Design

The therapeutic effects of the compounds were tested in the rat CIA model. Rats were randomly divided into equal groups and each group contained 10 rats. All rats were immunized on day 1 and boosted on day 9. Therapeutic dosing lasted from day 16 to day 30. The negative control group was treated with vehicle (MC 0.5%) and the positive control group with Enbrel (10 mg/kg, 3× week. s.c.). A compound of interest was typically tested at 3 doses, e.g. 3, 10, 30 mg/kg, p.o.

6.1.5. Clinical Assessment of Arthritis

Arthritis is scored according to the method of (Khachigian, 2006; Lin et al., 2007; Nishida et al., 2004). The swelling of each of the four paws is ranked with the arthritic score as follows: 0-no symptoms; 1-mild, but definite redness and swelling of one type of joint such as the ankle or wrist, or apparent redness and swelling limited to individual digits, regardless of the number of affected digits; 2-moderate redness and swelling of two or more types of joints; 3-severe redness and swelling of the entire paw including digits; 4-maximally inflamed limb with involvement of multiple joints (maximum cumulative clinical arthritis score 16 per animal) (Nishida et al., 2004).

To permit the meta-analysis of multiple studies the clinical score values were normalised as follows:

AUC of clinical score (AUC score): The area under the curve (AUC) from day 1 to day 14 was calculated for each individual rat. The AUC of each animal was divided by the average AUC obtained for the vehicle in the study from which the data on that animal was obtained and multiplied by 100 (i.e. the AUC was expressed as a percentage of the average vehicle AUC per study).

Clinical score increase from day 1 to day 14 (End point score): The clinical score difference for each animal was divided by the average clinical score difference obtained for the vehicle in the study from which the data on that animal was obtained and multiplied by 100 (i.e. the difference was expressed as a percentage of the average clinical score difference for the vehicle per study).

6.1.6. Change in Body Weight (%) after Onset of Arthritis

Clinically, body weight loss is associated with arthritis (Rall and Roubenoff, 2004; Shelton et al., 2005; Walsmith et al., 2004). Hence, changes in body weight after onset of arthritis can be used as a non-specific endpoint to evaluate the effect of therapeutics in the rat model. The change in body weight (%) after onset of arthritis was calculated as follows:

$$\text{Mice:} \frac{\text{Body Weight}_{(week6)} - \text{Body Weight}_{(week5)}}{\text{Body Weight}_{(week5)}} \times 100\%$$

$$\text{Rats:} \frac{\text{Body Weight}_{(week4)} - \text{Body Weight}_{(week3)}}{\text{Body Weight}_{(week3)}} \times 100\%$$

6.1.7. Radiology

X-ray photos were taken of the hind paws of each individual animal A random blind identity number was assigned to each of the photos, and the severity of bone erosion was ranked by two independent scorers with the radiological Larsen's score system as follows: 0—normal with intact bony outlines and normal joint space; 1—slight abnormality with any one or two of the exterior metatarsal bones showing slight bone erosion; 2—definite early abnormality with any 3 to 5 of the exterior metatarsal bones showing bone erosion; 3—medium destructive abnormality with all the exterior metatarsal bones as well as any one or two of the interior metatarsal bones showing definite bone erosions; 4—severe destructive abnormality with all the metatarsal bones showing definite bone erosion and at least one of the inner metatarsal joints completely eroded leaving some bony joint outlines partly preserved; 5—mutilating abnormality without bony outlines. This scoring system is a modification from (Bush et al., 2002; Jou et al., 2005; Salvemini et al., 2001; Sims et al., 2004).

6.1.8. Histology

After radiological analysis, the hind paws of mice were fixed in 10% phosphate-buffered formalin (pH 7.4), decalcified with rapid bone decalcifiant for fine histology (Laboratories Eurobio) and embedded in paraffin. To ensure extensive evaluation of the arthritic joints, at least four serial sections (5 μm thick) were cut and each series of sections were 100 μm in between. The sections were stained with hematoxylin and eosin (H&E). Histologic examinations for synovial inflammation and bone and cartilage damage were performed double blind. In each paw, four parameters were assessed using a four-point scale. The parameters were cell infiltration, pannus severity, cartilage erosion and bone erosion. Scoring was performed according as follows: 1—normal, 2—mild, 3—moderate, 4—marked. These four scores are summed together and represented as an additional score, namely the 'RA total score'.

6.1.9. Micro-Computed Tomography (μCT) Analysis of Calcaneus (Heel Bone):

Bone degradation observed in RA occurs especially at the cortical bone and can be revealed by μCT analysis (Oste et al., 2007; Sims et al., 2004). After scanning and 3D volume reconstruction of the calcaneus bone, bone degradation is measured as the number of discrete objects present per slide, isolated in silico perpendicular to the longitudinal axis of the bone. The more the bone is degraded, the more discrete objects are measured. 1000 slices, evenly distributed along the calcaneus (spaced by about 10.8 μm), are analyzed.

6.1.10. Steady State PK

At day 7 or 11, blood samples were collected at the retro-orbital sinus with lithium heparin as anti-coagulant at the following time points: predose, 1, 3 and 6 h. Whole blood samples were centrifuged and the resulting plasma samples were stored at −20° C. pending analysis. Plasma concentrations of each test compound were determined by an LC-MS/MS method in which the mass spectrometer was operated in positive electrospray mode. Pharmacokinetic parameters were calculated using Winnonlin®(Pharsight®, United States) and it was assumed that the predose plasma levels were equal to the 24 h plasma levels.

6.2. Oncology Models

In vivo models to validate efficacy of small molecules towards JAK2-driven myeoproliferative diseases are described (Geron et al., 2008; Wernig et al., 2008).

6.3. Mouse IBD Model

In vitro and in vivo models to validate efficacy of small molecules towards IBD are described (Wirtz and Neurath, 2007).

6.4. Mouse Asthma model

In vitro and in vivo models to validate efficacy of small molecules towards asthma are described (Ip et al., 2006; Kudlacz et al., 2008; Nials and Uddin, 2008; Pernis and Rothman, 2002).

6.5. Murine Model of Psoriatic-Like Epidermal Hyperplasia Induced by Intradermal Injections of IL22 or IL23

6.5.1. Materials

Mouse recombinant IL22 (582-ML-CF), carrier free is provided by R&D systems. Mouse recombinant IL23, carrier free (14-8231, CF) is provided by e-Bioscience.

6.5.2. Animals

Balb/c mice (female, 18-20 g body weight) are obtained from CERJ (France). Mice are kept on a 12 h light/dark cycle (07:00-19:00). Temperature is maintained at 22° C., food and water are provided ad libitum.

6.5.3. Study Design

The design of the study is adapted from Rizzo et al, 2011.

On the first day (D1), the mice are shaved around the two ears.

For 4 consecutive days (D1 to D4), the mice received a daily intradermal dose of mouse recombinant IL22 or IL23 (1 μg/20 μL in PBS/0.1% BSA) in the right pinna ear and 20 μL of PBS/0.1% BSA in the left pinna ear under anesthesia induced by inhalation of isoflurane.

From D1 to D5, mice are dosed with test-compound (10, 30, or 100 mg/kg, po, qd in MC 0.5%), 1 h prior IL23/IL22 injection or with vehicle.

6.5.4. Assessment of Disease

The thickness of both ears is measured daily with an automatic caliper. Body weight is assessed at initiation and at sacrifice. On fifth day, 2 hrs after the last dosing, the mice are sacrificed. The pinnae of the ear are cut, excluding cartilage. The pinnae are weighed and then, placed in vial containing 1 mL of RNAlater solution or in formaldehyde.

At D4, blood samples are also collected from the retro-orbital sinus for PK profile just before dosing (T0) and 1 h, 3 h, 6 h post-dosing.

There are 8 mice per group. The results are expressed as mean±sem and statistical analysis is performed using one-way Anova followed by Dunnett's post-hoc test versus IL22 or IL23 vehicle groups.

6.5.5. Histology

After sacrifice, ears are collected and fixed in 3.7% formaldehyde before embedding in paraffin. Two μm thick sections are done and stained with hematoxylin and eosin. Ear epidermis thickness is measured by image analysis (Sis'Ncom software) with 6 images per ear captured at magnification ×20. Data are expressed as mean±sem and statistical analysis is performed using one-way Anova followed by Dunnett's post-hoc test versus IL22 or IL23 vehicle groups.

6.5.6. RNA Extraction, RT-PCR and Real-Time PCR

IL-17a, IL-22, IL-1β, LCN2 and S100A9 transcript levels in ear tissue are determined using real-time quantitative PCR.

Example 7

Pharmacokinetic, ADME and Toxicity Assays 7.1. Thermodynamic Solubility

The test compound is added to 0.2M phosphate buffer pH 7.4 or 0.1M citrate buffer pH 3.0 at a concentration of 1 mg/mL in a glass vial.

The samples are rotated in a Rotator drive STR 4 (Stuart Scientific, Bibby) at speed 3.0 at room temperature for 24 h.

After 24 h, 800 μL of the sample is transferred to an eppendorf tube and centrifuged 5 min at 14000 rpm. 200 μL of the supernatant of the sample is then transferred to a MultiscreenR Solubility Plate (Millipore, MSSLBPC50) and the supernatant is filtered (10-12" Hg) with the aid of a vacuum manifold into a clean Greiner polypropylene V-bottom 96 well plate (Cat no. 651201). 5 μL of the filtrate is diluted into 95 μL (F20) of the same buffer used to incubate in the plate containing the standard curve (Greiner, Cat no. 651201).

The standard curve for the compound is prepared freshly in DMSO starting from a 10 mM DMSO stock solution diluted factor 2 in DMSO (5000 µM) and then further diluted in DMSO up to 19.5 µM. 3 µL of the dilution series as from 5000 µM is then transferred to a 97 µL acetonitrile-buffer mixture (50/50). The final concentration range is 2.5 to 150 µM.

The plate is sealed with sealing mats (MA96RD-045, www.kinesis.co.uk) and samples are measured at room temperature on LC-MS (ZQ 1525 from Waters) under optimized conditions using Quanoptimize to determine the appropriate mass of the molecule.

The samples are analyzed on LC-MS with a flow rate of 1 mL/min. Solvent A is 15 mM ammonia and solvent B is acetonitrile. The sample is run under positive ion spray on an XBridge C18 3.5 µM (2.1×30 mm) column, from Waters. The solvent gradient has a total run time of 2 min and ranges from 5% B to 95% B.

Peak areas are analyzed with the aid of Masslynx software package and peak areas of the samples are plotted against the standard curve to obtain the solubility of the compound.

Solubility values are reported in µM or µg/mL.

7.2. Aqueous Solubility

Starting from a 10 mM stock in DMSO, a serial dilution of the compound is prepared in DMSO. The dilution series is transferred to a 96 NUNC Maxisorb plate F-bottom (Cat no. 442404) and 0.1M phosphate buffer pH7.4 or 0.1M citrate buffer pH3.0 at room temperature is added.

The final concentration ranges from 300 µM to 18.75 µM in 5 equal dilution steps. The final DMSO concentration does not exceed 3%. 200 µM Pyrene is added to the corner points of each 96 well plate and serves as a reference point for calibration of Z-axis on the microscope.

The assay plates are sealed and incubated for 1 h at 37° C. while shaking at 230 rpm. The plates are then scanned under a white light microscope, yielding individual pictures of the precipitate per concentration. The precipitate is analyzed and converted into a number with a software tool which can be plotted onto a graph. The first concentration at which the compound appears completely dissolved is the concentration reported; however the true concentration lies somewhere between this concentration and one dilution step higher.

Solubility values measured according to this protocol are reported in µg/mL.

7.3. Plasma Protein Binding (Equilibrium Dialysis)

A 10 mM stock solution of the compound in DMSO is diluted with a factor 5 in DMSO. This solution is further diluted in freshly thawed human, rat, mouse or dog plasma (BioReclamation INC) with a final concentration of 5 µM and final DMSO concentration of 0.5% (5.5 µL in 1094.5 µL plasma in a PP-Masterblock 96well (Greiner, Cat no. 780285))

A Pierce Red Device plate with inserts (ThermoScientific, Cat no. 89809) is prepared and filled with 750 µL PBS in the buffer chamber and 500 µL of the spiked plasma in the plasma chamber. The plate is incubated for 4 h at 37° C. while shaking at 230 rpm. After incubation, 120 µL of both chambers is transferred to 360 µL acetonitrile in a 96-well round bottom, PP deep-well plates (Nunc, Cat no. 278743) and sealed with an aluminum foil lid. The samples are mixed and placed on ice for 30 min. This plate is then centrifuged 30 min at 1200 rcf at 4° C. and the supernatant is transferred to a 96 v-bottom PP plate (Greiner, 651201) for analysis on LC-MS.

The plate is sealed with sealing mats (MA96RD-04S) of www.kinesis.co.uk and samples are measured at room temperature on LC-MS (ZQ 1525 from Waters) under optimized conditions using Quanoptimize to determine the appropriate mass of the molecule.

The samples are analyzed on LC-MS with a flow rate of 1 mL/min. Solvent A is 15 mM ammonia and solvent B is acetonitrile. The sample is run under positive ion spray on an XBridge C18 3.5 µM (2.1×30 mm) column, from Waters. The solvent gradient has a total run time of 2 min and ranges from 5% B to 95% B.

Peak area from the compound in the buffer chamber and the plasma chamber are considered to be 100% compound. The percentage bound to plasma is derived from these results and is reported as percentage bound to plasma.

The solubility of the compound in the final test concentration in PBS is inspected by microscope to indicate whether precipitation is observed or not.

7.4. Aldehyde Oxidase Stability

A 10 mM stock solution of test compound in DMSO is first diluted with water (5 fold) to obtain a 50 µM working solution. A selective inhibitor of aldehyde oxidase (hydralazine) is prepared in water as 5 mM solution.

Incubation mixtures are prepared by adding 10 µL of liver S9 suspension (human and rat, BD Bioscience Gentest, 20 mg/mL) to 86 µL of 50 mM potassium phosphate buffer, pH 7.4 at 37° C. 2 µL of 5 mM hydralazine is added (for incubation with the addition of selective inhibitor) or 2 µL of water (for incubation without the addition of the inhibitor).

After 5 min pre-warming, the reaction is initiated by the addition of 2 µL of 50 µM test compound to the incubation mixtures. After 0, 3, 6, 12, 18, and 30 min of incubation, the reaction (100 µL) is terminated with 300 µL of MeCN:MeOH (2:1) with 1% acetic acid mixture containing 10 ng/mL of warfarin as analytical internal standard.

Samples are mixed, centrifuged, and the supernatant analysed by LC-MS.

Test compounds are considered as a substrate of aldehyde oxidase if clearance by S9 is inhibited by hydralazine. Species specific clearance of test compound may also indicate metabolism by aldehyde oxidase.

Phtalazine is included as a positive control.

The instrument responses (peak area ratio of test compound and internal standard) are referenced to the zero time-point samples (considered as 100%) in order to determine the percentage of compound remaining Plots of the percentage of test compounds remaining are used to determine the half-life ($T_{1/2}$) and intrinsic clearance in the S9 incubations using Graph Pad Prism software.

To calculate the in vitro intrinsic clearance ($CL_{int}$ (µL/min/mg), the following formula is used:

$$CLint = \frac{0.693}{T1/2} * \frac{\text{incubation volume}}{\text{protein amount}} * 1000$$

7.5. Liver Microsomal Stability

A 10 mM stock solution of compound in DMSO is diluted to 6 µM in a 105 mM phosphate buffer, pH 7.4 in a 96 deep well plate (Greiner, Cat no. 780285) and pre-warmed at 37° C.

A Glucose-6-phosphate-dehydrogenase (G6PDH, Roche, 10127671001) working stock solution of 700 U/mL is diluted with a factor 1:700 in a 105 mM phosphate buffer, pH7.4. A co-factor mix containing 0.528M $MgCl_2.6H_2O$ (Sigma, M2670), 0.528M glucose-6-phosphate (Sigma, G-7879) and 0.208M NADP+ (Sigma, N-0505) is diluted with a factor 1:8 in a 105 mM phosphate buffer, pH7.4.

A working solution is made containing 1 mg/mL liver microsomes (Xenotech) of the species of interest (human, mouse, rat, dog . . . ), 0.8 U/mL G6PDH and co-factor mix (6.6 mM $MgCl_2$, 6.6 mM glucose-6-phosphate, 2.6 mM NADP+). This mix is pre-incubated for 15 min, but never more than 20 min, at room temperature.

After pre-incubation, compound dilution and the mix containing the microsomes, are added together in equal amount and incubated for 30 min at 300 rpm. For the time point of 0 min, two volumes of MeOH are added to the compound dilution before the microsome mix is added. The final concentration during incubation are: 3 μM test compound or control compound, 0.5 mg/mL microsomes, 0.4 U/mL G6PDH, 3.3 mM $MgCl_2$, 3.3 mM glucose-6-phosphate and 1.3 mM NaDP+.

After 30 min of incubation, the reaction is stopped with 2 volumes of MeOH.

Of both time points, samples are mixed, centrifuged and the supernatant is harvested for analysis on LC-MS/MS. The instrument responses (i.e. peak heights) are referenced to the zero time-point samples (as 100%) in order to determine the percentage of compound remaining Standard compounds Propanolol and Verapamil are included in the assay design.

The data on microsomal stability are expressed as a percentage of the total amount of compound remaining after 30 min 7.6. Hepatocyte Stability Models to evaluate metabolic clearance in hepatocyte are described by McGinnity et al. Drug Metabolism and Disposition 2008, 32, 11, 1247.

7.7. Caco2 Permeability

Bi-directional Caco-2 assays are performed as described below. Caco-2 cells are obtained from European Collection of Cell Cultures (ECACC, cat 86010202) and used after a 21 day cell culture in 24-well Transwell plates (Fisher TKT-545-020B).

$2 \times 10^5$ cells/well are seeded in plating medium consisting of DMEM+GlutaMAXI+1% NEAA+10% FBS (FetalClone II)+1% Pen/Strep. The medium is changed every 2-3 days.

Test and reference compounds (propranolol and rhodamine123 or vinblastine, all purchased from Sigma) are prepared in Hanks' Balanced Salt Solution containing 25 mM HEPES (pH7.4) and added to either the apical (125 μL) or basolateral (600 μL) chambers of the Transwell plate assembly at a concentration of 10 μM with a final DMSO concentration of 0.25%.

50 μM Lucifer Yellow (Sigma) is added to the donor buffer in all wells to assess integrity of the cell layers by monitoring Lucifer Yellow permeation. As Lucifer Yellow (LY) cannot freely permeate lipophilic barriers, a high degree of LY transport indicates poor integrity of the cell layer.

After a 1 h incubation at 37° C. while shaking at an orbital shaker at 150 rpm, 70 μL aliquots are taken from both apical (A) and basal (B) chambers and added to 100 μL1 50:50 acetonitrile:water solution containing analytical internal standard (0.5 μM carbamazepine) in a 96 well plate.

Lucifer yellow is measured with a Spectramax Gemini XS (Ex 426 nm and Em 538 nm) in a clean 96 well plate containing 150 μL of liquid from basolateral and apical side.

Concentrations of compound in the samples are measured by high performance liquid-chromatography/mass spectroscopy (LC-MS/MS).

Apparent permeability ($P_{app}$) values are calculated from the relationship:

$$P_{APP} = [\text{compound}]_{acceptor\,final} \times V_{acceptor} / ([\text{compound}]_{donor\,initial} \times V_{donor}) / T_{inc} \times V_{donor} / \text{surface area} \times 60 \times 10^{-6} \text{ cm/s}$$

V=chamber volume
$T_{inc}$=incubation time.
Surface area=0.33 $cm^2$

The Efflux ratios, as an indication of active efflux from the apical cell surface, are calculated using the ratio of $P_{app}B>A/P_{app}A>B$.

The following assay acceptance criteria are used:
Propranolol: $P_{app}$ (A>B) value $\geq 20(\times 10^{-6}$ cm/s)
Rhodamine 123 or Vinblastine: $P_{app}$ (A>B) value <5 ($\times 10^{-6}$ cm/s) with Efflux ratio $\geq 5$.
Lucifer yellow permeability: ≤100 nm/s 7.8. MDCKII-MDR1 Permeability MDCKII-MDR1 cells are Madin-Darby canine kidney epithelial cells, over-expressing human multi-drug resistance (MDR1) gene, coding for P-glycoprotein (P-gp). Cells are obtained from Netherlands Cancer Institute and used after a 3-4 day cell culture in 24-well Millicell cell culture insert plates (Millipore, PSRP010R5). Bi-directional MDCKII-MDR1 permeability assay is performed as described below.

$3 \times 10^5$ cells/mL ($1.2 \times 10^5$ cells/well) are seeded in plating medium consisting of DMEM+1% Glutamax-100+1% Antibiotic/Antimycotic+10% FBS (Biowest, S1810). Cells are left in $CO_2$ incubator for 3-4 days. The medium is changed 24 h after seeding and on the day of experiment.

Test and reference compounds (amprenavir and propranolol) are prepared in Dulbecco's phosphate buffer saline (D-PBS, pH7.4) and added to either the apical (400 μL) or basolateral (800 μL) chambers of the Millicell cell culture insert plates assembly at a final concentration of 10 μM (0.5 μM in case of amprenavir) with a final DMSO concentration of 1%.

100 μM Lucifer Yellow (Sigma) is added to the all donor buffer solutions, in order to assess integrity of the cell monolayers by monitoring Lucifer Yellow permeation. Lucifer yellow is a fluorescent marker for the paracellular pathway and it is used as an internal control in every monolayer to verify tight junction integrity during the assay.

After a 1 h incubation at 37° C. while shaking at an orbital shaker at 150 rpm, 75 μL aliquots are taken from both apical (A) and basal (B) chambers and added to 225 μL acetonitrile: water solution (2:1) containing analytical internal standard (10 ng/mL warfarin) in a 96 well plate. Aliquoting is also performed at the beginning of the experiment from donor solutions to obtain initial (Co) concentration.

Concentration of compound in the samples is measured by high performance liquid-chromatography/mass spectroscopy (LC-MS/MS).

Lucifer yellow is measured with a Fluoroscan Ascent FL Thermo Scientific (Ex 485 nm and Em 530 nm) in a 96 well plate containing 150 μL of liquid from all receiver wells (basolateral or apical side).

7.9. Pharmacokinetic Study in Rodents 7.9.1. Animals

Sprague-Dawley rats (male, 5-6 weeks old) are obtained from Janvier (France). Rats are acclimatized for at least 7 days before treatment and are kept on a 12 h light/dark cycle (0700-1900). Temperature is maintained at approximately 22° C., and food and water are provided ad libitum. Two days before administration of the test compounds, rats underwent surgery to place a catheter in the jugular vein under isoflurane anesthesia. After the surgery, rats are housed individually. Rats are deprived of food for at least 16 h before oral dosing and 6 h after. Water is provided ad libitum.

7.9.2. Pharmacokinetic Study

Compounds are formulated in PEG200/physiological saline (60/40) for the intravenous route and in 0.5% methylcellulose and 10% hydroxylpropyl-β-cyclodextrine pH 3 for the oral route. Test compounds are orally dosed as a single esophageal gavage at 5 mg/kg under a dosing volume of 5 mL/kg and intravenously dosed as a bolus via the caudal vein at 1 mg/kg under a dosing volume of 5 mL/kg. Each group consisted of 3 rats. Blood samples are collected via the jugular vein with lithium heparin as anti-coagulant at the following time points: 0.05, 0.25, 0.5, 1, 3, 5 and 8 h (intravenous route), and 0.25, 0.5, 1, 3, 5, 8 and 24 h (oral route). Alternatively, blood samples are collected at the retro-orbital sinus with lithium heparin as anti-coagulant at the following time points 0.25, 1, 3 and 6 h (oral route). Whole blood samples are centrifuged at 5000 rpm for 10 min and the resulting plasma samples are stored at −20° C. pending analysis.

7.9.3. Quantification of Compound Levels in Plasma

Plasma concentrations of each test compound are determined by an LC-MS/MS method in which the mass spectrometer is operated in positive electrospray mode.

7.9.4. Determination of Pharmacokinetic Parameters

Pharmacokinetic parameters are calculated using Winnonlin® (Pharsight®, United States).

7.10. 7-Day Rat Toxicity Study

A 7-day oral toxicity study with test compounds is performed in Sprague-Dawley male rats to assess their toxic potential and toxicokinetics, at daily doses of 100, 300 and 500 mg/kg/day, by gavage, at the constant dosage-volume of 5 mL/kg/day.

The test compounds are formulated in 30% (v/v) HPβCD in purified water. Each group included 5 principal male rats as well as 3 satellite animals for toxicokinetics. A fourth group is given 30% (v/v) HPβCD in water only, at the same frequency, dosage volume and by the same route of administration, and acted as the vehicle control group.

The goal of the study is to determine the lowest dose that resulted in no adverse events being identified (no observable adverse effect level—NOAEL).

7.11. Liability for QT Prolongation

Potential for QT prolongation is assessed in the hERG patch clamp assay.

Whole-cell patch-clamp recordings are performed using an EPC10 amplifier controlled by Pulse v8.77 software (HEKA). Series resistance is typically less than 10 MΩ and compensated by greater than 60%, recordings are not leak subtracted. Electrodes are manufactured from GC150TF pipette glass (Harvard).

The external bathing solution contained: 135 mM NaCl, 5 mM KCl, 1.8 mM $CaCl_2$, 5 mM Glucose, 10 mM HEPES, pH 7.4.

The internal patch pipette solution contained: 100 mM Kgluconate, 20 mM KCl, 1 mM $CaCl_2$, 1 mM $MgCl_2$, 5 mM $Na_2ATP$, 2 mM Glutathione, 11 mM EGTA, 10 mM HEPES, pH 7.2.

Drugs are perfused using a Biologic MEV-9/EVH-9 rapid perfusion system.

All recordings are performed on HEK293 cells stably expressing hERG channels. Cells are cultured on 12 mm round coverslips (German glass, Bellco) anchored in the recording chamber using two platinum rods (Goodfellow). hERG currents are evoked using an activating pulse to +40 mV for 1000 ms followed by a tail current pulse to −50 mV for 2000 ms, holding potential is −80 mV. Pulses are applied every 20 s and all experiments are performed at room temperature.

Final Remarks

It will be appreciated by those skilled in the art that the foregoing descriptions are exemplary and explanatory in nature, and intended to illustrate the invention and its preferred embodiments. Through routine experimentation, an artisan will recognize apparent modifications and variations that may be made without departing from the spirit of the invention. All such modifications coming within the scope of the appended claims are intended to be included therein. Thus, the invention is intended to be defined not by the above description, but by the following claims and their equivalents.

All publications, including but not limited to patents and patent applications, cited in this specification are herein incorporated by reference as if each individual publication are specifically and individually indicated to be incorporated by reference herein as though fully set forth.

It should be understood that factors such as the differential cell penetration capacity of the various compounds can contribute to discrepancies between the activity of the compounds in the in vitro biochemical and cellular assays.

At least some of the chemical names of compound of the invention as given and set forth in this application, may have been generated on an automated basis by use of a commercially available chemical naming software program, and have not been independently verified. Representative programs performing this function include the Lexichem naming tool sold by Open Eye Software, Inc. and the Autonom Software tool sold by MDL, Inc. In the instance where the indicated chemical name and the depicted structure differ, the depicted structure will control.

REFERENCES

Bundgaard, H., 1985. Design of prodrugs. Elsevier.
Bush, K. A., Farmer, K. M., Walker, J. S., Kirkham, B. W., 2002. Reduction of joint inflammation and bone erosion in rat adjuvant arthritis by treatment with interleukin-17 receptor IgG1 Fc fusion protein. Arthritis Rheum. 46, 802-805. doi:10.1002/art.10173
Choy, E. H. S., Panayi, G. S., 2001. Cytokine Pathways and Joint Inflammation in Rheumatoid Arthritis. N. Engl. J. Med. 344, 907-916. doi:10.1056/NEJM200103223441207
Clegg, D. O., Reda, D. J., Harris, C. L., Klein, M. A., O'Dell, J. R., Hooper, M. M., Bradley, J. D., Bingham, C. O., Weisman, M. H., Jackson, C. G., Lane, N. E., Cush, J. J., Moreland, L. W., Schumacher, H. R., Oddis, C. V., Wolfe, F., Molitor, J. A., Yocum, D. E., Schnitzer, T. J., Furst, D. E., Sawitzke, A. D., Shi, H., Brandt, K. D., Moskowitz, R. W., Williams, H. J., 2006. Glucosamine, Chondroitin Sulfate, and the Two in Combination for Painful Knee Osteoarthritis. N. Engl. J. Med. 354, 795-808. doi: 10.1056/NEJMoa052771
Constantinescu, S. N., Girardot, M., Pecquet, C., 2008. Mining for JAK-STAT mutations in cancer. Trends Biochem. Sci. 33, 122-131. doi:10.1016/j.tibs.2007.12.002
Firestein, G. S., 2003. Evolving concepts of rheumatoid arthritis. Nature 423, 356-361. doi:10.1038/nature01661
Geron, I., Abrahamsson, A. E., Barroga, C. F., Kavalerchik, E., Gotlib, J., Hood, J. D., Durocher, J., Mak, C. C., Noronha, G., Soll, R. M., Tefferi, A., Kaushansky, K., Jamieson, C. H. M., 2008. Selective Inhibition of JAK2-Driven Erythroid Differentiation of Polycythemia Vera Progenitors. Cancer Cell 13, 321-330. doi:10.1016/j.ccr.2008.02.017

Ip, W. K., Wong, C. K., Lam, C. W. K., 2006. Interleukin (IL)-4 and IL-13 up-regulate monocyte chemoattractant protein-1 expression in human bronchial epithelial cells: involvement of p38 mitogen-activated protein kinase, extracellular signal-regulated kinase 1/2 and Janus kinase-2 but not c-Jun NH2-terminal kinase 1/2 signalling pathways. Clin. Exp. Immunol. 145, 162-172. doi:10.1111/j.1365-2249.2006.03085.x Jou, I.-M., Shiau, A.-L., Chen, S.-Y., Wang, C.-R., Shieh, D.-B., Tsai, C.-S., Wu, C.-L., 2005. Thrombospondin 1 as an effective gene therapeutic strategy in collagen-induced arthritis. Arthritis Rheum. 52, 339-344. doi:10.1002/art.20746

Kan, Z., Zheng, H., Liu, X., Li, S., Barber, T. D., Gong, Z., Gao, H., Hao, K., Willard, M. D., Xu, J., Hauptschein, R., Rejto, P. A., Fernandez, J., Wang, G., Zhang, Q., Wang, B., Chen, R., Wang, J., Lee, N. P., Zhou, W., Lin, Z., Peng, Z., Yi, K., Chen, S., Li, L., Fan, X., Yang, J., Ye, R., Ju, J., Wang, K., Estrella, H., Deng, S., Wei, P., Qiu, M., Wulur, I. H., Liu, J., Ehsani, M. E., Zhang, C., Loboda, A., Sung, W. K., Aggarwal, A., Poon, R. T., Fan, S. T., Wang, J., Hardwick, J., Reinhard, C., Dai, H., Li, Y., Luk, J. M., Mao, M., 2013. Whole-genome sequencing identifies recurrent mutations in hepatocellular carcinoma. Genome Res. 23, 1422-1433. doi:10.1101/gr.154492.113

Khachigian, L. M., 2006. Collagen antibody-induced arthritis. Nat. Protoc. 1, 2512-2516. doi:10.1038/nprot.2006.393

Kopf, M., Bachmann, M. F., Marsland, B. J., 2010. Averting inflammation by targeting the cytokine environment. Nat. Rev. Drug Discov. 9, 703-718. doi:10.1038/nrd2805

Kudlacz, E., Conklyn, M., Andresen, C., Whitney-Pickett, C., Changelian, P., 2008. The JAK-3 inhibitor CP-690550 is a potent anti-inflammatory agent in a murine model of pulmonary eosinophilia. Eur. J. Pharmacol. 582, 154-161. doi:10.1016/j.ejphar.2007.12.024 Lee, D. M., Weinblatt, M. E., 2001. Rheumatoid arthritis. The Lancet 358, 903-911. doi:10.1016/50140-6736(01)06075-5

Legendre, F., Dudhia, J., Pujol, J.-P., Bogdanowicz, P., 2003. JAK/STAT but Not ERK1/ERK2 Pathway Mediates Interleukin (IL)-6/Soluble IL-6R Down-regulation of Type II Collagen, Aggrecan Core, and Link Protein Transcription in Articular Chondrocytes ASSOCIATION WITH A DOWN-REGULATION OF SOX9 EXPRESSION. J. Biol. Chem. 278, 2903-2912. doi:10.1074/jbc.M110773200

Levy, D. E., Loomis, C. A., 2007. STAT3 Signaling and the Hyper-IgE Syndrome. N. Engl. J. Med. 357, 1655-1658. doi:10.1056/NEJMe078197

Lin, H.-S., Hu, C.-Y., Chan, H.-Y., Liew, Y.-Y., Huang, H.-P., Lepescheux, L., Bastianelli, E., Baron, R., Rawadi, G., Clément-Lacroix, P., 2007. Anti-rheumatic activities of histone deacetylase (HDAC) inhibitors in vivo in collagen-induced arthritis in rodents. Br. J. Pharmacol. 150, 862-872. doi:10.1038/sj.bjp.0707165

Li, W. Q., Dehnade, F., Zafarullah, M., 2001. Oncostatin M-Induced Matrix Metalloproteinase and Tissue Inhibitor of Metalloproteinase-3 Genes Expression in Chondrocytes Requires Janus Kinase/STAT Signaling Pathway. J. Immunol. 166, 3491-3498.

Menet, C. J. M., Schmitt, B. A., Geney, R. J. J., Doyle, K. J., Peach, J., Palmer, N. J., Jones, G. P., Hardy, D., Duffy, J. E. S., 2013. Imidazo[4,5-C] Pyridine Derivatives Useful for the Treatment of Degenerative and Inflammatory Diseases. WO2013117645 (A1).

Mullighan, C. G., Zhang, J., Harvey, R. C., Collins-Underwood, J. R., Schulman, B. A., Phillips, L. A., Tasian, S. K., Loh, M. L., Su, X., Liu, W., Devidas, M., Atlas, S. R., Chen, I.-M., Clifford, R. J., Gerhard, D. S., Carroll, W. L., Reaman, G. H., Smith, M., Downing, J. R., Hunger, S. P., Willman, C. L., 2009. JAK mutations in high-risk childhood acute lymphoblastic leukemia. Proc. Natl. Acad. Sci. U.S.A. 106, 9414-9418. doi:10.1073/pnas.0811761106

Naka, T., Nishimoto, N., Kishimoto, T., 2002. The paradigm of IL-6: from basic science to medicine. Arthritis Res. 4, S233-S242. doi:10.1186/ar565

Nials, A. T., Uddin, S., 2008. Mouse models of allergic asthma: acute and chronic allergen challenge. Dis. Model. Mech. 1, 213-220. doi:10.1242/dmm.000323

Nishida, K., Komiyama, T., Miyazawa, S., Shen, Z.-N., Furumatsu, T., Doi, H., Yoshida, A., Yamana, J., Yamamura, M., Ninomiya, Y., Inoue, H., Asahara, H., 2004. Histone deacetylase inhibitor suppression of autoantibody-mediated arthritis in mice via regulation of p16INK4a and p21WAF1/Cip1 expression. Arthritis Rheum. 50, 3365-3376. doi:10.1002/art.20709

O'Dell, J. R., 2004. Therapeutic Strategies for Rheumatoid Arthritis. N. Engl. J. Med. 350, 2591-2602. doi:10.1056/NEJMra040226

Osaki, M., Tan, L., Choy, B. K., Yoshida, Y., Cheah, K. S. E., Auron, P. E., Goldring, M. B., 2003. The TATA-containing core promoter of the type II collagen gene (COL2A1) is the target of interferon-gamma-mediated inhibition in human chondrocytes: requirement for Stat1 alpha, Jak1 and Jak2. Biochem. J. 369, 103-115. doi:10.1042/BJ20020928

O'Shea, J. J., Pesu, M., Borie, D. C., Changelian, P. S., 2004. A new modality for immunosuppression: targeting the JAK/STAT pathway. Nat. Rev. Drug Discov. 3, 555-564. doi:10.1038/nrd1441

Oste, L., Salmon, P., Dixon, G., van Rompaey, L., 2007. A high throughput method of measuring bone architectural disturbance in a murine CIA model by micro-CT morphometry.

O×Sullivan, L. A., Liongue, C., Lewis, R. S., Stephenson, S. E. M., Ward, A. C., 2007. Cytokine receptor signaling through the Jak-Stat-Socs pathway in disease. Mol. Immunol 44, 2497-2506. doi:10.1016/j.molimm.2006.11.025

Otero, M., Lago, R., Lago, F., Reino, J. J. G., Gualillo, O., 2005. Signalling pathway involved in nitric oxide synthase type II activation in chondrocytes: synergistic effect of leptin with interleukin-1. Arthritis Res. Ther. 7, R581-R591. doi:10.1186/ar1708

Pernis, A. B., Rothman, P. B., 2002. JAK-STAT signaling in asthma. J. Clin. Invest. 109, 1279-1283. doi:10.1172/JCI15786

Rall, L. C., Roubenoff, R., 2004. Rheumatoid cachexia: metabolic abnormalities, mechanisms and interventions. Rheumatology 43, 1219-1223. doi:10.1093/rheumatology/keh321

Rodig, S. J., Meraz, M. A., White, J. M., Lampe, P. A., Riley, J. K., Arthur, C. D., King, K. L., Sheehan, K. C. F., Yin, L., Pennica, D., Johnson Jr., E. M., Schreiber, R. D., 1998. Disruption of the Jak1 Gene Demonstrates Obligatory and Nonredundant Roles of the Jaks in Cytokine-Induced Biologic Responses. Cell 93, 373-383. doi:10.1016/S0092-8674(00)81166-6

Salvemini, D., Mazzon, E., Dugo, L., Serraino, I., De Sarro, A., Caputi, A. P., Cuzzocrea, S., 2001. Amelioration of joint disease in a rat model of collagen-induced arthritis by M40403, a superoxide dismutase mimetic. Arthritis Rheum. 44, 2909-2921.

Shelton, D. L., Zeller, J., Ho, W.-H., Pons, J., Rosenthal, A., 2005. Nerve growth factor mediates hyperalgesia and cachexia in auto-immune arthritis. Pain 116, 8-16. doi:10.1016/j.pain.2005.03.039

Sims, N. A., Green, J. R., Glatt, M., Schlict, S., Martin, T. J., Gillespie, M. T., Romas, E., 2004. Targeting osteoclasts with zoledronic acid prevents bone destruction in collagen-induced arthritis. Arthritis Rheum. 50, 2338-2346. doi:10.1002/art.20382

Smolen, J. S., Steiner, G., 2003. Therapeutic strategies for rheumatoid arthritis. Nat. Rev. Drug Discov. 2, 473-488. doi:10.1038/nrd1109

Staerk, J., Kallin, A., Demoulin, J.-B., Vainchenker, W., Constantinescu, S. N., 2005. JAK1 and Tyk2 Activation by the Homologous Polycythemia Vera JAK2 V617F Mutation CROSS-TALK WITH IGF1 RECEPTOR. J. Biol. Chem. 280, 41893-41899. doi:10.1074/jbc.C500358200

Tam, L., McGlynn, L. M., Traynor, P., Mukherjee, R., Bartlett, J. M. S., Edwards, J., 2007. Expression levels of the JAK/STAT pathway in the transition from hormone-sensitive to hormone-refractory prostate cancer. Br. J. Cancer 97, 378-383. doi:10.1038/sj.bjc.6603871

Vainchenker, W., Dusa, A., Constantinescu, S. N., 2008. JAKs in pathology: Role of Janus kinases in hematopoietic malignancies and immunodeficiencies. Semin. Cell Dev. Biol. 19, 385-393. doi:10.1016/j.semcdb.2008.07.002

Vandeghinste, N., Tomme, P., Michiels, F., Ma, L., Mille-Baker, B., Van, E., 2005. Methods and Means for Treatment of Osteoarthritis. WO2005124342 (A2).

Walsmith, J., Abad, L., Kehayias, J., Roubenoff, R., 2004. Tumor necrosis factor-alpha production is associated with less body cell mass in women with rheumatoid arthritis. J. Rheumatol. 31, 23-29.

Wernig, G., Kharas, M. G., Okabe, R., Moore, S. A., Leeman, D. S., Cullen, D. E., Gozo, M., McDowell, E. P., Levine, R. L., Doukas, J., Mak, C. C., Noronha, G., Martin, M., Ko, Y. D., Lee, B. H., Soll, R. M., Tefferi, A., Hood, J. D., Gilliland, D. G., 2008. Efficacy of TG101348, a selective JAK2 inhibitor, in treatment of a murine model of JAK2V617F-induced polycythemia vera. Cancer Cell 13, 311-320. doi:10.1016/j.ccr.2008.02.009

Wieland, H. A., Michaelis, M., Kirschbaum, B. J., Rudolphi, K. A., 2005. Osteoarthritis—an untreatable disease? Nat. Rev. Drug Discov. 4, 331-344. doi:10.1038/nrd1693

Wirtz, S., Neurath, M. F., 2007. Mouse models of inflammatory bowel disease. Adv. Drug Deliv. Rev. 59, 1073-1083. doi:10.1016/j.addr.2007.07.003

Xiang, Z., Zhao, Y., Mitaksov, V., Fremont, D. H., Kasai, Y., Molitoris, A., Ries, R. E., Miner, T. L., McLellan, M. D., DiPersio, J. F., Link, D. C., Payton, J. E., Graubert, T. A., Watson, M., Shannon, W., Heath, S. E., Nagarajan, R., Mardis, E. R., Wilson, R. K., Ley, T. J., Tomasson, M. H., 2008. Identification of somatic JAK1 mutations in patients with acute myeloid leukemia. Blood 111, 4809-4812. doi:10.1182/blood-2007-05-090308

Zenatti, P. P., Ribeiro, D., Li, W., Zuurbier, L., Silva, M. C., Paganin, M., Tritapoe, J., Hixon, J. A., Silveira, A. B., Cardoso, B. A., Sarmento, L. M., Correia, N., Toribio, M. L., Kobarg, J., Horstmann, M., Pieters, R., Brandalise, S. R., Ferrando, A. A., Meijerink, J. P., Durum, S. K., Yunes, J. A., Barata, J. T., 2011. Oncogenic IL7R gain-of-function mutations in childhood T-cell acute lymphoblastic leukemia. Nat. Genet. 43, 932-939. doi:10.1038/ng.924

The invention claimed is:

1. A compound according to Formula I:

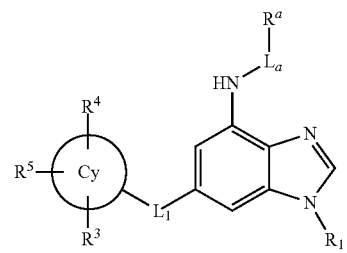

wherein
$R^1$ is H, or Me;
$L_1$ is —$NR^2$—; —O—, or —$CH_2$—;
Cy is pyridinyl;
$R^2$ is H, or $C_{1-4}$ alkyl;
$R^3$ is H, halo, $C_{1-4}$ alkyl optionally substituted with one or more halo, or $C_{1-4}$ alkoxy optionally substituted with one or more halo;
$R^4$ is H, or halo;
$R^5$ is —CN, halo, or is -$L_2$-$R^6$;
-$L_2$ is absent, or is —C(=O)—, —C(=O)$NR^7$—, —$NR^7$C(=O)—, —$SO_2$—, —$SO_2NR^7$—, or —$NR^7SO_2$—;
$R^6$ is H, or $C_{1-6}$ alkyl optionally substituted with one or more independently selected $R^8$ groups;
$R^7$ is H, or $C_{1-4}$ alkyl;
$R^8$ is OH, CN, halo, or $C_{1-4}$ alkoxy,
$L_a$ is absent, or is —C(=O)—, —C(=O)O—, or —C(=O)NH—;
$R^a$ is:
H,
$C_{1-4}$ alkyl optionally substituted with one or more independently selected $R^b$, or
$C_{3-7}$ monocyclic cycloalkyl optionally substituted with one or more independently selected $R^c$;
$R^b$ is
halo,
CN,
OH,
$C_{1-4}$ alkoxy,
$C_{3-7}$ cycloalkyl,
—$SO_2$—$C_{1-4}$ alkyl, or
—C(=O)$NR^{b1}R^{b2}$
$R^c$ is
halo,
CN,
OH,
$C_{1-4}$ alkyl,
—C(=O)OH, or
—C(=O)$NR^{c1}R^{c2}$; and
each $R^{b1}$, $R^{b2}$, $R^{c1}$ and $R^{c2}$ is independently selected from H, and $C_{1-4}$ alkyl, or a pharmaceutically acceptable salt thereof.

2. A compound or pharmaceutically acceptable salt according to claim 1, wherein $R^1$ is Me.

3. A compound or pharmaceutically acceptable salt according to claim 1, wherein the compound is according to Formula IIb, or IIc:

IIb
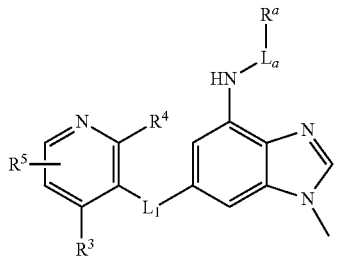

IIc
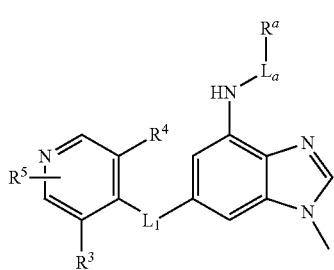

wherein $L_1$, $R^3$, $R^4$, $L_a$, $R^a$ and $R^5$ are as described in claim 1.

4. A compound or pharmaceutically acceptable salt according to claim 1, wherein the compound is according to Formula IVb, IVc, IVe or IVf:

IVb
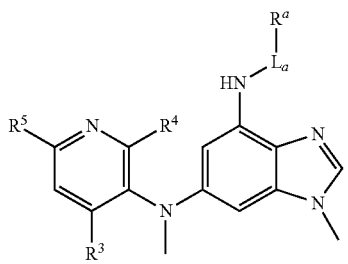

IVc
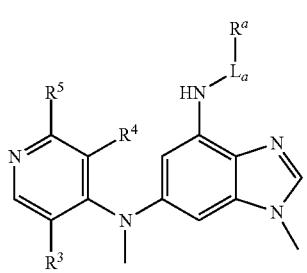

IVe
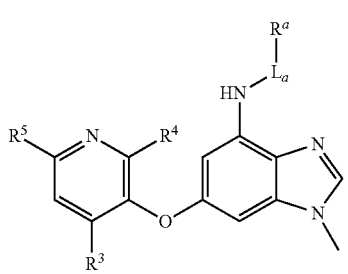

IVf
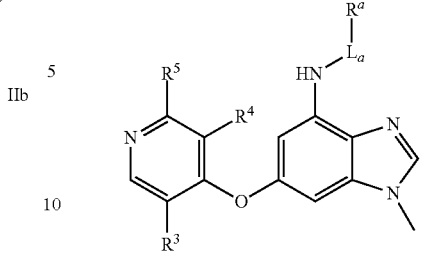

wherein $R^3$, $R^4$, $R^5$, $L_a$, and $R^a$ are as described in claim 1.

5. A compound or pharmaceutically acceptable salt according to claim 1, wherein the compound is according to Formula Vb, Vc, Ve or Vf:

Vb
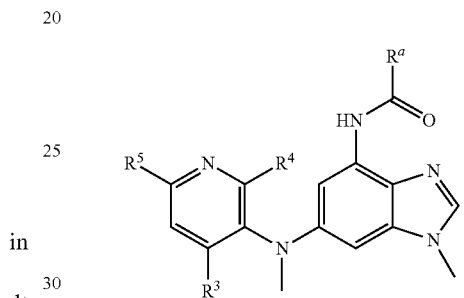

Vc
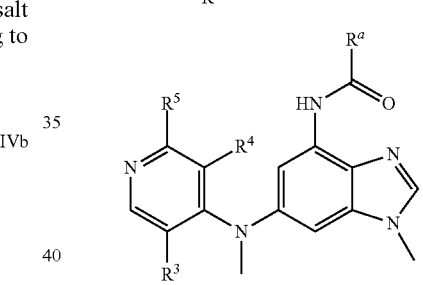

Ve
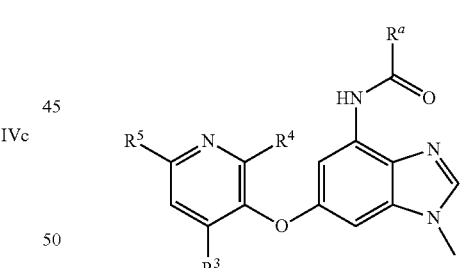

Vf
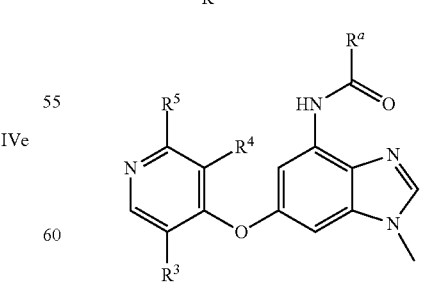

wherein $R^3$, $R^4$, $R^5$, $L_a$, and $R^a$ are as described in claim 1.

6. A compound or pharmaceutically acceptable salt according to claim 1, wherein $R^4$ is H, F, or Cl.

7. A compound or pharmaceutically acceptable salt according to claim 1, wherein R³ is H, Me, or Et.

8. A compound or pharmaceutically acceptable salt according to claim 1, wherein R⁵ is CN, F, Cl, —SO₂Me or —SO₂Et.

9. A compound or pharmaceutically acceptable salt according to claim 1, wherein $R^a$ is:

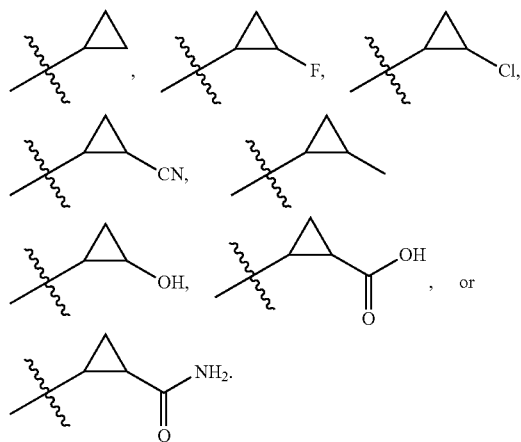

10. A compound, or pharmaceutically acceptable salt thereof, according to claim 1 wherein the compound is (1R,2R)—N-[6-[(6-cyano-4-methyl-3-pyridyl)oxy]-1-methyl-benzimidazol-4-yl]-2-fluoro-cyclopropanecarboxamide.

11. A pharmaceutical composition comprising a pharmaceutically acceptable carrier and a pharmaceutically effective amount of a compound, or a pharmaceutically acceptable salt thereof, according to claim 1.

12. A compound or pharmaceutically acceptable salt according to claim 1, wherein La is —C(═O)—, —C(═O)O—, or —C(═O)NH—.

13. A compound or pharmaceutically acceptable salt according to claim 1, wherein Ra is Me, or Et.

14. A compound or pharmaceutically acceptable salt according to claim 1, wherein the compound is selected from N-(6-(((6-cyano-4-ethylpyridin-3-yl)(methyl)amino)-1-methyl-1H-benzo[d]imidazol-4-yl)cyclopropanecarboxamide;

Methyl 6-((6-cyano-4-ethylpyridin-3-yl)(methyl)amino)-1-methyl-1H-benzo[d]imidazol-4-ylcarbamate;

(1R,2R)—N-[6-[(6-cyano-4-ethyl-3-pyridyl)oxy]-1-methyl-benzimidazol-4-yl]-2-fluoro-cyclopropanecarboxamide;

(1R,2R)—N-(6-((6-cyano-4-ethylpyridin-3-yl)(methyl)amino)-1-methyl-1H-benzo[d]imidazol-4-yl)-2-fluoro-cyclopropanecarboxamide;

(1R,2R)—N-(6-((6-cyano-4-methylpyridin-3-yl)(methyl)amino)-1-methyl-1H-benzo[d]imidazol-4-yl)-2-fluoro-cyclopropanecarboxamide;

(1R,2R)-2-fluoro-N-[6-[(6-fluoro-4-methyl-3-pyridyl)-methyl-amino]-1-methyl-benzimidazol-4-yl]cyclopropanecarboxamide;

(1R,2R)—N-[6-[(2,6-difluoro-3-pyridyl)-methyl-amino]-1-methyl-benzimidazol-4-yl]-2-fluoro-cyclopropanecarboxamide;

(1R,2R)—N-[6-[(6-cyano-2-fluoro-3-pyridyl)-methyl-amino]-1-methyl-benzimidazol-4-yl]-2-fluoro-cyclopropanecarboxamide;

N-[6-[(4-ethyl-6-methyl sulfonyl-3-pyridyl)-methyl-amino]-1-methyl-benzimidazol-4-yl]cyclopropanecarboxamide;

(1R,2R)—N-[6-[(6-cyano-4-methyl-3-pyridyl)oxy]-1-methyl-benzimidazol-4-yl]-2-fluoro-cyclopropanecarboxamide;

(1R,2R)—N-[6-[(6-cyano-2-fluoro-4-methyl-3-pyridyl)-methyl-amino]-1-methyl-benzimidazol-4-yl]-2-fluoro-cyclopropanecarboxamide;

(1R,2R)—N-[6-[(2-cyano-3-fluoro-5-methyl-4-pyridyl)-methyl-amino]-1-methyl-benzimidazol-4-yl]-2-fluoro-cyclopropanecarboxamide;

N-[6-[(6-cyano-4-methyl-3-pyridyl)oxy]-1-methyl-benzimidazol-4-yl]cyclopropanecarboxamide;

5-((4-(cyclopropanecarboxamido)-1-methyl-1H-benzo[d]imidazol-6-yl)(methyl)amino)-4-ethylpicolinamide;

4-ethyl-5-((4-((1R,2R)-2-fluorocyclopropanecarboxamido)-1-methyl-1H-benzo[d]imidazol-6-yl)(methyl)amino)picolinamide;

5-(7-amino-3-methyl-benzimidazol-5-yl)oxy-4-methyl-pyridine-2-carbonitrile;

N-[6-[(4-ethyl-6-methyl sulfonyl-3-pyridyl)oxy]-1-methyl-benzimidazol-4-yl]cyclopropanecarboxamide;

5-[7-[[(1R,2R)-2-fluorocyclopropanecarbonyl]amino]-3-methyl-benzimidazol-5-yl]oxy-4-methyl-pyridine-2-carboxamide;

1-[6-[(6-cyano-4-methyl-3-pyridyl)oxy]-1-methyl-benzimidazol-4-yl]-3-isopropyl-urea;

4-methyl-5-[3-methyl-7-(methylamino)benzimidazol-5-yl]oxy-pyridine-2-carbonitrile;

5-[7-(dimethylamino)-3-methyl-benzimidazol-5-yl]oxy-4-methyl-pyridine-2-carbonitrile; and 1-[6-[(6-cyano-4-methyl-3-pyridyl)oxy]-1-methyl-benzimidazol-4-yl]-3-isopropyl-urea.

* * * * *